US011998540B2

(12) United States Patent
Liau et al.

(10) Patent No.: US 11,998,540 B2
(45) Date of Patent: Jun. 4, 2024

(54) COMPOSITIONS AND METHODS FOR TREATING DRUG-TOLERANT GLIOBLASTOMA

(71) Applicant: THE GENERAL HOSPITAL CORPORATION, Boston, MA (US)

(72) Inventors: Brian B. Liau, Boston, MA (US); Anoop P. Patel, Boston, MA (US); Cem Sievers, Boston, MA (US); Bradley E. Bernstein, Boston, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 16/060,852

(22) PCT Filed: Mar. 24, 2016

(86) PCT No.: PCT/US2016/024083

§ 371 (c)(1),
(2) Date: Jun. 8, 2018

(87) PCT Pub. No.: WO2017/099829

PCT Pub. Date: Jun. 15, 2017

(65) Prior Publication Data

US 2019/0000831 A1 Jan. 3, 2019

Related U.S. Application Data

(60) Provisional application No. 62/266,544, filed on Dec. 11, 2015.

(51) Int. Cl.

| | |
|---|---|
| *A61K 31/4709* | (2006.01) |
| *A61K 31/44* | (2006.01) |
| *A61K 31/506* | (2006.01) |
| *A61K 31/55* | (2006.01) |
| *A61K 31/5513* | (2006.01) |
| *A61K 45/06* | (2006.01) |
| *A61P 35/00* | (2006.01) |

(52) U.S. Cl.
CPC .......... *A61K 31/4709* (2013.01); *A61K 31/44* (2013.01); *A61K 31/506* (2013.01); *A61K 31/55* (2013.01); *A61K 31/5513* (2013.01); *A61K 45/06* (2013.01); *A61P 35/00* (2018.01); *A61K 2300/00* (2013.01)

(58) Field of Classification Search
CPC .. A61K 31/44; A61K 31/4709; A61K 31/506; A61K 31/55; A61K 31/5513; A61K 45/06; A61K 2300/00; A61P 35/00
See application file for complete search history.

(56) References Cited

U.S. PATENT DOCUMENTS

2011/0178046 A1 7/2011 Ross et al.
2014/0371214 A1* 12/2014 Labelle ................ C07D 401/04 514/228.8

FOREIGN PATENT DOCUMENTS

WO 2012071469 A2 5/2012
WO WO 2014053491 * 4/2014

OTHER PUBLICATIONS

Xing et al., Elevated expression of Notch-1 and EGFR induced apoptosis in glioblastoma multiforme patients. Clinical Neurology and Neurosurgery, vol. 131, pp. 54-58 (Year: 2015).*
Lathia et al., Cancer stem cells in glioblastoma. Genes & Development, vol. 29, pp. 1203-1717 (Year: 2015).*
Hulleman et al., A role for the transcription faction HEY1 in glioblastoma. J. Cell. Mol. vol. 13(1), pp. 136-146 (Year: 2009).*
Chudnovsky et al. ZFHX4 interacts with the NuRD core member CHD4 and regulates the glioblastoma tumor initiating cell state. Cell Rep. vol. 30(6), pp. 313-324 (Year: 2014).*
Suva et al., Reconstructing and reprogramming the tumor propagating potential of glioblastoma stem-like cells. Cell. vol. 157(3), pp. 580-594 (Year: 2014).*
Truffaux et al., "Preclinical evaluation of dasatinib alone and in combination with cabozantinib for the treatment of diffuse intrinsic pontine glioma", Neuro-Oncology, 17(7), pp. 953-964 (Year: 2015).*
Cenciarelli et al., PDGF receptor alpha inhibition induces apoptosis in glioblastoma cancer stem cells refractory to anti-Notch and anti_EGFR treatment. Molecular Cancer, vol. 13, 347 (Year: 2014).*
Supplemental European Search Report, dated Jul. 19, 2019, as received in corresponding European Patent Application No. 16873494.5 (7 pages).
Cenciarelli et al., "PDGF receptor alpha inhibition induces apoptosis in glioblastoma cancer stem cells refractory to anti-Notch and anit-EGFR treatment," vol. 13:247, Mol. Cancer (2014).
Hashizume et al., "Pharmacologic inhibition of histone demethylation as a therapy for pediatric brainstem glioma," Nat Med., vol. 20(12), pp. 1394-1396 (2014).
Lassman et al., "Phase 2 trial of dasatinib in target-selected patients with recurrent glioblastoma (RTOG 0627)," Neuro Oncol., vol. 17(7), pp. 992-998 (2015).
Vandyke et al., "The tyrosine kinase inhibitor dasatinib (SPRYCEL) inhibits chondrocyte activity and proliferation," Blood Cancer J., vol. 1(2):e2, pp. 1-4 (2011).
Chan et al., "The histone H3.3K27M mutation in pediatric glioma reprograms H3K27 methylation and gene expression," Genes Dev., vol. 27(9), pp. 985-990 (2013).

(Continued)

*Primary Examiner* — Barbara P Badio
(74) *Attorney, Agent, or Firm* — Melissa Hunter-Ensor; Scott Goncher; Greenberg Traurig, LLP

(57) ABSTRACT

The present invention provides compositions and methods for the treatment of drug-tolerant glioblastoma, and in particular glioblastoma stem cells. Specifically, the methods comprise contacting a glioblastoma stem cell with a platelet-derived growth factor receptor alpha inhibitor and one or more of a histone lysine demethylase inhibitor and a Notch inhibitor.

1 Claim, 64 Drawing Sheets

Specification includes a Sequence Listing.

(56) References Cited

OTHER PUBLICATIONS

Nehoff et al., "A combination of tyrosine kinase inhibitors, crizotinib and dasatinib for the treatment of glioblastoma multiforme," Oncotarget, vol. 6(35), pp. 37948-64 (2015).
International Search Report and Written Opinion for corresponding PCT patent application PCT/US2016/24083, dated Jul. 14, 2016 (13 pages).
Baxter J, et al, "Histone hypomethylation is an indicator of epigenetic plasticity in quiescent lymphocytes," The EMBO Journal 23 (2004): 4462-4472.
Chen J, et al, "A restricted cell population propagates glioblastoma growth following chemotherapy," Nature 488 (2012): 522-526.
Kidder, BJ, et al, "KDM5B focuses H3K4 methylation near promoters and enhancers during embryonic stem cell self-renewal and differentiation," Genome Biology 15 (2014): R32.
Ntziachristos, P, et al., "Contrasting roles for histone 3 lysine 27 demethylases in acute lymphoblastic leukemia," Nature 514 (2014): 513-517.
Pollard SM, et al, "Glioma Stem Cell Lines Expanded in Adherent Culture Have Tumor-Specific Phenotypes and Are Suitable for Chemical and Genetic Screens," Cell Stem Cell 4 (2009): 568-580.
Rheinbay, E, et al, "An Aberrant Transcription Factor Network Essential for Wnt Signaling and Stem Cell Maintenance In Glioblastoma," Cell Reports 3 (2013): 1567-1579.
Benayoun et al., "H3K4me3 Breadth Is Linked to Cell Identity and Transcriptional Consistency," Cell, Jul. 31, 2014, vol. 158, pp. 673-688.
Chicas et al., "H3K4 demethylation by Jarid1a and Jarid1b contributes to retinoblastoma-mediated gene silencing during cellular senescence," Proceedings of the National Academy of Sciences of the United States of America, PNAS, Jun. 5, 2012, vol. 109, No. 23, pp. 8971-8976.
Heinemann et al., "Inhibition of demethylases by GSK-J1/J4," Nature, Oct. 2, 2014, vol. 514, pp. E1-E2.
Kruidenier et al., "A selective jumonji H3K27 demethylase inhibitor modulates the proinflammatory macrophage response," Nature, Aug. 16, 2012, vol. 488, pp. 404-408.
Examination Report dated Feb. 23, 2021 in corresponding European Patent Application No. 16873494.5 (6 pages).
Office Action dated Jan. 19, 2022 in corresponding European Patent Application No. 16873494.5 (6 pages).

* cited by examiner

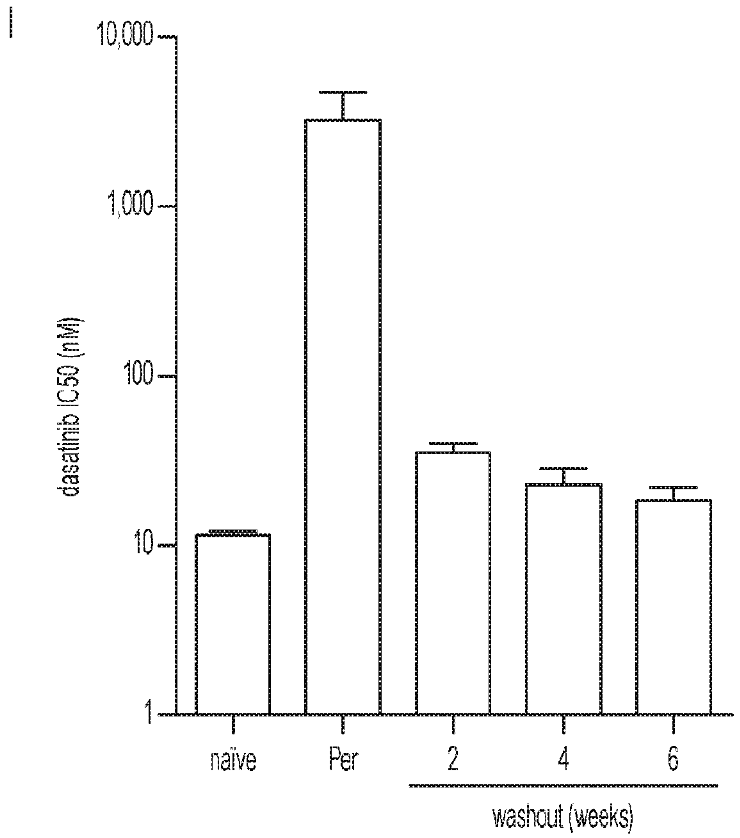
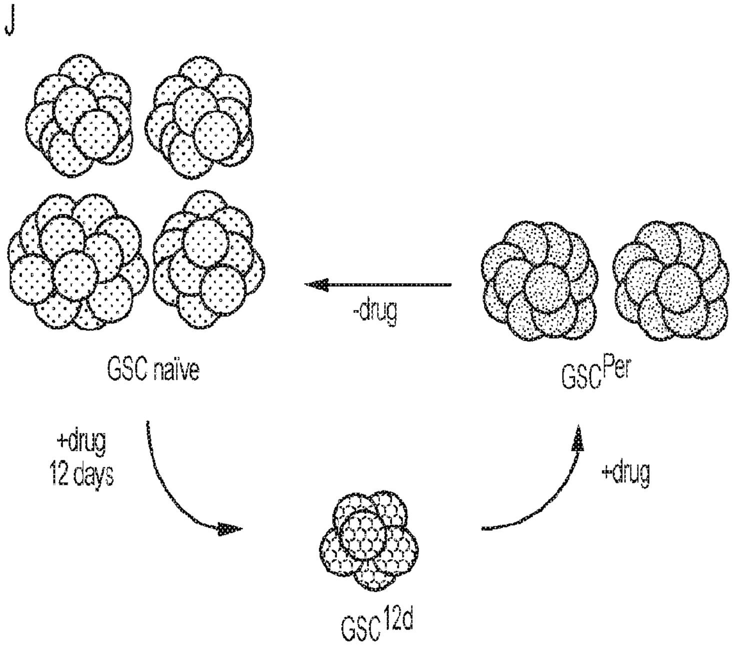
FIG. 1
CONTINUED

| % viable cells in S/G2/M | Mean | s.e.m. |
|---|---|---|
| naive | 42.8 | 0.6 |
| das4d | 6.2 | 0.2 |
| das12d | 12.3 | 0.7 |
| das25d | 14.6 | 1.2 |
| dasPer | 24.7 | 2.1 |
| washout | 36.7 | 2.0 |

A

| | Enriched Signatures | P-value |
|---|---|---|
| cluster 1 | mitochondrion<br>mitotic cell cycle | $10^{-43}$<br>$10^{-16}$ |
| cluster 2 | cell cycle<br>DNA metabolic process | $10^{-29}$<br>$10^{-19}$ |
| cluster 3 | translational elongation<br>Hsiao Housekeeping Genes | $10^{-112}$<br>$10^{-82}$ |
| cluster 4 | Veerhak Proneural<br>negative regulation of transcription | $10^{-33}$<br>$10^{-5}$ |
| cluster 5 | nucleus<br>transcription regulation | $10^{-14}$<br>$10^{-9}$ |
| cluster 6 | cell morphogenesis<br>neuron development | $10^{-5}$<br>$10^{-5}$ |

B

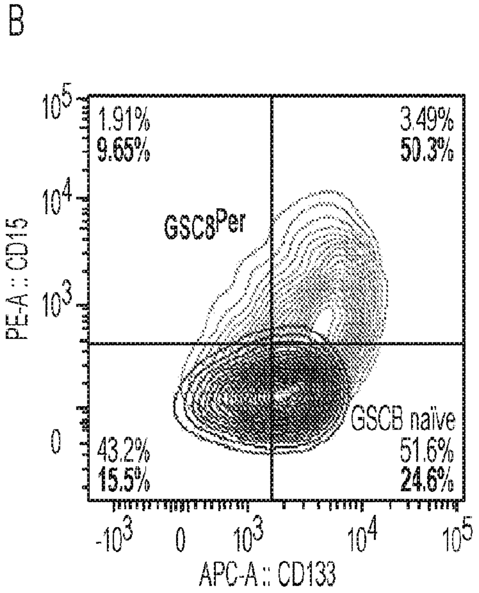

FIG. 6

DLX2 polypeptide sequence

LOCUS NP_004396 328 aa linear PRI 15-MAR-2015
DEFINITION homeobox protein DLX-2 [Homo sapiens].
ORIGIN

```
  1 mtgvfdslva dmhstqiaas styhqhqqpp sgggagpggn ssssslhkp qesptlpvst
 61 atdssyytnq qhpaggggg gspyahmgsy qyqasglnnv pysakssydl gytaaytsya
121 pygtssspan nepekedlep eirivngkpk kvrkprtiys sfqlaalqrr fqktqylalp
181 eraelaaslg ltqtqvkiwf qnrrskfkkm wksgeipseq hpgasasppc asppvsapas
241 wdfgvpqrma ggggpgsggs gagssgssps saasaflgny pwyhqtsgsa shlqatapll
301 hptqtpqphh hhhhhggga pvsagtif
```

DLX2 nucleic acid sequence

LOCUS NM_004405 2308 bp mRNA linear PRI 15-MAR-2015
DEFINITION Homo sapiens distal-less homeobox 2 (DLX2), mRNA.
ORIGIN

```
   1 aagaggatgc gaccagaggc agctgtcccg agcagcgcac ggtgatcgcc tccccccggag
  61 gaggaggcgc ctagacggtt gcctcctttc ttgtttcccc accaccaccc ccgtaattac
 121 attggctgct ggaggggacc gggagagaca gaggaggcgc ctggcttccc ccgcacgccc
 181 gccacctctg ctctttcccg tctcgggcca ggatgactgg agtctttgac agtctagtgg
 241 ctgatatgca ctcgacccag atcgccgcct ccagcacgta ccaccagcac cagcagcccc
 301 cgagcggcgg cggcgccggc ccgggtggca acagcagcag cagcagcagc ctccacaagc
 361 cccaggagtc gcccacccttt ccggtgtcca ccgccaccga cagcagctac tacaccaacc
 421 agcagcaccc ggcgggcggc ggcggcggcg ggggctcgcc ctacgcgcac atgggttcct
 481 accagtacca agccagcggc ctcaacaacg tcccttactc cgccaagagc agctatgacc
 541 tgggctacac cgccgcctac acctcctacg ctccctatgg aaccagttcg tccccagcca
 601 acaacgagcc tgagaaggag gaccttgagc ctgaaattcg gatagtgaac gggaagccaa
 661 agaaagtccg gaaaccccgc accatctact ccagtttcca gctggcggct cttcagcggc
 721 gtttccaaaa gactcaatac ttggccttgc cggagcgagc cgagctggcg gcctctctgg
 781 gcctcaccca gactcaggtc aaaatctggt tccagaaccg ccggtccaag ttcaagaaga
 841 tgtggaaaag tggtgagatc ccctcggagc agcaccctgg ggccagcgct tctccacctt
 901 gtgcttcgcc gccagtctca gcgccggcct cctgggactt tggtgtgccg cagcggatgg
 961 cgggcggcgg tggtccgggc agtggcggca gcggcgccgg cagctcgggc tccagcccga
1021 gcagcgcggc ctcggctttt ctgggcaact acccctggta ccaccagacc tcgggatccg
1081 cctcacacct gcaggccacg gcgccgctgc tgcaccccac tcagaccccg cagccgcatc
1141 accaccacca ccatcacggc ggcgggggcg ccccggtgag cgcggggacg attttctaac
1201 cccagggaga actcgccaga gactgagagc agagaccact tatcctcatt gcttaccccg
```

FIG. 16

```
1261 agccggggtt ccctcctccc ggcccgctgc cgccacccac ctctcctgca ggctgcgacc
1321 tgcagtggcc cgtctcaggc cctgctcact cccggggcca ccaaacgggc ccctctctcg
1381 ggggaaccgg acagcagctt ggcaaaggcc tccctaaaag gccgcatttc tgacctgagc
1441 cccgggtctc ggctgtttcg agccccgcct cggacttgcc ttccctcccc tccgggtgag
1501 cctgtctggc gccttcctcg ccccgggctg agagctgggt cccgggagat ggaagcctcc
1561 caggcgcgcg aggcttcccg ggcgctctga ggcttctttc tcctcgcccg ctcccctggg
1621 ctcagctcgg acgctgcagt tattgacctc ccggtcccgc ctgcccgccc tcccccacgt
1681 ggccccttga cccgggcggc cccgccgctt ctttccttcc tgcagttccc agccctcgga
1741 gcccccatcc cttatcttac ccccaccgcg ctcccccagg agcgctccct cagctctctc
1801 ctcatccatc accagtggag ttttttttatt tgttattttt ttaaaagttt aggtgccttt
1861 gcggatgacc tcattttgac gttgaaaaaa tgatttttta atatgtgaac actgcaaaaa
1921 tgtgtttaaa ttatcttttt taaaacctat tcaggattat tagcctggac ttggacacag
1981 agtttgtaaa taaaggtgtc tgtgcagatt ttcccactga tttatttgta taaaaatact
2041 catcttttca gactttttttg taaacccccca gttgtgaaaa ctgcagttta gcagtgacct
2101 cagcaacccc tcctttttat tttttccttt aaaaacattt cagttaaatt aagctactga
2161 tttggatttg ttttatcgta tcctaaagtc tttgttgttg aaatgaaagg tattttgggg
2221 ttatttatta tgaaaacaac atgctcttaa tgttgatttt acaatatgaa gagattattt
2281 aaataaatta ttgttttcat tggaaaaa
```

FABP7 polypeptide sequence

```
LOCUS       NP_001437               132 aa            linear   PRI 10-FEB-
2016
DEFINITION  fatty acid-binding protein, brain isoform 1 [Homo sapiens].
ORIGIN
        1 mveafcatwk ltnsqnfdey mkalgvgfat rqvgnvtkpt viisqegdkv virtlstfkn
       61 teisfqlgee fdettaddrn cksvvsldgd klvhiqkwdg ketnfvreik dgkmvmtltf
      121 gdvvavrhye ka
```

FABP7 nucleic acid sequence

```
LOCUS       NM_001446              1047 bp    mRNA    linear   PRI 10-FEB-
2016
DEFINITION  Homo sapiens fatty acid binding protein 7, brain (FABP7),
            transcript variant 1, mRNA.
ORIGIN
        1 tttctcaggc ataagggctg tagtgtgagg attgggagga actcgaccta ctccgctaac
       61 ccagtggcct gagccaatca caaagaggat tggagcctca ctcgagcgct ccttcccttc
      121 tcctctctct gtgacagcct cttggaaaga gggacactgg aggggtgtgt ttgcaattta
      181 aatcactgga tttttgccca ccctctttcc aaataagaag gcaggagctg cttgctgagg
```

FIG. 16
CONTINUED

```
 241 tgtaaagggt cttctgagct gcagtggcaa ttagaccaga agatccccgc tcctgtctct
 301 aaagagggga aagggcaagg atggtggagg ctttctgtgc tacctggaag ctgaccaaca
 361 gtcagaactt tgatgagtac atgaaggctc taggcgtggg ctttgccact aggcaggtgg
 421 gaaatgtgac caaaccaacg gtaattatca gtcaagaagg agacaaagtg gtcatcagga
 481 ctctcagcac attcaagaac acggagatta gtttccagct gggagaagag tttgatgaaa
 541 ccactgcaga tgatagaaac tgtaagtctg ttgttagcct ggatggagac aaacttgttc
 601 acatacagaa atgggatggc aaagaaacaa attttgtaag agaaattaag gatggcaaaa
 661 tggttatgac ccttactttt ggtgatgtgg ttgctgttcg ccactatgag aaggcataaa
 721 aatgttcctg gtcggggctt ggaagagctc ttcagttttt ctgtttcctc aagtctcagt
 781 gctatcctat tacaacatgg ctgatcatta attagaaggt tatccttggt gtggaggtgg
 841 aaaatggtga tttaaaaact tgttactcca agcaacttgc ccaattttaa tctgaaaatt
 901 tatcatgttt tataatttga attaaagttt tgtccccccc ccccttttttt ttataaacaa
 961 gtgaatacat tttataattt cttttggaat gtaaatcaaa tttgaataaa aatcttacac
1021 gtgaaattta aaaaaaaaaa aaaaaaa
```

HES5 polypeptide sequence

LOCUS NP_001010926 166 aa linear PRI 15-MAR-2015
DEFINITION transcription factor HES-5 [Homo sapiens].
ORIGIN

```
  1 mapstvavel lspkeknrlr kpvvekmrrd rinssieqlk llleqefarh qpnsklekad
 61 ilemavsylk hskafvaaag pkslhqdyse gyswclqeav qfltlhaasd tqmkllyhfq
121 rppaapaapa kepkapgaap ppalsakata aaaaahqpac glwrpw
```

HES5 nucleic acid sequence

LOCUS NM_001010926 1319 bp mRNA linear PRI 15-MAR-2015
DEFINITION Homo sapiens hes family bHLH transcription factor 5 (HES5), mRNA.
ORIGIN

```
  1 cgcgcttggc cttgcccgcg cccgctcgcc tcgtctcgcc cggcctcccc gcgtcgcctc
 61 gtcgcctgtt ccgcgccagg catggccccc agcactgtgg ccgtggagct gctcagcccc
121 aaagagaaaa accgactgcg gaagccggtg gtggagaaga tgcgccgcga ccgcatcaac
181 agcagcatcg agcagctgaa gctgctgctg gagcaggagt tcgcgcggca ccagcccaac
241 tccaagctgg agaaggccga catcctggag atggctgtca gctacctgaa gcacagcaaa
301 gccttcgtcg ccgccgccgg ccccaagagc ctgcaccagg actacagcga aggctactcg
361 tggtgcctgc aggaggccgt gcagttcctg acgctccacg ccgccagcga cacgcagatg
421 aagctgctgt accacttcca gcggcccccg gccgcgcccg ccgcgcccgc caaggagccc
```

FIG. 16
CONTINUED 481 aaggcgccgg gcgccgcgcc cccgcccgcg ctctccgcca aggccaccgc cgccgccgcc
541 gccgcgcacc agcccgcctg cggcctctgg cggccctggt gacccggcgg gacctgcggg
601 cgcgcggccc gacgaccaga gggcgagcct gctcctctcg cctgtaggga agcgccttcc
661 cgccgtcgtc cgcccccgggc ttggacgcgc ccttctccgg aaggctctgg ccccaagctg
721 gccggcccgc aggagcccca ttctcagaga atgtgtgtgc agagtccctg ccgttttagg
781 acaatcaggg cccatcttct gccaagtgtc tgaccccatg gggttgttct gtgtttgcat
841 ttaagcaagt gacttctggg aagtccccgg ccgccccgggg ttctatgata tttgtagtgc
901 cggggctcgc acactgctgc ccccagcctg tagaggactt tcttcagggc ccgtagctgc
961 tgggcgtacc cctggcaggc gggctgtgcc gcgggcacat ttgccttttg tgaaggccga
1021 actcgagctg tatcctcata ggaaacagtg atcaccccgg acgggcgtcc aggaccctga
1081 gggccatggc caaaaggctc ctgagtgtgc ctggtggtct ggctggggct cacggtgggc
1141 tgtctgggga gggtgggtgc ctccactatg atccttaaag gattcctctg tgtgggtgga
1201 tgcgtgtggg cacgactttg tactcagaaa ttgaactctc agtcacgtgg aagccacggg
1261 actgctccga agccgccata ataaaatctg attgttcagc cccaaaaaaa aaaaaaaaa HEY1 polypeptide sequence LOCUS NP_001035798 308 aa linear PRI 25-FEB-2016
DEFINITION hairy/enhancer-of-split related with YRPW motif protein 1 isoform b [Homo sapiens].

ORIGIN
1 mkrahpeyss sdseldetie vekesadeng nlssalgsms pttssqilar krrrgiiekr
61 rrdrinnsls elrrlvpsaf ekqvmeqgsa klekaeilqm tvdhlkmlht aggkgyfdah
121 alamdyrslg freclaevar ylsiieglda sdplrvrlvs hlnnyasqre aasgahaglg
181 hipwgtvfgh hphiahplll pqnghgnagt tasptephhq grlgsahpea palrappsgs
241 lgpvlpvvts asklspplls svaslsafpf sfgsfhllsp nalspsaptq aanlgkpyrp
301 wgteigaf HEY1 nucleic acid sequence LOCUS NM_001040708 2331 bp mRNA linear PRI 25-FEB-2016
DEFINITION Homo sapiens hes related family bHLH transcription factor with YRPW motif 1 (HEY1), transcript variant 2, mRNA.

ORIGIN
1 ttccccactc ccccgccctc cccagggccc tgggaagggg ctcagcgtgg gaaaggatgg
61 ttgagtttta accagaggca aagcgtgagc gggatcagtg tgtgcggaac gcaagcagcc
121 gagagcggag aggcgccgct gtagttaact cctccctgcc cgccgcgccg accctcccca
181 ggaacccccca gggagccagc atgaagcgag ctcaccccga gtacagctcc tcggacagcg

FIG. 16
CONTINUED

```
 241 agctggacga gaccatcgag gtggagaagg agagtgcgga cgagaatgga aacttgagtt
 301 cggctctagg ttccatgtcc ccaactacat cttcccagat tttggccaga aaaagacgga
 361 gaggaataat tgagaagcgc cgacgagacc ggatcaataa cagtttgtct gagctgagaa
 421 ggctggtacc cagtgctttt gagaagcagg taatggagca aggatctgct aagctagaaa
 481 aagccgagat cctgcagatg accgtggatc acctgaaaat gctgcatacg gcaggaggga
 541 aaggttactt tgacgcgcac gcccttgcta tggactatcg gagtttggga tttcgggaat
 601 gcctggcaga agttgcgcgt tatctgagca tcattgaagg actagatgcc tctgacccgc
 661 ttcgagttcg actggtttcg catctcaaca actacgcttc ccagcgggaa gccgcgagcg
 721 gcgcccacgc gggcctcgga cacattccct gggggaccgt cttcggacat cacccgcaca
 781 tcgcgcaccc gctgttgctg ccccagaacg gccacgggaa cgcgggcacc acggcctcac
 841 ccacggaacc gcaccaccag ggcaggctgg gctcggcaca tccggaggcg cctgctttgc
 901 gagcgccccc tagcggcagc ctcggaccgg tgctccctgt ggtcacctcc gcctccaaac
 961 tgtcgccgcc tctgctctcc tcagtggcct ccctgtcggc cttccccttc tctttcggct
1021 ccttccactt actgtctccc aatgcactga gcccttcagc acccacgcag gctgcaaacc
1081 ttggcaagcc ctatagacct tgggggacgg agatcggagc tttttaaaga actgatgtag
1141 aatgagggag gggaaagttt aaaatcccag ctgggctgga ctgttgccaa catcacctta
1201 aagtcgtcag taaaagtaaa aaggaaaaag gtacactttc agataatttt ttttttaaag
1261 actaaaggtt tgttggttta cttttatctt ttttaatgtt tttttcatca tgtcatgtat
1321 tagcagtttt taaaaactag ttgttaaatt ttgttcaaga cattaaattg aaatagtgag
1381 tataagccaa cactttgtga taggtttgta ctgtgcctaa tttactttgt aaaccagaat
1441 gattccgttt ttgcctcaaa atttggggaa tcttaacatt tagtattttt ggtctgtttt
1501 tctccttgta tagttatggt ctgtttttag aattaatttt ccaaaccact atgcttaatg
1561 ttaacatgat tctgtttgtt aatattttga cagattaagg tgttgtataa ataatattct
1621 tttgggggga ggggaactat attgaatttt atatttctga gcaaagcgtt gacaaatcag
1681 atgatcagct ttatccaaga aagaagacta gtaaattgtc tgcctcctat agcagaaagg
1741 tgaatgtaca aactgttggt ggccctgaat ccatctgacc agctgctggt atctgccagg
1801 actggcagtt ctgatttagt taggagagag ccgctgatag gttaggtctc atttggagtg
1861 ttggtggaaa ggaaactgaa ggtaattgaa tagaatacgc ctgcatttac cagcccccagc
1921 aacacaaaga atttttaatc acacggatct caaattcaca aatgttaaca tggataagtg
1981 atcatggtgt gcgagtggtc aattgagtag tacagtggaa actgttaaat gcataaccta
2041 attttcctgg gactgccata ttttctttta actggaaatt tttatgtgag ttttcctttt
2101 ggtgcatgga actgtggttg ccaaggtatt taaaagggct ttcctgcctc cttctctttg
2161 atttatttaa tttgatttgg gctataaaat atcatttttc aggtttattc ttttagcagg
2221 tgtagttaaa cgacctccac tgaactgggt ttgacctctg ttgtactgat gtgttgtgac
2281 taaataaaaa agaaagaaca aagtaaaaaa aaaaaaaaaa aaaaaaaaaa a
```

KDM6A polypeptide sequence

FIG. 16
CONTINUED

```
LOCUS       NP_001278344            1453 aa            linear   PRI 14-FEB-
2016
DEFINITION  lysine-specific demethylase 6A isoform 1 [Homo sapiens].

ORIGIN
        1 mkscgvslat aaaaaaafgd eekkmaagka sgeseeasps ltaeerealg gldsrlfgfv
       61 rfhedgartk allgkavrcy eslilkaegk vesdffcqlg hfnllledyp kalsayqryy
      121 slqsdywkna aflyglglvy fhynafqwai kafqevlyvd psfcrakeih lrlglmfkvn
      181 tdyesslkhf qlalvdcnpc tlsnaeiqfh iahlyetqrk yhsakeayeq llqtenlsaq
      241 vkatvlqqlg wmhhtvdllg dkatkesyai qylqkslead pnsgqswyfl grcyssigkv
      301 qdafisyrqs idkseasadt wcsigvlyqq qnqpmdalqa yicavqldhg haaawmdlgt
      361 lyescnqpqd aikcylnatr skscsntsal aarikylqaq lcnlpqgslq nktkllpsie
      421 eawslpipae ltsrqgamnt aqqackphhp ntepvlglsq tpisqqslpl hmipssqvdd
      481 lsspakrkrt ssptkntsdn wsgghavshp pvqqqahswc ltpqklqhle qlranrnnln
      541 paqklmleql esqfvlmqqh qmrptgvaqv rstgipngpt adsslptnsv sgqqpqlalt
      601 rvpsvsqpgv rpacpgqpla ngpfsaghvp cstsrtlgst dtilignnhi tgsgsngnvp
      661 ylqrnaltlp hnrtnltssa eepwknqlsn stqglhkgqs shsagpnger plsstgpsqh
      721 lqaagsgiqn qnghptlpsn svtqgaalnh lsshtatsgg qqgitltkes kpsgniltvp
      781 etsrhtgetp nstasveglp nhvhqmtada vcspshgdsk spgllssdnp qlsallmgka
      841 nnnvgtgtcd kvnnihpavh tktdnsvass pssaistatp spksteqttt nsvtslnsph
      901 sglhtingeg meesqspmkt dlllvnhkps pqiipsmsvs iypssaevlk acrnlgkngl
      961 snssilldkc ppprppsspy pplpkdklnp ptpsiylenk rdaffpplhq fctnpnnpvt
     1021 virglagalk ldlglfstkt lveannehmv evrtqllqpa denwdptgtk kiwhcesnrs
     1081 httiakyaqy qassfqeslr eenekrshhk dhsdsestss dnsgrrrkgp fktikfgtni
     1141 dlsddkkwkl qlheltklpa fvrvvsagnl lshvghtilg mntvqlymkv pgsrtpghqe
     1201 nnnfcsvnin igpgdcewfv vpegywgvln dfceknnlnf lmgswwpnle dlyeanvpvy
     1261 rfiqrpgdlv winagtvhwv qaigwcnnia wnvgpltacq yklaveryew nklqsvksiv
     1321 pmvhlswnma rnikvsdpkl femikycllr tlkqcqtlre aliaagkeii whgrtkeepa
     1381 hycsicevev fdllfvtnes nsrktyivhc qdcarktsgn lenfvvleqy kmedlmqvyd
     1441 qftlapplps ass
```

KDM6A nucleic acid sequence

```
LOCUS       NM_001291415            5941 bp    mRNA    linear   PRI 14-FEB-
2016
DEFINITION  Homo sapiens lysine demethylase 6A (KDM6A), transcript variant 1,
            mRNA.

ORIGIN
        1 gtgtgacaca attacaacaa ctttgtgctg gtgccgggga agtttgtgtc tccaacgaat
       61 cccctcagtg ctccccagcc ccgcgcgctc cggccgttcc cgccgtcccc gcctgtggct
```

FIG. 16
CONTINUED 121 gcccctgcc caacccgcg atgtgaccct acagccgaaa gccgccgctg ccgacccggg
181 ggctccgcag cccctgccgc cgccgccgcc gccttcaccg ccgccgcgtt gggatttttc
241 gtcgccgccg cccgcggcgg aggaggaggc ggcgataaag ttggtgtgct ggtcccgcgc
301 gcagattggg ggcgtcactg cgggccccgg tccgaggggg ggtgtcggcg ttggagttgt
361 gaattcgctg cgtttccatg aaatcctgcg gagtgtcgct cgctaccgcc gccgctgccg
421 ccgccgcttt cggtgatgag gaaaagaaaa tggcggcggg aaaagcgagc ggcgagagcg
481 aggaggcgtc cccagcctg acagccgagg agagggaggc gctcggcgga ctggacagcc
541 gcctctttgg gttcgtgaga tttcatgaag atggcgccag gacgaaggcc ctactgggca
601 aggctgttcg ctgctatgaa tctctaatct taaaagctga aggaaaagtg gagtctgatt
661 tcttttgtca attaggtcac ttcaacctct tattggaaga ttatccaaaa gcattatctg
721 cataccagag gtactacagt ttacagtctg actactggaa gaatgctgcc tttttatatg
781 gtcttggttt ggtctacttc cattataatg catttcagtg ggcaattaaa gcatttcagg
841 aggtgcttta tgttgatccc agcttttgtc gagccaagga aattcattta cgacttgggc
901 ttatgttcaa agtgaacaca gactatgagt ctagtttaaa gcattttcag ttagctttgg
961 ttgactgtaa tccctgcact ttgtccaatg ctgaaattca atttcacatt gcccacttat
1021 atgaaaccca gaggaaatat cattctgcaa aagaagctta tgaacaactt ttgcagacag
1081 agaatctttc tgcacaagta aaagcaactg tcttacaaca gttaggttgg atgcatcaca
1141 ctgtagatct cctgggagat aaagccacca aggaaagcta tgctattcag tatctccaaa
1201 agtccttgga agcagatcct aattctggcc agtcctggta tttcctcgga aggtgctatt
1261 caagtattgg gaaagttcag gatgccttta tatcttacag gcagtctatt gataaatcag
1321 aagcaagtgc agatacatgg tgttcaatag gtgtgctata tcagcagcaa aatcagccca
1381 tggatgcttt acaggcctat atttgtgctg tacaattgga ccatggccat gctgcagcct
1441 ggatggacct aggcactctc tatgaatcct gcaaccagcc tcaggatgcc attaaatgct
1501 acttaaatgc aactagaagc aaaagttgta gtaatacctc tgcacttgca gcacgaatta
1561 agtatttaca ggctcagttg tgtaaccttc cacaaggtag tctacagaat aaaactaaat
1621 tacttcctag tattgaggag gcgtggagcc taccaattcc cgcagagctt acctccaggc
1681 agggtgccat gaacacagca cagcaggcat gtaaacctca tcatccaaat actgaacctg
1741 tattaggcct cagtcaaaca ccaatttcac agcaatcctt gccactacac atgattcctt
1801 ctagccaagt agatgacctg tccagtcctg ccaagaggaa aagaacatct agtccaacaa
1861 agaatacttc tgacaattgg agtggtggac atgctgtgtc acatcctcca gtacagcaac
1921 aagctcattc atggtgtttg acaccacaga aattacagca tttggaacag ctccgcgcaa
1981 atagaaataa tttaaatcca gcacagaaac tgatgctgga acagctggaa agtcagtttg
2041 tcttaatgca acaacaccaa atgagaccaa caggagttgc acaggtacga tctactggaa
2101 ttcctaatgg gccaacagct gactcatcac tgcctacaaa ctcagtctct ggccagcagc
2161 cacagcttgc tctgaccaga gtgcctagcg tctctcagcc tggagtccgt cctgcctgcc
2221 ctgggcagcc tttggccaat ggaccctttt ctgcaggcca tgttccctgt agcacatcaa
2281 gaacgctggg aagtacagac actattttga taggcaataa tcatataaca ggaagtggaa
2341 gtaatggaaa cgtgccttac ctgcagcgaa acgcactcac tctacctcat aaccgcacaa

FIG. 16
CONTINUED 2401 acctgaccag cagcgcagag gagccgtgga aaaaccaact atctaactcc actcaggggc
2461 ttcacaaagg tcagagttca cattcggcag gtcctaatgg tgaacgacct ctctcttcca
2521 ctgggccttc ccagcatctc caggcagctg gctctggtat tcagaatcag aacggacatc
2581 ccaccctgcc tagcaattca gtaacacagg gggctgctct caatcacctc tcctctcaca
2641 ctgctacctc aggtggacaa caaggcatta ccttaaccaa agagagcaag ccttcaggaa
2701 acatattgac ggtgcctgaa acaagcaggc acactggaga gacacctaac agcactgcca
2761 gtgtcgaggg acttcctaat catgtccatc agatgacggc agatgctgtt tgcagtccta
2821 gccatggaga ttctaagtca ccaggtttac taagttcaga caatcctcag ctctctgcct
2881 tgttgatggg aaaagccaat aacaatgtgg gtactggaac ctgtgacaaa gtcaataaca
2941 tccacccagc tgttcataca aagactgata actctgttgc ctcttcacca tcttcagcca
3001 tttcaacagc aacaccttct ccaaaatcca ctgagcagac aaccacaaac agtgttacca
3061 gccttaacag ccctcacagt gggctacaca caattaatgg agaagggatg gaagaatctc
3121 agagccccat gaaaacagat ctgcttctgg ttaaccacaa acctagtcca cagatcatac
3181 catcaatgtc tgtgtccata taccccagct cagcagaagt tctgaaggca tgcaggaatc
3241 taggtaaaaa tggcttatct aacagtagca ttttgttgga taaatgtcca cctccaagac
3301 caccatcttc accataccct cccttgccaa aggacaagtt gaatccacct acacctagta
3361 tttacttgga aaataaacgt gatgcttttct ttcctccatt acatcaattt tgtacaaatc
3421 cgaacaaccc tgttacagta atacgtggcc ttgctggagc tcttaagtta gacctgggac
3481 ttttctctac taaaactttg gtggaagcta acaatgaaca tatggtagaa gtgaggacac
3541 agttgttgca gccagcagat gaaaactggg atcccactgg aacaaagaaa atctggcatt
3601 gtgaaagtaa tagatctcat actacaattg ctaaatatgc acagtaccag gcctcctcat
3661 tccaggaatc attgagagaa gaaaatgaaa aaagaagtca tcataaagac cactcagata
3721 gtgaatctac atcgtcagat aattctggga ggaggaggaa aggacccttt aaaaccataa
3781 agtttgggac caatattgac ctatctgatg acaaaaagtg gaagttgcag ctacatgagc
3841 tgactaaact tcctgctttt gtgcgtgtcg tatcagcagg aaatcttcta agccatgttg
3901 gtcataccat attgggcatg aacacagttc aactatacat gaaagttcca gggagcagaa
3961 caccaggtca tcaggaaaat aacaacttct gttcagttaa cataaatatt ggcccaggtg
4021 actgtgaatg gtttgttgtt cctgaaggtt actggggtgt tctgaatgac ttctgtgaaa
4081 aaaataattt gaatttccta atgggttctt ggtggcccaa tcttgaagat ctttatgaag
4141 caaatgttcc agtgtatagg tttattcagc gacctggaga tttggtctgg ataaatgcag
4201 gcactgttca ttgggttcag gctattggct ggtgcaacaa cattgcttgg aatgttggtc
4261 cacttacagc ctgccagtat aaattggcag tggaacggta cgaatggaac aaattgcaaa
4321 gtgtgaagtc aatagtaccc atggttcatc tttcctggaa tatggcacga aatatcaagg
4381 tctcagatcc aaagcttttt gaaatgatta agtattgtct tctaagaact ctgaagcaat
4441 gtcagacatt gagggaagct ctcattgctg caggaaaaga gattatatgg catgggcgga
4501 caaaagaaga accagctcat tactgtagca tttgtgaagt ggaggttttt gatctgcttt
4561 ttgtcactaa tgagagtaat tcacgaaaga cctacatagt acattgccaa gattgtgcac
4621 gaaaaacaag cggaaacttg gaaaactttg tggtgctaga acagtacaaa atggaggacc

FIG. 16
CONTINUED

```
4681 tgatgcaagt ctatgaccaa tttacattag ctcctccatt accatccgcc tcatcttgat
4741 attgttccat ggacattaaa tgagaccttt tctgctattc aggaaataac ccagttctgc
4801 accactggtt tttgtagcta tctcgtaagg ctgctggctg aaaactgtgt ctatgcaacc
4861 ttccaagtgc ggagtgtcaa ccaactggac gggagagagt actgctccta ctccaggact
4921 ctcacaaagc tgatgagctg tacttcagaa aaaaataata atttccatgt tttgtatata
4981 tctgacaaaa ctggcaacat cttacagact actgacttga agacaacctc ttttatattt
5041 ctctatttct gggctgatga atttgttttc atctgtcttt tcccccttca gaattttcct
5101 tggaaaaaaa atactagcct agctggtcat ttctttgtaa ggtagttagc aattttaagt
5161 ctttctttgg tcaacttttt tttaatgtga aaagttaggt aagacacttt tttactgctt
5221 ttatgttttt ctgtcttgtt ttgagaccat gatggttaca cttttggttc ctaaataaaa
5281 tttaaaaaat taacagccaa gtcacaaagg taatggattg cacatagact aaggaataaa
5341 cttcagattt gtgatttttg tttctaatct tgatgtaaat ttacactatt tataaataca
5401 tatttattgc ttgaaaatat ttgtgaatgg aatgctgtta ttttttccag atttacctgc
5461 cattgaaatt ttaaggagtt ctgtaatttc aaacactact cctattacat tttctatgtg
5521 taaataaaac tgcttagcat tgtacagaaa cttttattaa aattgtttaa tgtttaaaga
5581 gttttctatt gtttgagttt taaaaaagac tttatgtaca gtgcccagtt tttgttcatt
5641 tttgaaatct gattatatat atttatata tacttatgta tgtatatata atatatatag
5701 aaatctggat atatatgtat aaatctttag aacttaaatt tttctcgttt taagtttcac
5761 atctatggta gatttttgag gtgtctactg taaagtattg cttacaaaaa gtatgattat
5821 ttttaaagaa atatatatgg tatgtatcct caagacctaa aatgtcagac tggtttattg
5881 ttaagttgca attactgcaa tgacagacca ataaacaatt gctgccaaaa tgtagtataa
5941 a
```

KDM6B polypeptide sequence

```
LOCUS       NP_001073893            1682 aa            linear   PRI 14-FEB-
2016
DEFINITION  lysine-specific demethylase 6B [Homo sapiens].

ORIGIN
        1 mhravdppga raareafalg glscagawss cpphppprsa wlpggrcsas igqpplpapl
       61 ppshgsssgh pskpyyapga ptprplhgkl eslhgcvqal lrepaqpglw eqlgqlyese
      121 hdseeatrcy hsalryggsf aelgprigrl qqaqlwnfht gscqhrakvl ppleqvwnll
      181 hlehkrnyga krggppvkra aeppvvqpvp paalsgpsge eglspggkrr rgcnseqtgl
      241 ppglplpppp lppppppppp ppplpglat sppfqltkpg lwstlhgdaw gperkgsapp
      301 ergeqrhslp hpypypapay tahppghrlv paappgpgpr ppgaeshgcl patrppgsdl
      361 resrvqrsrm dssvspaatt acvpyapsrp pglpgtttss ssssssntgl rgvepnpgip
      421 gadhyqtpal evshhgrlgp sahssrkpfl gapaatphls lppgpssppp ppcprllrpp
      481 pppawlkgpa craaredgei leelffgteg pprpappplp hregflgppa srfsvgtqds
      541 htpptpptpt tsssnsnsgs hsssspagpvs fppppylars idplprppsp aqnpqdpplv
```

FIG. 16
CONTINUED 601 pltlalppap psschqntsg sfrrpesprp rvsfpktpev gpgpppgpls kapqpvppgv
661 gelpargprl fdfpptpled qfeepaefki lpdglanimk mldesirkee eqqqheagva
721 pqpplkepfa slqspfptdt apttttapava vttttttttt ttatqeeekk pppalppppp
781 lakfpppsqp qppppppppsp asllkslasv legqkycyrg tgaavstrpg plpttqyspg
841 ppsgatalpp tsaapsaqgs pqpsassssq fstsggpwar errageepvp gpmtptqppp
901 plslpparse sevleeisra cetlvervgr satdpadpvd taepadsgte rllppaqake
961 eaggvaavsg sckrrqkehq kehrrhrrac kdsvgrrpre grakakakvp keksrrvlgn
1021 ldlqseeiqg reksrpdlgg askakpptap appsapapsa qptppsasvp gkkareeapg
1081 ppgvsradml klrslsegpp kelkirlikv esgdketfia seveerrlrm adltishcaa
1141 dvvrasrnak vkgkfresyl spaqsvkpki nteeklprek lnpptpsiyl eskrdafspv
1201 llqfctdprn pitvirglag slrlnlglfs tktlveasge htvevrtqvq qpsdenwdlt
1261 gtrqiwpces srshttiaky aqyqassfqe slqeekesed eeseepdstt gtppssapdp
1321 knhhiikfgt nidlsdakrw kpqlqellkl pafmrvtstg nmlshvghti lgmntvqlym
1381 kvpgsrtpgh qennnfcsvn inigpgdcew favhehywet isafcdrhgv dyltgswwpi
1441 lddlyasnip vyrfvqrpgd lvwinagtvh wvqatgwcnn iawnvgplta yqyqlalery
1501 ewnevknvks ivpmihvswn vartvkisdp dlfkmikfcl lqsmkhcqvq reslvragkk
1561 iayqgrvkde payycnecdv evfnilfvts engsrntylv hcegcarrrs aglqgvvvle
1621 qyrteelaqa ydaftlvrar rargqrrral gqaagtgfgs paapfpeppp afspqapast
1681 sr KDM6B nucleic acid sequence LOCUS NM_001080424 6704 bp mRNA linear PRI 14-FEB-2016
DEFINITION Homo sapiens lysine demethylase 6B (KDM6B), mRNA.
ORIGIN
1 ggcaacatgc cagccccgta gcactgccca ccccacccac tgtggtctgt tgtaccccac
61 tgctggggtg gtggttccaa tgagacaggg cacaccaaac tccatctggc tgttactgag
121 gcggagacac gggtgatgat tggctttctg gggagagagg aagtcctgtg attggccaga
181 tctctggagc ttgccgacgc ggtgtgagga cgctcccacg gaggccggaa ttggctgtga
241 aaggactgag gcagccatct gggggtagcg ggcactctta tcagagcggc tggagccgga
301 ccatcgtccc agagagctgg ggcagggggc cgtgcccaat ctccagggct cctggggcca
361 ctgctgacct ggctggatgc atcgggcagt ggaccctcca ggggcccgcg ctgcacggga
421 agcctttgcc cttgggggcc tgagctgtgc tggggcctgg agctcctgcc cgcctcatcc
481 ccctcctcgt agcgcatggc tgcctggagg cagatgctca gccagcattg ggcagccccc
541 gcttcctgct cccctacccc cttcacatgg cagtagttct gggcaccccca gcaaaccata
601 ttatgctcca ggggcgccca ctccaagacc cctccatggg aagctggaat ccctgcatgg
661 ctgtgtgcag gcattgctcc gggagccagc ccagccaggg ctttgggaac agcttgggca
721 actgtacgag tcagagcacg atagtgagga ggccacacgc tgctaccaca gcgcccttcg

FIG. 16
CONTINUED 781 atacggagga agcttcgctg agctggggcc ccgcattggc cgactgcagc aggcccagct
841 ctggaacttt catactggct cctgccagca ccgagccaag gtcctgcccc cactggagca
901 agtgtggaac ttgctacacc ttgagcacaa acggaactat ggagccaagc ggggaggtcc
961 cccggtgaag cgagctgctg aaccccccagt ggtgcagcct gtgcctcctg cagcactctc
1021 aggcccctca ggggaggagg gcctcagccc tggaggcaag cgaaggagag gctgcaactc
1081 tgaacagact ggccttcccc cagggctgcc actgcctcca ccaccattac caccaccacc
1141 accaccacca ccaccaccac caccacccct gcctggcctg gctaccagcc ccccatttca
1201 gctaaccaag ccagggctgt ggagtaccct gcatggagat gcctggggcc cagagcgcaa
1261 gggttcagca cccccagagc gccaggagca gcggcactcg ctgcctcacc catatccata
1321 cccagctcca gcgtacaccg cgcacccccc tggccaccgg ctggtcccgg ctgctccccc
1381 aggcccaggc ccccgccccc caggagcaga gagccatggc tgcctgcctg ccacccgtcc
1441 ccccggaagt gaccttagag agagcagagt tcagaggtcg cggatggact ccagcgtttc
1501 accagcagca accaccgcct gcgtgcctta cgccccttcc cggccccctg gcctccccgg
1561 caccaccacc agcagcagca gtagcagcag cagcaacact ggtctccggg gcgtggagcc
1621 gaacccaggc attcccggcg ctgaccatta ccaaactccc gcgctggagg tctctcacca
1681 tggccgcctg gggccctcgg cacacagcag tcggaaaccg ttcttggggg ctcccgctgc
1741 cactccccac ctatccctgc cacctggacc ttcctcaccc cctccacccc cctgtccccg
1801 cctcttacgc cccccaccac cccctgcctg gttgaagggt ccggcctgcc gggcagcccg
1861 agaggatgga gagatcttag aagagctctt ctttgggact gagggacccc cccgccctgc
1921 cccaccaccc ctcccccatc gcgagggctt cttggggcct ccggcctccc gcttttctgt
1981 gggcactcag gattctcaca cccctcccac tcccccaacc ccaaccacca gcagtagcaa
2041 cagcaacagt ggcagccaca gcagcagccc tgctgggcct gtgtcctttc ccccaccacc
2101 ctatctggcc agaagtatag acccccttcc ccggcctccc agcccagcac agaacccccca
2161 ggacccacct cttgtacccc tgactcttgc cctgcctcca gcccctcctt cctcctgcca
2221 ccaaaatacc tcaggaagct tcaggcgccc ggagagcccc cggcccaggg tctccttccc
2281 aaagaccccc gaggtggggc cggggccacc cccaggcccc ctgagtaaag ccccccagcc
2341 tgtgccgccc ggggttgggg agctgcctgc ccgaggccct cgactctttg attttccccc
2401 cactccgctg gaggaccagt ttgaggagcc agccgaattc aagatcctac ctgatgggct
2461 ggccaacatc atgaagatgc tggacgaatc cattcgcaag gaagaggaac agcaacaaca
2521 cgaagcaggc gtggcccccc aacccccgct gaaggagccc tttgcatctc tgcagtctcc
2581 tttccccacc gacacagccc ccaccactac tgctcctgct gtcgccgtca ccaccaccac
2641 caccaccacc accaccacca cggccaccca ggaagaggag aagaagccac caccagccct
2701 accaccacca ccgcctctag ccaagttccc tccaccctct cagccacagc caccaccacc
2761 cccacccccc agcccggcca gcctgctcaa atccttggcc tccgtgctgg agggacaaaa
2821 gtactgttat cggggggactg gagcagctgt ttccacccgg cctgggccct tgcccaccac
2881 tcagtattcc cctggccccc catcaggtgc taccgccctg ccgcccacct cagcggcccc
2941 tagcgcccag ggctccccac agccctctgc ttcctcgtca tctcagttct ctacctcagg
3001 cgggccctgg gcccgggagc gcagggcggg cgaagagcca gtcccgggcc ccatgacccc

FIG. 16
CONTINUED 3061 cacccaaccg cccccacccc tatctctgcc ccctgctcgc tctgagtctg aggtgctaga
3121 agagatcagc cgggcttgcg agacccttgt ggagcgggtg ggccggagtg ccactgaccc
3181 agccgaccca gtggacacag cagagccagc ggacagtggg actgagcgac tgctgccccc
3241 cgcacaggcc aaggaggagg ctggcggggt ggcggcagtg tcaggcagct gtaagcggcg
3301 acagaaggag catcagaagg agcatcggcg gcacaggcgg gcctgtaagg acagtgtggg
3361 tcgtcggccc cgtgagggca gggcaaaggc caaggccaag gtccccaaag aaaagagccg
3421 ccgggtgctg gggaacctgg acctgcagag cgaggagatc cagggtcgtg agaagtcccg
3481 gcccgatctt ggcggggcct ccaaggccaa gccacccaca gctccagccc ctccatcagc
3541 tcctgcacct tctgcccagc ccacaccccc gtcagcctct gtccctggaa agaaggctcg
3601 ggaggaagcc ccagggccac cgggtgtcag ccgggccgac atgctgaagc tgcgctcact
3661 tagtgagggg ccccccaagg agctgaagat ccggctcatc aaggtagaga gtggtgacaa
3721 ggagaccttt atcgcctctg aggtggaaga gcggcggctg cgcatggcag acctcaccat
3781 cagccactgt gctgctgacg tcgtgcgcgc cagcaggaat gccaaggtga aagggaagtt
3841 tcgagagtcc tacctttccc ctgcccagtc tgtgaaaccg aagatcaaca ctgaggagaa
3901 gctgccccgg gaaaaactca acccccctac acccagcatc tatctggaga gcaaacggga
3961 tgccttctca cctgtcctgc tgcagttctg tacagaccct cgaaatccca tcacagtgat
4021 ccggggcctg gcggggctccc tgcggctcaa cttgggcctc ttctccacca agaccctggt
4081 ggaagcgagt ggcgaacaca ccgtggaagt tcgcacccag gtgcagcagc cctcagatga
4141 gaactgggat ctgacaggca ctcggcagat ctggccttgt gagagctccc gttcccacac
4201 caccattgcc aagtacgcac agtaccaggc ctcatccttc caggagtctc tgcaggagga
4261 gaaggagagt gaggatgagg agtcagagga gccagacagc accactggaa cccctcctag
4321 cagcgcacca gacccgaaga accatcacat catcaagttt ggcaccaaca tcgacttgtc
4381 tgatgctaag cggtggaagc cccagctgca ggagctgctg aagctgcccg ccttcatgcg
4441 ggtaacatcc acgggcaaca tgctgagcca cgtgggccac accatcctgg gcatgaacac
4501 ggtgcagctg tacatgaagg tgcccggcag ccgaacgcca ggccaccagg agaataacaa
4561 cttctgctcc gtcaacatca acattggccc aggcgactgc gagtggttcg cggtgcacga
4621 gcactactgg gagaccatca gcgctttctg tgatcggcac ggcgtggact acttgacggg
4681 ttcctggtgg ccaatcctgg atgatctcta tgcatccaat attcctgtgt accgcttcgt
4741 gcagcgaccc ggagacctcg tgtggattaa tgcggggact gtgcactggg tgcaggccac
4801 cggctggtgc aacaacattg cctggaacgt ggggcccctc accgcctatc agtaccagct
4861 ggccctggaa cgatacgagt ggaatgaggt gaagaacgtc aaatccatcg tgcccatgat
4921 tcacgtgtca tggaacgtgg ctcgcacggt caaaatcagc gaccccgact tgttcaagat
4981 gatcaagttc tgcctgctgc agtccatgaa gcactgccag gtgcaacgcg agagcctggt
5041 gcgggcaggg aagaaaatcg cttaccaggg ccgtgtcaag gacgagccag cctactactg
5101 caacgagtgc gatgtggagg tgtttaacat cctgttcgtg acaagtgaga atggcagccg
5161 caacacgtac ctggtacact gcgagggctg tgcccggcgc cgcagcgcag gcctgcaggg
5221 cgtggtggtg ctggagcagt accgcactga ggagctggct caggcctacg acgccttcac
5281 gctggtgagg gcccggcggg cgcgcgggca gcggaggagg gcactggggc aggctgcagg

FIG. 16
CONTINUED

```
5341 gacgggcttc gggagcccgg ccgcgccttt ccctgagccc ccgccggctt tctcccccca
5401 ggccccagcc agcacgtcgc gatgaggccg gacgccccgc ccgcctgcct gcccgcgcaa
5461 ggcgccgcgg ggccaccagc acatgcctgg gctggaccta ggtcccgcct gtggccgaga
5521 agggggtcgg gcccagccct tccaccccat tggcagctcc cctcacttaa tttattaaga
5581 aaaacttttt tttttttttt agcaaatatg aggaaaaaag gaaaaaaaat gggagacggg
5641 ggaggggggct ggcagcccct cgcccaccag cgcctcccct caccgacttt ggcctttttta
5701 gcaacagaca caaggaccag gctccggcgg cggcgggggt cacatacggg ttccctcacc
5761 ctgccagccg cccgcccgcc cggcgcagat gcacgcggct cgtgtatgta catagacgtt
5821 acggcagccg aggtttttaa tgagattctt tctatgggct ttacccctcc cccggaacct
5881 cctttttttac ttccaatgct agctgtgacc cctgtacatg tctctttatt cacttggtta
5941 tgatttgtat tttttgttct tttcttgttt ttttgttttt aatttataac agtcccactc
6001 acctctattt attcattttt gggaaaaccc gacctcccac accccccaagc catcctgccc
6061 gcccctccag ggaccgcccg tcgccgggct ctccccgcgc cccagtgtgt gtccgggccc
6121 ggcccgaccg tctccacccg tccgcccgcg gctccagccg ggttctcatg gtgctcaaac
6181 ccgctcccct cccctacgtc ctgcactttc tcggaccagt ccccccactc ccgacccgac
6241 cccagcccca cctgagggtg agcaactcct gtactgtagg ggaagaagtg ggaactgaaa
6301 tggtattttg taaaaaaaat aaataaaata aaaaaattaa aggttttaaa gaaagaacta
6361 tgaggaaaag gaaccccgtc cttcccagcc ccggccaact ttaaaaaaca cagaccttca
6421 cccccacccc cttttctttt taagtgtgaa acaacccagg gccagggcct cactggggca
6481 gggacacccc ggggtgagtt tctctggggc tttattttcg ttttgttggt tgttttttct
6541 ccacgctggg gctgcggagg ggtgggggggt ttacagtccc gcaccctcgc actgcactgt
6601 ctctctgccc caggggcaga ggggtcttcc caaccctacc cctattttcg gtgatttttg
6661 tgtgagaata ttaatattaa aaataaacgg agaaaaaaaa tcct
```

Notch polypeptide sequence

```
LOCUS       NP_060087              2555 aa            linear   PRI 10-FEB-
2016
DEFINITION  neurogenic locus notch homolog protein 1 preproprotein [Homo
            sapiens].
ORIGIN
        1 mppllapllc lallpalaar gprcsqpget clnggkceaa ngteacvcgg afvgprcqdp
       61 npclstpckn agtchvvdrr gvadyacsca lgfsgplclt pldnacltnp crnggtcdll
      121 tlteykcrcp pgwsgkscqq adpcasnpca ngggclpfea syichcppsf hgptcrqdvn
      181 ecgqkpglcr hggtchnevg syrcvcrath tgpncerpyv pcspspcqng gtcrptgdvt
      241 hecaclpgft gqnceenidd cpgnncknggg acvdgvntyn crcppewtgq yctedvdecq
      301 lmpnacqngg tchnthggyn cvcvngwtge dcseniddca saacfhgatc hdrvasfyce
      361 cphgrtgllc hlndacisnp cnegsncdtn pvngkaictc psgytgpacs qdvdecslga
      421 npcehagkci ntlgsfecqc lqgytgprce idvnecvsnp cqndatcldq igefqcicmp
```

FIG. 16
CONTINUED 481 gyegvhcevn tdecasspcl hngrcldkin efqcecptgf tghlcqydvd ecastpckng
541 akcldgpnty tcvctegytg thcevdidec dpdpchygsc kdgvatftcl crpgytghhc
601 etninecssq pcrhggtcqd rdnaylcfcl kgttgpncei nlddcasspc dsgtcldkid
661 gyecacepgy tgsmcninid ecagnpchng gtcedgingf tcrcpegyhd ptclsevnec
721 nsnpcvhgac rdslngykcd cdpgwsgtnc dinnnecesn pcvnggtckd mtsgyvctcr
781 egfsgpncqt ninecasnpc lnqgtciddv agykcncllp ytgatcevvl apcapspcrn
841 ggecrqsedy esfscvcptg wqgqtcevdi necvlspcrh gascqnthgg yrchcqagys
901 grncetdidd crpnpchngg sctdgintaf cdclpgfrgt fceedineca sdpcrnganc
961 tdcvdsytct cpagfsgihc enntpdctes scfnggtcvd ginsftclcp pgftgsycqh
1021 dvnecdsqpc lhggtcqdgc gsyrctcpqg ytgpncqnlv hwcdsspckn ggkcwqthtq
1081 yrcecpsgwt glycdvpsvs cevaaqrqgv dvarlcqhgg lcvdagnthh crcqagytgs
1141 ycedlvdecs pspcqngatc tdylggysck cvagyhgvnc seeideclsh pcqnggtcld
1201 lpntykcscp rgtqgvhcei nvddcnppvd pvsrspkcfn ngtcvdqvgg ysctcppgfv
1261 gercegdvne clsnpcdarg tqncvqrvnd fhcecraght grrcesving ckgkpckngg
1321 tcavasntar gfickcpagf egatcendar tcgslrclng gtcisgprsp tclclgpftg
1381 pecqfpassp clggnpcynq gtceptsesp fyrclcpakf ngllchildy sfgggagrdi
1441 ppplieeace lpecqedagn kvcslqcnnh acgwdggdcs lnfndpwknc tqslqcwkyf
1501 sdghcdsqcn sagclfdgfd cqraegqcnp lydqyckdhf sdghcdqgcn saecewdgld
1561 caehvperla agtlvvvvlm ppeqlrnssf hflrelsrvl htnvvfkrda hgqqmifpyy
1621 greeelrkhp ikraaegwaa pdallgqvka sllpggsegg rrrreldpmd vrgsivylei
1681 dnrqcvqass qcfqsatdva aflgalaslg slnipykiea vqsetveppp paqlhfmyva
1741 aaafvllffv gcgvllsrkr rrqhgqlwfp egfkvseask kkrreplged svglkplkna
1801 sdgalmddnq newgdedlet kkfrfeepvv lpdlddqtdh rqwtqqhlda adlrmsamap
1861 tppqgevdad cmdvnvrgpd gftplmiasc sgggletgns eeeedapavi sdfiyqgasl
1921 hnqtdrtget alhlaarysr sdaakrllea sadaniqdnm grtplhaavs adaqgvfqil
1981 irnratdlda rmhdgttpli laarlavegm ledlinshad vnavddlgks alhwaaavnn
2041 vdaavvllkn gankdmqnnr eetplflaar egsyetakvl ldhfanrdit dhmdrlprdi
2101 aqermhhdiv rlldeynlvr spqlhgaplg gtptlspplc spngylgslk pgvqgkkvrk
2161 psskglacgs keakdlkarr kksqdgkgcl ldssgmlspv dslesphgyl sdvaspplp
2221 spfqqspsvp lnhlpgmpdt hlgighlnva akpemaalgg ggrlafetgp prlshlpvas
2281 gtstvlgsss ggalnftvgg stslngqcew lsrlqsgmvp nqynplrgsv apgplstqap
2341 slqhgmvgpl hsslaasals qmmsyqglps trlatqphlv qtqqvqpqnl qmqqqnlqpa
2401 niqqqqslqp pppppqphlg vssaasghlg rsflsgepsq advqplgpss lavhtilpqe
2461 spalptslps slvppvtaaq fltppsqhsy sspvdntpsh qlqvpehpfl tpspespdqw
2521 ssssphsnvs dwsegvsspp tsmqsqiari peafk Notch nucleic acid sequence

FIG. 16
CONTINUED

```
LOCUS       NM_017617           9322 bp    mRNA    linear   PRI 10-FEB-
2016
DEFINITION  Homo sapiens notch 1 (NOTCH1), mRNA.

ORIGIN

        1 atgccgccgc tcctggcgcc cctgctctgc ctggcgctgc tgcccgcgct cgccgcacga
       61 ggcccgcgat gctcccagcc cggtgagacc tgcctgaatg gcgggaagtg tgaagcggcc
      121 aatggcacgg aggcctgcgt ctgtggcggg gccttcgtgg gcccgcgatg ccaggacccc
      181 aacccgtgcc tcagcacccc ctgcaagaac gccgggacat gccacgtggt ggaccgcaga
      241 ggcgtggcag actatgcctg cagctgtgcc ctgggcttct ctgggcccct ctgcctgaca
      301 cccctggaca atgcctgcct caccaacccc tgccgcaacg gggcacctg cgacctgctc
      361 acgctgacgg agtacaagtg ccgctgcccg cccggctggt cagggaaatc gtgccagcag
      421 gctgacccgt gcgcctccaa cccctgcgcc aacggtggcc agtgcctgcc cttcgaggcc
      481 tcctacatct gccactgccc acccagcttc catggcccca cctgccggca ggatgtcaac
      541 gagtgtggcc agaagcccgg gctttgccgc cacggaggca cctgccacaa cgaggtcggc
      601 tcctaccgct gcgtctgccg cgccacccac actggcccca actgcgagcg gccctacgtg
      661 ccctgcagcc cctcgccctg ccagaacggg ggcacctgcc gccccacggg cgacgtcacc
      721 cacgagtgtg cctgcctgcc aggcttcacc ggccagaact gtgaggaaaa tatcgacgat
      781 tgtccaggaa acaactgcaa gaacgggggt gcctgtgtgg acggcgtgaa cacctacaac
      841 tgccgctgcc cgccagagtg gacaggtcag tactgtaccg aggatgtgga cgagtgccag
      901 ctgatgccaa atgcctgcca gaacggcggg acctgccaca acacccacgg tggctacaac
      961 tgcgtgtgtg tcaacggctg gactggtgag gactgcagcg agaacattga tgactgtgcc
     1021 agcgccgcct gcttccacgg cgccacctgc catgaccgtg tggcctcctt ctactgcgag
     1081 tgtccccatg gccgcacagg tctgctgtgc cacctcaacg acgcatgcat cagcaacccc
     1141 tgtaacgagg gctccaactg cgacaccaac cctgtcaatg gcaaggccat ctgcacctgc
     1201 ccctcggggt acacgggccc ggcctgcagc caggacgtgg atgagtgctc gctgggtgcc
     1261 aacccctgcg agcatgcggg caagtgcatc aacacgctgg gctccttcga gtgccagtgt
     1321 ctgcagggct acacgggccc ccgatgcgag atcgacgtca acgagtgcgt ctcgaacccg
     1381 tgccagaacg acgccacctg cctggaccag attggggagt tccagtgcat ctgcatgccc
     1441 ggctacgagg gtgtgcactg cgaggtcaac acagacgagt gtgccagcag cccctgcctg
     1501 cacaatggcc gctgcctgga caagatcaat gagttccagt gcgagtgccc cacgggcttc
     1561 actgggcatc tgtgccagta cgatgtggac gagtgtgcca gcacccccctg caagaatggt
     1621 gccaagtgcc tggacggacc caacacttac acctgtgtgt gcacggaagg gtacacgggg
     1681 acgcactgcg aggtggacat cgatgagtgc gaccccgacc cctgccacta cggctcctgc
     1741 aaggacggcg tcgccacctt cacctgcctc tgccgcccag gctacacggg ccaccactgc
     1801 gagaccaaca tcaacgagtg ctccagccag ccctgccgcc acgggggcac ctgccaggac
     1861 cgcgacaacg cctacctctg cttctgcctg aaggggacca caggacccaa ctgcgagatc
     1921 aacctggatg actgtgccag cagcccctgc gactcgggca cctgtctgga caagatcgat
     1981 ggctacgagt gtgcctgtga gccgggctac acagggagca tgtgtaacat caacatcgat
```

FIG. 16
CONTINUED 2041 gagtgtgcgg gcaacccctg ccacaacggg ggcacctgcg aggacggcat caatggcttc
2101 acctgccgct gccccgaggg ctaccacgac cccacctgcc tgtctgaggt caatgagtgc
2161 aacagcaacc cctgcgtcca cggggcctgc cgggacagcc tcaacgggta caagtgcgac
2221 tgtgaccctg ggtggagtgg gaccaactgt gacatcaaca acaatgagtg tgaatccaac
2281 ccttgtgtca acggcggcac ctgcaaagac atgaccagtg gctacgtgtg cacctgccgg
2341 gagggcttca gcggtcccaa ctgccagacc aacatcaacg agtgtgcgtc caacccatgt
2401 ctgaaccagg gcacgtgtat tgacgacgtt gccgggtaca agtgcaactg cctgctgccc
2461 tacacaggtg ccacgtgtga ggtggtgctg gccccgtgtg cccccagccc ctgcagaaac
2521 ggcggggagt gcaggcaatc cgaggactat gagagcttct cctgtgtctg ccccacgggc
2581 tggcaagggc agacctgtga ggtcgacatc aacgagtgcg ttctgagccc gtgccggcac
2641 ggcgcatcct gccagaacac ccacggcggc taccgctgcc actgccaggc cggctacagt
2701 gggcgcaact gcgagaccga catcgacgac tgccggccca acccgtgtca caacgggggc
2761 tcctgcacag acggcatcaa cacggccttc tgcgactgcc tgcccggctt ccggggcact
2821 ttctgtgagg aggacatcaa cgagtgtgcc agtgacccct gccgcaacgg ggccaactgc
2881 acggactgcg tggacagcta cacgtgcacc tgccccgcag gcttcagcgg gatccactgt
2941 gagaacaaca cgcctgactg cacagagagc tcctgcttca acggtggcac ctgcgtggac
3001 ggcatcaact cgttcacctg cctgtgtcca cccggcttca cgggcagcta ctgccagcac
3061 gatgtcaatg agtgcgactc acagccctgc ctgcatggcg gcacctgtca ggacggctgc
3121 ggctcctaca ggtgcacctg cccccagggc tacactggcc ccaactgcca gaaccttgtg
3181 cactggtgtg actcctcgcc ctgcaagaac ggcggcaaat gctggcagac ccacacccag
3241 taccgctgcg agtgccccag cggctggacc ggcctttact gcgacgtgcc cagcgtgtcc
3301 tgtgaggtgg ctgcgcagcg acaaggtgtt gacgttgccc gcctgtgcca gcatggaggg
3361 ctctgtgtgg acgcgggcaa cacgcaccac tgccgctgcc aggcgggcta cacaggcagc
3421 tactgtgagg acctggtgga cgagtgctca cccagcccct gccagaacgg ggccacctgc
3481 acggactacc tgggcggcta ctcctgcaag tgcgtggccg gctaccacgg ggtgaactgc
3541 tctgaggaga tcgacgagtg cctctcccac ccctgccaga acgggggcac ctgcctcgac
3601 ctccccaaca cctacaagtg ctcctgccca cggggcactc agggtgtgca ctgtgagatc
3661 aacgtggacg actgcaatcc ccccgttgac cccgtgtccc ggagccccaa gtgctttaac
3721 aacggcacct gcgtggacca ggtgggcggc tacagctgca cctgcccgcc gggcttcgtg
3781 ggtgagcgct gtgaggggga tgtcaacgag tgcctgtcca atccctgcga cgcccgtggc
3841 acccagaact gcgtgcagcg cgtcaatgac ttccactgcg agtgccgtgc tggtcacacc
3901 gggcgccgct gcgagtccgt catcaatggc tgcaaaggca agccctgcaa gaatgggggc
3961 acctgcgccg tggcctccaa caccgcccgc gggttcatct gcaagtgccc tgcgggcttc
4021 gagggcgcca cgtgtgagaa tgacgctcgt acctgcggca gcctgcgctg cctcaacggc
4081 ggcacatgca tctccggccc gcgcagcccc acctgcctgt gcctgggccc cttcacgggc
4141 cccgaatgcc agttcccggc cagcagcccc tgcctgggcg gcaacccctg ctacaaccag
4201 gggacctgtg agcccacatc cgagagcccc ttctaccgtt gcctgtgccc cgccaaattc
4261 aacgggctct tgtgccacat cctggactac agcttcgggg gtggggccgg gcgcgacatc

FIG. 16
CONTINUED 4321 cccccgccgc tgatcgagga ggcgtgcgag ctgcccgagt gccaggagga cgcgggcaac
4381 aaggtctgca gcctgcagtg caacaaccac gcgtgcggct gggacggcgg tgactgctcc
4441 ctcaacttca atgacccctg gaagaactgc acgcagtctc tgcagtgctg gaagtacttc
4501 agtgacggcc actgtgacag ccagtgcaac tcagccggct gcctcttcga cggctttgac
4561 tgccagcgtg cggaaggcca gtgcaacccc ctgtacgacc agtactgcaa ggaccacttc
4621 agcgacgggc actgcgacca gggctgcaac agcgcggagt gcgagtggga cgggctggac
4681 tgtgcggagc atgtacccga gaggctggcg gccggcacgc tggtggtggt ggtgctgatg
4741 ccgccggagc agctgcgcaa cagctccttc cacttcctgc gggagctcag ccgcgtgctg
4801 cacaccaacg tggtcttcaa gcgtgacgca cacggccagc agatgatctt cccctactac
4861 ggccgcgagg aggagctgcg caagcacccc atcaagcgtg ccgccgaggg ctgggccgca
4921 cctgacgccc tgctgggcca ggtgaaggcc tcgctgctcc ctggtggcag cgagggtggg
4981 cggcggcgga gggagctgga ccccatggac gtccgcggct ccatcgtcta cctggagatt
5041 gacaaccggc agtgtgtgca ggcctcctcg cagtgcttcc agagtgccac cgacgtggcc
5101 gcattcctgg gagcgctcgc ctcgctgggc agcctcaaca tcccctacaa gatcgaggcc
5161 gtgcagagtg agaccgtgga gccgcccccg ccggcgcagc tgcacttcat gtacgtggcg
5221 gcggccgcct ttgtgcttct gttcttcgtg ggctgcgggg tgctgctgtc ccgcaagcgc
5281 cggcggcagc atggccagct ctggttccct gagggcttca aagtgtctga ggccagcaag
5341 aagaagcggc gggagcccct cggcgaggac tccgtgggcc tcaagcccct gaagaacgct
5401 tcagacggtg ccctcatgga cgacaaccag aatgagtggg gggacgagga cctggagacc
5461 aagaagttcc ggttcgagga gcccgtggtt ctgcctgacc tggacgacca gacagaccac
5521 cggcagtgga ctcagcagca cctggatgcc gctgacctgc gcatgtctgc catggccccc
5581 acaccgcccc agggtgaggt tgacgccgac tgcatggacg tcaatgtccg cgggcctgat
5641 ggcttcaccc cgctcatgat cgcctcctgc agcgggggcg gcctggagac gggcaacagc
5701 gaggaagagg aggacgcgcc ggccgtcatc tccgacttca tctaccaggg cgccagcctg
5761 cacaaccaga cagaccgcac gggcgagacc gccttgcacc tggccgcccg ctactcacgc
5821 tctgatgccg ccaagcgcct gctggaggcc agcgcagatg ccaacatcca ggacaacatg
5881 ggccgcaccc cgctgcatgc ggctgtgtct gccgacgcac aaggtgtctt ccagatcctg
5941 atccggaacc gagccacaga cctggatgcc cgcatgcatg atggcacgac gccactgatc
6001 ctggctgccc gcctggccgt ggagggcatg ctggaggacc tcatcaactc acacgccgac
6061 gtcaacgccg tagatgacct gggcaagtcc gccctgcact gggccgccgc cgtgaacaat
6121 gtggatgccg cagttgtgct cctgaagaac ggggctaaca aagatatgca gaacaacagg
6181 gaggagacac ccctgtttct ggccgcccgg gagggcagct acgagaccgc caaggtgctg
6241 ctggaccact ttgccaaccg ggacatcacg gatcatatgg accgcctgcc gcgcgacatc
6301 gcacaggagc gcatgcatca cgacatcgtg aggctgctgg acgagtacaa cctggtgcgc
6361 agcccgcagc tgcacggagc ccgctggggg ggcacgccca ccctgtcgcc cccgctctgc
6421 tcgcccaacg gctacctggg cagcctcaag cccggcgtgc agggcaagaa ggtccgcaag
6481 cccagcagca aaggcctggc ctgtggaagc aaggaggcca aggacctcaa ggcacggagg
6541 aagaagtccc aggacggcaa gggctgcctg ctggacagct ccggcatgct ctcgcccgtg

FIG. 16
CONTINUED 6601 gactccctgg agtcacccca tggctacctg tcagacgtgg cctcgccgcc actgctgccc
6661 tccccgttcc agcagtctcc gtccgtgccc ctcaaccacc tgcctgggat gcccgacacc
6721 cacctgggca tcgggcacct gaacgtggcg gccaagcccg agatggcggc gctgggtggg
6781 ggcggccggc tggcctttga gactggccca cctcgtctct cccacctgcc tgtggcctct
6841 ggcaccagca ccgtcctggg ctccagcagc ggaggggccc tgaatttcac tgtgggcggg
6901 tccaccagtt tgaatggtca atgcgagtgg ctgtcccggc tgcagagcgg catggtgccg
6961 aaccaataca accctctgcg ggggagtgtg gcaccaggcc ccctgagcac acaggccccc
7021 tccctgcagc atggcatggt aggcccgctg cacagtagcc ttgctgccag cgccctgtcc
7081 cagatgatga gctaccaggg cctgcccagc acccggctgg ccacccagcc tcacctggtg
7141 cagacccagc aggtgcagcc acaaaactta cagatgcagc agcagaacct gcagccagca
7201 aacatccagc agcagcaaag cctgcagccg ccaccaccac caccacagcc gcaccttggc
7261 gtgagctcag cagccagcgg ccacctgggc cggagcttcc tgagtggaga gccgagccag
7321 gcagacgtgc agccactggg ccccagcagc ctggcggtgc acactattct gccccaggag
7381 agccccgccc tgcccacgtc gctgccatcc tcgctggtcc cacccgtgac cgcagcccag
7441 ttcctgacgc ccccctcgca gcacagctac tcctcgcctg tggacaacac ccccagccac
7501 cagctacagg tgcctgagca cccccttcctc accccgtccc ctgagtcccc tgaccagtgg
7561 tccagctcgt ccccgcattc caacgtctcc gactggtccg agggcgtctc cagccctccc
7621 accagcatgc agtcccagat cgcccgcatt ccggaggcct tcaagtaaac ggcgcgcccc
7681 acgagacccc ggcttccttt cccaagcctt cgggcgtctg tgtgcgctct gtggatgcca
7741 gggccgacca gaggagcctt tttaaaacac atgtttttat acaaaataag aacgaggatt
7801 ttaatttttt ttagtattta tttatgtact tttattttac acagaaacac tgccttttta
7861 tttatatgta ctgttttatc tggccccagg tagaaacttt tatctattct gagaaaacaa
7921 gcaagttctg agagccaggg ttttcctacg taggatgaaa agattcttct gtgtttataa
7981 aatataaaca aagattcatg atttataaat gccatttatt tattgattcc tttttttcaaa
8041 atccaaaaag aaatgatgtt ggagaaggga agttgaacga gcatagtcca aaaagctcct
8101 ggggcgtcca ggccgcgccc tttccccgac gcccacccaa ccccaagcca gcccggccgc
8161 tccaccagca tcacctgcct gttaggagaa gctgcatcca gaggcaaacg gaggcaaagc
8221 tggctcacct tccgcacgcg gattaatttg catctgaaat aggaaacaag tgaaagcata
8281 tgggttagat gttgccatgt gttttagatg gtttcttgca agcatgcttg tgaaaatgtg
8341 ttctcggagt gtgtatgcca agagtgcacc catggtacca atcatgaatc tttgtttcag
8401 gttcagtatt atgtagttgt tcgttggtta tacaagttct tggtccctcc agaaccaccc
8461 cggccccctg cccgttcttg aaatgtaggc atcatgcatg tcaaacatga gatgtgtgga
8521 ctgtggcact tgcctgggtc acacacggag gcatcctacc cttttctggg gaaagacact
8581 gcctgggctg accccggtgg cggccccagc acctcagcct gcacagtgtc cccccaggttc
8641 cgaagaagat gctccagcaa cacagcctgg gccccagctc gcgggacccg acccccccgtg
8701 ggctcccgtg ttttgtagga gacttgccag agccgggcac attgagctgt gcaacgccgt
8761 gggctgcgtc ctttggtcct gtccccgcag ccctggcagg gggcatgcgg tcgggcaggg
8821 gctggaggga ggcgggggct gcccttgggc cacccctcct agtttgggag gagcagattt

FIG. 16
CONTINUED

```
8881 ttgcaatacc aagtatagcc tatggcagaa aaaatgtctg taaatatgtt tttaaaggtg
8941 gattttgttt aaaaaatctt aatgaatgag tctgttgtgt gtcatgccag tgagggacgt
9001 cagacttggc tcagctcggg gagccttagc cgcccatgca ctggggacgc tccgctgccg
9061 tgccgcctgc actcctcagg gcagcctccc ccggctctac gggggccgcg tggtgccatc
9121 cccagggggc atgaccagat gcgtcccaag atgttgattt ttactgtgtt ttataaaata
9181 gagtgtagtt tacagaaaaa gactttaaaa gtgatctaca tgaggaactg tagatgatgt
9241 atttttttca tctttttttgt taactgattt gcaataaaaa tgatactgat ggtgatctgg
9301 cttccaaaaa aaaaaaaaaa aa
```

PDGFRA polypeptide sequence

```
LOCUS       NP_006197              1089 aa            linear   PRI 21-FEB-
2016
DEFINITION  platelet-derived growth factor receptor alpha precursor [Homo
            sapiens].
ORIGIN
        1 mgtshpaflv lgclltglsl ilcqlslpsi lpnenekvvq lnssfslrcf gesevswqyp
       61 mseeessdve irneennsgl fvtvlevssa saahtglytc yynhtqteen elegrhiyiy
      121 vpdpdvafvp lgmtdylviv edddsaiipc rttdpetpvt lhnsegvvpa sydsrqgfng
      181 tftvgpyice atvkgkkfqt ipfnvyalka tseldlemea lktvyksget ivvtcavfnn
      241 evvdlqwtyp gevkgkgitm leeikvpsik lvytltvpea tvkdsgdyec aarqatrevk
      301 emkkvtisvh ekgfieikpt fsqleavnlh evkhfvvevr aypppriswl knnltlienl
      361 teittdveki qeiryrsklk lirakeedsg hytivaqned avksytfell tqvpssildl
      421 vddhhgstgg qtvrctaegt plpdiewmic kdikkcnnet swtilannvs niiteihsrd
      481 rstvegrvtf akveetiavr claknllgae nrelklvapt lrseltvaaa vlvllvivii
      541 slivlvviwk qkpryeirwr viesispdgh eyiyvdpmql pydsrwefpr dglvlgrvlg
      601 sgafgkvveg tayglsrsqp vmkvavkmlk ptarssekqa lmselkimth lgphlnivnl
      661 lgactksgpi yiiteycfyg dlvnylhknr dsflshhpek pkkeldifgl npadestrsy
      721 vilsfenngd ymdmkqadtt qyvpmlerke vskysdiqrs lydrpasykk ksmldsevkn
      781 llsddnsegl tlldllsfty qvargmefla skncvhrdla arnvllaqgk ivkicdfgla
      841 rdimhdsnyv skgstflpvk wmapesifdn lyttlsdvws ygillweifs lggtpypgmm
      901 vdstfynkik sgyrmakpdh atsevyeimv kcwnsepekr psfyhlseiv enllpgqykk
      961 syekihldfl ksdhpavarm rvdsdnayig vtykneedkl kdweggldeq rlsadsgyii
     1021 plpdidpvpe eedlgkrnrh ssqtseesai etgsssstfi kredetiedi dmmddigids
     1081 sdlvedsfl
```

PDGFRA nucleic acid sequence

FIG. 16
CONTINUED

```
LOCUS       NM_006206            6574 bp    mRNA    linear   PRI 21-FEB-
2016
DEFINITION  Homo sapiens platelet derived growth factor receptor alpha
            (PDGFRA), mRNA.
ORIGIN
        1 aagagcaaaa agcgaaggcg caatctggac actgggagat tcggagcgca gggagtttga
       61 gagaaacttt tattttgaag agaccaaggt tgaggggggg cttatttcct gacagctatt
      121 tacttagagc aaatgattag ttttagaagg atggactata acattgaatc aattacaaaa
      181 cgcggttttt gagcccatta ctgttggagc tacagggaga gaaacagagg aggagactgc
      241 aagagatcat tggaggccgt gggcacgctc tttactccat gtgtgggaca ttcattgcgg
      301 aataacatcg gaggagaagt ttcccagagc tatggggact tcccatccgg cgttcctggt
      361 cttaggctgt cttctcacag ggctgagcct aatcctctgc cagctttcat taccctctat
      421 ccttccaaat gaaaatgaaa aggttgtgca gctgaattca tccttttctc tgagatgctt
      481 tggggagagt gaagtgagct ggcagtaccc catgtctgaa gaagagagct ccgatgtgga
      541 aatcagaaat gaagaaaaca acagcggcct tttgtgacg gtcttggaag tgagcagtgc
      601 ctcggcggcc cacacagggt tgtacacttg ctattacaac cacactcaga cagaagagaa
      661 tgagcttgaa ggcaggcaca tttacatcta tgtgccagac ccagatgtag cctttgtacc
      721 tctaggaatg acggattatt tagtcatcgt ggaggatgat gattctgcca ttataccttg
      781 tcgcacaact gatcccgaga ctcctgtaac cttacacaac agtgaggggg tggtacctgc
      841 ctcctacgac agcagacagg gctttaatgg gaccttcact gtagggccct atatctgtga
      901 ggccaccgtc aaaggaaaga agttccagac catcccattt aatgtttatg ctttaaaagc
      961 aacatcagag ctggatctag aaatggaagc tcttaaaacc gtgtataagt caggggaaac
     1021 gattgtggtc acctgtgctg tttttaacaa tgaggtggtt gaccttcaat ggacttaccc
     1081 tggagaagtg aaaggcaaag gcatcacaat gctggaagaa atcaaagtcc catccatcaa
     1141 attggtgtac actttgacgg tccccgaggc cacggtgaaa gacagtggag attacgaatg
     1201 tgctgcccgc caggctacca gggaggtcaa agaaatgaag aaagtcacta tttctgtcca
     1261 tgagaaaggt ttcattgaaa tcaaacccac cttcagccag ttggaagctg tcaacctgca
     1321 tgaagtcaaa cattttgttg tagaggtgcg ggcctaccca cctcccagga tatcctggct
     1381 gaaaaacaat ctgactctga ttgaaaatct cactgagatc accactgatg tggaaaagat
     1441 tcaggaaata aggtatcgaa gcaaattaaa gctgatccgt gctaaggaag aagacagtgg
     1501 ccattatact attgtagctc aaaatgaaga tgctgtgaag agctatactt ttgaactgtt
     1561 aactcaagtt ccttcatcca ttctggactt ggtcgatgat caccatggct caactggggg
     1621 acagacggtg aggtgcacag ctgaaggcac gccgcttcct gatattgagt ggatgatatg
     1681 caaagatatt aagaaatgta ataatgaaac ttcctggact attttggcca acaatgtctc
     1741 aaacatcatc acggagatcc actcccgaga caggagtacc gtggagggcc gtgtgacttt
     1801 cgccaaagtg gaggagacca tcgccgtgcg atgcctggct aagaatctcc ttggagctga
     1861 gaaccgagag ctgaagctgg tggctcccac cctgcgttct gaactcacgg tggctgctgc
     1921 agtcctggtg ctgttggtga ttgtgatcat ctcacttatt gtcctggttg tcatttggaa
     1981 acagaaaccg aggtatgaaa ttcgctggag ggtcattgaa tcaatcagcc cagatggaca
```

FIG. 16
CONTINUED 2041 tgaatatatt tatgtggacc cgatgcagct gccttatgac tcaagatggg agtttccaag
2101 agatggacta gtgcttggtc gggtcttggg gtctggagcg tttgggaagg tggttgaagg
2161 aacagcctat ggattaagcc ggtcccaacc tgtcatgaaa gttgcagtga agatgctaaa
2221 acccacggcc agatccagtg aaaaacaagc tctcatgtct gaactgaaga taatgactca
2281 cctggggcca catttgaaca ttgtaaactt gctgggagcc tgcaccaagt caggccccat
2341 ttacatcatc acagagtatt gcttctatgg agatttggtc aactatttgc ataagaatag
2401 ggatagcttc ctgagccacc acccagagaa gccaaagaaa gagctggata tctttggatt
2461 gaaccctgct gatgaaagca cacggagcta tgttatttta tcttttgaaa acaatggtga
2521 ctacatggac atgaagcagg ctgatactac acagtatgtc cccatgctag aaaggaaaga
2581 ggtttctaaa tattccgaca tccagagatc actctatgat cgtccagcct catataagaa
2641 gaaatctatg ttagactcag aagtcaaaaa cctcctttca gatgataact cagaaggcct
2701 tactttattg gatttgttga gcttcaccta tcaagttgcc cgaggaatgg agtttttggc
2761 ttcaaaaaat tgtgtccacc gtgatctggc tgctcgcaac gtcctcctgg cacaaggaaa
2821 aattgtgaag atctgtgact ttggcctggc cagagacatc atgcatgatt cgaactatgt
2881 gtcgaaaggc agtacctttc tgcccgtgaa gtggatggct cctgagagca tctttgacaa
2941 cctctacacc acactgagtg atgtctggtc ttatggcatt ctgctctggg agatcttttc
3001 ccttggtggc accccttacc ccggcatgat ggtggattct actttctaca ataagatcaa
3061 gagtgggtac cggatggcca agcctgacca cgctaccagt gaagtctacg agatcatggt
3121 gaaatgctgg aacagtgagc cggagaagag accctccttt taccacctga gtgagattgt
3181 ggagaatctg ctgcctggac aatataaaaa gagttatgaa aaaattcacc tggacttcct
3241 gaagagtgac catcctgctg tggcacgcat gcgtgtggac tcagacaatg catacattgg
3301 tgtcacctac aaaaacgagg aagacaagct gaaggactgg gagggtggtc tggatgagca
3361 gagactgagc gctgacagtg gctacatcat tcctctgcct gacattgacc ctgtccctga
3421 ggaggaggac ctgggcaaga ggaacagaca cagctcgcag acctctgaag agagtgccat
3481 tgagacgggt tccagcagtt ccaccttcat caagagagag gacgagacca ttgaagacat
3541 cgacatgatg gatgacatcg gcatagactc ttcagacctg gtggaagaca gcttcctgta
3601 actggcggat tcgaggggtt ccttccactt ctggggccac ctctggatcc cgttcagaaa
3661 accactttat tgcaatgcag aggttgagag gaggacttgg ttgatgttta aagagaagtt
3721 cccagccaag ggcctcgggg agcgttctaa atatgaatga atgggatatt ttgaaatgaa
3781 ctttgtcagt gttgcctctt gcaatgcctc agtagcatct cagtggtgtg tgaagtttgg
3841 agatagatgg ataagggaat aataggccac agaaggtgaa ctttgtgctt caaggacatt
3901 ggtgagagtc caacagacac aatttatact gcgacagaac ttcagcattg taattatgta
3961 aataactcta accaaggctg tgtttagatt gtattaacta tcttctttgg acttctgaag
4021 agaccactca atccatccat gtacttccct cttgaaacct gatgtcagct gctgttgaac
4081 tttttaaaga agtgcatgaa aaaccatttt tgaaccttaa aaggtactgg tactatagca
4141 ttttgctatc ttttttagtg ttaaagagat aaagaataat aattaaccaa ccttgtttaa
4201 tagatttggg tcatttagaa gcctgacaac tcattttcat attgtaatct atgtttataa
4261 tactactact gttatcagta atgctaaatg tgtaataatg taacatgatt tccctccaga

FIG. 16
CONTINUED 4321 gaaagcacaa tttaaaacaa tccttactaa gtaggtgatg agtttgacag tttttgacat
4381 ttatattaaa taacatgttt ctctataaag tatggtaata gctttagtga attaaattta
4441 gttgagcata gagaacaaag taaaagtagt gttgtccagg aagtcagaat ttttaactgt
4501 actgaatagg ttccccaatc catcgtatta aaaaacaatt aactgccctc tgaaataatg
4561 ggattagaaa caaacaaaac tcttaagtcc taaaagttct caatgtagag gcataaacct
4621 gtgctgaaca taacttctca tgtatattac ccaatggaaa atataatgat cagcaaaaag
4681 actggatttg cagaagtttt tttttttttt ttcttcatgc ctgatgaaag ctttggcgac
4741 cccaatatat gtattttttg aatctatgaa cctgaaaagg gtcagaagga tgcccagaca
4801 tcagcctcct tctttcaccc cttaccccaa agagaaagag tttgaaactc gagaccataa
4861 agatattctt tagtggaggc tggatgtgca ttagcctgga tcctcagttc tcaaatgtgt
4921 gtggcagcca ggatgactag atcctgggtt tccatccttg agattctgaa gtatgaagtc
4981 tgagggaaac cagagtctgt atttttctaa actccctggc tgttctgatc ggccagtttt
5041 cggaaacact gacttaggtt tcaggaagtt gccatgggaa acaaataatt tgaactttgg
5101 aacagggttg gcattcaacc acgcaggaag cctactattt aaatccttgg cttcaggtta
5161 gtgacattta atgccatcta gctagcaatt gcgaccttaa tttaactttc cagtcttagc
5221 tgaggctgag aaagctaaag tttggttttg acaggttttc caaaagtaaa gatgctactt
5281 cccactgtat gggggagatt gaactttccc cgtctcccgt cttctgcctc ccactccata
5341 ccccgccaag gaaaggcatg tacaaaaatt atgcaattca gtgttccaag tctctgtgta
5401 accagctcag tgttttggtg gaaaaaacat tttaagtttt actgataatt tgaggttaga
5461 tgggaggatg aattgtcaca tctatccaca ctgtcaaaca ggttggtgtg ggttcattgg
5521 cattctttgc aatactgctt aattgctgat accatatgaa tgaaacatgg gctgtgatta
5581 ctgcaatcac tgtgctatcg gcagatgatg ctttggaaga tgcagaagca ataataaagt
5641 acttgactac ctactggtgt aatctcaatg caagccccaa ctttcttatc caactttttc
5701 atagtaagtg cgaagactga gccagattgg ccaattaaaa acgaaaacct gactaggttc
5761 tgtagagcca attagacttg aaatacgttt gtgtttctag aatcacagct caagcattct
5821 gtttatcgct cactctccct tgtacagcct tattttgttg gtgctttgca ttttgatatt
5881 gctgtgagcc ttgcatgaca tcatgaggcc ggatgaaact tctcagtcca gcagtttcca
5941 gtcctaacaa atgctcccac ctgaatttgt atatgactgc atttgtgtgt gtgtgtgtgt
6001 tttcagcaaa ttccagattt gtttcctttt ggcctcctgc aaagtctcca gaagaaaatt
6061 tgccaatctt tcctactttc tatttttatg atgacaatca aagccggcct gagaaacact
6121 atttgtgact ttttaaacga ttagtgatgt ccttaaaatg tggtctgcca atctgtacaa
6181 aatggtccta tttttgtgaa gagggacata agataaaatg atgttataca tcaatatgta
6241 tatatgtatt tctatataga cttggagaat actgccaaaa catttatgac aagctgtatc
6301 actgccttcg tttatatttt tttaactgtg ataatcccca caggcacatt aactgttgca
6361 cttttgaatg tccaaaattt atattttaga aataataaaa agaaagatac ttacatgttc
6421 ccaaaacaat ggtgtggtga atgtgtgaga aaaactaact tgatagggtc taccaataca
6481 aaatgtatta cgaatgcccc tgttcatgtt tttgttttaa aacgtgtaaa tgaagatctt
6541 tatatttcaa taaatgatat ataatttaaa gtta

FIG. 16
CONTINUED

SALL2 polypeptide sequence

LOCUS NP_005398 1007 aa linear PRI 17-APR-2013
DEFINITION sal-like protein 2 [Homo sapiens].
ORIGIN

```
  1 msrrkqrkpq qlisdcegps asengdasee dhpqvcakcc aqftdptefl ahqnacstdp
 61 pvmviiggqe npnnssasse prpeghnnpq vmdtehsnpp dsgssvptdp twgperrgee
121 spghflvaat gtaagggggl ilaspklgat plppestpap pppppppppp gvgsghlnip
181 lileelrvlq qrqihqmqmt eqicrqvlll gslgqtvgap aspselpgtg tasstkpllp
241 lfspikpvqt sktlasssss sssssgaetp kqaffhlyhp lgsqhpfsag gvgrshkptp
301 apspalpgst dqliasphla fpsttgllaa qclgaargle ataspgllkp kngsgelsyg
361 evmgplekpg grhkcrfcak vfgsdsalqi hlrshtgerp ykcnvcgnrf ttrgnlkvhf
421 hrhrekyphv qmnphpvpeh ldyvitssgl pygmsvppek aeeeaatpgg gverkplvas
481 ttalsatesl tllstsagta tapglpafnk fvlmkavepk nkadentppg segsaisgva
541 esstatrmql sklvtslpsw alltnhfkst gsfpfpyvle plgaspsets klqqlvekid
601 rqgavavtsa asgapttsap apsssassgp nqcviclrvl scpralrlhy gqhggerpfk
661 ckvcgrafst rgnlrahfvg hkaspaaraq nscpicqkkf tnavtlqqhv rmhlggqipn
721 ggtalpeggg aaqengseqs tvsgagsfpq qqsqqpspee elseeeeeed eeeeedvtde
781 dslagrgses ggekaisvrg dseeasgaee evgtvaaaat agkemdsnek ttqqsslppp
841 pppdsldqpq pmeqgssgvl ggkeeggkpe rssspasalt pegeatsvtl veelslqeam
901 rkepgesssr kacevcgqaf psqaaleehq kthpkegplf tcvfcrqgfl eratlkkhml
961 lahhqvqpfa phgpqniaal slvpgcspsi tstglspfpr kddptip
```

SALL2 nucleic acid sequence

LOCUS NM_005407 4931 bp mRNA linear PRI 17-APR-2013
DEFINITION Homo sapiens sal-like 2 (Drosophila) (SALL2), mRNA.

ORIGIN

```
  1 gagctgcaga agcgtaggga agaagctgaa gaaaaaaagg gggcgtctcc cctttaaaga
 61 cttgcaaaga ttgagagaga aagagagaga gtcaagaaca gagaatcaga gagagagaga
121 gagtctgtgt ctctgggaaa gaagaacatc tctgcttcac agtgatttgc gctgggggag
181 aggcatcaat tggcttcgga cccaaggggg agacgagacc aggtcacccc ggttaagacc
241 aagtgagcgt tgcccctccc tctcccaact ctctacccgg gaatgtctcg gcgaaagcag
301 cggaaacccc aacagttaat ctcggactgc gaaggtccca gcgcgtctga gaacggtgat
361 gctagcgagg aggatcaccc ccaagtctgt gccaagtgct gcgcacaatt cactgaccca
421 actgaattcc tcgcccacca gaacgcatgt tctactgacc ctcctgtaat ggtgataatt
```

FIG. 16 CONTINUED 481 gggggccagg agaaccccaa caactcttcg gcctcctctg aaccccggcc tgagggtcac
541 aataatcctc aggtcatgga cacagagcat agcaaccccc cagattctgg gtcctccgtg
601 cccacggatc ccacctgggg cccagagagg agaggagagg agtctccagg gcatttcctg
661 gtcgctgcca caggtacagc ggctgggga ggcgggggcc tgatcttggc cagtcccaag
721 ctgggagcaa ccccattacc tccagaatcg accccctgcac cccctcctcc tccaccaccc
781 cctccgcccc caggggtagg cagtggccac ttgaatatcc ccctgatctt ggaagagcta
841 cgggtgctgc agcagcggca gatccatcag atgcagatga ctgagcaaat ctgcaggcag
901 gtgctgttgc ttggctcctt aggccagacg gtgggtgccc ctgccagtcc ctcagagcta
961 cctgggacag ggactgcctc ttccaccaag cccctactac ccctcttcag ccccatcaag
1021 cctgtccaaa ccagcaagac actggcatct tcctcctcct cctcctcttc ctcttcaggg
1081 gcagaaacgc ccaagcaggc cttcttccac ctttaccacc cactggggtc acagcatcct
1141 ttctctgctg gaggggttgg gcgaagccac aaacccaccc ctgccccttc cccagccttg
1201 ccaggcagca cagatcagct gattgcctcg cctcatctgg cattcccaag caccacggga
1261 ctactggcag cacagtgtct tggggcagcc cgaggccttg aggccactgc ctccccaggg
1321 ctcctgaagc caaagaatgg aagtggtgag ctgagctacg gagaagtgat gggtcccttg
1381 gagaagcctg gtggaaggca caaatgccgc ttctgtgcca aagtatttgg cagtgacagt
1441 gccctgcaga tccaccttcg ttcccacacg ggtgagaggc cctataagtg caatgtctgt
1501 ggaaaccgtt ttaccacccg tggcaacctc aaagtgcatt tccaccggca tcgtgagaag
1561 tacccacatg tgcagatgaa cccacaccca gtaccagagc acctagacta tgtcattacc
1621 agcagtggct tgccttatgg tatgtccgtg ccaccagaga aggccgagga ggaggcagcc
1681 actccaggtg gaggggttga gcgcaagcct ctggtggcct ccacaacagc actcagtgcc
1741 acagagagcc tgactctgct ctccaccagt gcaggcacag ccacggctcc aggactccct
1801 gctttcaata agtttgtgct catgaaagca gtggaaccca agaataaagc tgatgaaaac
1861 acccccccag ggagtgaggg ctcagccatc agtggagtgg cagaaagtag cacggcaact
1921 cgcatgcaac taagtaagtt ggtgacttca ctaccaagct gggcactgct taccaaccac
1981 ttcaagtcca ctggcagctt ccccttcccc tatgtgctag agcccttggg ggcctcaccc
2041 tctgagacat caaagctgca gcaactggta gaaaagattg accggcaagg agctgtggcg
2101 gtgacctcag ctgcctcagg agcccccacc acctctgccc ctgcaccttc atcctcagcc
2161 tcttctggac ctaaccagtg tgtcatctgt ctccgagtgc ttagctgtcc tcgggcccta
2221 cgccttcatt atggccaaca tggaggtgag aggcccttca aatgcaaagt gtgtggcaga
2281 gccttctcca ccaggggtaa tctgcgtgca catttcgtgg gccacaaggc cagtccagct
2341 gcccgggcac agaattcctg ccccatctgc cagaagaagt tcaccaatgc tgtcactctg
2401 cagcagcatg tccggatgca cctgggggc cagatcccca acggtggtac tgcactccct
2461 gaaggtggag gagctgctca ggagaatggc tccgagcaat ctacagtctc cggggcaggg
2521 agtttccccc agcagcagtc ccagcagcca tcaccggaag aggagttgtc tgaggaggag
2581 gaagaggagg atgaggaaga agaggaagat gtgactgatg aagattccct ggcagggaga
2641 ggctcagaga gtggaggtga gaaggcaata tcagtgagag gtgattcaga agaggcatct
2701 ggggcagagg aggaggtggg gacagtggcg gcagcagcca cagctgggaa ggagatggac

FIG. 16
CONTINUED 2761 agtaatgaga aaactactca acagtcttct ttgccaccac caccaccacc tgacagcctg
2821 gatcagcctc agccaatgga gcagggaagc agtggtgttt taggaggcaa ggaagagggg
2881 ggcaaaccgg agagaagctc aagtccggca tcagcactca ccccagaagg ggaagccacc
2941 agcgtgacct tggtagagga gctgagcctg caggaggcaa tgagaaagga gccaggagag
3001 agcagcagca gaaaggcctg cgaagtgtgt ggccaggcct ttccctccca ggcagctctg
3061 gaggagcatc agaagaccca ccccaaggag gggccgctct tcacttgtgt tttctgcagg
3121 cagggctttc ttgagcgggc taccctcaag aagcatatgc tcctggcaca ccaccaggta
3181 cagccctttg ccccccatgg ccctcagaat attgctgctc tttctctagt ccctggctgt
3241 tcgccttcca tcacctccac agggctctcc cccttccccc gaaaagatga ccccacgatc
3301 ccatgagcct gtttttctgt acctgctgct ctttgtccca cagagcagaa acagcttcac
3361 aaaaggacct cccagagtta tgagccctga ttttgtcttt ttctctaagt tcttaacatg
3421 ttatgtccct agtggctttt ctgtagtccc tgagcttgga aattactgtg cttacaaggg
3481 gatggccccc taaggaattt ttcttccctc ctcattcttt gtacctgagg aacatagatt
3541 ctctgcagct ttctcaaggg gaaccctctc cagcttccct ggtgtgaccc ttcttccccc
3601 tcctctctcc tctccctttc cctttggtag gtgcacctga gcacctacat ttggcattgc
3661 agcctagcca aaaagggctg gcagctgtct ctggagggcc cagtgccact cctctggggt
3721 gacctttctg ctcagctggt gggtatgggt cccctatctt tctagaacca gtatgtggca
3781 ttcctgtcaa atggcctgcc catgaagccc tggaattcca gctccacctc cactaccact
3841 ccaagcctgg ccccaccagt gctgtttggc ctaggaactg tggctgggaa ggtgcctcca
3901 acaatgggat ccagggaagc caaggagaag acagcccccc tcctatttca gcctcctgca
3961 cccaaggcag tgcctgagaa gcccatcata gacaagaagt agcaaactgt acattccttc
4021 ttcctccccc tgctccagaa ggtgccggta ctgaagatgc tccagtaatt ggtgacccaa
4081 ccctaggaag tagggagaaa tgaaggaagg gcataggaaa attttcccag taaatcccct
4141 gatggtcaca ttaaggtaaa ggttttggct ggtcagtgtg ccaagacctc tccagcttct
4201 cattcatgat gacctctcaa agttgggaaa caagctgatt tcttgccaag aggtctccca
4261 ggagatattt gggaaatgtg aagttcgtat ctttaaggag catttttggt cagcatggtt
4321 gatgaactaa tgatgagaga gttaaggaat gttgctagaa catagggctt gctggtacct
4381 atgtgactaa gaaagggaca tgatgtaagg gaaaaggcct caaattcttg tgaatgtgga
4441 cattctcgtt aatattcttt tgggctaata gtgacatagt gtgcagaggt gtaccaggga
4501 tcatggggga tttcctagca ctagtatgct tctagtttta gataactccc tcctttattc
4561 cctggcccct tgtattttcc ttatcttcct ctttcaagac ccctacccat tttgcctatc
4621 cgtaggctgg ggcttgtgtc tttgtcattg tctggttctt aagagtccca gctccaggtg
4681 gcgtcctccc tgcctctccg tcttgtaatg agttgtagta tttactctta acataggatc
4741 atttggaaca ggagttctga ggaggagaga gtgagggttt tgctattgac tgacttgaac
4801 gatggcttct cctcaagctg taggctccag agcttcctaa cctagtaaaa tgtcaagaac
4861 agacgggaga tattagtgtc tttccctcta tcattaaagg tgttttaacc aaaaaaaaaa
4921 aaaaaaaaaa a

FIG. 16
CONTINUED

ZFHX4 polypeptide sequence

```
LOCUS       NP_078997              3616 aa            linear   PRI 15-MAR-
2015
DEFINITION  zinc finger homeobox protein 4 [Homo sapiens].
ORIGIN
        1 metcdsppis rqengqstsk lcgttqldne vpekvagmep drensstddn lktderksea
       61 llgfsvenaa atqvtsakei pcnecatsfp slqkymehhc pnarlpvlkd dneseisele
      121 dsdvenltge ivyqpdgsay iiedskesgq naqtganskl fstamfldsl asageksdqs
      181 asapmsfypq iintfhiass lgkpftadqa fpntsalagv gpvlhsfrvy dlrhkrekdy
      241 ltsdgsakns cvskdvpnnv dlskfdgcvs dgkrkpvlmc flcklsfgyi rsfvthavhd
      301 hrmtlndeeq kllsnkcvsa iiqgigkdke plisflepkk stsvyphfst tnligpdptf
      361 rglwsafhve ngdslpagfa flkgsastss saeqplgitq mpkaevnlgg lsslvvntpi
      421 tsvslshsss esskmseskd qenncerpke snvlhpngec pvkseptepg dedeedaysn
      481 elddeevlge ltdsignkdf pllnqsispl sssvlkfiek gtssssatvs ddtekkkqta
      541 avrasgsvas nygisgkdfa dasaskdsat aahpseiarg dedssatphq hgftpstpgt
      601 pgpggdgspg sgiecpkcdt vlgssrslgg hmtmmhsrns cktlkcpkcn whykyqqtle
      661 ahmkekhpep ggscvycktg qphprlarge sytcgykpfr cevcnysttt kgnlsihmqs
      721 dkhlnnvqnl qngngeqvfg hsapapntsl sgcgtpspsk pkqkptwrce vcdyetnvar
      781 nlrihmtsek hmhnmmllqq nmkqiqhnlh lglapaeael yqyylaqnig ltgmklenpa
      841 dpqlminpfq ldpataaala pglvnnelpp eirlasgqlm gddlslltag elspyisdpa
      901 lklfqcavcn kftsdsleal svhvssersl peeewravig diyqcklcny ntqlkanfql
      961 hcktdkhmqk yqlvahikeg gksnewrlkc iaignpvhlk cnacdyytns vdklrlhttn
     1021 hrheaalkly khlqkqegav npescyyyca vcdyttkvkl nlvqhvrsvk hqqteglrkl
     1081 qlhqqglape ednlseiffv kdcppnelet aslgartcdd dlteqqlrst seeqseeaeg
     1141 aikptavaed dekdtserdn segknsnkds giitpekelk vsvaggtqpl llakeedvat
     1201 krskptednk fcheqfyqcp ycnynsrdqs riqmhvlsqh svqpviccpl cqdvlsnkmh
     1261 lqlhlthlhs vspdcvekll mtvpvpdvmm pnsmllpaaa sekserdtpa avtaegsgky
     1321 sgespmddks magledskan vevkneeqkp tkeplevsew nknsskdvki pdtlqdqlne
     1381 qqkrqplsvs drhvykyrcn hcslafktmq klqihsqyha iraatmcnlc qrsfrtfqal
     1441 kkhleaghpe lseaelqqly aslpvngelw aesetmsqdd hgleqemere yevdhegkas
     1501 pvgsdsssip ddmgsepkrt lpfrkgpnft mekfldpsrp ykctvckesf tqknillvhy
     1561 nsvshlhklk kvlqeasspv pqetnsntdn kpykcsicnv aysqsstlei hmrsvlhqtk
     1621 araaklepsg hvagghsiaa nvnspgqgml dsmslaavns kdthldakel nkkqtpdlis
     1681 aqpahhppqs paqiqmqlqh elqqqaaffq pqflnpaflp hfpmtpeall qfqqpqflfp
     1741 fyipgtefsl gpdlglpgsa tfgmpgmtgm agslledlkq qiqtqhhvgq tqlqilqqqa
     1801 qqyqatqpql qpqkqqqqpp ppqqqqqqqa skllkqeqsn ivsadcqimk dvpsykeaed
     1861 isekpekpkq efisegeglk egkdtkkqks lepsipppri asgargnaak allenfgfel
```

FIG. 16
CONTINUED 1921 viqynenrqk vqkkgksgeg entdklecgt cgklfsnvli lkshqehvhg qffpyaalek
1981 farqyreayd klypispssp etpppppppp plppappqps smgpvkipnt vstplqappp
2041 tppppppppp pppppppppp psappqvqlp vsldlplfps immqpvqhpa lppqlalqlp
2101 qmdalsadlt qlcqqqlgld pnflrhsqfk rprtritddq lkilrayfdi nnspseeqiq
2161 emaeksglsq kvikhwfrnt lfkerqrnkd spynfsnppi tvlediridp qptslehyks
2221 dasfskrssr trftdyqlrv lqdffdtnay pkddeieqls tvlnlptrvi vvwfqnarqk
2281 arksyenqae tkdnekrelt neryirtsnm qyqckkcnvv fprifdlith qkkqcykded
2341 ddaqdesqte dsmdatdqvv ykhctvsgqt daaknaaapa assgsgtstp lipspkpepe
2401 ktspkpeypa ekpkqsdpsp psqgtkpalp lastssdppq astaqpqpqp qppkqpqlig
2461 rppsasqtpv pssplqismt slqnslppql lqyqcdqctv afptlelwqe hqhmhflaaq
2521 nqflhspfle rpmdmpymif dpnnplmtgq llgssltqmp pqassshtta pttvaaslkr
2581 klddkednnc sekeggnsge dqhrdkrlrt titpeqleil yekylldsnp trkmldhiar
2641 evglkkrvvq vwfqntrare rkgqfravgp aqshkrcpfc ralfkaksal eshirsrhwn
2701 egkqagyslp psplistedg gespqkyiyf dypslpltki dlssenelas tvstpvskta
2761 elspknllsp ssfkaecsed venlnappae agydqnktdf detssintai sdattgdegn
2821 temesttgss gdvkpalspk epktldtlpk pattpttevc ddkflfslts psihfndkdg
2881 dhdqsfyitd dpddnadrse tssiadpssp npfgssnpfk sksndrpghk rfrtqmsnlq
2941 lkvlkacfsd yrtptmqece mlgneiglpk rvvqvwfqna rakekkfkin igkpfminqg
3001 gteqtkpect lcgvkysarl sirdhifskq hiskvretvg sqldrekdyl apttvrqlma
3061 qqeldrikka sdvlgltvqq pgmmdssslh gislptaypg lpglppvllp gmngpsslpg
3121 fpqnsntltp pgagmlgfpt satsspalsl ssaptkpllq tppppppppp pppssslsgq
3181 qteqqnkese kkqtkpnkvk kikeeeleat kpekhpkkee kissalsvlg kvvgethvdp
3241 iqlqalqnai agdpasfigg qflpyfipgf asyftpqlpg tvqggyfppv cgmeslfpyg
3301 ptmpqtlagl spgallqqyq qyqqnlqesl qkqqkqqqeq qqkpvqakts kvesdqpqns
3361 ndasetkedk statestkee pqlesksadf sdtyvvpfvk yeficrkcqm mftdedaavn
3421 hqksfcyfgq plidpqetvl rvpvskyqcl acdvaisgne alsqhlqssl hkektikqam
3481 rnakehvrll phsvcspnpn ttstsqsaas snntyphlsc fsmkswpnil fqasarraas
3541 ppssppslsl pstvtsslcs tsgvqtslpt escsdesdse lsqkledldn slevkakpas
3601 gldgnfnsir mdmfsv ZFHX4 nucleic acid sequence LOCUS NM_024721 13975 bp mRNA linear PRI 15-MAR-2015
DEFINITION Homo sapiens zinc finger homeobox 4 (ZFHX4), mRNA.

ORIGIN
1 attttttaa acagggctaa aacgataata attagcagaa taaagacata tcggattttc
61 atttcctttc ctccttttcc caaccccttc acaaccaaac agcgagaccg cggtcggcac
121 atgctttaac tcctcccgga cccccgagga ccgctccatg ccccccactt tctgctccag

FIG. 16
CONTINUED 181 cgtttttatt ttcacccaat aaagttcgag gattattttt tatttttttt gttttttttaa
241 tgaaccctct cgttttactt ggatgtgatc agctgtaagt aaaataaaag caaaacaaaa
301 aagaggcgaa gatcgagtag gaactgcagg ggaaatggaa agtccctgac aggctggatg
361 aaatgagatc cccatgtagc aattgccatg gaaacctgtg actcccctcc tatctcaagg
421 caggaaaatg ggcagagcac atcaaagcta tgtggaacga cacaacttga taatgaggtg
481 ccagagaaag ttgcagggat ggagcctgac agggaaaaca gctccacaga tgacaacctg
541 aaaacggatg agcgcaaaag tgaagccttg ctgggtttca gcgttgagaa tgcagctgcc
601 actcaggtta cctcagcaaa ggagataccc tgcaacgaat gtgccacttc ttttcccagt
661 ttacagaaat acatggaaca ccactgccct aatgcccgcc ttcctgtcct gaaggatgac
721 aacgagagcg agatcagcga gttagaggac agtgacgtgg aaaatctaac aggggagatc
781 gtttaccagc ctgatgggtc agcatatata attgaggact ccaaagaaag tgggcagaat
841 gcacagactg ggcaaatag caaactcttt tctacagcga tgttcctgga ctccctggca
901 tctgctggag agaagagtga tcagtctgct tctgcaccta tgtcgttcta cccacagatc
961 atcaacactt ttcatatcgc ttcatccctc gggaaaccat ttacagccga tcaggctttc
1021 ccaaatacct cagcattagc aggagttggt cctgtgttgc acagtttccg tgtctatgat
1081 ctccgacaca agagagagaa agactatcta accagtgatg gctcagccaa aaactcctgt
1141 gtgtccaaag atgtccctaa caatgtggac ttgtccaaat tcgatggttg tgttagcgat
1201 gggaaaagga aacctgtttt aatgtgtttc ttgtgcaagt tgtcttttgg ttatatcagg
1261 tcatttgtaa cccatgctgt gcatgatcat cggatgaccc tcaatgacga ggagcagaag
1321 ctcctcagta ataaatgcgt ctccgccata atacagggga ttggcaaaga caaagaacct
1381 cttataagct ttctggaacc aaaaaaatcc acttctgttt atccccattt ttctactaca
1441 aacctcatag gacccgatcc aaccttccgc ggtttatgga gcgcttttca tgttgaaaat
1501 ggtgactctt tgccggctgg ctttgccttc ttaaaaggaa gcgcgagcac ctcgagctca
1561 gcagagcagc cgctggggat tacccaaatg ccaaaggctg aagtgaatct gggggggctg
1621 tctagtttag tagtgaacac cccaattacc tctgtctccc tcagccactc atcgtctgag
1681 tctagcaaga tgtcagagag caaagaccaa gagaacaact gtgaaaggcc aaaagaaagc
1741 aacgttttac acccaaacgg ggagtgccct gtcaaaagtg aacccactga accgggagat
1801 gaggatgaag aagatgcgta ctccaatgaa cttgatgacg aggaagtatt aggtgaactc
1861 accgatagta ttggtaacaa agatttccct ctcttaaacc aaagcatttc tcctttatca
1921 tccagtgtgc taaaatttat tgaaaagggt acctcgtcct cctcggcgac tgtttctgat
1981 gacacagaaa agaaaaaaca gactgctgct gttagggcca gtggcagtgt tgctagtaac
2041 tatggcatca gtggcaagga ctttgcagac gcaagtgcca gtaaagacag tgccacagct
2101 gctcatccaa gtgaaatagc ccgggggagac gaagacagtt cagccactcc tcaccagcat
2161 ggctttaccc cgagtactcc tggcacacca gggcctggag gagacggctc accgggcagt
2221 ggcatcgagt gtccaaagtg cgacactgtg ttggggtctt cgaggtctct tggtggtcat
2281 atgactatga tgcactcgag gaactcatgc aaaaccctca aatgtcctaa atgtaactgg
2341 cactacaaat atcagcagac cctggaggcc catatgaagg agaaacaccc tgagccgggt
2401 ggctcttgtg tttattgtaa gactggacag cctcacccca ggcttgcccg gggtgagagt

FIG. 16
CONTINUED 2461 tacacgtgtg gctataaacc cttccgttgt gaggtttgta actactctac cactaccaaa
2521 ggcaacctca gtattcatat gcagtcggac aagcacctga acaatgttca gaatctccaa
2581 aatggcaatg gtgagcaggt gtttggccac tctgccccag cccccaacac cagcctcagt
2641 ggctgcggaa caccctctcc gtccaaaccc aaacagaaac ccacctggcg gtgtgaagtt
2701 tgtgattatg aaaccaatgt cgccaggaac ctccgaattc atatgaccag cgaaaagcac
2761 atgcataata tgatgctttt gcagcagaac atgaagcaga tccagcataa tctgcacttg
2821 ggcctcgccc cggcggaagc agagctttat cagtactacc tagcccagaa cataggcctg
2881 accggaatga agctggaaaa ccctgccgac cctcagctga tgatcaatcc attccagctg
2941 gatccagcga cagcagcggc tttggcacca gggctcgtaa ataatgagct gccgcctgaa
3001 atccggcttg ccagtggtca gctaatgggt gatgacctgt ccctccttac tgcaggagag
3061 ctgtcacctt atatcagtga cccagcgctg aagctattcc agtgtgctgt ttgcaacaaa
3121 ttcacctctg acagcctgga ggccctaagt gtgcatgtga gcagtgagcg ctctctccct
3181 gaagaggaat ggagggcagt aattggagat atctaccagt gcaagctctg caactacaac
3241 actcagctca aagccaactt ccagctacac tgcaagactg ataaacatat gcagaaatat
3301 caactggtgg ctcacattaa agaaggggc aaaagcaatg agtggaggtt gaagtgtatt
3361 gccattggca accctgttca cctaaaatgt aacgcctgtg actattacac caacagtgtg
3421 gataaattac gcttgcatac caccaatcac aggcacgagg cggccctgaa gctctacaag
3481 cacttgcaga agcaagaggg tgcagtgaat cccgaatcct gctattacta ctgtgccgtg
3541 tgtgattaca ccaccaaggt caagttgaat ctggtacaac atgtccgttc ggtgaagcat
3601 cagcagactg agggcctacg gaagctccag ctccaccagc aaggcctggc accagaggag
3661 gacaacctca gtgagatctt ttttgttaaa gattgcccac caaatgagct tgaaactgcc
3721 tcattgggag ccaggacttg tgatgatgat cttacagagc agcagttgag atcgacctca
3781 gaagaacaaa gtgaggaggc agaaggagct attaagccta cagcagtggc cgaggacgat
3841 gaaaaagaca caagtgagag agacaatagt gaaggcaaaa actctaataa agactctggg
3901 ataatcacac cagagaagga actaaaagtt agtgtggcag ggggtaccca gccactcctg
3961 ctggcaaaag aagaggatgt tgcaacaaaa aggtcaaaac ctacagagga caataaattc
4021 tgtcatgaac agttctatca atgtccttat tgtaactaca atagtaggga ccaaagtcgt
4081 atccagatgc acgtcctatc acagcactcg gtgcagccgg tcatctgctg tcctctctgt
4141 caggacgtcc tcagcaacaa aatgcatctc caactgcatc tgacgcattt gcacagtgtg
4201 tctccagact gtgtggagaa gctgcttatg acagtgcctg tccctgatgt gatgatgcca
4261 aacagtatgc tactgccagc agctgcctct gagaaatcag agcgggacac acctgcagcc
4321 gtgacagctg aggggtctgg gaaatattca ggtgaaagtc caatggatga caaaagcatg
4381 gcaggtctcg aggattcaaa ggctaatgtg gaagtaaaga atgaggagca gaaaccgact
4441 aaagaaccct tggaagtctc agaatggaat aaaaatagca gtaaggatgt gaaaatcccc
4501 gacacactgc aagatcaatt aaatgaacag caaaaaaggc aaccgctctc tgtttctgac
4561 cgtcatgtct acaagtatcg ctgtaaccat tgtagcttgg ctttcaaaac tatgcagaag
4621 cttcagatac attcccagta tcatgcaatt cgggctgcga caatgtgtaa cctctgccag
4681 cgcagtttcc gtacattcca ggctttaaaa aaacacttgg aagcaggcca ccctgaactg

FIG. 16
CONTINUED 4741 agtgaagctg aacttcaaca gctatatgcc tccttgcccg tgaatggaga actgtgggca
4801 gagagcgaaa ctatgtccca ggatgaccat ggcctagagc aggaaatgga gagagagtat
4861 gaggtggacc acgaagggaa agcaagtcct gtaggaagtg atagtagctc tattccagat
4921 gacatgggct ctgaaccaaa gcggacctta cctttagaa aagggcccaa ttttacgatg
4981 gaaaaattcc ttgatccatc tcgtccatat aaatgtacag tgtgtaaaga gtcattcacc
5041 caaaagaaca ttctcttggt ccactataat tcagtttctc acttgcataa gctgaaaaaa
5101 gttttgcagg aagcctccag tcctgtccca caagaaacca acagcaacac agataacaaa
5161 ccctacaagt gcagcatctg caatgttgca tacagccaaa gctcaacatt ggaaatccac
5221 atgaggtctg tgctccacca gacaaaggct agggctgcaa agctggagcc cagtggtcat
5281 gtggctggtg ggcacagcat tgcagcaaat gtcaacagcc ctggccaggg gatgttagat
5341 tccatgagtt tagcagctgt aaacagcaaa gatacccatt tagatgccaa agaattaaat
5401 aaaaagcaaa ctcctgattt aatctctgct caacctgcac atcacccacc acagtcacca
5461 gcacaaattc agatgcaact acagcacgaa ttacaacagc aagccgcatt ctttcagcct
5521 cagtttctaa acccagcctt tttgcctcat tttcctatga ccccagaagc actgctgcag
5581 tttcagcagc ctcagtttct ctttccattt tatatacctg ggacggagtt cagcttgggg
5641 ccagatttgg gcttgccagg ctctgccaca tttgggatgc ctggcatgac aggaatggct
5701 ggctccttgc ttgaagacct aaagcagcag attcaaaccc aacatcacgt tggtcaaact
5761 caactccaga tactacagca acaagcacaa caataccaag ccacacagcc ccagctgcag
5821 cctcaaaaac aacagcagca gccaccacct ccacagcagc agcagcaaca gcaggcaagc
5881 aaattattga aacaagagca aagtaacata gtgagtgcag actgccaaat catgaaggat
5941 gtgccatctt ataaggaggc agaagatatt tctgaaaagc cagaaaaacc aaagcaggaa
6001 tttataagtg aaggtgaagg actcaaagaa ggcaaagaca caaagaagca aaaatccttg
6061 gaaccatcca tcccaccacc ccgaatagct tcaggggcca gaggaaatgc tgccaaagcg
6121 ttattggaaa actttggttt tgaactggtc attcagtata acgaaaacag gcagaaggta
6181 cagaagaagg gcaaaagtgg tgaaggcgaa aacactgaca aactagaatg tggaacatgt
6241 ggtaaattgt tttccaatgt tcttatttta aagagtcacc aagaacatgt acatgggcaa
6301 ttttttccat atgcagcgct agaaaaattt gctcgtcaat acagggaggc ctatgacaag
6361 ctttatccaa tttctccatc ttctccagaa acgccgcccc cgccacctcc tcctcctccc
6421 ttgcctccgg ctcctccaca gccttcttct atgggtcctg taaagatccc caacacggtt
6481 tctactcctc tgcaagctcc accacccact cctcccccac caccaccacc tcctcctcct
6541 cctcctcctc cccccccacc tcctccacct tctgctcctc cacaggtcca actgccggtt
6601 tctctggacc tgccgctctt tccttccatt atgatgcaac ctgtgcaaca ccctgcgctt
6661 cctcccccagc ttgccctgca gctgccacag atggacgcac tctctgcaga cctcacccaa
6721 ctttgccagc agcagctcgg attagatccc aacttcttaa gacattctca gttcaaacgc
6781 ccacggacaa gaattacaga tgatcagcta aaaatcctga gggcttattt tgacattaat
6841 aattctccaa gtgaagaaca gatccaggaa atggcagaga aatctggcct ctcccaaaaa
6901 gttatcaaac actggtttag aaatacgctt tttaaggaac gacagagaaa taaagattca
6961 ccatacaact tcagtaaccc tcctataacg gttttagaag atatcagaat tgatccacag

FIG. 16
CONTINUED 7021 cccacctctt tagaacatta caaatctgat gcatcattca gtaaaaggtc ttctagaacg
7081 agatttactg actaccagct tagggttctg caagactttt ttgacacaaa cgcttaccca
7141 aaagatgatg aaatagaaca actctccact gttctcaatc tgcctacccg ggttattgtt
7201 gtatggttcc agaatgctcg tcagaaagca cgaaagagtt atgagaatca agcagaaaca
7261 aaagataatg aaaaaagaga actcactaat gaacggtaca ttcgaacaag caacatgcag
7321 taccagtgta aaaagtgcaa tgtggttttc cccaggatct ttgacttgat tacgcatcag
7381 aaaaagcagt gttacaagga tgaagatgat gatgcccaag atgaaagcca aacagaagac
7441 tccatggatg ccactgatca agtggtatac aagcattgca cagtgtctgg ccaaacggat
7501 gcagctaaaa acgctgctgc ccctgcagca agttctggct ctgggaccag cacccccctg
7561 attccatcac ccaaaccaga acctgagaag acttctccaa aacctgaata tcccgcagaa
7621 aagccaaagc agagtgaccc ctctcccct tctcaaggca ccaaaccagc cctgccatta
7681 gcatcgactt cctcggaccc accacaggca tccacagccc agccacagcc acagccacag
7741 ccaccaaaac aaccccaact tatcggaaga cctccctcgg cctctcaaac accggtccct
7801 tccagtccac tgcaaatttc catgacgtct ctccagaaca gtctacctcc acagttacta
7861 caataccaat gtgatcagtg tacagttgcc ttcccaactc tggaactctg gcaggaacac
7921 cagcacatgc acttccttgc tgctcaaaac caattccttc actctccgtt cttggaaagg
7981 cccatggaca tgccctacat gatatttgac cccaacaatc cgctgatgac tggacaactg
8041 ctgggcagtt ccctcactca aatgcccccct caggccagtt cctcccacac cacagccccc
8101 acaacggttg ctgcttccct aaaaaggaaa ctagacgata aagaagataa taattgcagt
8161 gaaaaagaag gagggaatag cggtgaagac caacaccgag ataaacgctt gagaaccacg
8221 atcaccccgg aacagctgga aatactctat gaaaaatact tgctggattc caatcctacc
8281 agaaaaatgc ttgatcatat tgcccgcgaa gtcgggctga aaaaaagggt cgtgcaagtc
8341 tggttccaga atacacgagc gcgggagagg aaaggccagt tccgggcggt gggtccagca
8401 cagtctcata aacggtgtcc gttttgccga gccctgttta aagcaaagtc ggccttagaa
8461 agccacattc gctctcggca ctggaatgaa ggaaagcagg caggttacag cttgccacca
8521 agccctttaa tatccaccga agatgggggga gaaagcccac agaaatacat ctattttgat
8581 tacccatctt tgccattaac taaaattgat ctatcaagtg agaatgaatt ggcttctaca
8641 gtgtcaacac ctgttagtaa aacagcagag ctgtcaccga agaatctttt aagcccttct
8701 tcttttaaag cagagtgttc tgaggatgta gagaatttaa atgcccctcc tgctgaggct
8761 gggtatgatc aaaataaaac cgattttgat gagacttcat cgattaatac ggcaatcagt
8821 gacgccacca ccggagacga gggaaacact gaaatggaaa gcaccacagg aagttccgga
8881 gatgtgaaac cggctttgtc tcccaaagag ccaaaaactc tggatactct gccaaaacct
8941 gcaaccacac ctaccacgga ggtctgcgat gacaaatttc tcttttctct cacaagccca
9001 tccatccatt tcaatgacaa agatggcgac cacgaccaaa gcttttacat cacagatgac
9061 ccggatgaca acgccgaccg cagcgaaacg tccagcatag cggacccgag ctccccaaat
9121 ccattcggat ccagcaatcc ctttaaatcc aaaagtaatg atcggccggg tcacaagcgt
9181 tttcgaacgc aaatgagcaa tcttcaactc aaggttctca aggcttgctt tagtgactac
9241 cgaactccaa ccatgcaaga atgtgaaatg ttagggaatg agattggtct gcccaaacgc

FIG. 16
CONTINUED 9301 gtagtccagg tgtggttcca aaatgcaagg gcaaaggaaa agaaatttaa aattaacata
9361 gggaagcctt tcatgatcaa tcaaggcgga acggaaggca ccaaaccaga gtgtaccctc
9421 tgcggggtga agtactctgc ccgcttgtcc atcagagatc acattttctc caaacagcac
9481 atttcaaaag tgagggagac cgttggcagt cagctcgatc gggagaaaga ttacttggct
9541 ccgaccacgg ttcggcagct gatggcacag caagaacttg atcgtataaa gaaagcttca
9601 gacgtgctgg gcttgacggt acagcagcca ggcatgatgg acagcagttc tctccacggc
9661 atcagcctgc caacagccta ccccggactc cccggccttc ctccagtcct tctccccgga
9721 atgaacggtc catcctcctt gccgggattt ccacaaaatt caaacacttt aacacctccc
9781 ggtgcaggca tgcttgggtt tcctacttca gctacttcgt ctcctgccct gtctctcagc
9841 agtgccccca ccaaaccttt gctgcagact ccaccacctc caccacctcc tcctcctcct
9901 cctccttcat cctctctgtc aggacagcag accgagcaac agaacaaaga atctgagaaa
9961 aagcaaacta agccaaacaa ggtgaaaaaa atcaaagagg aggaattaga ggccaccaaa
10021 cccgaaaaac accccaaaaa agaggaaaaa atctcatctg ctctttcagt gttgggcaaa
10081 gttgtaggtg aaacacatgt cgatcctatt cagttgcagg cattacagaa tgcaattgct
10141 ggtgacccag cttcctttat aggcggacag ttcttgccat actttatccc tgggtttgct
10201 tcttatttta cacctcagct ccctggaaca gtgcaggggg gatacttccc acctgtctgt
10261 ggcatggaga gcctctttcc ttatggccct acaatgcccc agacactggc aggtctgtcc
10321 ccaggtgcac tgttgcagca gtaccaacag tatcagcaga acctgcagga gtccctgcaa
10381 aagcagcaaa agcaacagca agaacagcag cagaaaccag ttcaggcaaa gacatccaaa
10441 gtagaaagtg accagccgca aaactccaac gatgcttcag aaacaaagga agacaaaagt
10501 actgctacag aaagcacaaa agaagaaccc cagttagaat ccaaaagtgc agacttttca
10561 gacacttacg ttgttccatt cgtcaagtat gagtttatat gcagaaagtg ccagatgatg
10621 tttactgatg aagacgccgc agtaaatcat caaaagtcct tctgttattt cggtcagcct
10681 ttgattgacc cacaagagac agtgcttcgt gtcccagtca gcaaatatca gtgtcttgcc
10741 tgtgatgtgg ctatcagtgg gaatgaagca cttagccaac acctccagtc aagcttgcac
10801 aaagagaaaa caatcaaaca agcaatgaga aatgccaaag agcatgttag attattacct
10861 cactcagtct gctcccctaa tcctaacacc acatctacct cgcagtctgc agcttcttct
10921 aataacacct atcctcatct ttcttgcttc tccatgaagt cctggcctaa tatccttttc
10981 caagcgtctg ccaggagagc tgcttctccc ccttcttctc ctccttccct ttccttgcct
11041 tcaacggtta cctcaagttt gtgcagcacc tcaggggttc aaacctcact acccacagaa
11101 agttgttcag atgagtctga cagtgagctg agccagaagc tagaagactt agataattct
11161 ttggaagtga aggctaagcc tgcttctggc ctagatggta atttcaatag catccgaatg
11221 gatatgttca gtgtgtagga gtgaagacag gatcccgtgc ttaaaaaaat aaaaaataaa
11281 aaaataaaaa aaaaataaga ctttaactgc agttccaaag cttctctaac ccaaaaatta
11341 cagtaccaaa tgattgactc aggattgttt ttcccatatt gatatgctgg caatatagga
11401 tggtatgtaa tggacagaac tgatgcagat ggttgaatgc gcttgtacta tatgctaaaa
11461 tatggaaaag gaaaaaaaaa tctcacaagt tcttttggaa cttgtttcaa gccaaaaact
11521 ctcaagaaag caaattgcac ctcagctgga ttgatttcca aatgctagca tgtactgtat

FIG. 16
CONTINUED 11581 gggaggatga tccagatgtt tcaaagagaa tttctcttag tttagttagg tgtaattcag
11641 tagctttaaa ttctcaggtc agaacataac atttctcatt tgttaaaagc agcaagaagc
11701 ctggtaaaac tgtgactttt ccccaaacgt caatctttat tagaaagcat tttctaggtg
11761 tgtttagtgt acaaagagac tttataaccc ttactggaca acacacagat ccttgagctc
11821 acgctgcagg atagtacagt tttaccgcag agggaatctg gaacagtgga atcatgtgtc
11881 tgccctgtgt attgcagttt gtattgccac aagctatatt tataccagtg tcaccctttt
11941 cttgtagaat atactaataa tctgtgccaa ctctaccttc tcacttttac ctctgacgtc
12001 attctttttt tctgaaagag gtaataattc tagttttgat agactctgag gattatgtga
12061 acaggacatt tttcatttgt gaatttaatg ctatactgtc aaggtacttg cttgtgtctg
12121 aactctagtg cacttatgat tttgtagacc atgtgaaatt taataagata cctttttttt
12181 cctttctttg tgtgtagtgc agcaacagtt tggtctgcat ttgttagaag tttaactcct
12241 aacaacccaa agacctattt aacaattggt gcataaatga aagtagtact gtatacttga
12301 aactgtttaa gtacaagttg aacaaaaatt atgaaaaggt atatttgctt ctcgggaaag
12361 caaagaagct gctttaaaaa ataaaaaggg gactaaaaat ttgttttgta taaagaggtt
12421 agccctgcgc acgtaggact gaattcagtg atatccctat acactgccat ttagtggata
12481 ggttattgta cttccattca tactctgggc acttgtgttg tattgttctg ttacatactt
12541 tttttaacct gttttgtttt atcatatatg cattaaaagt attatcttta tcaacatttg
12601 ctgctactgt gttaacattt ttgttttgct tgccatgaat ttcaacttcc accacccagt
12661 gaattgattt ataaattgct atgctttgct gtttttctgt tgctgtggaa cttaaagaat
12721 gtgaaagctg tcaaagggta ttttacgaat cacttttgtg tttgatatag taaaacaatg
12781 tgattcattc caaagtaaca gaaggttatt tgtaagaaag ttaaaggctt gtgaacaaag
12841 aaagctaagc tgttgtacat atttgtagtt ggctgtgcat ggtacaaatt tattaatatg
12901 aagaaatgca aaatgtattg cttttgatat ttctcttccg agatgaacaa gtagcatgta
12961 atgcaactgt ttgacagttt aactcaagtc atgcttcaaa ctgttttaat gatcaaatca
13021 agacacattt cattttacat tttattattg tacagttttt gtttcggatg atgatcacag
13081 caatctttat tctatacatt ttatgtgaac ttttttaatg tctttaattt ggattttttt
13141 tttttttagt attttaacat ttattttaat cctgaagaca ctttttttgat tgtgtttcgt
13201 aagagacaac atggcctcct aaggtgcaat cctgccgcta tagtgagcta atgtcctgaa
13261 tccaaaggct tcagaaaatt gcttttgcct ttttcatgaa tgttaagcag cagcattgtg
13321 agatcgatct gtcctggcag ttaacacgat gtgcaacagt gtgttagcat ggaacagaac
13381 gcttttcaca aaacaaagga ctgttttaca aatgattatt ccgacagtgt gtcgacataa
13441 acttttacaa ctgcacagca gccaaaaaaa gaaaaaaaaa agaaaaaaaa ctttaactgg
13501 atggacgttg ttagggtgag aaataaaagg acagcctcca aaggttgaga atgagaattg
13561 tttttcctg gatatcaaag ggattatcac agcgcaatca ttgtctacac aacatgtact
13621 ctcaacgcct gggttacata ggaaatgcac cctgaggttt taataaaagc ccctatggct
13681 ataactttaa ataaactaaa ccaaaaatgt tattgatgtt ttatatatag agagtagtct
13741 cattagtttt tgttactgta atgtttgaag tctcaaatgc accgtattac ggtaaataac
13801 atggttttga aaactttttt ttattttgtc acagacctgt tgtcatagtt gaaatgatgt

FIG. 16
CONTINUED 13861 ttattgtaga tggtatttga acttattctt ctggaaatag ttcatcaagt atgtttgttg
13921 ctcattgtga tacattaaaa actgtatcta catatttaaa aaaaaaaaaa aaaaa SOX2 polypeptide sequence LOCUS NP_003097 317 aa linear PRI 16-JUN-2013
DEFINITION transcription factor SOX-2 [Homo sapiens].

ORIGIN 1 mynmmetelk ppgpqqtsgg gggnstaaaa ggnqknspdr vkrpmnafmv wsrgqrrkma
61 qenpkmhnse iskrlgaewk llsetekrpf ideakrlral hmkehpdyky rprrktktlm
121 kkdkytlpgg llapggnsma sgvgvgaglg agvnqrmdsy ahmngwsngs ysmmqdqlgy
181 pqhpglnahg aaqmqpmhry dvsalqynsm tssqtymngs ptysmsysqq gtpgmalgsm
241 gsvvkseass sppvvtsssh srapcqagdl rdmismylpg aevpepaaps rlhmsqhyqs
301 gpvpgtaing tlplshm SOX2 nucleic acid sequence LOCUS NM_003106 2520 bp mRNA linear PRI 16-JUN-2013
DEFINITION Homo sapiens SRY (sex determining region Y)-box 2 (SOX2), mRNA.

ORIGIN 1 ggatggttgt ctattaactt gttcaaaaaa gtatcaggag ttgtcaaggc agagaagaga
61 gtgtttgcaa aagggggaaa gtagtttgct gcctctttaa gactaggact gagagaaaga
121 agaggagaga gaaagaaagg gagagaagtt tgagccccag gcttaagcct ttccaaaaaa
181 taataataac aatcatcggc ggcggcagga tcggccagag gaggagggaa gcgctttttt
241 tgatcctgat tccagtttgc ctctctcttt ttttcccccca aattattctt cgcctgattt
301 tcctcgcgga gccctgcgct cccgacaccc ccgcccgcct cccctcctcc tctccccccg
361 cccgcgggcc ccccaaagtc ccggccgggc cgagggtcgg cggccgccgg cgggccgggc
421 ccgcgcacag cgccccgcatg tacaacatga tggagacgga gctgaagccg ccgggcccgc
481 agcaaacttc gggggggcggc ggcggcaact ccaccgcggc ggcggccggc ggcaaccaga
541 aaaacagccc ggaccgcgtc aagcggccca tgaatgcctt catggtgtgg tcccgcgggc
601 agcggcgcaa gatggcccag gagaacccca agatgcacaa ctcggagatc agcaagcgcc
661 tgggcgccga gtggaaactt ttgtcggaga cggagaagcg gccgttcatc gacgaggcta
721 agcggctgcg agcgctgcac atgaaggagc acccggatta taaataccgg ccccggcgga
781 aaaccaagac gctcatgaag aaggataagt acacgctgcc cggcgggctg ctggcccccg
841 gcggcaatag catggcgagc ggggtcgggg tgggcgccgg cctgggcgcg ggcgtgaacc
901 agcgcatgga cagttacgcg cacatgaacg gctggagcaa cggcagctac agcatgatgc
961 aggaccagct gggctacccg cagcaccccgg gcctcaatgc gcacggcgca gcgcagatgc

FIG. 16
CONTINUED

```
1021 agcccatgca ccgctacgac gtgagcgccc tgcagtacaa ctccatgacc agctcgcaga
1081 cctacatgaa cggctcgccc acctacagca tgtcctactc gcagcagggc acccctggca
1141 tggctcttgg ctccatgggt tcggtggtca agtccgaggc cagctccagc ccccctgtgg
1201 ttacctcttc ctcccactcc agggcgccct gccaggccgg ggacctccgg gacatgatca
1261 gcatgtatct ccccggcgcc gaggtgccgg aacccgccgc ccccagcaga cttcacatgt
1321 cccagcacta ccagagcggc ccggtgcccg gcacggccat taacggcaca ctgcccctct
1381 cacacatgtg agggccggac agcgaactgg aggggggaga aattttcaaa gaaaaacgag
1441 ggaaatggga ggggtgcaaa agaggagagt aagaaacagc atggagaaaa cccggtacgc
1501 tcaaaaagaa aaaggaaaaa aaaaaatccc atcacccaca gcaaatgaca gctgcaaaag
1561 agaacaccaa tcccatccac actcacgcaa aaaccgcgat gccgacaaga aaacttttat
1621 gagagagatc ctggacttct ttttggggga ctatttttgt acagagaaaa cctggggagg
1681 gtggggaggg cgggggaatg gaccttgtat agatctggag gaaagaaagc tacgaaaaac
1741 tttttaaaag ttctagtggt acggtaggag ctttgcagga agtttgcaaa agtctttacc
1801 aataatattt agagctagtc tccaagcgac gaaaaaaatg ttttaatatt tgcaagcaac
1861 ttttgtacag tatttatcga gataaacatg gcaatcaaaa tgtccattgt ttataagctg
1921 agaatttgcc aatatttttc aaggagaggc ttcttgctga attttgattc tgcagctgaa
1981 atttaggaca gttgcaaacg tgaaaagaag aaaattattc aaatttggac attttaattg
2041 tttaaaaatt gtacaaaagg aaaaaattag aataagtact ggcgaaccat ctctgtggtc
2101 ttgtttaaaa agggcaaaag ttttagactg tactaaattt tataacttac tgttaaaagc
2161 aaaaatggcc atgcaggttg acaccgttgg taatttataa tagcttttgt tcgatcccaa
2221 ctttccattt tgttcagata aaaaaaacca tgaaattact gtgtttgaaa tattttctta
2281 tggtttgtaa tatttctgta aatttattgt gatattttaa ggttttcccc cctttatttt
2341 ccgtagttgt attttaaaag attcggctct gtattatttg aatcagtctg ccgagaatcc
2401 atgtatatat ttgaactaat atcatcctta taacaggtac attttcaact taagttttta
2461 ctccattatg cacagtttga gataaataaa tttttgaaat atggacactg aaaaaaaaaa
```

OLIG2 polypeptide sequence

```
LOCUS       NP_005797               323 aa            linear   PRI 17-APR-
2013
DEFINITION  oligodendrocyte transcription factor 2 [Homo sapiens].
ORIGIN
        1 mdsdaslvss rpsspepddl flparskgss gsaftggtvs sstpsdcppe lsaelrgamg
       61 sagahpgdkl ggsgfkssss stsssstssaa asstkkdkkq mtepelqqlr lkinsrerkr
      121 mhdlniamdg lrevmpyahg psvrklskia tlllarnyil mltnsleemk rlvseiyggh
      181 hagfhpsacg glahsaplpa atahpaaaah aahhpavhhp ilppaaaaaa aaaaaaavss
      241 aslpgsglps vgsirpphgl lkspsaaaaa plgggggsgg asggfqhwgg mpcpcsmcqv
      301 ppphhhvsam gagslprlts dak
```

FIG. 16
CONTINUED

OLIG2 nucleic acid sequence
LOCUS NM_005806 2521 bp mRNA linear PRI 17-APR-2013
DEFINITION Homo sapiens oligodendrocyte lineage transcription factor 2 (OLIG2), mRNA.
ORIGIN 1 aaaaaccggc cgagccccta aaggtgcgga tgcttattat agatcgacgc gacaccagcg
61 cccggtgcca ggttctcccc tgaggctttt cggagcgagc tcctcaaatc gcatccagat
121 tttcgggtcc gagggaagga ggaccctgcg aaagctgcga cgactatctt cccctggggc
181 catggactcg gacgccagcc tggtgtccag ccgcccgtcg tcgccagagc ccgatgacct
241 ttttctgccg gcccggagta agggcagcag cggcagcgcc ttcactgggg gcaccgtgtc
301 ctcgtccacc ccgagtgact gcccgccgga gctgagcgcc gagctgcgcg gcgctatggg
361 ctctgcgggc gcgcatcctg gggacaagct aggaggcagt ggcttcaagt catcctcgtc
421 cagcacctcg tcgtctacgt cgtcggcggc tgcgtcgtcc accaagaagg acaagaagca
481 aatgacagag ccggagctgc agcagctgcg tctcaagatc aacagccgcg agcgcaagcg
541 catgcacgac ctcaacatcg ccatggatgg cctccgcgag gtcatgccgt acgcacacgg
601 cccttcggtg cgcaagcttt ccaagatcgc cacgctgctg ctggcgcgca actacatcct
661 catgctcacc aactcgctgg aggagatgaa gcgactggtg agcgagatct acgggggcca
721 ccacgctggc ttccacccgt cggcctgcgg cggcctggcg cactccgcgc ccctgcccgc
781 cgccaccgcg cacccggcag cagcagcgca cgccgcacat caccccgcgg tgcaccaccc
841 catcctgccg cccgccgccg cagcggctgc tgccgccgct gcagccgcgg ctgtgtccag
901 cgcctctctg cccggatccg ggctgccgtc ggtcggctcc atccgtccac cgcacggcct
961 actcaagtct ccgtctgctg ccgcggccgc cccgctgggg ggcgggggcg gcggcagtgg
1021 ggcgagcggg ggcttccagc actggggcgg catgccctgc ccctgcagca tgtgccaggt
1081 gccgccgccg caccaccacg tgtcggctat gggcgccggc agcctgccgc gcctcacctc
1141 cgacgccaag tgagccgact ggcgccggcg cgttctggcg acaggggagc caggggccgc
1201 ggggaagcga ggactggcct gcgctgggct cgggagctct gtcgcgagga ggggcgcagg
1261 accatggact gggggtgggg catggtgggg attccagcat ctgcgaaccc aagcaatggg
1321 ggcgcccaca gagcagtggg gagtgagggg atgttctctc cgggacctga tcgagcgctg
1381 tctggcttta acctgagctg gtccagtaga catcgtttta tgaaaaggta ccgctgtgtg
1441 cattcctcac tagaactcat ccgacccccg acccccacct ccgggaaaag attctaaaaa
1501 cttctttccc tgagagcgtg gcctgacttg cagactcggc ttgggcagca cttcgggggg
1561 ggagggggtg ttatgggagg gggacacatt ggggccttgc tcctcttcct cctttcttgg
1621 cgggtgggag actccgggta gccgcactgc agaagcaaca gcccgaccgc gccctccagg
1681 gtcgtccctg gcccaaggcc aggggccaca agttagttgg aagccggcgt tcggtatcag
1741 aagcgctgat ggtcatatcc aatctcaata tctgggtcaa tccacaccct cttagaactg
1801 tggccgttcc tccctgtctc tcgttgattt gggagaatat ggttttctaa taaatctgtg

FIG. 16
CONTINUED 1861 gatgttcctt cttcaacagt atgagcaagt ttatagacat tcagagtaga accacttgtg
1921 gattggaata acccaaaact gccgatttca ggggcgggtg cattgtagtt attattttaa
1981 aatagaaact accccaccga ctcatctttc cttctctaag cacaaagtga tttggttatt
2041 ttggtacctg agaacgtaac agaattaaaa ggcagttgct gtggaaacag tttgggttat
2101 ttgggggttc tgttggcttt ttaaaatttt ctttttgga tgtgtaaatt tatcaatgat
2161 gaggtaagtg cgcaatgcta agctgtttgc tcacgtgact gccagcccca tcggagtcta
2221 agccggcttt cctctatttt ggtttatttt tgccacgttt aacacaaatg gtaaactcct
2281 ccacgtgctt cctgcgttcc gtgcaagccg cctcggcgct gcctgcgttg caaactgggc
2341 tttgtagcgt ctgccgtgta acacccttcc tctgatcgca ccgcccctcg cagagagtgt
2401 atcatctgtt ttatttttgt aaaaacaaag tgctaaataa tatttattac ttgtttggtt
2461 gcaaaaacgg aataaatgac tgagtgttga gattttaaat aaaatttaaa gtaaaaaaaa
2521 a POU3F2 polypeptide sequence LOCUS NP_005595 443 aa linear PRI 17-JUN-2013
DEFINITION POU domain, class 3, transcription factor 2 [Homo sapiens].
ORIGIN 1 mataasnhys lltssasivh aeppggmqqg aggyreaqsl vqgdygalqs nghplshahq
61 witalshggg gggggggggg gggggggggdg spwstsplgq pdikpsvvvq qggrgdelhg
121 pgalqqqhqq qqqqqqqqqq qqqqqqqqqr pphlvhhaan hhpgpgawrs aaaaahlpps
181 mgasnggllly sqpsftvngm lgagggpagl hhhglrdahd ephhadhhph phshphqqpp
241 pppppqgppg hpgahhdphs dedtptsddl eqfakqfkqr riklgftqad vglalgtlyg
301 nvfsqtticr fealqlsfkn mcklkpllnk wleeadsssg sptsidkiaa qgrkrkkrts
361 ievsvkgale shflkcpkps aqeitslads lqlekevvrv wfcnrrqkek rmtppggtlp
421 gaedvyggsr dtpphhgvqt pvq POU3F2 nucleic acid sequence LOCUS NM_005604 4108 bp mRNA linear PRI 17-JUN-2013
DEFINITION Homo sapiens POU class 3 homeobox 2 (POU3F2), mRNA.
ORIGIN 1 agtaatagca ggagcagcaa cagaaggcgt cggagcgggc gtcggagctg cccgctgtgg
61 gagagagagg agacagaaag agcgagcgag gagagggagc ccgaggcgaa aaagtaactg
121 tcaaatgcgc ggctccttta accggagcgc tcagtccggc tccgagagtc atggcgaccg
181 cagcgtctaa ccactacagc ctgctcacct ccagcgcctc catcgtgcac gccgagccgc

FIG. 16
CONTINUED 241 ccggcggcat gcagcagggc gcggggggct accgcgaagc gcagagcctg gtgcagggcg
301 actacggcgc tctgcagagc aacggacacc cgctcagcca cgctcaccag tggatcaccg
361 cgctgtccca cggcggcggc ggcgggggcg gtggcggcgg cggggggggc gggggcggcg
421 gcgggggcgg cggcgacggc tccccgtggt ccaccagccc cctgggccag ccggacatca
481 agccctcggt ggtggtgcag cagggcggcc gcggagacga gctgcacggg ccaggcgccc
541 tgcagcagca gcatcagcag cagcaacagc aacagcagca gcaacagcag caacagcagc
601 agcagcagca gcaacagcgg ccgccgcatc tggtgcacca cgccgctaac caccaccccgg
661 gacccggggc atggcggagc gcggcggctg cagcgcacct cccaccctcc atgggagcgt
721 ccaacggcgg cttgctctac tcgcagccca gcttcacggt gaacggcatg ctgggcgccg
781 gcgggcagcc ggccggtctg caccaccacg gcctgcggga cgcgcacgac gagccacacc
841 atgccgacca ccaccccgcac ccgcactcgc acccacacca gcagccgccg cccccgccgc
901 ccccgcaggg tccgcctggc cacccaggcg cgcaccacga cccgcactcg gacgaggaca
961 cgccgacctc ggacgacctg gagcagttcg ccaagcagtt caagcagcgg cggatcaaac
1021 tgggatttac ccaagcggac gtggggctgg ctctgggcac cctgtatggc aacgtgttct
1081 cgcagaccac catctgcagg tttgaggccc tgcagctgag cttcaagaac atgtgcaagc
1141 tgaagccttt gttgaacaag tggttggagg aggcggactc gtcctcgggc agccccacga
1201 gcatagacaa gatcgcagcg caagggcgca agcggaaaaa gcggacctcc atcgaggtga
1261 gcgtcaaggg ggctctggag agccatttcc tcaaatgccc caagccctcg gcccaggaga
1321 tcacctccct cgcggacagc ttacagctgg agaaggaggt ggtgagagtt tggttttgta
1381 acaggagaca gaaagagaaa aggatgaccc ctcccggagg gactctgccg ggcgccgagg
1441 atgtgtacgg ggggagtagg gacactccac cacaccacgg ggtgcagacg cccgtccagt
1501 gaactcgagc tgggggaggg gcagagcgcg gggctccccc tccccttcgg tccttggccc
1561 tttcccggcc ctcttgttcc ctctctaact tctgattgtt cttttatttt taattattat
1621 ttccccgtcc cttaaaaaga caaaaaaaat aaggcaaaag gaaagcaact aagacactgg
1681 actatccttt aaaggtagca ggtgtaatga tgtgttttga cctttgcagg cgagtaacca
1741 ggcaatggag tggagtgtct cctggagaga gtgaggagag tgtgtgatag ctagaaagag
1801 agagagacag agagatggca agcactgaga taaatacctg gcaaaactaa ataaattacc
1861 aaaaaggaaa aaaaatccac caaaccatga taaacacaaa atgcagcttc ctgatgctta
1921 gagttggcac atgctgctgt gtttatttat tgtggattcc catcaggaaa gaggaaaaaa
1981 tacacatgtt ctttcatata ggcaaaattt aaccacataa atttgcactg caagaaaatt
2041 gaagtttacg tgaacaaatt catgagcata ttttctcttt ctccccaccg ttaatttggg
2101 agttgccgtt ttgggggatt ttgttttgct ttgctttatt catcggagag agttgaagcc
2161 agctcttggc cactctccat ttctaatgtt cttgtgttgc cccttcttcg tactgtttgt
2221 gaactttggt taccttcaca ttccccttac gagggtgtaa catctatttg ttcctcttac
2281 caaagcaaaa ggattggctt catacaaaat agacaattct ctgatttcag gaaatgtgca
2341 tggtctaccc gctttatcga aggcaagaat ccggtttgga atataaaaat aagcattggt
2401 tgttcttacc agccacaaag taaacttcat tttcaggcag tgtttctggg ggaggttatg
2461 gagggaagaa aaaagaaaaa tcgatagtga gtgactgatt gcttcatttt atcaggcggg

FIG. 16
CONTINUED 2521 cccattgtga aagagctcag gggaaatgtg gaggttaaat atatttccag agttgtccag
2581 cagaaagaaa gtggcacttt gaagagaact agggaagtac atatcttcag atatccctat
2641 atagttctct accttcagtt ttagtaacaa ttatgaagaa ttatttgtgc tgacagcagc
2701 agttaaactt tgtttctcta atagcttttt ttttacataa aaaaagaccc aggaacttaa
2761 tagtgtatgc ataagactgt gttttttagc acacagatac ccacagcata cactgacgat
2821 ctccacgcag tagacaggtt ttgtcttcac tagctcattt gtttatcaag tcatatttag
2881 ggtcccacac cctcttttcc tgtaatttat tgcagaatac accactttga cttggacagc
2941 tttctgcccc ctctttcact aaggaaggca aatgaagtga aaaaaaaaaa tgccattttc
3001 aatccttcct ttctcccctt tgttaatagt tttaagtgaa tttttgacct tatcttaatg
3061 gaaaacggtt aactccaaac acaaaagact ctactggaaa gtgtaggtga aaaaacttgt
3121 aactgtattg aaaataaata ccattaaact gtgatcagtt aaaatttaaa agaaaaatca
3181 gcacaaaagg gcgctaaaag ggaaaacact ttttattaat cttaaaagtt tggggggtttt
3241 tttccagtta ggtattagat aaatttttat tttaaaaaat gaaagtctca ctaccataaa
3301 attatggttc agcatcagat tagcattgca ctcagtagtc tttaaggttt taggaaatat
3361 gctttatatt gtcttttcaa acacctgtga ttgtttcatt ttccatgttt ttgcaagata
3421 aatggtgact tataatgggc atatttattt gcctgtattt catttccccc aatgaatgtc
3481 acaaggagat gggcacggag ctgcttcggg tgcatcacgc tgctcgttcc tgaggtatgg
3541 gaactggcct ttagtgaagc tatccagagc agggcaaata gccactggta aagggaggaa
3601 atgaatttcc agatacttat taccaagtag gtaaggtcag aagctggagt tcagagaatg
3661 tgtctacagc ttctctgact cttataggtt tactaagatg aaagttacca ctgaacctta
3721 ccactatgta tatatgttta atatctgtct tttgaaatgc agaaatagtt taaatgtttc
3781 tttgtctatt tttctttttt tttaatgcta cccagggaaa tattttcata tcatttttaa
3841 gtggcctgcc tcaatgtata tttatttctt ttgaaacaaa aaggttctgg aaactgtttt
3901 tctgtagctt taaatgaata ggtgagcaaa atctatatgg gatgtaattt ttttgttcag
3961 tctcttaaaa aatactttgt tttggtacat ttggttgtgc ttgtggggaa aataaaaacg
4021 cagagatcct tatatattta tgttaaagta atattttatt atctacataa aacagaaatg
4081 cacaataaaa aaaaaaaaaa aaaaaaaa LSD1 isoform b polypeptide sequence LOCUS NP_055828 852 aa linear PRI 09-JUN-2013
DEFINITION lysine-specific histone demethylase 1A isoform b [Homo sapiens].
ORIGIN 1 mlsgkkaaaa aaaaaaaatg teagpgtagg sengsevaaq paglsgpaev gpgavgertp
61 rkkepprasp pgglaeppgs agpqagptvv pgsatpmetg iaetpegrrt srrkrakvey
121 remdeslanl sedeyyseee rnakaekekk lpppppqapp eeenesepee psgvegaafq
181 srlphdrmts qeaacfpdii sgpqqtqkvf lfirnrtlql wldnpkiqlt featlqqlea

FIG. 16
CONTINUED

```
241 pynsdtvlvh rvhsylerhg linfgiykri kplptkktgk viiigsgvsg laaarqlqsf
301 gmdvtllear drvggrvatf rkgnyvadlg amvvtglggn pmavvskqvn melakikqkc
361 plyeangqav pkekdemveq efnrlleats ylshqldfnv lnnkpvslgq alevviqlqe
421 khvkdeqieh wkkivktqee lkellnkmvn lkekikelhq qykeasevkp prditaeflv
481 kskhrdltal ckeydelaet qgkleeklqe leanppsdvy lssrdrqild whfanlefan
541 atplstlslk hwdqdddfef tgshltvrng yscvpvalae gldiklntav rqvrytasgc
601 eviavntrst sqtfiykcda vlctlplgvl kqqppavqfv pplpewktsa vqrmgfgnln
661 kvvlcfdrvf wdpsvnlfgh vgsttasrge lflfwnlyka pillalvage aagimenisd
721 dvivgrclai lkgifgssav pqpketvvsr wradpwargs ysyvaagssg ndydlmaqpi
781 tpgpsipgap qpiprlffag ehtirnypat vhgallsglr eagriadqfl gamytlprqa
841 tpgvpaqqsp sm
```

LSD1 isoform b nucleic acid sequence

```
LOCUS       NM_015013            3053 bp    mRNA    linear   PRI 09-JUN-2013
DEFINITION  Homo sapiens lysine (K)-specific demethylase 1A (KDM1A), transcript
            variant 2, mRNA.
ORIGIN
        1 ggcgcggcgg gagcgcgctt ggcgcgtgcg tacgcgacgg cggttggcgg cgcgcgggca
       61 gcgtgaagcg aggcgaggca aggcttttcg gacccacgga gcgacagagc gagcggcccc
      121 tacggccgtc ggcggcccgg cggcccgaga tgttatctgg gaagaaggcg gcagccgcgg
      181 cggcggcggc tgcagcggca gcaaccggga cggaggctgg ccctgggaca gcaggcggct
      241 ccgagaacgg gtctgaggtg gccgcgcagc ccgcgggcct gtcgggccca gccgaggtcg
      301 ggccgggggc ggtgggggag cgcacacccc gcaagaaaga gcctccgcgg gcctcgcccc
      361 ccgggggcct ggcggaaccg ccggggtccg cagggcctca ggccggccct actgtcgtgc
      421 ctgggtctgc gacccccatg gaaactggaa tagcagagac tccggagggg cgtcggacca
      481 gccggcgcaa gcgggcgaag gtagagtaca gagagatgga tgaaagcttg gccaacctct
      541 cagaagatga gtattattca gaagaagaga gaaatgccaa agcagagaag gaaaagaagc
      601 ttcccccacc accccctcaa gccccacctg aggaagaaaa tgaaagtgag cctgaagaac
      661 catcgggtgt ggagggcgca gctttccaga gccgacttcc tcatgaccgg atgacttctc
      721 aagaagcagc ctgttttcca gatattatca gtggaccaca acagacccag aaggtttttc
      781 ttttcattag aaaccgcaca ctgcagttgt ggttggataa tccaaagatt cagctgacat
      841 ttgaggctac tctccaacaa ttagaagcac cttataacag tgatactgtg cttgtccacc
      901 gagttcacag ttatttagag cgtcatggtc ttatcaactt cggcatctat aagaggataa
      961 aacccctacc aactaaaaag acaggaaagg taattattat aggctctggg gtctcaggct
     1021 tggcagcagc tcgacagtta caaagttttg gaatggatgt cacacttttg gaagccaggg
     1081 atcgtgtggg tggacgagtt gccacatttc gcaaaggaaa ctatgtagct gatcttggag
```

FIG. 16
CONTINUED 1141 ccatggtggt aacaggtctt ggagggaatc ctatggctgt ggtcagcaaa caagtaaata
1201 tggaactggc caagatcaag caaaaatgcc cactttatga agccaacgga caagctgttc
1261 ctaaagagaa agatgaaatg gtagagcaag agtttaaccg gttgctagaa gctacatctt
1321 accttagtca tcaactagac ttcaatgtcc tcaataataa gcctgtgtcc cttggccagg
1381 cattggaagt tgtcattcag ttacaagaga agcatgtcaa agatgagcag attgaacatt
1441 ggaagaagat agtgaaaact caggaagaat tgaaagaact tcttaataag atggtaaatt
1501 tgaaagagaa aattaaagaa ctccatcagc aatacaaaga agcatctgaa gtaaagccac
1561 ccagagatat tactgccgag ttcttagtga aaagcaaaca cagggatctg accgccctat
1621 gcaaggaata tgatgaatta gctgaaacac aaggaaagct agaagaaaaa cttcaggagt
1681 tggaagcgaa tcccccaagt gatgtatatc tctcatcaag agacagacaa atacttgatt
1741 ggcattttgc aaatcttgaa tttgctaatg ccacacctct ctcaactctc tcccttaagc
1801 actgggatca ggatgatgac tttgagttca ctggcagcca cctgacagta aggaatggct
1861 actcgtgtgt gcctgtggct ttagcagaag gcctagacat taaactgaat acagcagtgc
1921 gacaggttcg ctacacggct tcaggatgtg aagtgatagc tgtgaatacc cgctccacga
1981 gtcaaacctt tatttataaa tgcgacgcag ttctctgtac ccttcccctg ggtgtgctga
2041 agcagcagcc accagccgtt cagtttgtgc cacctctccc tgagtggaaa acatctgcag
2101 tccaaaggat gggatttggc aaccttaaca aggtggtgtt gtgttttgat cgggtgttct
2161 gggatccaag tgtcaatttg ttcgggcatg ttggcagtac gactgccagc aggggtgagc
2221 tcttcctctt ctggaacctc tataaagctc caatactgtt ggcactagtg gcaggagaag
2281 ctgctggtat catggaaaac ataagtgacg atgtgattgt tggccgatgc ctggccattc
2341 tcaaagggat tttggtagc agtgcagtac ctcagcccaa agaaactgtg gtgtctcgtt
2401 ggcgtgctga tccctgggct cggggctctt attcctatgt tgctgcagga tcatctggaa
2461 atgactatga tttaatggct cagccaatca ctcctggccc ctcgattcca ggtgccccac
2521 agccgattcc acgactcttc tttgcgggag aacatacgat ccgtaactac ccagccacag
2581 tgcatggtgc tctgctgagt gggctgcgag aagcgggaag aattgcagac cagtttttgg
2641 gggccatgta tacgctgcct cgccaggcca caccaggtgt tcctgcacag cagtccccaa
2701 gcatgtgaga cagatgcatt ctaagggaag aggcccatgt gcctgtttct gccatgtaag
2761 gaaggctctt ctagcaatac tagatcccac tgagaaaatc caccctggca tctgggctcc
2821 tgatcagctg atggagctcc tgatttgaca aaggagcttg cctcctttga atgacctaga
2881 gcacagggag gaacttgtcc attagtttgg aattgtgttc ttcgtaaaga ctgaggcaag
2941 caagtgctgt gaaataacat catcttagtc ccttggtgtg tggggttttt gttttttttt
3001 tatattttga gaataaaact tcatataaaa ttggcaaaaa aaaaaaaaaa aaa LSD1 isoform a polypeptide sequence LOCUS NP_001009999 876 aa linear PRI 09-JUN-2013
DEFINITION lysine-specific histone demethylase 1A isoform a [Homo sapiens].

FIG. 16
CONTINUED

ORIGIN

```
  1 mlsgkkaaaa aaaaaaaatg teagpgtagg sengsevaaq paglsgpaev gpgavgertp
 61 rkkepprasp pgglaeppgs agpqagptvv pgsatpmetg iaetpegrrt srrkrakvey
121 remdeslanl sedeyyseee rnakaekekk lppppppqapp eeenesepee psgqaggl qd
181 dssggygdgq asgvegaafq srlphdrmts qeaacfpdii sgpqqtqkvf lfirnrtlql
241 wldnpkiqlt featlqqlea pynsdtvlvh rvhsylerhg linfgiykri kplptkktgk
301 viiigsgvsg laaarqlqsf gmdvtllear drvggrvatf rkgnyvadlg amvvtglggn
361 pmavvskqvn melakikqkc plyeangqad tvkvpkekde mveqefnrll eatsylshql
421 dfnvlnnkpv slgqalevvi qlqekhvkde qiehwkkivk tqeelkelln kmvnlkekik
481 elhqqykeas evkpprdita eflvkskhrd ltalckeyde laetqgklee klqeleanpp
541 sdvylssrdr qildwhfanl efanatplst lslkhwdqdd dfeftgshlt vrngyscvpv
601 alaegldikl ntavrqvryt asgceviavn trstsqtfiy kcdavlctlp lgvlkqqppa
661 vqfvpplpew ktsavqrmgf gnlnkvvlcf drvfwdpsvn lfghvgstta srgelflfwn
721 lykapillal vageaagime nisddvivgr clailkgifg ssavpqpket vvsrwradpw
781 argsysyvaa gssgndydlm aqpitpgpsi pgapqpiprl ffagehtirn ypatvhgall
841 sglreagria dqflgamytl prqatpgvpa qqspsm
```

LSD1 isoform a nucleic acid sequence

```
LOCUS       NM_001009 999          3125 bp    mRNA    linear   PRI 09   -JUN-
2013
DEFINITION  Homo sapiens lysine (K)  -specific demethylase 1A (KDM1A),
transcript
             variant 1, mRNA.
```

ORIGIN

```
  1 ggcgcggcgg gagcgcgctt ggcgcgtgcg tacgcgacgg cggttggcgg cgcgcgggca
 61 gcgtgaagcg aggcgaggca aggcttttcg gacccacgga gcgacagagc gagcggcccc
121 tacggccgtc ggcggcccgg cggcccgaga tgttatctgg gaagaaggcg gcagccgcgg
181 cggcggcggc tgcagcggca gcaaccggga cggaggctgg ccctgggaca gcaggcggct
241 ccgagaacgg gtctgaggtg gccgcgcagc ccgcgggcct gtcgggccca gccgaggtcg
301 ggccgggggc ggtgggggag cgcacacccc gcaagaaaga gcctccgcgg gcctcgcccc
361 ccgggggcct ggcggaaccg ccggggtccg cagggcctca ggccggccct actgtcgtgc
421 ctgggtctgc gaccccatg gaaactggaa tagcagagac tccggagggg cgtcggacca
481 gccggcgcaa gcgggcgaag gtagagtaca gagagatgga tgaaagcttg gccaacctct
541 cagaagatga gtattattca gaagaagaga gaaatgccaa agcagagaag gaaaagaagc
601 ttcccccacc acccccctcaa gccccacctg aggaagaaaa tgaaagtgag cctgaagaac
661 catcggggca agcaggagga cttcaagacg acagttctgg agggtatgga gacggccaag
721 catcaggtgt ggagggcgca gctttccaga gccgacttcc tcatgaccgg atgacttctc
781 aagaagcagc ctgttttcca gatattatca gtggaccaca acagacccag aaggtttttc
```

FIG. 16
CONTINUED 841 ttttcattag aaaccgcaca ctgcagttgt ggttggataa tccaaagatt cagctgacat
901 ttgaggctac tctccaacaa ttagaagcac cttataacag tgatactgtg cttgtccacc
961 gagttcacag ttatttagag cgtcatggtc ttatcaactt cggcatctat aagaggataa
1021 aacccctacc aactaaaaag acaggaaagg taattattat aggctctggg gtctcaggct
1081 tggcagcagc tcgacagtta caaagttttg gaatggatgt cacacttttg gaagccaggg
1141 atcgtgtggg tggacgagtt gccacatttc gcaaaggaaa ctatgtagct gatcttggag
1201 ccatggtggt aacaggtctt ggagggaatc ctatggctgt ggtcagcaaa caagtaaata
1261 tggaactggc caagatcaag caaaaatgcc cactttatga agccaacgga caagctgaca
1321 ctgtcaaggt tcctaaagag aaagatgaaa tggtagagca agagtttaac cggttgctag
1381 aagctacatc ttaccttagt catcaactag acttcaatgt cctcaataat aagcctgtgt
1441 cccttggcca ggcattggaa gttgtcattc agttacaaga gaagcatgtc aaagatgagc
1501 agattgaaca ttggaagaag atagtgaaaa ctcaggaaga attgaaagaa cttcttaata
1561 agatggtaaa tttgaaagag aaaattaaag aactccatca gcaatacaaa gaagcatctg
1621 aagtaaagcc acccagagat attactgccg agttcttagt gaaaagcaaa cacagggatc
1681 tgaccgccct atgcaaggaa tatgatgaat tagctgaaac acaaggaaag ctagaagaaa
1741 aacttcagga gttggaagcg aatcccccaa gtgatgtata tctctcatca agagacagac
1801 aaatacttga ttggcatttt gcaaatcttg aatttgctaa tgccacacct ctctcaactc
1861 tctcccttaa gcactgggat caggatgatg actttgagtt cactggcagc cacctgacag
1921 taaggaatgg ctactcgtgt gtgcctgtgg ctttagcaga aggcctagac attaaactga
1981 atacagcagt gcgacaggtt cgctacacgg cttcaggatg tgaagtgata gctgtgaata
2041 cccgctccac gagtcaaacc tttatttata aatgcgacgc agttctctgt acccttcccc
2101 tgggtgtgct gaagcagcag ccaccagccg ttcagtttgt gccacctctc cctgagtgga
2161 aaacatctgc agtccaaagg atgggatttg gcaaccttaa caaggtggtg ttgtgttttg
2221 atcgggtgtt ctgggatcca agtgtcaatt tgttcgggca tgttggcagt acgactgcca
2281 gcaggggtga gctcttcctc ttctggaacc tctataaagc tccaatactg ttggcactag
2341 tggcaggaga agctgctggt atcatggaaa acataagtga cgatgtgatt gttggccgat
2401 gcctggccat tctcaaaggg atttttggta gcagtgcagt acctcagccc aaagaaactg
2461 tggtgtctcg ttggcgtgct gatccctggg ctcggggctc ttattcctat gttgctgcag
2521 gatcatctgg aaatgactat gatttaatgg ctcagccaat cactcctggc ccctcgattc
2581 caggtgcccc acagccgatt ccacgactct tctttgcggg agaacatacg atccgtaact
2641 acccagccac agtgcatggt gctctgctga gtgggctgcg agaagcggga agaattgcag
2701 accagttttt gggggccatg tatacgctgc ctcgccaggc cacaccaggt gttcctgcac
2761 agcagtcccc aagcatgtga gacagatgca ttctaaggga agaggcccat gtgcctgttt
2821 ctgccatgta aggaaggctc ttctagcaat actagatccc actgagaaaa tccaccctgg
2881 catctgggct cctgatcagc tgatggagct cctgatttga caaaggagct tgcctccttt
2941 gaatgaccta gagcacaggg aggaacttgt ccattagttt ggaattgtgt tcttcgtaaa
3001 gactgaggca agcaagtgct gtgaaataac atcatcttag tcccttggtg tgtggggttt
3061 ttgttttttt tttatatttt gagaataaaa cttcatataa aattggcaaa aaaaaaaaaa

FIG. 16
CONTINUED 3121 aaaaa

RCOR2 polypeptide sequence

LOCUS NP_775858 523 aa linear PRI 17-APR-2013
DEFINITION REST corepressor 2 [Homo sapiens].

ORIGIN 1 mpsvmekpsa gsgilsrsra ktvpnggqph seddsseeeh shdsmirvgt nyqavipeck
61 pesparysnk elkgmlvwsp nhcvsdakld kyiamakekh gynieqalgm llwhkhdvek
121 sladlanftp fpdewtvedk vlfeqafgfh gkcfqriqqm lpdklipslv kyyyswkktr
181 srtsvmdrqa rrlggrkdke dsdeleegrg gvsegepdpa dpkreplpsr plnarpgpgk
241 kevqvsqyrh hplrtrrrpp kgmylspegl tavsgspdla nltlrgldsq lislkrqvqs
301 mkqtnsslrq aleggidplr ppeantkfns rwttdeqlla vqairrygkd fgaiaevign
361 ktltqvktff vsyrrrfnle evlqeweaeq dgapgapvpm eearrgaplp apaleeddev
421 qitsvstsvp rsvppapppp ppptslsqpp pllrpplpta ptllrqpppl qqgrflqprl
481 apnqppppli rpalaaprhs arpgpqpppt ligtpleppa psl RCOR2 nucleic acid sequence LOCUS NM_173587 2621 bp mRNA linear PRI 17-APR-2013
DEFINITION Homo sapiens REST corepressor 2 (RCOR2), mRNA.
ORIGIN 1 gcgcccagcc gctgaacggc gtgggcaggt gggcggtggg gttccagggc gccccgagga
61 caggggggccc cgacttcagg ggaaccccaa ccctgagggg cgtacatagt aatcacgccc
121 cagccgcacc ggaccttgcg ctcatccctt gcgtccccca cttctgcaca aacttttctg
181 acgccctggc tcgtgggggt cgtggagagc gctggggcta ccaggtgggc tcccaccccg
241 ccggacccta gccacgctga cctcctgcct ctcctaacct cagtggcgac ctctccaggc
301 cgggccgggc tcggcactcg gagcgagtgc ggcaaccact gtcgctctcc gaaggctcct
361 gcgccccccg gggcagctgg gcggggtaat gccctcagtg atggagaagc cgagcgcggg
421 ctctgggatc ctgtcccgta gccgggccaa gacggtgccc aacggcggac agccccactc
481 ggaggatgac agcagcgagg aggagcactc gcacgacagc atgatccgcg ttggaaccaa
541 ttaccaggcc gtaattccgg agtgcaagcc tgagagcccc gcacgctaca gcaacaagga
601 gctgaagggg atgctggtgt ggtcacccaa ccactgtgtg tcagatgcca agcttgacaa
661 gtacattgcg atggccaagg agaagcatgg ctacaacatt gagcaggcgc tgggcatgct
721 tctgtggcat aagcacgatg tggagaagtc gctggccgac ctggccaact tcaccccatt
781 ccctgacgag tggacagtag aggacaaggt gctgtttgaa caggcctttg gcttccatgg
841 caaatgcttc cagcggatcc agcagatgct gcctgacaag ttgattccca gcctggtgaa

FIG. 16
CONTINUED 901 atactactac tcttggaaga agacccgcag ccgaactagt gtgatggaca gacaggcccg
961 gcggctgggg ggccgcaagg acaaagaaga cagtgatgag ctcgaagagg gtcgaggagg
1021 cgtgagtgag ggagagcccg atcctgcaga tcccaagaga gagcctctac cctctcggcc
1081 cctgaatgca cgcccaggcc ctgggaaaaa ggaggtccag gtgtctcagt accgccacca
1141 tcccttgcga acccggcgtc gcccacccaa gggcatgtac ctgagccctg aaggcctcac
1201 ggcagtgtca ggaagcccgg accttgccaa cctcacgctc cgaggtcttg actctcagct
1261 catctccctc aagcgccagg tacagagcat gaagcagacg aacagcagcc tgcgccaagc
1321 cctggagggc ggtattgatc cactacgccc cccggaggcc aacaccaagt tcaactcccg
1381 ctggaccaca gatgagcagc ttttggctgt tcaagccatc cgtaggtatg gcaaagactt
1441 tggggctatt gcagaggtga ttgggaacaa gactctgacc caggtgaaga ctttctttgt
1501 gagctaccgg cgccgcttca atctggagga ggtgctgcag gaatgggagg ctgagcagga
1561 tggggcccct ggagccccag tccccatgga ggaggctagg agagggggctc cattgccagc
1621 cccagcccta gaggaagatg atgaggtcca gattacatcg gtctccacgt ccgtgccccg
1681 atcagtgccc cctgcgccac cacccctcc acctcccacc tcgctgtccc agccaccccc
1741 gctgctgagg ccacctttgc ccacggctcc cactctgctc cgacagccac ccccactgca
1801 gcagggccgc ttcctccagc cccggctggc ccccaaccag cccccaccgc ctctcatccg
1861 ccccgctctg gctgcccccc gccacagcgc ccgccctggc cctcagcccc cacccaccct
1921 gattggaacc cctctggagc cccagcacc ctcactctga gccctgacgt cctccaccaa
1981 ccacgggctc caggacccct ttgctggcca tccccaggca tctctggtgt cactgaggac
2041 agaagggact agggctctgg cggggtcttt gtaagaccag agtttcggac agcccagccc
2101 cgccctttgg gttctgcatg tgttcctggc agctgggcct gtctcctggg gccatggccg
2161 ggctcagggg cctttgagct ggcctgaggg cactttcgct tcctggccgg tactggaatg
2221 gctgtgtcct agtctgctgg ggcttggcct ctgggtcctg ccctttgtgt gtccggggta
2281 gtgaccttag cgtggagtgg ggagagggca gttgggtgtg ctggctgttc tcattcctct
2341 ttcccttctt ttagcaataa gtctggggtg aggtggggag ggaggctgca gggggggagg
2401 tgggcagagg ggccttacag cagcagaggc tggaagagaa gctctgtctt caggggccag
2461 ctgggaaatg ctaaggagct gagggtgccc accaagccca ccttccagaa acttggagaa
2521 atgggggttg ggaacttatg cagacatgga tttatttttc aacatttttt aaaaattaaa
2581 aaaaataaaa tctaagctta ctgaaaaaaa aaaaaaaaaa a

FIG. 16
CONTINUED

SEQUENCE LISTING

<160> NUMBER OF SEQ ID NOS: 55

<210> SEQ ID NO 1
<211> LENGTH: 328
<212> TYPE: PRT
<213> ORGANISM: Homo sapiens

<400> SEQUENCE: 1

```
Met Thr Gly Val Phe Asp Ser Leu Val Ala Asp Met His Ser Thr Gln
1               5                   10                  15
```

-continued

```
Ile Ala Ala Ser Ser Thr Tyr His Gln His Gln Gln Pro Pro Ser Gly
            20                  25                  30

Gly Gly Ala Gly Pro Gly Gly Asn Ser Ser Ser Ser Ser Ser Leu His
        35                  40                  45

Lys Pro Gln Glu Ser Pro Thr Leu Pro Val Ser Thr Ala Thr Asp Ser
    50                  55                  60

Ser Tyr Tyr Thr Asn Gln Gln His Pro Ala Gly Gly Gly Gly Gly Gly
65                  70                  75                  80

Gly Ser Pro Tyr Ala His Met Gly Ser Tyr Gln Tyr Gln Ala Ser Gly
                85                  90                  95

Leu Asn Asn Val Pro Tyr Ser Ala Lys Ser Ser Tyr Asp Leu Gly Tyr
            100                 105                 110

Thr Ala Ala Tyr Thr Ser Tyr Ala Pro Tyr Gly Thr Ser Ser Ser Pro
        115                 120                 125

Ala Asn Asn Glu Pro Glu Lys Glu Asp Leu Glu Pro Glu Ile Arg Ile
    130                 135                 140

Val Asn Gly Lys Pro Lys Lys Val Arg Lys Pro Arg Thr Ile Tyr Ser
145                 150                 155                 160

Ser Phe Gln Leu Ala Ala Leu Gln Arg Arg Phe Gln Lys Thr Gln Tyr
                165                 170                 175

Leu Ala Leu Pro Glu Arg Ala Glu Leu Ala Ala Ser Leu Gly Leu Thr
            180                 185                 190

Gln Thr Gln Val Lys Ile Trp Phe Gln Asn Arg Arg Ser Lys Phe Lys
        195                 200                 205

Lys Met Trp Lys Ser Gly Glu Ile Pro Ser Glu Gln His Pro Gly Ala
    210                 215                 220

Ser Ala Ser Pro Pro Cys Ala Ser Pro Pro Val Ser Ala Pro Ala Ser
225                 230                 235                 240

Trp Asp Phe Gly Val Pro Gln Arg Met Ala Gly Gly Gly Gly Pro Gly
                245                 250                 255

Ser Gly Gly Ser Gly Ala Gly Ser Ser Gly Ser Ser Pro Ser Ser Ala
            260                 265                 270

Ala Ser Ala Phe Leu Gly Asn Tyr Pro Trp Tyr His Gln Thr Ser Gly
        275                 280                 285

Ser Ala Ser His Leu Gln Ala Thr Ala Pro Leu Leu His Pro Thr Gln
    290                 295                 300

Thr Pro Gln Pro His His His His His His His Gly Gly Gly Gly Ala
305                 310                 315                 320

Pro Val Ser Ala Gly Thr Ile Phe
                325
```

<210> SEQ ID NO 2
<211> LENGTH: 2308
<212> TYPE: DNA
<213> ORGANISM: Homo sapiens

<400> SEQUENCE: 2

```
aagaggatgc gaccagaggc agctgtcccg agcagcgcac ggtgatcgcc tcccccggag      60

gaggaggcgc ctagacggtt gcctcctttc ttgtttcccc accaccaccc ccgtaattac     120

attggctgct ggaggggacc gggagagaca gaggaggcgc ctggcttccc ccgcacgccc     180

gccacctctg ctctttcccg tctcgggcca ggatgactgg agtctttgac agtctagtgg     240

ctgatatgca ctcgacccag atcgccgcct ccagcacgta ccaccagcac cagcagcccc     300

cgagcggcgg cggcgccggc ccgggtggca acagcagcag cagcagcagc ctccacaagc     360
```

-continued

```
cccaggagtc gcccaccctt ccggtgtcca ccgccaccga cagcagctac tacaccaacc    420

agcagcaccc ggcgggcggc ggcggcggcg ggggctcgcc ctacgcgcac atgggttcct    480

accagtacca agccagcggc ctcaacaacg tcccttactc cgccaagagc agctatgacc    540

tgggctacac cgccgcctac acctcctacg ctccctatgg aaccagttcg tccccagcca    600

acaacgagcc tgagaaggag gaccttgagc ctgaaattcg gatagtgaac gggaagccaa    660

agaaagtccg gaaaccccgc accatctact ccagtttcca gctggcggct cttcagcggc    720

gtttccaaaa gactcaatac ttggccttgc cggagcgagc cgagctggcg gcctctctgg    780

gcctcaccca gactcaggtc aaaatctggt tccagaaccg ccggtccaag ttcaagaaga    840

tgtggaaaag tggtgagatc ccctcggagc agcaccctgg ggccagcgct tctccacctt    900

gtgcttcgcc gccagtctca gcgccggcct cctgggactt tggtgtgccg cagcggatgg    960

cgggcggcgg tggtccgggc agtggcggca gcggcgccgg cagctcgggc tccagcccga   1020

gcagcgcggc ctcggctttt ctgggcaact accccctggta ccaccagacc tcgggatccg   1080

cctcacacct gcaggccacg gcgccgctgc tgcaccccac tcagaccccg cagccgcatc   1140

accaccacca ccatcacggc ggcgggggcg ccccggtgag cgcggggacg attttctaac   1200

cccagggaga actcgccaga gactgagagc agagaccact tatcctcatt gcttaccccg   1260

agccggggtt ccctcctccc ggcccgctgc cgccacccac ctctcctgca ggctgcgacc   1320

tgcagtggcc cgtctcaggc cctgctcact cccggggcca ccaaacgggc ccctctctcg   1380

ggggaaccgg acagcagctt ggcaaaggcc tccctaaaag gccgcatttc tgacctgagc   1440

cccgggtctc ggctgtttcg agccccgcct cggacttgcc ttccctcccc tccgggtgag   1500

cctgtctggc gccttcctcg ccccgggctg agagctgggt cccgggagat ggaagcctcc   1560

caggcgcgcg aggcttcccg ggcgctctga ggcttctttc tcctcgcccg ctcccctggg   1620

ctcagctcgg acgctgcagt tattgacctc ccggtcccgc ctgcccgccc tcccccacgt   1680

ggccccttga cccgggcggc cccgccgctt ctttccttcc tgcagttccc agccctcgga   1740

gcccccatcc cttatcttac ccccaccgcg ctcccccagg agcgctccct cagctctctc   1800

ctcatccatc accagtggag tttttttatt tgttattttt ttaaaagttt aggtgccttt   1860

gcggatgacc tcattttgac gttgaaaaaa tgatttttta atatgtgaac actgcaaaaa   1920

tgtgtttaaa ttatcttttt taaaacctat tcaggattat tagcctggac ttggacacag   1980

agtttgtaaa taaaggtgtc tgtgcagatt ttcccactga tttatttgta taaaaatact   2040

catcttttca gactttttg taaaccccca gttgtgaaaa ctgcagttta gcagtgacct   2100

cagcaacccc tcctttttat tttttccttt aaaaacattt cagttaaatt aagctactga   2160

tttggatttg ttttatcgta tcctaaagtc tttgttgttg aaatgaaagg tattttgggg   2220

ttatttatta tgaaaacaac atgctcttaa tgttgatttt acaatatgaa gagattattt   2280

aaataaatta ttgttttcat tggaaaaa                                      2308
```

<210> SEQ ID NO 3
<211> LENGTH: 132
<212> TYPE: PRT
<213> ORGANISM: Homo sapiens

<400> SEQUENCE: 3

```
Met Val Glu Ala Phe Cys Ala Thr Trp Lys Leu Thr Asn Ser Gln Asn
1               5                   10                  15

Phe Asp Glu Tyr Met Lys Ala Leu Gly Val Gly Phe Ala Thr Arg Gln
```

```
            20                  25                  30

Val Gly Asn Val Thr Lys Pro Thr Val Ile Ile Ser Gln Glu Gly Asp
        35                  40                  45

Lys Val Val Ile Arg Thr Leu Ser Thr Phe Lys Asn Thr Glu Ile Ser
    50                  55                  60

Phe Gln Leu Gly Glu Glu Phe Asp Glu Thr Thr Ala Asp Asp Arg Asn
65                  70                  75                  80

Cys Lys Ser Val Val Ser Leu Asp Gly Asp Lys Leu Val His Ile Gln
                85                  90                  95

Lys Trp Asp Gly Lys Glu Thr Asn Phe Val Arg Glu Ile Lys Asp Gly
            100                 105                 110

Lys Met Val Met Thr Leu Thr Phe Gly Asp Val Val Ala Val Arg His
        115                 120                 125

Tyr Glu Lys Ala
    130


<210> SEQ ID NO 4
<211> LENGTH: 1047
<212> TYPE: DNA
<213> ORGANISM: Homo sapiens

<400> SEQUENCE: 4

tttctcaggc ataagggctg tagtgtgagg attgggagga actcgaccta ctccgctaac     60

ccagtggcct gagccaatca caaagaggat tggagcctca ctcgagcgct ccttcccttc    120

tcctctctct gtgacagcct cttggaaaga gggacactgg aggggtgtgt ttgcaattta    180

aatcactgga tttttgccca ccctctttcc aaataagaag gcaggagctg cttgctgagg    240

tgtaaagggt cttctgagct gcagtggcaa ttagaccaga agatccccgc tcctgtctct    300

aaagagggga aagggcaagg atggtggagg ctttctgtgc tacctggaag ctgaccaaca    360

gtcagaactt tgatgagtac atgaaggctc taggcgtggg ctttgccact aggcaggtgg    420

gaaatgtgac caaaccaacg gtaattatca gtcaagaagg agacaaagtg gtcatcagga    480

ctctcagcac attcaagaac acggagatta gtttccagct gggagaagag tttgatgaaa    540

ccactgcaga tgatagaaac tgtaagtctg ttgttagcct ggatggagac aaacttgttc    600

acatacagaa atgggatggc aaagaaacaa attttgtaag agaaattaag gatggcaaaa    660

tggttatgac ccttactttt ggtgatgtgg ttgctgttcg ccactatgag aaggcataaa    720

aatgttcctg gtcggggctt ggaagagctc ttcagttttt ctgtttcctc aagtctcagt    780

gctatcctat tacaacatgg ctgatcatta attagaaggt tatccttggt gtggaggtgg    840

aaaatggtga tttaaaaact tgttactcca agcaacttgc ccaattttaa tctgaaaatt    900

tatcatgttt tataatttga attaaagttt tgtccccccc cccctttttt ttataaacaa    960

gtgaatacat tttataattt cttttggaat gtaaatcaaa tttgaataaa aatcttacac   1020

gtgaaattta aaaaaaaaaa aaaaaaa                                        1047


<210> SEQ ID NO 5
<211> LENGTH: 166
<212> TYPE: PRT
<213> ORGANISM: Homo sapiens

<400> SEQUENCE: 5

Met Ala Pro Ser Thr Val Ala Val Glu Leu Leu Ser Pro Lys Glu Lys
1               5                   10                  15

Asn Arg Leu Arg Lys Pro Val Val Glu Lys Met Arg Arg Asp Arg Ile
```

```
            20                  25                  30

Asn Ser Ser Ile Glu Gln Leu Lys Leu Leu Leu Glu Gln Glu Phe Ala
        35                  40                  45

Arg His Gln Pro Asn Ser Lys Leu Glu Lys Ala Asp Ile Leu Glu Met
    50                  55                  60

Ala Val Ser Tyr Leu Lys His Ser Lys Ala Phe Val Ala Ala Ala Gly
65                  70                  75                  80

Pro Lys Ser Leu His Gln Asp Tyr Ser Glu Gly Tyr Ser Trp Cys Leu
                85                  90                  95

Gln Glu Ala Val Gln Phe Leu Thr Leu His Ala Ala Ser Asp Thr Gln
            100                 105                 110

Met Lys Leu Leu Tyr His Phe Gln Arg Pro Pro Ala Ala Pro Ala Ala
        115                 120                 125

Pro Ala Lys Glu Pro Lys Ala Pro Gly Ala Ala Pro Pro Pro Ala Leu
    130                 135                 140

Ser Ala Lys Ala Thr Ala Ala Ala Ala Ala Ala His Gln Pro Ala Cys
145                 150                 155                 160

Gly Leu Trp Arg Pro Trp
                165


<210> SEQ ID NO 6
<211> LENGTH: 1319
<212> TYPE: DNA
<213> ORGANISM: Homo sapiens

<400> SEQUENCE: 6

cgcgcttggc cttgcccgcg cccgctcgcc tcgtctcgcc cggcctcccc gcgtcgcctc     60

gtcgcctgtt ccgcgccagg catggccccc agcactgtgg ccgtggagct gctcagcccc    120

aaagagaaaa accgactgcg gaagccggtg gtggagaaga tgcgccgcga ccgcatcaac    180

agcagcatcg agcagctgaa gctgctgctg gagcaggagt tcgcgcggca ccagcccaac    240

tccaagctgg agaaggccga catcctggag atggctgtca gctacctgaa gcacagcaaa    300

gccttcgtcg ccgccgccgg ccccaagagc ctgcaccagg actacagcga aggctactcg    360

tggtgcctgc aggaggccgt gcagttcctg acgctccacg ccgccagcga cacgcagatg    420

aagctgctgt accacttcca gcggcccccg gccgcgcccg ccgcgcccgc caaggagccc    480

aaggcgccgg gcgccgcgcc cccgcccgcg ctctccgcca aggccaccgc cgccgccgcc    540

gccgcgcacc agcccgcctg cggcctctgg cggccctggt gacccggcgg gacctgcggg    600

cgcgcggccc gacgaccaga gggcgagcct gctcctctcg cctgtaggga agcgccttcc    660

cgccgtcgtc cgccccgggc ttggacgcgc ccttctccgg aaggctctgg ccccaagctg    720

gccggcccgc aggagcccca ttctcagaga atgtgtgtgc agagtccctg ccgttttagg    780

acaatcaggg cccatcttct gccaagtgtc tgaccccatg ggttgttct gtgtttgcat    840

ttaagcaagt gacttctggg aagtccccgg ccgcccgggg ttctatgata tttgtagtgc    900

cggggctcgc acactgctgc ccccagcctg tagaggactt tcttcagggc ccgtagctgc    960

tgggcgtacc cctggcaggc gggctgtgcc gcgggcacat ttgccttttg tgaaggccga   1020

actcgagctg tatcctcata ggaaacagtg atcaccccgg acgggcgtcc aggaccctga   1080

gggccatggc caaaaggctc ctgagtgtgc ctggtggtct ggctggggct cacggtgggc   1140

tgtctgggga gggtgggtgc ctccactatg atccttaaag gattcctctg tgtgggtgga   1200

tgcgtgtggg cacgactttg tactcagaaa ttgaactctc agtcacgtgg aagccacggg   1260
```

actgctccga agccgccata ataaaatctg attgttcagc ccccaaaaaa aaaaaaaaa 1319

<210> SEQ ID NO 7
<211> LENGTH: 308
<212> TYPE: PRT
<213> ORGANISM: Homo sapiens

<400> SEQUENCE: 7

Met Lys Arg Ala His Pro Glu Tyr Ser Ser Ser Asp Ser Glu Leu Asp
1 5 10 15

Glu Thr Ile Glu Val Glu Lys Glu Ser Ala Asp Glu Asn Gly Asn Leu
20 25 30

Ser Ser Ala Leu Gly Ser Met Ser Pro Thr Thr Ser Ser Gln Ile Leu
35 40 45

Ala Arg Lys Arg Arg Arg Gly Ile Ile Glu Lys Arg Arg Arg Asp Arg
50 55 60

Ile Asn Asn Ser Leu Ser Glu Leu Arg Arg Leu Val Pro Ser Ala Phe
65 70 75 80

Glu Lys Gln Val Met Glu Gln Gly Ser Ala Lys Leu Glu Lys Ala Glu
85 90 95

Ile Leu Gln Met Thr Val Asp His Leu Lys Met Leu His Thr Ala Gly
100 105 110

Gly Lys Gly Tyr Phe Asp Ala His Ala Leu Ala Met Asp Tyr Arg Ser
115 120 125

Leu Gly Phe Arg Glu Cys Leu Ala Glu Val Ala Arg Tyr Leu Ser Ile
130 135 140

Ile Glu Gly Leu Asp Ala Ser Asp Pro Leu Arg Val Arg Leu Val Ser
145 150 155 160

His Leu Asn Asn Tyr Ala Ser Gln Arg Glu Ala Ala Ser Gly Ala His
165 170 175

Ala Gly Leu Gly His Ile Pro Trp Gly Thr Val Phe Gly His His Pro
180 185 190

His Ile Ala His Pro Leu Leu Leu Pro Gln Asn Gly His Gly Asn Ala
195 200 205

Gly Thr Thr Ala Ser Pro Thr Glu Pro His His Gln Gly Arg Leu Gly
210 215 220

Ser Ala His Pro Glu Ala Pro Ala Leu Arg Ala Pro Pro Ser Gly Ser
225 230 235 240

Leu Gly Pro Val Leu Pro Val Val Thr Ser Ala Ser Lys Leu Ser Pro
245 250 255

Pro Leu Leu Ser Ser Val Ala Ser Leu Ser Ala Phe Pro Phe Ser Phe
260 265 270

Gly Ser Phe His Leu Leu Ser Pro Asn Ala Leu Ser Pro Ser Ala Pro
275 280 285

Thr Gln Ala Ala Asn Leu Gly Lys Pro Tyr Arg Pro Trp Gly Thr Glu
290 295 300

Ile Gly Ala Phe
305

<210> SEQ ID NO 8
<211> LENGTH: 2331
<212> TYPE: DNA
<213> ORGANISM: Homo sapiens

<400> SEQUENCE: 8
ttccccactc ccccgccctc cccagggccc tgggaagggg ctcagcgtgg gaaaggatgg 60

```
ttgagtttta accagaggca aagcgtgagc gggatcagtg tgtgcggaac gcaagcagcc    120
gagagcggag aggcgccgct gtagttaact cctccctgcc cgccgcgccg accctcccca    180
ggaaccccca gggagccagc atgaagcgag ctcaccccga gtacagctcc tcggacagcg    240
agctggacga gaccatcgag gtggagaagg agagtgcgga cgagaatgga aacttgagtt    300
cggctctagg ttccatgtcc ccaactacat cttcccagat tttggccaga aaaagacgga    360
gaggaataat tgagaagcgc cgacgagacc ggatcaataa cagtttgtct gagctgagaa    420
ggctggtacc cagtgctttt gagaagcagg taatggagca aggatctgct aagctagaaa    480
aagccgagat cctgcagatg accgtggatc acctgaaaat gctgcatacg gcaggaggga    540
aaggttactt tgacgcgcac gcccttgcta tggactatcg gagtttggga tttcgggaat    600
gcctggcaga agttgcgcgt tatctgagca tcattgaagg actagatgcc tctgacccgc    660
ttcgagttcg actggtttcg catctcaaca actacgcttc ccagcgggaa gccgcgagcg    720
gcgcccacgc gggcctcgga cacattccct gggggaccgt cttcggacat cacccgcaca    780
tcgcgcaccc gctgttgctg ccccagaacg gccacgggaa cgcgggcacc acggcctcac    840
ccacggaacc gcaccaccag ggcaggctgg gctcggcaca tccggaggcg cctgctttgc    900
gagcgccccc tagcggcagc ctcggaccgg tgctccctgt ggtcacctcc gcctccaaac    960
tgtcgccgcc tctgctctcc tcagtggcct ccctgtcggc cttccccttc tctttcggct   1020
ccttccactt actgtctccc aatgcactga gcccttcagc acccacgcag gctgcaaacc   1080
ttggcaagcc ctatagacct tgggggacgg agatcggagc tttttaaaga actgatgtag   1140
aatgagggag gggaaagttt aaaatcccag ctgggctgga ctgttgccaa catcacctta   1200
aagtcgtcag taaaagtaaa aaggaaaaag gtacactttc agataatttt tttttaaag   1260
actaaaggtt tgttggttta cttttatctt ttttaatgtt tttttcatca tgtcatgtat   1320
tagcagtttt taaaaactag ttgttaaatt ttgttcaaga cattaaattg aaatagtgag   1380
tataagccaa cactttgtga taggtttgta ctgtgcctaa tttactttgt aaaccagaat   1440
gattccgttt ttgcctcaaa atttggggaa tcttaacatt tagtattttt ggtctgtttt   1500
tctccttgta tagttatggt ctgtttttag aattaatttt ccaaaccact atgcttaatg   1560
ttaacatgat tctgtttgtt aatattttga cagattaagg tgttgtataa ataatattct   1620
tttgggggga ggggaactat attgaatttt atatttctga gcaaagcgtt gacaaatcag   1680
atgatcagct ttatccaaga aagaagacta gtaaattgtc tgcctcctat agcagaaagg   1740
tgaatgtaca aactgttggt ggccctgaat ccatctgacc agctgctggt atctgccagg   1800
actggcagtt ctgatttagt taggagagag ccgctgatag gttaggtctc atttggagtg   1860
ttggtggaaa ggaaactgaa ggtaattgaa tagaatacgc ctgcatttac cagccccagc   1920
aacacaaaga atttttaatc acacggatct caaattcaca aatgttaaca tggataagtg   1980
atcatggtgt gcgagtggtc aattgagtag tacagtggaa actgttaaat gcataaccta   2040
attttcctgg gactgccata ttttctttta actggaaatt tttatgtgag ttttcctttt   2100
ggtgcatgga actgtggttg ccaaggtatt taaaagggct ttcctgcctc cttctctttg   2160
atttatttaa tttgatttgg gctataaaat atcatttttc aggtttattc ttttagcagg   2220
tgtagttaaa cgacctccac tgaactgggt ttgacctctg ttgtactgat gtgttgtgac   2280
taaataaaaa agaaagaaca aagtaaaaaa aaaaaaaaaa aaaaaaaaaa a            2331
```

<210> SEQ ID NO 9

<211> LENGTH: 1453
<212> TYPE: PRT
<213> ORGANISM: Homo sapiens

<400> SEQUENCE: 9

```
Met Lys Ser Cys Gly Val Ser Leu Ala Thr Ala Ala Ala Ala Ala Ala
1               5                   10                  15

Ala Phe Gly Asp Glu Glu Lys Lys Met Ala Ala Gly Lys Ala Ser Gly
            20                  25                  30

Glu Ser Glu Glu Ala Ser Pro Ser Leu Thr Ala Glu Glu Arg Glu Ala
        35                  40                  45

Leu Gly Gly Leu Asp Ser Arg Leu Phe Gly Phe Val Arg Phe His Glu
    50                  55                  60

Asp Gly Ala Arg Thr Lys Ala Leu Leu Gly Lys Ala Val Arg Cys Tyr
65                  70                  75                  80

Glu Ser Leu Ile Leu Lys Ala Glu Gly Lys Val Glu Ser Asp Phe Phe
                85                  90                  95

Cys Gln Leu Gly His Phe Asn Leu Leu Leu Glu Asp Tyr Pro Lys Ala
            100                 105                 110

Leu Ser Ala Tyr Gln Arg Tyr Tyr Ser Leu Gln Ser Asp Tyr Trp Lys
        115                 120                 125

Asn Ala Ala Phe Leu Tyr Gly Leu Gly Leu Val Tyr Phe His Tyr Asn
    130                 135                 140

Ala Phe Gln Trp Ala Ile Lys Ala Phe Gln Glu Val Leu Tyr Val Asp
145                 150                 155                 160

Pro Ser Phe Cys Arg Ala Lys Glu Ile His Leu Arg Leu Gly Leu Met
                165                 170                 175

Phe Lys Val Asn Thr Asp Tyr Glu Ser Ser Leu Lys His Phe Gln Leu
            180                 185                 190

Ala Leu Val Asp Cys Asn Pro Cys Thr Leu Ser Asn Ala Glu Ile Gln
        195                 200                 205

Phe His Ile Ala His Leu Tyr Glu Thr Gln Arg Lys Tyr His Ser Ala
    210                 215                 220

Lys Glu Ala Tyr Glu Gln Leu Leu Gln Thr Glu Asn Leu Ser Ala Gln
225                 230                 235                 240

Val Lys Ala Thr Val Leu Gln Gln Leu Gly Trp Met His His Thr Val
                245                 250                 255

Asp Leu Leu Gly Asp Lys Ala Thr Lys Glu Ser Tyr Ala Ile Gln Tyr
            260                 265                 270

Leu Gln Lys Ser Leu Glu Ala Asp Pro Asn Ser Gly Gln Ser Trp Tyr
        275                 280                 285

Phe Leu Gly Arg Cys Tyr Ser Ser Ile Gly Lys Val Gln Asp Ala Phe
    290                 295                 300

Ile Ser Tyr Arg Gln Ser Ile Asp Lys Ser Glu Ala Ser Ala Asp Thr
305                 310                 315                 320

Trp Cys Ser Ile Gly Val Leu Tyr Gln Gln Gln Asn Gln Pro Met Asp
                325                 330                 335

Ala Leu Gln Ala Tyr Ile Cys Ala Val Gln Leu Asp His Gly His Ala
            340                 345                 350

Ala Ala Trp Met Asp Leu Gly Thr Leu Tyr Glu Ser Cys Asn Gln Pro
        355                 360                 365

Gln Asp Ala Ile Lys Cys Tyr Leu Asn Ala Thr Arg Ser Lys Ser Cys
    370                 375                 380

Ser Asn Thr Ser Ala Leu Ala Ala Arg Ile Lys Tyr Leu Gln Ala Gln
```

-continued

```
385                 390                 395                 400

Leu Cys Asn Leu Pro Gln Gly Ser Leu Gln Asn Lys Thr Lys Leu Leu
                405                 410                 415

Pro Ser Ile Glu Glu Ala Trp Ser Leu Pro Ile Pro Ala Glu Leu Thr
            420                 425                 430

Ser Arg Gln Gly Ala Met Asn Thr Ala Gln Gln Ala Cys Lys Pro His
        435                 440                 445

His Pro Asn Thr Glu Pro Val Leu Gly Leu Ser Gln Thr Pro Ile Ser
    450                 455                 460

Gln Gln Ser Leu Pro Leu His Met Ile Pro Ser Ser Gln Val Asp Asp
465                 470                 475                 480

Leu Ser Ser Pro Ala Lys Arg Lys Arg Thr Ser Ser Pro Thr Lys Asn
                485                 490                 495

Thr Ser Asp Asn Trp Ser Gly Gly His Ala Val Ser His Pro Pro Val
            500                 505                 510

Gln Gln Gln Ala His Ser Trp Cys Leu Thr Pro Gln Lys Leu Gln His
        515                 520                 525

Leu Glu Gln Leu Arg Ala Asn Arg Asn Asn Leu Asn Pro Ala Gln Lys
    530                 535                 540

Leu Met Leu Glu Gln Leu Glu Ser Gln Phe Val Leu Met Gln Gln His
545                 550                 555                 560

Gln Met Arg Pro Thr Gly Val Ala Gln Val Arg Ser Thr Gly Ile Pro
                565                 570                 575

Asn Gly Pro Thr Ala Asp Ser Ser Leu Pro Thr Asn Ser Val Ser Gly
            580                 585                 590

Gln Gln Pro Gln Leu Ala Leu Thr Arg Val Pro Ser Val Ser Gln Pro
        595                 600                 605

Gly Val Arg Pro Ala Cys Pro Gly Gln Pro Leu Ala Asn Gly Pro Phe
    610                 615                 620

Ser Ala Gly His Val Pro Cys Ser Thr Ser Arg Thr Leu Gly Ser Thr
625                 630                 635                 640

Asp Thr Ile Leu Ile Gly Asn Asn His Ile Thr Gly Ser Gly Ser Asn
                645                 650                 655

Gly Asn Val Pro Tyr Leu Gln Arg Asn Ala Leu Thr Leu Pro His Asn
            660                 665                 670

Arg Thr Asn Leu Thr Ser Ser Ala Glu Glu Pro Trp Lys Asn Gln Leu
        675                 680                 685

Ser Asn Ser Thr Gln Gly Leu His Lys Gly Gln Ser Ser His Ser Ala
    690                 695                 700

Gly Pro Asn Gly Glu Arg Pro Leu Ser Ser Thr Gly Pro Ser Gln His
705                 710                 715                 720

Leu Gln Ala Ala Gly Ser Gly Ile Gln Asn Gln Asn Gly His Pro Thr
                725                 730                 735

Leu Pro Ser Asn Ser Val Thr Gln Gly Ala Ala Leu Asn His Leu Ser
            740                 745                 750

Ser His Thr Ala Thr Ser Gly Gly Gln Gln Gly Ile Thr Leu Thr Lys
        755                 760                 765

Glu Ser Lys Pro Ser Gly Asn Ile Leu Thr Val Pro Glu Thr Ser Arg
    770                 775                 780

His Thr Gly Glu Thr Pro Asn Ser Thr Ala Ser Val Glu Gly Leu Pro
785                 790                 795                 800

Asn His Val His Gln Met Thr Ala Asp Ala Val Cys Ser Pro Ser His
                805                 810                 815
```

-continued

```
Gly Asp Ser Lys Ser Pro Gly Leu Leu Ser Ser Asp Asn Pro Gln Leu
            820                 825                 830

Ser Ala Leu Leu Met Gly Lys Ala Asn Asn Asn Val Gly Thr Gly Thr
        835                 840                 845

Cys Asp Lys Val Asn Asn Ile His Pro Ala Val His Thr Lys Thr Asp
    850                 855                 860

Asn Ser Val Ala Ser Ser Pro Ser Ser Ala Ile Ser Thr Ala Thr Pro
865                 870                 875                 880

Ser Pro Lys Ser Thr Glu Gln Thr Thr Thr Asn Ser Val Thr Ser Leu
                885                 890                 895

Asn Ser Pro His Ser Gly Leu His Thr Ile Asn Gly Glu Gly Met Glu
            900                 905                 910

Glu Ser Gln Ser Pro Met Lys Thr Asp Leu Leu Leu Val Asn His Lys
        915                 920                 925

Pro Ser Pro Gln Ile Ile Pro Ser Met Ser Val Ser Ile Tyr Pro Ser
    930                 935                 940

Ser Ala Glu Val Leu Lys Ala Cys Arg Asn Leu Gly Lys Asn Gly Leu
945                 950                 955                 960

Ser Asn Ser Ser Ile Leu Leu Asp Lys Cys Pro Pro Pro Arg Pro Pro
                965                 970                 975

Ser Ser Pro Tyr Pro Pro Leu Pro Lys Asp Lys Leu Asn Pro Pro Thr
            980                 985                 990

Pro Ser Ile Tyr Leu Glu Asn Lys  Arg Asp Ala Phe Phe  Pro Pro Leu
        995                 1000                1005

His Gln  Phe Cys Thr Asn Pro  Asn Asn Pro Val Thr  Val Ile Arg
    1010                1015                1020

Gly Leu  Ala Gly Ala Leu Lys  Leu Asp Leu Gly Leu  Phe Ser Thr
    1025                1030                1035

Lys Thr  Leu Val Glu Ala Asn  Asn Glu His Met Val  Glu Val Arg
    1040                1045                1050

Thr Gln  Leu Leu Gln Pro Ala  Asp Glu Asn Trp Asp  Pro Thr Gly
    1055                1060                1065

Thr Lys  Lys Ile Trp His Cys  Glu Ser Asn Arg Ser  His Thr Thr
    1070                1075                1080

Ile Ala  Lys Tyr Ala Gln Tyr  Gln Ala Ser Ser Phe  Gln Glu Ser
    1085                1090                1095

Leu Arg  Glu Glu Asn Glu Lys  Arg Ser His His Lys  Asp His Ser
    1100                1105                1110

Asp Ser  Glu Ser Thr Ser Ser  Asp Asn Ser Gly Arg  Arg Arg Lys
    1115                1120                1125

Gly Pro  Phe Lys Thr Ile Lys  Phe Gly Thr Asn Ile  Asp Leu Ser
    1130                1135                1140

Asp Asp  Lys Lys Trp Lys Leu  Gln Leu His Glu Leu  Thr Lys Leu
    1145                1150                1155

Pro Ala  Phe Val Arg Val Val  Ser Ala Gly Asn Leu  Leu Ser His
    1160                1165                1170

Val Gly  His Thr Ile Leu Gly  Met Asn Thr Val Gln  Leu Tyr Met
    1175                1180                1185

Lys Val  Pro Gly Ser Arg Thr  Pro Gly His Gln Glu  Asn Asn Asn
    1190                1195                1200

Phe Cys  Ser Val Asn Ile Asn  Ile Gly Pro Gly Asp  Cys Glu Trp
    1205                1210                1215
```

```
Phe Val  Val Pro Glu Gly Tyr  Trp Gly Val Leu Asn  Asp Phe Cys
    1220                 1225                 1230

Glu Lys  Asn Asn Leu Asn Phe  Leu Met Gly Ser Trp  Trp Pro Asn
    1235                 1240                 1245

Leu Glu  Asp Leu Tyr Glu Ala  Asn Val Pro Val Tyr  Arg Phe Ile
    1250                 1255                 1260

Gln Arg  Pro Gly Asp Leu Val  Trp Ile Asn Ala Gly  Thr Val His
    1265                 1270                 1275

Trp Val  Gln Ala Ile Gly Trp  Cys Asn Asn Ile Ala  Trp Asn Val
    1280                 1285                 1290

Gly Pro  Leu Thr Ala Cys Gln  Tyr Lys Leu Ala Val  Glu Arg Tyr
    1295                 1300                 1305

Glu Trp  Asn Lys Leu Gln Ser  Val Lys Ser Ile Val  Pro Met Val
    1310                 1315                 1320

His Leu  Ser Trp Asn Met Ala  Arg Asn Ile Lys Val  Ser Asp Pro
    1325                 1330                 1335

Lys Leu  Phe Glu Met Ile Lys  Tyr Cys Leu Leu Arg  Thr Leu Lys
    1340                 1345                 1350

Gln Cys  Gln Thr Leu Arg Glu  Ala Leu Ile Ala Ala  Gly Lys Glu
    1355                 1360                 1365

Ile Ile  Trp His Gly Arg Thr  Lys Glu Glu Pro Ala  His Tyr Cys
    1370                 1375                 1380

Ser Ile  Cys Glu Val Glu Val  Phe Asp Leu Leu Phe  Val Thr Asn
    1385                 1390                 1395

Glu Ser  Asn Ser Arg Lys Thr  Tyr Ile Val His Cys  Gln Asp Cys
    1400                 1405                 1410

Ala Arg  Lys Thr Ser Gly Asn  Leu Glu Asn Phe Val  Val Leu Glu
    1415                 1420                 1425

Gln Tyr  Lys Met Glu Asp Leu  Met Gln Val Tyr Asp  Gln Phe Thr
    1430                 1435                 1440

Leu Ala  Pro Pro Leu Pro Ser  Ala Ser Ser
    1445                 1450
```

<210> SEQ ID NO 10
<211> LENGTH: 5941
<212> TYPE: DNA
<213> ORGANISM: Homo sapiens

<400> SEQUENCE: 10

```
gtgtgacaca attacaacaa ctttgtgctg gtgccgggga agtttgtgtc tccaacgaat     60

cccctcagtg ctccccagcc ccgcgcgctc cggccgttcc cgccgtcccc gcctgtggct    120

gccccctgcc caaccccgcg atgtgaccct acagccgaaa gccgccgctg ccgacccggg    180

ggctccgcag cccctgccgc cgccgccgcc gccttcaccg ccgccgcgtt gggatttttc    240

gtcgccgccg cccgcggcgg aggaggaggc ggcgataaag ttggtgtgct ggtcccgcgc    300

gcagattggg ggcgtcactg cgggccccgg tccgaggggg ggtgtcggcg ttggagttgt    360

gaattcgctg cgtttccatg aaatcctgcg gagtgtcgct cgctaccgcc gccgctgccg    420

ccgccgcttt cggtgatgag gaaaagaaaa tggcggcggg aaaagcgagc ggcgagagcg    480

aggaggcgtc ccccagcctg acagccgagg agagggaggc gctcggcgga ctggacagcc    540

gcctctttgg gttcgtgaga tttcatgaag atggcgccag gacgaaggcc ctactgggca    600

aggctgttcg ctgctatgaa tctctaatct taaaagctga aggaaaagtg gagtctgatt    660

tcttttgtca attaggtcac ttcaacctct tattggaaga ttatccaaaa gcattatctg    720
```

```
cataccagag gtactacagt ttacagtctg actactggaa gaatgctgcc tttttatatg    780
gtcttggttt ggtctacttc cattataatg catttcagtg ggcaattaaa gcatttcagg    840
aggtgcttta tgttgatccc agcttttgtc gagccaagga aattcattta cgacttgggc    900
ttatgttcaa agtgaacaca gactatgagt ctagtttaaa gcattttcag ttagctttgg    960
ttgactgtaa tccctgcact ttgtccaatg ctgaaattca atttcacatt gcccacttat   1020
atgaaaccca gaggaaatat cattctgcaa aagaagctta tgaacaactt ttgcagacag   1080
agaatctttc tgcacaagta aaagcaactg tcttacaaca gttaggttgg atgcatcaca   1140
ctgtagatct cctgggagat aaagccacca aggaaagcta tgctattcag tatctccaaa   1200
agtccttgga agcagatcct aattctggcc agtcctggta tttcctcgga aggtgctatt   1260
caagtattgg gaaagttcag gatgccttta tatcttacag gcagtctatt gataaatcag   1320
aagcaagtgc agatacatgg tgttcaatag gtgtgctata tcagcagcaa aatcagccca   1380
tggatgcttt acaggcctat atttgtgctg tacaattgga ccatggccat gctgcagcct   1440
ggatggacct aggcactctc tatgaatcct gcaaccagcc tcaggatgcc attaaatgct   1500
acttaaatgc aactagaagc aaaagttgta gtaatacctc tgcacttgca gcacgaatta   1560
agtatttaca ggctcagttg tgtaaccttc cacaaggtag tctacagaat aaaactaaat   1620
tacttcctag tattgaggag gcgtggagcc taccaattcc cgcagagctt acctccaggc   1680
agggtgccat gaacacagca cagcaggcat gtaaacctca tcatccaaat actgaacctg   1740
tattaggcct cagtcaaaca ccaatttcac agcaatcctt gccactacac atgattcctt   1800
ctagccaagt agatgacctg tccagtcctg ccaagaggaa aagaacatct agtccaacaa   1860
agaatacttc tgacaattgg agtggtggac atgctgtgtc acatcctcca gtacagcaac   1920
aagctcattc atggtgtttg acaccacaga aattacagca tttggaacag ctccgcgcaa   1980
atagaaataa tttaaatcca gcacagaaac tgatgctgga acagctggaa agtcagtttg   2040
tcttaatgca acaacaccaa atgagaccaa caggagttgc acaggtacga tctactggaa   2100
ttcctaatgg gccaacagct gactcatcac tgcctacaaa ctcagtctct ggccagcagc   2160
cacagcttgc tctgaccaga gtgcctagcg tctctcagcc tggagtccgt cctgcctgcc   2220
ctgggcagcc tttggccaat ggaccctttt ctgcaggcca tgttccctgt agcacatcaa   2280
gaacgctggg aagtacagac actattttga taggcaataa tcatataaca ggaagtggaa   2340
gtaatggaaa cgtgccttac ctgcagcgaa acgcactcac tctacctcat aaccgcacaa   2400
acctgaccag cagcgcagag gagccgtgga aaaaccaact atctaactcc actcaggggc   2460
ttcacaaagg tcagagttca cattcggcag gtcctaatgg tgaacgacct ctctcttcca   2520
ctgggccttc ccagcatctc caggcagctg gctctggtat tcagaatcag aacggacatc   2580
ccaccctgcc tagcaattca gtaacacagg gggctgctct caatcacctc tcctctcaca   2640
ctgctacctc aggtggacaa caaggcatta ccttaaccaa agagagcaag ccttcaggaa   2700
acatattgac ggtgcctgaa acaagcaggc acactggaga gacacctaac agcactgcca   2760
gtgtcgaggg acttcctaat catgtccatc agatgacggc agatgctgtt tgcagtccta   2820
gccatggaga ttctaagtca ccaggtttac taagttcaga caatcctcag ctctctgcct   2880
tgttgatggg aaaagccaat aacaatgtgg gtactggaac ctgtgacaaa gtcaataaca   2940
tccacccagc tgttcataca aagactgata actctgttgc ctcttcacca tcttcagcca   3000
tttcaacagc aacaccttct ccaaaatcca ctgagcagac aaccacaaac agtgttacca   3060
```

-continued

```
gccttaacag ccctcacagt gggctacaca caattaatgg agaagggatg gaagaatctc   3120
agagccccat gaaaacagat ctgcttctgg ttaaccacaa acctagtcca cagatcatac   3180
catcaatgtc tgtgtccata taccccagct cagcagaagt tctgaaggca tgcaggaatc   3240
taggtaaaaa tggcttatct aacagtagca ttttgttgga taaatgtcca cctccaagac   3300
caccatcttc accatacccct cccttgccaa aggacaagtt gaatccacct acacctagta   3360
tttacttgga aaataaacgt gatgctttct ttcctccatt acatcaattt tgtacaaatc   3420
cgaacaaccc tgttacagta atacgtggcc ttgctggagc tcttaagtta gacctgggac   3480
ttttctctac taaaactttg gtggaagcta acaatgaaca tatggtagaa gtgaggacac   3540
agttgttgca gccagcagat gaaaactggg atcccactgg aacaaagaaa atctggcatt   3600
gtgaaagtaa tagatctcat actacaattg ctaaatatgc acagtaccag gcctcctcat   3660
tccaggaatc attgagagaa gaaaatgaaa aaagaagtca tcataaagac cactcagata   3720
gtgaatctac atcgtcagat aattctggga ggaggaggaa aggacccttt aaaaccataa   3780
agtttgggac caatattgac ctatctgatg acaaaaagtg gaagttgcag ctacatgagc   3840
tgactaaact tcctgctttt gtgcgtgtcg tatcagcagg aaatcttcta agccatgttg   3900
gtcataccat attgggcatg aacacagttc aactatacat gaaagttcca gggagcagaa   3960
caccaggtca tcaggaaaat aacaacttct gttcagttaa cataaatatt ggcccaggtg   4020
actgtgaatg gtttgttgtt cctgaaggtt actggggtgt tctgaatgac ttctgtgaaa   4080
aaaataattt gaatttccta atgggttctt ggtggcccaa tcttgaagat ctttatgaag   4140
caaatgttcc agtgtatagg tttattcagc gacctggaga tttggtctgg ataaatgcag   4200
gcactgttca ttgggttcag gctattggct ggtgcaacaa cattgcttgg aatgttggtc   4260
cacttacagc ctgccagtat aaattggcag tggaacggta cgaatggaac aaattgcaaa   4320
gtgtgaagtc aatagtaccc atggttcatc tttcctggaa tatggcacga aatatcaagg   4380
tctcagatcc aaagcttttt gaaatgatta agtattgtct tctaagaact ctgaagcaat   4440
gtcagacatt gagggaagct ctcattgctg caggaaaaga gattatatgg catgggcgga   4500
caaaagaaga accagctcat tactgtagca tttgtgaagt ggaggttttt gatctgcttt   4560
ttgtcactaa tgagagtaat tcacgaaaga cctacatagt acattgccaa gattgtgcac   4620
gaaaaacaag cggaaacttg gaaaactttg tggtgctaga acagtacaaa atggaggacc   4680
tgatgcaagt ctatgaccaa tttacattag ctcctccatt accatccgcc tcatcttgat   4740
attgttccat ggacattaaa tgagaccttt tctgctattc aggaaataac ccagttctgc   4800
accactggtt tttgtagcta tctcgtaagg ctgctggctg aaaactgtgt ctatgcaacc   4860
ttccaagtgc ggagtgtcaa ccaactggac gggagagagt actgctccta ctccaggact   4920
ctcacaaagc tgatgagctg tacttcagaa aaaaataata atttccatgt tttgtatata   4980
tctgacaaaa ctggcaacat cttacagact actgacttga agacaacctc ttttatattt   5040
ctctatttct gggctgatga atttgttttc atctgtcttt tccccccttca gaattttcct   5100
tggaaaaaaa atactagcct agctggtcat ttctttgtaa ggtagttagc aattttaagt   5160
ctttctttgg tcaacttttt tttaatgtga aaagttaggt aagacacttt tttactgctt   5220
ttatgttttt ctgtcttgtt ttgagaccat gatggttaca cttttggttc ctaaataaaa   5280
tttaaaaaat taacagccaa gtcacaaagg taatggattg cacatagact aaggaataaa   5340
cttcagattt gtgatttttg tttctaatct tgatgtaaat ttacactatt tataaataca   5400
tatttattgc ttgaaaatat ttgtgaatgg aatgctgtta ttttttccag atttacctgc   5460
```

```
cattgaaatt ttaaggagtt ctgtaatttc aaacactact cctattacat tttctatgtg   5520

taaataaaac tgcttagcat tgtacagaaa cttttattaa aattgtttaa tgtttaaaga   5580

gttttctatt gtttgagttt taaaaaagac tttatgtaca gtgcccagtt tttgttcatt   5640

tttgaaatct gattatatat attttatata tacttatgta tgtatatata atatatatag   5700

aaatctggat atatatgtat aaatctttag aacttaaatt tttctcgttt taagtttcac   5760

atctatggta gatttttgag gtgtctactg taaagtattg cttacaaaaa gtatgattat   5820

ttttaaagaa atatatatgg tatgtatcct caagacctaa aatgtcagac tggtttattg   5880

ttaagttgca attactgcaa tgacagacca ataaacaatt gctgccaaaa tgtagtataa   5940

a                                                                   5941


<210> SEQ ID NO 11
<211> LENGTH: 1682
<212> TYPE: PRT
<213> ORGANISM: Homo sapiens

<400> SEQUENCE: 11

Met His Arg Ala Val Asp Pro Pro Gly Ala Arg Ala Ala Arg Glu Ala
1               5                   10                  15

Phe Ala Leu Gly Gly Leu Ser Cys Ala Gly Ala Trp Ser Ser Cys Pro
            20                  25                  30

Pro His Pro Pro Pro Arg Ser Ala Trp Leu Pro Gly Gly Arg Cys Ser
        35                  40                  45

Ala Ser Ile Gly Gln Pro Pro Leu Pro Ala Pro Leu Pro Pro Ser His
    50                  55                  60

Gly Ser Ser Ser Gly His Pro Ser Lys Pro Tyr Tyr Ala Pro Gly Ala
65                  70                  75                  80

Pro Thr Pro Arg Pro Leu His Gly Lys Leu Glu Ser Leu His Gly Cys
                85                  90                  95

Val Gln Ala Leu Leu Arg Glu Pro Ala Gln Pro Gly Leu Trp Glu Gln
            100                 105                 110

Leu Gly Gln Leu Tyr Glu Ser Glu His Asp Ser Glu Glu Ala Thr Arg
        115                 120                 125

Cys Tyr His Ser Ala Leu Arg Tyr Gly Gly Ser Phe Ala Glu Leu Gly
    130                 135                 140

Pro Arg Ile Gly Arg Leu Gln Gln Ala Gln Leu Trp Asn Phe His Thr
145                 150                 155                 160

Gly Ser Cys Gln His Arg Ala Lys Val Leu Pro Pro Leu Glu Gln Val
                165                 170                 175

Trp Asn Leu Leu His Leu Glu His Lys Arg Asn Tyr Gly Ala Lys Arg
            180                 185                 190

Gly Gly Pro Pro Val Lys Arg Ala Ala Glu Pro Pro Val Val Gln Pro
        195                 200                 205

Val Pro Pro Ala Ala Leu Ser Gly Pro Ser Gly Glu Glu Gly Leu Ser
    210                 215                 220

Pro Gly Gly Lys Arg Arg Arg Gly Cys Asn Ser Glu Gln Thr Gly Leu
225                 230                 235                 240

Pro Pro Gly Leu Pro Leu Pro Pro Pro Pro Leu Pro Pro Pro Pro Pro
                245                 250                 255

Pro Pro Pro Pro Pro Pro Pro Pro Leu Pro Gly Leu Ala Thr Ser Pro
            260                 265                 270

Pro Phe Gln Leu Thr Lys Pro Gly Leu Trp Ser Thr Leu His Gly Asp
```

```
        275                 280                 285

Ala Trp Gly Pro Glu Arg Lys Gly Ser Ala Pro Pro Glu Arg Gln Glu
    290                 295                 300

Gln Arg His Ser Leu Pro His Pro Tyr Pro Tyr Pro Ala Pro Ala Tyr
305                 310                 315                 320

Thr Ala His Pro Pro Gly His Arg Leu Val Pro Ala Ala Pro Pro Gly
                325                 330                 335

Pro Gly Pro Arg Pro Pro Gly Ala Glu Ser His Gly Cys Leu Pro Ala
            340                 345                 350

Thr Arg Pro Pro Gly Ser Asp Leu Arg Glu Ser Arg Val Gln Arg Ser
        355                 360                 365

Arg Met Asp Ser Ser Val Ser Pro Ala Ala Thr Thr Ala Cys Val Pro
    370                 375                 380

Tyr Ala Pro Ser Arg Pro Pro Gly Leu Pro Gly Thr Thr Thr Ser Ser
385                 390                 395                 400

Ser Ser Ser Ser Ser Ser Asn Thr Gly Leu Arg Gly Val Glu Pro Asn
                405                 410                 415

Pro Gly Ile Pro Gly Ala Asp His Tyr Gln Thr Pro Ala Leu Glu Val
            420                 425                 430

Ser His His Gly Arg Leu Gly Pro Ser Ala His Ser Ser Arg Lys Pro
        435                 440                 445

Phe Leu Gly Ala Pro Ala Ala Thr Pro His Leu Ser Leu Pro Pro Gly
    450                 455                 460

Pro Ser Ser Pro Pro Pro Pro Pro Cys Pro Arg Leu Leu Arg Pro Pro
465                 470                 475                 480

Pro Pro Pro Ala Trp Leu Lys Gly Pro Ala Cys Arg Ala Ala Arg Glu
                485                 490                 495

Asp Gly Glu Ile Leu Glu Glu Leu Phe Phe Gly Thr Glu Gly Pro Pro
            500                 505                 510

Arg Pro Ala Pro Pro Pro Leu Pro His Arg Glu Gly Phe Leu Gly Pro
        515                 520                 525

Pro Ala Ser Arg Phe Ser Val Gly Thr Gln Asp Ser His Thr Pro Pro
    530                 535                 540

Thr Pro Pro Thr Pro Thr Thr Ser Ser Ser Asn Ser Asn Ser Gly Ser
545                 550                 555                 560

His Ser Ser Ser Pro Ala Gly Pro Val Ser Phe Pro Pro Pro Pro Tyr
                565                 570                 575

Leu Ala Arg Ser Ile Asp Pro Leu Pro Arg Pro Pro Ser Pro Ala Gln
            580                 585                 590

Asn Pro Gln Asp Pro Pro Leu Val Pro Leu Thr Leu Ala Leu Pro Pro
        595                 600                 605

Ala Pro Pro Ser Ser Cys His Gln Asn Thr Ser Gly Ser Phe Arg Arg
    610                 615                 620

Pro Glu Ser Pro Arg Pro Arg Val Ser Phe Pro Lys Thr Pro Glu Val
625                 630                 635                 640

Gly Pro Gly Pro Pro Pro Gly Pro Leu Ser Lys Ala Pro Gln Pro Val
                645                 650                 655

Pro Pro Gly Val Gly Glu Leu Pro Ala Arg Gly Pro Arg Leu Phe Asp
            660                 665                 670

Phe Pro Pro Thr Pro Leu Glu Asp Gln Phe Glu Glu Pro Ala Glu Phe
        675                 680                 685

Lys Ile Leu Pro Asp Gly Leu Ala Asn Ile Met Lys Met Leu Asp Glu
    690                 695                 700
```

-continued

```
Ser Ile Arg Lys Glu Glu Glu Gln Gln Gln His Glu Ala Gly Val Ala
705                 710                 715                 720

Pro Gln Pro Pro Leu Lys Glu Pro Phe Ala Ser Leu Gln Ser Pro Phe
                725                 730                 735

Pro Thr Asp Thr Ala Pro Thr Thr Thr Ala Pro Ala Val Ala Val Thr
            740                 745                 750

Thr Thr Thr Thr Thr Thr Thr Thr Thr Thr Ala Thr Gln Glu Glu Glu
        755                 760                 765

Lys Lys Pro Pro Pro Ala Leu Pro Pro Pro Pro Pro Leu Ala Lys Phe
    770                 775                 780

Pro Pro Pro Ser Gln Pro Gln Pro Pro Pro Pro Pro Pro Pro Ser Pro
785                 790                 795                 800

Ala Ser Leu Leu Lys Ser Leu Ala Ser Val Leu Glu Gly Gln Lys Tyr
                805                 810                 815

Cys Tyr Arg Gly Thr Gly Ala Ala Val Ser Thr Arg Pro Gly Pro Leu
            820                 825                 830

Pro Thr Thr Gln Tyr Ser Pro Gly Pro Pro Ser Gly Ala Thr Ala Leu
        835                 840                 845

Pro Pro Thr Ser Ala Ala Pro Ser Ala Gln Gly Ser Pro Gln Pro Ser
    850                 855                 860

Ala Ser Ser Ser Ser Gln Phe Ser Thr Ser Gly Gly Pro Trp Ala Arg
865                 870                 875                 880

Glu Arg Arg Ala Gly Glu Glu Pro Val Pro Gly Pro Met Thr Pro Thr
                885                 890                 895

Gln Pro Pro Pro Pro Leu Ser Leu Pro Pro Ala Arg Ser Glu Ser Glu
            900                 905                 910

Val Leu Glu Glu Ile Ser Arg Ala Cys Glu Thr Leu Val Glu Arg Val
        915                 920                 925

Gly Arg Ser Ala Thr Asp Pro Ala Asp Pro Val Asp Thr Ala Glu Pro
    930                 935                 940

Ala Asp Ser Gly Thr Glu Arg Leu Leu Pro Pro Ala Gln Ala Lys Glu
945                 950                 955                 960

Glu Ala Gly Gly Val Ala Ala Val Ser Gly Ser Cys Lys Arg Arg Gln
                965                 970                 975

Lys Glu His Gln Lys Glu His Arg Arg His Arg Arg Ala Cys Lys Asp
            980                 985                 990

Ser Val Gly Arg Arg Pro Arg Glu  Gly Arg Ala Lys Ala  Lys Ala Lys
        995                 1000                1005

Val Pro  Lys Glu Lys Ser Arg  Arg Val Leu Gly Asn  Leu Asp Leu
    1010                1015                1020

Gln Ser  Glu Glu Ile Gln Gly  Arg Glu Lys Ser Arg  Pro Asp Leu
    1025                1030                1035

Gly Gly  Ala Ser Lys Ala Lys  Pro Pro Thr Ala Pro  Ala Pro Pro
    1040                1045                1050

Ser Ala  Pro Ala Pro Ser Ala  Gln Pro Thr Pro Pro  Ser Ala Ser
    1055                1060                1065

Val Pro  Gly Lys Lys Ala Arg  Glu Glu Ala Pro Gly  Pro Pro Gly
    1070                1075                1080

Val Ser  Arg Ala Asp Met Leu  Lys Leu Arg Ser Leu  Ser Glu Gly
    1085                1090                1095

Pro Pro  Lys Glu Leu Lys Ile  Arg Leu Ile Lys Val  Glu Ser Gly
    1100                1105                1110
```

```
Asp Lys  Glu Thr Phe Ile Ala  Ser Glu Val Glu Glu  Arg Arg Leu
    1115                 1120                 1125

Arg Met  Ala Asp Leu Thr Ile  Ser His Cys Ala Ala  Asp Val Val
    1130                 1135                 1140

Arg Ala  Ser Arg Asn Ala Lys  Val Lys Gly Lys Phe  Arg Glu Ser
    1145                 1150                 1155

Tyr Leu  Ser Pro Ala Gln Ser  Val Lys Pro Lys Ile  Asn Thr Glu
    1160                 1165                 1170

Glu Lys  Leu Pro Arg Glu Lys  Leu Asn Pro Pro Thr  Pro Ser Ile
    1175                 1180                 1185

Tyr Leu  Glu Ser Lys Arg Asp  Ala Phe Ser Pro Val  Leu Leu Gln
    1190                 1195                 1200

Phe Cys  Thr Asp Pro Arg Asn  Pro Ile Thr Val Ile  Arg Gly Leu
    1205                 1210                 1215

Ala Gly  Ser Leu Arg Leu Asn  Leu Gly Leu Phe Ser  Thr Lys Thr
    1220                 1225                 1230

Leu Val  Glu Ala Ser Gly Glu  His Thr Val Glu Val  Arg Thr Gln
    1235                 1240                 1245

Val Gln  Gln Pro Ser Asp Glu  Asn Trp Asp Leu Thr  Gly Thr Arg
    1250                 1255                 1260

Gln Ile  Trp Pro Cys Glu Ser  Ser Arg Ser His Thr  Thr Ile Ala
    1265                 1270                 1275

Lys Tyr  Ala Gln Tyr Gln Ala  Ser Ser Phe Gln Glu  Ser Leu Gln
    1280                 1285                 1290

Glu Glu  Lys Glu Ser Glu Asp  Glu Glu Ser Glu Glu  Pro Asp Ser
    1295                 1300                 1305

Thr Thr  Gly Thr Pro Pro Ser  Ser Ala Pro Asp Pro  Lys Asn His
    1310                 1315                 1320

His Ile  Ile Lys Phe Gly Thr  Asn Ile Asp Leu Ser  Asp Ala Lys
    1325                 1330                 1335

Arg Trp  Lys Pro Gln Leu Gln  Glu Leu Leu Lys Leu  Pro Ala Phe
    1340                 1345                 1350

Met Arg  Val Thr Ser Thr Gly  Asn Met Leu Ser His  Val Gly His
    1355                 1360                 1365

Thr Ile  Leu Gly Met Asn Thr  Val Gln Leu Tyr Met  Lys Val Pro
    1370                 1375                 1380

Gly Ser  Arg Thr Pro Gly His  Gln Glu Asn Asn Asn  Phe Cys Ser
    1385                 1390                 1395

Val Asn  Ile Asn Ile Gly Pro  Gly Asp Cys Glu Trp  Phe Ala Val
    1400                 1405                 1410

His Glu  His Tyr Trp Glu Thr  Ile Ser Ala Phe Cys  Asp Arg His
    1415                 1420                 1425

Gly Val  Asp Tyr Leu Thr Gly  Ser Trp Trp Pro Ile  Leu Asp Asp
    1430                 1435                 1440

Leu Tyr  Ala Ser Asn Ile Pro  Val Tyr Arg Phe Val  Gln Arg Pro
    1445                 1450                 1455

Gly Asp  Leu Val Trp Ile Asn  Ala Gly Thr Val His  Trp Val Gln
    1460                 1465                 1470

Ala Thr  Gly Trp Cys Asn Asn  Ile Ala Trp Asn Val  Gly Pro Leu
    1475                 1480                 1485

Thr Ala  Tyr Gln Tyr Gln Leu  Ala Leu Glu Arg Tyr  Glu Trp Asn
    1490                 1495                 1500

Glu Val  Lys Asn Val Lys Ser  Ile Val Pro Met Ile  His Val Ser
```

```
    1505                1510                1515

Trp Asn  Val Ala Arg Thr Val  Lys Ile Ser Asp Pro  Asp Leu Phe
    1520                1525                1530

Lys Met  Ile Lys Phe Cys Leu  Leu Gln Ser Met Lys  His Cys Gln
    1535                1540                1545

Val Gln  Arg Glu Ser Leu Val  Arg Ala Gly Lys Lys  Ile Ala Tyr
    1550                1555                1560

Gln Gly  Arg Val Lys Asp Glu  Pro Ala Tyr Tyr Cys  Asn Glu Cys
    1565                1570                1575

Asp Val  Glu Val Phe Asn Ile  Leu Phe Val Thr Ser  Glu Asn Gly
    1580                1585                1590

Ser Arg  Asn Thr Tyr Leu Val  His Cys Glu Gly Cys  Ala Arg Arg
    1595                1600                1605

Arg Ser  Ala Gly Leu Gln Gly  Val Val Val Leu Glu  Gln Tyr Arg
    1610                1615                1620

Thr Glu  Glu Leu Ala Gln Ala  Tyr Asp Ala Phe Thr  Leu Val Arg
    1625                1630                1635

Ala Arg  Arg Ala Arg Gly Gln  Arg Arg Arg Ala Leu  Gly Gln Ala
    1640                1645                1650

Ala Gly  Thr Gly Phe Gly Ser  Pro Ala Ala Pro Phe  Pro Glu Pro
    1655                1660                1665

Pro Pro  Ala Phe Ser Pro Gln  Ala Pro Ala Ser Thr  Ser Arg
    1670                1675                1680


<210> SEQ ID NO 12
<211> LENGTH: 6704
<212> TYPE: DNA
<213> ORGANISM: Homo sapiens

<400> SEQUENCE: 12

ggcaacatgc cagccccgta gcactgccca ccccacccac tgtggtctgt tgtaccccac     60

tgctggggtg gtggttccaa tgagacaggg cacaccaaac tccatctggc tgttactgag    120

gcggagacac gggtgatgat tggctttctg ggagagaggg aagtcctgtg attggccaga    180

tctctggagc ttgccgacgc ggtgtgagga cgctcccacg gaggccggaa ttggctgtga    240

aaggactgag gcagccatct gggggtagcg ggcactctta tcagagcggc tggagccgga    300

ccatcgtccc agagagctgg ggcagggggc cgtgcccaat ctccagggct cctggggcca    360

ctgctgacct ggctggatgc atcgggcagt ggaccctcca ggggcccgcg ctgcacggga    420

agcctttgcc cttgggggcc tgagctgtgc tggggcctgg agctcctgcc cgcctcatcc    480

ccctcctcgt agcgcatggc tgcctggagg cagatgctca gccagcattg ggcagccccc    540

gcttcctgct cccctacccc cttcacatgg cagtagttct gggcacccca gcaaaccata    600

ttatgctcca ggggcgccca ctccaagacc cctccatggg aagctggaat ccctgcatgg    660

ctgtgtgcag gcattgctcc gggagccagc ccagccaggg ctttgggaac agcttgggca    720

actgtacgag tcagagcacg atagtgagga ggccacacgc tgctaccaca gcgcccttcg    780

atacggagga agcttcgctg agctggggcc ccgcattggc cgactgcagc aggcccagct    840

ctggaacttt catactggct cctgccagca ccgagccaag gtcctgcccc cactggagca    900

agtgtggaac ttgctacacc ttgagcacaa acggaactat ggagccaagc ggggaggtcc    960

cccggtgaag cgagctgctg aaccccccagt ggtgcagcct gtgcctcctg cagcactctc   1020

aggcccctca ggggaggagg gcctcagccc tggaggcaag cgaaggagag gctgcaactc   1080
```

tgaacagact ggccttcccc cagggctgcc actgcctcca ccaccattac caccaccacc 1140
accaccacca ccaccaccac caccacccct gcctggcctg gctaccagcc ccccatttca 1200
gctaaccaag ccagggctgt ggagtaccct gcatggagat gcctggggcc cagagcgcaa 1260
gggttcagca cccccagagc gccaggagca gcggcactcg ctgcctcacc catatccata 1320
cccagctcca gcgtacaccg cgcacccccc tggccaccgg ctggtcccgg ctgctccccc 1380
aggcccaggc ccccgccccc caggagcaga gagccatggc tgcctgcctg ccacccgtcc 1440
ccccggaagt gaccttagag agagcagagt tcagaggtcg cggatggact ccagcgtttc 1500
accagcagca accaccgcct gcgtgcctta cgccccttcc cggccccctg gcctccccgg 1560
caccaccacc agcagcagca gtagcagcag cagcaacact ggtctccggg gcgtggagcc 1620
gaacccaggc attcccggcg ctgaccatta ccaaactccc gcgctggagg tctctcacca 1680
tggccgcctg gggccctcgg cacacagcag tcggaaaccg ttcttggggg ctcccgctgc 1740
cactccccac ctatccctgc cacctggacc ttcctcaccc cctccacccc cctgtccccg 1800
cctcttacgc cccccaccac cccctgcctg gttgaagggt ccggcctgcc gggcagcccg 1860
agaggatgga gagatcttag aagagctctt ctttgggact gagggacccc cccgccctgc 1920
cccaccaccc ctcccccatc gcgagggctt cttggggcct ccggcctccc gcttttctgt 1980
gggcactcag gattctcaca cccctcccac tcccccaacc ccaaccacca gcagtagcaa 2040
cagcaacagt ggcagccaca gcagcagccc tgctgggcct gtgtcctttc ccccaccacc 2100
ctatctggcc agaagtatag accccccttcc ccggcctccc agcccagcac agaaccccca 2160
ggacccacct cttgtacccc tgactcttgc cctgcctcca gcccctcctt cctcctgcca 2220
ccaaaatacc tcaggaagct tcaggcgccc ggagagcccc cggcccaggg tctccttccc 2280
aaagaccccc gaggtggggc cggggccacc cccaggcccc ctgagtaaag ccccccagcc 2340
tgtgccgccc ggggttgggg agctgcctgc ccgaggccct cgactctttg attttccccc 2400
cactccgctg gaggaccagt ttgaggagcc agccgaattc aagatcctac ctgatgggct 2460
ggccaacatc atgaagatgc tggacgaatc cattcgcaag gaagaggaac agcaacaaca 2520
cgaagcaggc gtggcccccc aacccccgct gaaggagccc tttgcatctc tgcagtctcc 2580
tttccccacc gacacagccc ccaccactac tgctcctgct gtcgccgtca ccaccaccac 2640
caccaccacc accaccacca cggccaccca ggaagaggag aagaagccac caccagccct 2700
accaccacca ccgcctctag ccaagttccc tccaccctct cagccacagc caccaccacc 2760
cccacccccc agcccggcca gcctgctcaa atccttggcc tccgtgctgg agggacaaaa 2820
gtactgttat cgggggactg gagcagctgt ttccacccgg cctgggccct tgcccaccac 2880
tcagtattcc cctggccccc catcaggtgc taccgccctg ccgcccacct cagcggcccc 2940
tagcgcccag ggctccccac agccctctgc ttcctcgtca tctcagttct ctacctcagg 3000
cgggccctgg gcccgggagc gcagggcggg cgaagagcca gtcccgggcc ccatgacccc 3060
cacccaaccg cccccacccc tatctctgcc ccctgctcgc tctgagtctg aggtgctaga 3120
agagatcagc cgggcttgcg agacccttgt ggagcgggtg ggccggagtg ccactgaccc 3180
agccgaccca gtggacacag cagagccagc ggacagtggg actgagcgac tgctgccccc 3240
cgcacaggcc aaggaggagg ctggcggggt ggcggcagtg tcaggcagct gtaagcggcg 3300
acagaaggag catcagaagg agcatcggcg gcacaggcgg gcctgtaagg acagtgtggg 3360
tcgtcggccc cgtgagggca gggcaaaggc caaggccaag gtccccaaag aaaagagccg 3420
ccgggtgctg gggaacctgg acctgcagag cgaggagatc cagggtcgtg agaagtcccg 3480

-continued

```
gcccgatctt ggcggggcct ccaaggccaa gccacccaca gctccagccc ctccatcagc   3540
tcctgcacct tctgcccagc ccacaccccc gtcagcctct gtccctggaa agaaggctcg   3600
ggaggaagcc ccagggccac cgggtgtcag ccgggccgac atgctgaagc tgcgctcact   3660
tagtgagggg ccccccaagg agctgaagat ccggctcatc aaggtagaga gtggtgacaa   3720
ggagaccttt atcgcctctg aggtggaaga gcggcggctg cgcatggcag acctcaccat   3780
cagccactgt gctgctgacg tcgtgcgcgc cagcaggaat gccaaggtga aagggaagtt   3840
tcgagagtcc tacctttccc ctgcccagtc tgtgaaaccg aagatcaaca ctgaggagaa   3900
gctgccccgg gaaaaactca accccctac acccagcatc tatctggaga gcaaacggga   3960
tgccttctca cctgtcctgc tgcagttctg tacagaccct cgaaatccca tcacagtgat   4020
ccggggcctg gcgggctccc tgcggctcaa cttgggcctc ttctccacca agaccctggt   4080
ggaagcgagt ggcgaacaca ccgtggaagt tcgcacccag gtgcagcagc cctcagatga   4140
gaactgggat ctgacaggca ctcggcagat ctggccttgt gagagctccc gttcccacac   4200
caccattgcc aagtacgcac agtaccaggc ctcatccttc caggagtctc tgcaggagga   4260
gaaggagagt gaggatgagg agtcagagga gccagacagc accactggaa cccctcctag   4320
cagcgcacca gacccgaaga accatcacat catcaagttt ggcaccaaca tcgacttgtc   4380
tgatgctaag cggtggaagc cccagctgca ggagctgctg aagctgcccg ccttcatgcg   4440
ggtaacatcc acgggcaaca tgctgagcca cgtgggccac accatcctgg gcatgaacac   4500
ggtgcagctg tacatgaagg tgcccggcag ccgaacgcca ggccaccagg agaataacaa   4560
cttctgctcc gtcaacatca acattggccc aggcgactgc gagtggttcg cggtgcacga   4620
gcactactgg gagaccatca gcgctttctg tgatcggcac ggcgtggact acttgacggg   4680
ttcctggtgg ccaatcctgg atgatctcta tgcatccaat attcctgtgt accgcttcgt   4740
gcagcgaccc ggagacctcg tgtggattaa tgcggggact gtgcactggg tgcaggccac   4800
cggctggtgc aacaacattg cctggaacgt ggggcccctc accgcctatc agtaccagct   4860
ggccctggaa cgatacgagt ggaatgaggt gaagaacgtc aaatccatcg tgcccatgat   4920
tcacgtgtca tggaacgtgg ctcgcacggt caaaatcagc gaccccgact tgttcaagat   4980
gatcaagttc tgcctgctgc agtccatgaa gcactgccag gtgcaacgcg agagcctggt   5040
gcgggcaggg aagaaaatcg cttaccaggg ccgtgtcaag gacgagccag cctactactg   5100
caacgagtgc gatgtggagg tgtttaacat cctgttcgtg acaagtgaga atggcagccg   5160
caacacgtac ctggtacact gcgagggctg tgcccggcgc cgcagcgcag gcctgcaggg   5220
cgtggtggtg ctggagcagt accgcactga ggagctggct caggcctacg acgccttcac   5280
gctggtgagg gcccggcggg cgcgcgggca gcggaggagg gcactggggc aggctgcagg   5340
gacgggcttc gggagcccgg ccgcgccttt ccctgagccc ccgccggctt tctcccccca   5400
ggccccagcc agcacgtcgc gatgaggccg gacgccccgc ccgcctgcct gcccgcgcaa   5460
ggcgccgcgg ggccaccagc acatgcctgg gctggaccta ggtcccgcct gtggccgaga   5520
agggggtcgg gcccagccct tccaccccat tggcagctcc cctcacttaa tttattaaga   5580
aaaacttttt ttttttttt agcaaatatg aggaaaaaag gaaaaaaaat gggagacggg   5640
ggagggggct ggcagcccct cgcccaccag cgcctcccct caccgacttt ggccttttta   5700
gcaacagaca caaggaccag gctccggcgg cggcgggggt cacatacggg ttccctcacc   5760
ctgccagccg cccgcccgcc cggcgcagat gcacgcggct cgtgtatgta catagacgtt   5820
```

-continued

```
acggcagccg aggtttttaa tgagattctt tctatgggct ttacccctcc cccggaacct   5880

ccttttttac ttccaatgct agctgtgacc cctgtacatg tctctttatt cacttggtta   5940

tgatttgtat tttttgttct tttcttgttt ttttgttttt aatttataac agtcccactc   6000

acctctattt attcattttt gggaaaaccc gacctcccac acccccaagc catcctgccc   6060

gcccctccag ggaccgcccg tcgccgggct ctccccgcgc cccagtgtgt gtccgggccc   6120

ggcccgaccg tctccacccg tccgcccgcg gctccagccg ggttctcatg gtgctcaaac   6180

ccgctcccct cccctacgtc ctgcactttc tcggaccagt ccccccactc ccgacccgac   6240

cccagcccca cctgagggtg agcaactcct gtactgtagg ggaagaagtg ggaactgaaa   6300

tggtattttg taaaaaaaat aaataaaata aaaaaattaa aggttttaaa gaaagaacta   6360

tgaggaaaag gaaccccgtc cttcccagcc ccggccaact ttaaaaaaca cagaccttca   6420

cccccacccc cttttctttt taagtgtgaa acaacccagg gccagggcct cactggggca   6480

gggacacccc ggggtgagtt tctctggggc tttattttcg ttttgttggt tgtttttttct  6540

ccacgctggg gctgcggagg ggtgggggt ttacagtccc gcaccctcgc actgcactgt   6600

ctctctgccc caggggcaga ggggtcttcc caaccctacc cctattttcg gtgatttttg   6660

tgtgagaata ttaatattaa aaataaacgg agaaaaaaaa tcct                   6704


<210> SEQ ID NO 13
<211> LENGTH: 2555
<212> TYPE: PRT
<213> ORGANISM: Homo sapiens

<400> SEQUENCE: 13

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220
```

Ser Pro Cys Gln Asn Gly Gly Thr Cys Arg Pro Thr Gly Asp Val Thr
225 230 235 240

His Glu Cys Ala Cys Leu Pro Gly Phe Thr Gly Gln Asn Cys Glu Glu
245 250 255

Asn Ile Asp Asp Cys Pro Gly Asn Asn Cys Lys Asn Gly Gly Ala Cys
260 265 270

Val Asp Gly Val Asn Thr Tyr Asn Cys Arg Cys Pro Pro Glu Trp Thr
275 280 285

Gly Gln Tyr Cys Thr Glu Asp Val Asp Glu Cys Gln Leu Met Pro Asn
290 295 300

Ala Cys Gln Asn Gly Gly Thr Cys His Asn Thr His Gly Gly Tyr Asn
305 310 315 320

Cys Val Cys Val Asn Gly Trp Thr Gly Glu Asp Cys Ser Glu Asn Ile
325 330 335

Asp Asp Cys Ala Ser Ala Ala Cys Phe His Gly Ala Thr Cys His Asp
340 345 350

Arg Val Ala Ser Phe Tyr Cys Glu Cys Pro His Gly Arg Thr Gly Leu
355 360 365

Leu Cys His Leu Asn Asp Ala Cys Ile Ser Asn Pro Cys Asn Glu Gly
370 375 380

Ser Asn Cys Asp Thr Asn Pro Val Asn Gly Lys Ala Ile Cys Thr Cys
385 390 395 400

Pro Ser Gly Tyr Thr Gly Pro Ala Cys Ser Gln Asp Val Asp Glu Cys
405 410 415

Ser Leu Gly Ala Asn Pro Cys Glu His Ala Gly Lys Cys Ile Asn Thr
420 425 430

Leu Gly Ser Phe Glu Cys Gln Cys Leu Gln Gly Tyr Thr Gly Pro Arg
435 440 445

Cys Glu Ile Asp Val Asn Glu Cys Val Ser Asn Pro Cys Gln Asn Asp
450 455 460

Ala Thr Cys Leu Asp Gln Ile Gly Glu Phe Gln Cys Ile Cys Met Pro
465 470 475 480

Gly Tyr Glu Gly Val His Cys Glu Val Asn Thr Asp Glu Cys Ala Ser
485 490 495

Ser Pro Cys Leu His Asn Gly Arg Cys Leu Asp Lys Ile Asn Glu Phe
500 505 510

Gln Cys Glu Cys Pro Thr Gly Phe Thr Gly His Leu Cys Gln Tyr Asp
515 520 525

Val Asp Glu Cys Ala Ser Thr Pro Cys Lys Asn Gly Ala Lys Cys Leu
530 535 540

Asp Gly Pro Asn Thr Tyr Thr Cys Val Cys Thr Glu Gly Tyr Thr Gly
545 550 555 560

Thr His Cys Glu Val Asp Ile Asp Glu Cys Asp Pro Asp Pro Cys His
565 570 575

Tyr Gly Ser Cys Lys Asp Gly Val Ala Thr Phe Thr Cys Leu Cys Arg
580 585 590

Pro Gly Tyr Thr Gly His His Cys Glu Thr Asn Ile Asn Glu Cys Ser
595 600 605

Ser Gln Pro Cys Arg His Gly Gly Thr Cys Gln Asp Arg Asp Asn Ala
610 615 620

Tyr Leu Cys Phe Cys Leu Lys Gly Thr Thr Gly Pro Asn Cys Glu Ile
625 630 635 640

```
Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Gly Gln
    850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
        995                 1000                1005

Cys Pro  Pro Gly Phe Thr Gly  Ser Tyr Cys Gln His  Asp Val Asn
    1010                1015                1020

Glu Cys  Asp Ser Gln Pro Cys  Leu His Gly Gly Thr  Cys Gln Asp
    1025                1030                1035

Gly Cys  Gly Ser Tyr Arg Cys  Thr Cys Pro Gln Gly  Tyr Thr Gly
    1040                1045                1050

Pro Asn  Cys Gln Asn Leu Val  His Trp Cys Asp Ser  Ser Pro Cys
```

-continued

```
    1055                1060                1065

Lys Asn  Gly Gly Lys Cys Trp  Gln Thr His Thr Gln  Tyr Arg Cys
    1070                1075                1080

Glu Cys  Pro Ser Gly Trp Thr  Gly Leu Tyr Cys Asp  Val Pro Ser
    1085                1090                1095

Val Ser  Cys Glu Val Ala Ala  Gln Arg Gln Gly Val  Asp Val Ala
    1100                1105                1110

Arg Leu  Cys Gln His Gly Gly  Leu Cys Val Asp Ala  Gly Asn Thr
    1115                1120                1125

His His  Cys Arg Cys Gln Ala  Gly Tyr Thr Gly Ser  Tyr Cys Glu
    1130                1135                1140

Asp Leu  Val Asp Glu Cys Ser  Pro Ser Pro Cys Gln  Asn Gly Ala
    1145                1150                1155

Thr Cys  Thr Asp Tyr Leu Gly  Gly Tyr Ser Cys Lys  Cys Val Ala
    1160                1165                1170

Gly Tyr  His Gly Val Asn Cys  Ser Glu Glu Ile Asp  Glu Cys Leu
    1175                1180                1185

Ser His  Pro Cys Gln Asn Gly  Gly Thr Cys Leu Asp  Leu Pro Asn
    1190                1195                1200

Thr Tyr  Lys Cys Ser Cys Pro  Arg Gly Thr Gln Gly  Val His Cys
    1205                1210                1215

Glu Ile  Asn Val Asp Asp Cys  Asn Pro Pro Val Asp  Pro Val Ser
    1220                1225                1230

Arg Ser  Pro Lys Cys Phe Asn  Asn Gly Thr Cys Val  Asp Gln Val
    1235                1240                1245

Gly Gly  Tyr Ser Cys Thr Cys  Pro Pro Gly Phe Val  Gly Glu Arg
    1250                1255                1260

Cys Glu  Gly Asp Val Asn Glu  Cys Leu Ser Asn Pro  Cys Asp Ala
    1265                1270                1275

Arg Gly  Thr Gln Asn Cys Val  Gln Arg Val Asn Asp  Phe His Cys
    1280                1285                1290

Glu Cys  Arg Ala Gly His Thr  Gly Arg Arg Cys Glu  Ser Val Ile
    1295                1300                1305

Asn Gly  Cys Lys Gly Lys Pro  Cys Lys Asn Gly Gly  Thr Cys Ala
    1310                1315                1320

Val Ala  Ser Asn Thr Ala Arg  Gly Phe Ile Cys Lys  Cys Pro Ala
    1325                1330                1335

Gly Phe  Glu Gly Ala Thr Cys  Glu Asn Asp Ala Arg  Thr Cys Gly
    1340                1345                1350

Ser Leu  Arg Cys Leu Asn Gly  Gly Thr Cys Ile Ser  Gly Pro Arg
    1355                1360                1365

Ser Pro  Thr Cys Leu Cys Leu  Gly Pro Phe Thr Gly  Pro Glu Cys
    1370                1375                1380

Gln Phe  Pro Ala Ser Ser Pro  Cys Leu Gly Gly Asn  Pro Cys Tyr
    1385                1390                1395

Asn Gln  Gly Thr Cys Glu Pro  Thr Ser Glu Ser Pro  Phe Tyr Arg
    1400                1405                1410

Cys Leu  Cys Pro Ala Lys Phe  Asn Gly Leu Leu Cys  His Ile Leu
    1415                1420                1425

Asp Tyr  Ser Phe Gly Gly Gly  Ala Gly Arg Asp Ile  Pro Pro Pro
    1430                1435                1440

Leu Ile  Glu Glu Ala Cys Glu  Leu Pro Glu Cys Gln  Glu Asp Ala
    1445                1450                1455
```

```
Gly Asn  Lys Val Cys Ser Leu  Gln Cys Asn Asn His  Ala Cys Gly
    1460                 1465                 1470

Trp Asp  Gly Gly Asp Cys Ser  Leu Asn Phe Asn Asp  Pro Trp Lys
    1475                 1480                 1485

Asn Cys  Thr Gln Ser Leu Gln  Cys Trp Lys Tyr Phe  Ser Asp Gly
    1490                 1495                 1500

His Cys  Asp Ser Gln Cys Asn  Ser Ala Gly Cys Leu  Phe Asp Gly
    1505                 1510                 1515

Phe Asp  Cys Gln Arg Ala Glu  Gly Gln Cys Asn Pro  Leu Tyr Asp
    1520                 1525                 1530

Gln Tyr  Cys Lys Asp His Phe  Ser Asp Gly His Cys  Asp Gln Gly
    1535                 1540                 1545

Cys Asn  Ser Ala Glu Cys Glu  Trp Asp Gly Leu Asp  Cys Ala Glu
    1550                 1555                 1560

His Val  Pro Glu Arg Leu Ala  Ala Gly Thr Leu Val  Val Val Val
    1565                 1570                 1575

Leu Met  Pro Pro Glu Gln Leu  Arg Asn Ser Ser Phe  His Phe Leu
    1580                 1585                 1590

Arg Glu  Leu Ser Arg Val Leu  His Thr Asn Val Val  Phe Lys Arg
    1595                 1600                 1605

Asp Ala  His Gly Gln Gln Met  Ile Phe Pro Tyr Tyr  Gly Arg Glu
    1610                 1615                 1620

Glu Glu  Leu Arg Lys His Pro  Ile Lys Arg Ala Ala  Glu Gly Trp
    1625                 1630                 1635

Ala Ala  Pro Asp Ala Leu Leu  Gly Gln Val Lys Ala  Ser Leu Leu
    1640                 1645                 1650

Pro Gly  Gly Ser Glu Gly Gly  Arg Arg Arg Arg Glu  Leu Asp Pro
    1655                 1660                 1665

Met Asp  Val Arg Gly Ser Ile  Val Tyr Leu Glu Ile  Asp Asn Arg
    1670                 1675                 1680

Gln Cys  Val Gln Ala Ser Ser  Gln Cys Phe Gln Ser  Ala Thr Asp
    1685                 1690                 1695

Val Ala  Ala Phe Leu Gly Ala  Leu Ala Ser Leu Gly  Ser Leu Asn
    1700                 1705                 1710

Ile Pro  Tyr Lys Ile Glu Ala  Val Gln Ser Glu Thr  Val Glu Pro
    1715                 1720                 1725

Pro Pro  Pro Ala Gln Leu His  Phe Met Tyr Val Ala  Ala Ala Ala
    1730                 1735                 1740

Phe Val  Leu Leu Phe Phe Val  Gly Cys Gly Val Leu  Leu Ser Arg
    1745                 1750                 1755

Lys Arg  Arg Arg Gln His Gly  Gln Leu Trp Phe Pro  Glu Gly Phe
    1760                 1765                 1770

Lys Val  Ser Glu Ala Ser Lys  Lys Lys Arg Arg Glu  Pro Leu Gly
    1775                 1780                 1785

Glu Asp  Ser Val Gly Leu Lys  Pro Leu Lys Asn Ala  Ser Asp Gly
    1790                 1795                 1800

Ala Leu  Met Asp Asp Asn Gln  Asn Glu Trp Gly Asp  Glu Asp Leu
    1805                 1810                 1815

Glu Thr  Lys Lys Phe Arg Phe  Glu Glu Pro Val Val  Leu Pro Asp
    1820                 1825                 1830

Leu Asp  Asp Gln Thr Asp His  Arg Gln Trp Thr Gln  Gln His Leu
    1835                 1840                 1845
```

```
Asp Ala  Ala Asp Leu Arg Met  Ser Ala Met Ala Pro  Thr Pro Pro
    1850                 1855                 1860

Gln Gly  Glu Val Asp Ala Asp  Cys Met Asp Val Asn  Val Arg Gly
    1865                 1870                 1875

Pro Asp  Gly Phe Thr Pro Leu  Met Ile Ala Ser Cys  Ser Gly Gly
    1880                 1885                 1890

Gly Leu  Glu Thr Gly Asn Ser  Glu Glu Glu Glu Asp  Ala Pro Ala
    1895                 1900                 1905

Val Ile  Ser Asp Phe Ile Tyr  Gln Gly Ala Ser Leu  His Asn Gln
    1910                 1915                 1920

Thr Asp  Arg Thr Gly Glu Thr  Ala Leu His Leu Ala  Ala Arg Tyr
    1925                 1930                 1935

Ser Arg  Ser Asp Ala Ala Lys  Arg Leu Leu Glu Ala  Ser Ala Asp
    1940                 1945                 1950

Ala Asn  Ile Gln Asp Asn Met  Gly Arg Thr Pro Leu  His Ala Ala
    1955                 1960                 1965

Val Ser  Ala Asp Ala Gln Gly  Val Phe Gln Ile Leu  Ile Arg Asn
    1970                 1975                 1980

Arg Ala  Thr Asp Leu Asp Ala  Arg Met His Asp Gly  Thr Thr Pro
    1985                 1990                 1995

Leu Ile  Leu Ala Ala Arg Leu  Ala Val Glu Gly Met  Leu Glu Asp
    2000                 2005                 2010

Leu Ile  Asn Ser His Ala Asp  Val Asn Ala Val Asp  Asp Leu Gly
    2015                 2020                 2025

Lys Ser  Ala Leu His Trp Ala  Ala Ala Val Asn Asn  Val Asp Ala
    2030                 2035                 2040

Ala Val  Val Leu Leu Lys Asn  Gly Ala Asn Lys Asp  Met Gln Asn
    2045                 2050                 2055

Asn Arg  Glu Glu Thr Pro Leu  Phe Leu Ala Ala Arg  Glu Gly Ser
    2060                 2065                 2070

Tyr Glu  Thr Ala Lys Val Leu  Leu Asp His Phe Ala  Asn Arg Asp
    2075                 2080                 2085

Ile Thr  Asp His Met Asp Arg  Leu Pro Arg Asp Ile  Ala Gln Glu
    2090                 2095                 2100

Arg Met  His His Asp Ile Val  Arg Leu Leu Asp Glu  Tyr Asn Leu
    2105                 2110                 2115

Val Arg  Ser Pro Gln Leu His  Gly Ala Pro Leu Gly  Gly Thr Pro
    2120                 2125                 2130

Thr Leu  Ser Pro Pro Leu Cys  Ser Pro Asn Gly Tyr  Leu Gly Ser
    2135                 2140                 2145

Leu Lys  Pro Gly Val Gln Gly  Lys Lys Val Arg Lys  Pro Ser Ser
    2150                 2155                 2160

Lys Gly  Leu Ala Cys Gly Ser  Lys Glu Ala Lys Asp  Leu Lys Ala
    2165                 2170                 2175

Arg Arg  Lys Lys Ser Gln Asp  Gly Lys Gly Cys Leu  Leu Asp Ser
    2180                 2185                 2190

Ser Gly  Met Leu Ser Pro Val  Asp Ser Leu Glu Ser  Pro His Gly
    2195                 2200                 2205

Tyr Leu  Ser Asp Val Ala Ser  Pro Pro Leu Leu Pro  Ser Pro Phe
    2210                 2215                 2220

Gln Gln  Ser Pro Ser Val Pro  Leu Asn His Leu Pro  Gly Met Pro
    2225                 2230                 2235

Asp Thr  His Leu Gly Ile Gly  His Leu Asn Val Ala  Ala Lys Pro
```

```
    2240                2245                2250

Glu Met  Ala Ala Leu Gly Gly  Gly Gly Arg Leu Ala  Phe Glu Thr
    2255                2260                2265

Gly Pro  Pro Arg Leu Ser His  Leu Pro Val Ala Ser  Gly Thr Ser
    2270                2275                2280

Thr Val  Leu Gly Ser Ser Ser  Gly Gly Ala Leu Asn  Phe Thr Val
    2285                2290                2295

Gly Gly  Ser Thr Ser Leu Asn  Gly Gln Cys Glu Trp  Leu Ser Arg
    2300                2305                2310

Leu Gln  Ser Gly Met Val Pro  Asn Gln Tyr Asn Pro  Leu Arg Gly
    2315                2320                2325

Ser Val  Ala Pro Gly Pro Leu  Ser Thr Gln Ala Pro  Ser Leu Gln
    2330                2335                2340

His Gly  Met Val Gly Pro Leu  His Ser Ser Leu Ala  Ala Ser Ala
    2345                2350                2355

Leu Ser  Gln Met Met Ser Tyr  Gln Gly Leu Pro Ser  Thr Arg Leu
    2360                2365                2370

Ala Thr  Gln Pro His Leu Val  Gln Thr Gln Gln Val  Gln Pro Gln
    2375                2380                2385

Asn Leu  Gln Met Gln Gln Gln  Asn Leu Gln Pro Ala  Asn Ile Gln
    2390                2395                2400

Gln Gln  Gln Ser Leu Gln Pro  Pro Pro Pro Pro Pro  Gln Pro His
    2405                2410                2415

Leu Gly  Val Ser Ser Ala Ala  Ser Gly His Leu Gly  Arg Ser Phe
    2420                2425                2430

Leu Ser  Gly Glu Pro Ser Gln  Ala Asp Val Gln Pro  Leu Gly Pro
    2435                2440                2445

Ser Ser  Leu Ala Val His Thr  Ile Leu Pro Gln Glu  Ser Pro Ala
    2450                2455                2460

Leu Pro  Thr Ser Leu Pro Ser  Ser Leu Val Pro Pro  Val Thr Ala
    2465                2470                2475

Ala Gln  Phe Leu Thr Pro Pro  Ser Gln His Ser Tyr  Ser Ser Pro
    2480                2485                2490

Val Asp  Asn Thr Pro Ser His  Gln Leu Gln Val Pro  Glu His Pro
    2495                2500                2505

Phe Leu  Thr Pro Ser Pro Glu  Ser Pro Asp Gln Trp  Ser Ser Ser
    2510                2515                2520

Ser Pro  His Ser Asn Val Ser  Asp Trp Ser Glu Gly  Val Ser Ser
    2525                2530                2535

Pro Pro  Thr Ser Met Gln Ser  Gln Ile Ala Arg Ile  Pro Glu Ala
    2540                2545                2550

Phe Lys
    2555


<210> SEQ ID NO 14
<211> LENGTH: 9322
<212> TYPE: DNA
<213> ORGANISM: Homo sapiens

<400> SEQUENCE: 14

atgccgccgc tcctggcgcc cctgctctgc ctggcgctgc tgcccgcgct cgccgcacga     60

ggcccgcgat gctcccagcc cggtgagacc tgcctgaatg gcgggaagtg tgaagcggcc    120

aatggcacgg aggcctgcgt ctgtggcggg gccttcgtgg gcccgcgatg ccaggacccc    180
```

-continued aacccgtgcc tcagcacccc ctgcaagaac gccgggacat gccacgtggt ggaccgcaga 240
ggcgtggcag actatgcctg cagctgtgcc ctgggcttct ctgggcccct ctgcctgaca 300
cccctggaca atgcctgcct caccaacccc tgccgcaacg gggggcacctg cgacctgctc 360
acgctgacgg agtacaagtg ccgctgcccg cccggctggt cagggaaatc gtgccagcag 420
gctgacccgt gcgcctccaa cccctgcgcc aacggtggcc agtgcctgcc cttcgaggcc 480
tcctacatct gccactgccc acccagcttc catggcccca cctgccggca ggatgtcaac 540
gagtgtggcc agaagcccgg gctttgccgc cacggaggca cctgccacaa cgaggtcggc 600
tcctaccgct gcgtctgccg cgccacccac actggcccca actgcgagcg gccctacgtg 660
ccctgcagcc cctcgccctg ccagaacggg ggcacctgcc gccccacggg cgacgtcacc 720
cacgagtgtg cctgcctgcc aggcttcacc ggccagaact gtgaggaaaa tatcgacgat 780
tgtccaggaa acaactgcaa gaacgggggt gcctgtgtgg acggcgtgaa cacctacaac 840
tgccgctgcc cgccagagtg gacaggtcag tactgtaccg aggatgtgga cgagtgccag 900
ctgatgccaa atgcctgcca gaacggcggg acctgccaca acacccacgg tggctacaac 960
tgcgtgtgtg tcaacggctg gactggtgag gactgcagcg agaacattga tgactgtgcc 1020
agcgccgcct gcttccacgg cgccacctgc catgaccgtg tggcctcctt ctactgcgag 1080
tgtccccatg gccgcacagg tctgctgtgc cacctcaacg acgcatgcat cagcaacccc 1140
tgtaacgagg gctccaactg cgacaccaac cctgtcaatg gcaaggccat ctgcacctgc 1200
ccctcggggt acacgggccc ggcctgcagc caggacgtgg atgagtgctc gctgggtgcc 1260
aacccctgcg agcatgcggg caagtgcatc aacacgctgg gctccttcga gtgccagtgt 1320
ctgcagggct acacgggccc ccgatgcgag atcgacgtca acgagtgcgt ctcgaacccg 1380
tgccagaacg acgccacctg cctggaccag attggggagt tccagtgcat ctgcatgccc 1440
ggctacgagg gtgtgcactg cgaggtcaac acagacgagt gtgccagcag cccctgcctg 1500
cacaatggcc gctgcctgga caagatcaat gagttccagt gcgagtgccc cacgggcttc 1560
actgggcatc tgtgccagta cgatgtggac gagtgtgcca gcacccccctg caagaatggt 1620
gccaagtgcc tggacggacc caacacttac acctgtgtgt gcacggaagg gtacacgggg 1680
acgcactgcg aggtggacat cgatgagtgc gaccccgacc cctgccacta cggctcctgc 1740
aaggacggcg tcgccacctt cacctgcctc tgccgcccag gctacacggg ccaccactgc 1800
gagaccaaca tcaacgagtg ctccagccag ccctgccgcc acgggggcac ctgccaggac 1860
cgcgacaacg cctacctctg cttctgcctg aaggggacca caggacccaa ctgcgagatc 1920
aacctggatg actgtgccag cagcccctgc gactcgggca cctgtctgga caagatcgat 1980
ggctacgagt gtgcctgtga gccgggctac acagggagca tgtgtaacat caacatcgat 2040
gagtgtgcgg gcaacccctg ccacaacggg ggcacctgcg aggacggcat caatggcttc 2100
acctgccgct gccccgaggg ctaccacgac cccacctgcc tgtctgaggt caatgagtgc 2160
aacagcaacc cctgcgtcca cggggcctgc cgggacagcc tcaacgggta caagtgcgac 2220
tgtgaccctg ggtggagtgg gaccaactgt gacatcaaca acaatgagtg tgaatccaac 2280
ccttgtgtca acggcggcac ctgcaaagac atgaccagtg gctacgtgtg cacctgccgg 2340
gagggcttca gcggtcccaa ctgccagacc aacatcaacg agtgtgcgtc caacccatgt 2400
ctgaaccagg gcacgtgtat tgacgacgtt gccgggtaca agtgcaactg cctgctgccc 2460
tacacaggtg ccacgtgtga ggtggtgctg gccccgtgtg cccccagccc ctgcagaaac 2520
ggcggggagt gcaggcaatc cgaggactat gagagcttct cctgtgtctg ccccacgggc 2580

-continued

```
tggcaagggc agacctgtga ggtcgacatc aacgagtgcg ttctgagccc gtgccggcac   2640
ggcgcatcct gccagaacac ccacggcggc taccgctgcc actgccaggc cggctacagt   2700
gggcgcaact gcgagaccga catcgacgac tgccggccca acccgtgtca caacgggggc   2760
tcctgcacag acggcatcaa cacggccttc tgcgactgcc tgcccggctt ccggggcact   2820
ttctgtgagg aggacatcaa cgagtgtgcc agtgacccct gccgcaacgg ggccaactgc   2880
acggactgcg tggacagcta cacgtgcacc tgccccgcag gcttcagcgg gatccactgt   2940
gagaacaaca cgcctgactg cacagagagc tcctgcttca acggtggcac ctgcgtggac   3000
ggcatcaact cgttcacctg cctgtgtcca cccggcttca cgggcagcta ctgccagcac   3060
gatgtcaatg agtgcgactc acagccctgc ctgcatggcg gcacctgtca ggacggctgc   3120
ggctcctaca ggtgcacctg cccccagggc tacactggcc ccaactgcca gaaccttgtg   3180
cactggtgtg actcctcgcc ctgcaagaac ggcggcaaat gctggcagac ccacacccag   3240
taccgctgcg agtgccccag cggctggacc ggcctttact gcgacgtgcc cagcgtgtcc   3300
tgtgaggtgg ctgcgcagcg acaaggtgtt gacgttgccc gcctgtgcca gcatggaggg   3360
ctctgtgtgg acgcgggcaa cacgcaccac tgccgctgcc aggcgggcta cacaggcagc   3420
tactgtgagg acctggtgga cgagtgctca cccagcccct gccagaacgg ggccacctgc   3480
acggactacc tgggcggcta ctcctgcaag tgcgtggccg gctaccacgg ggtgaactgc   3540
tctgaggaga tcgacgagtg cctctcccac ccctgccaga acgggggcac ctgcctcgac   3600
ctccccaaca cctacaagtg ctcctgccca cggggcactc agggtgtgca ctgtgagatc   3660
aacgtggacg actgcaatcc ccccgttgac cccgtgtccc ggagccccaa gtgctttaac   3720
aacggcacct gcgtggacca ggtgggcggc tacagctgca cctgcccgcc gggcttcgtg   3780
ggtgagcgct gtgaggggga tgtcaacgag tgcctgtcca atccctgcga cgcccgtggc   3840
acccagaact gcgtgcagcg cgtcaatgac ttccactgcg agtgccgtgc tggtcacacc   3900
gggcgccgct gcgagtccgt catcaatggc tgcaaaggca agccctgcaa gaatgggggc   3960
acctgcgccg tggcctccaa caccgcccgc gggttcatct gcaagtgccc tgcgggcttc   4020
gagggcgcca cgtgtgagaa tgacgctcgt acctgcggca gcctgcgctg cctcaacggc   4080
ggcacatgca tctccggccc gcgcagcccc acctgcctgt gcctgggccc cttcacgggc   4140
cccgaatgcc agttcccggc cagcagcccc tgcctgggcg gcaacccctg ctacaaccag   4200
gggacctgtg agcccacatc cgagagcccc ttctaccgtt gcctgtgccc cgccaaattc   4260
aacgggctct tgtgccacat cctggactac agcttcgggg gtggggccgg gcgcgacatc   4320
cccccgccgc tgatcgagga ggcgtgcgag ctgcccgagt gccaggagga cgcgggcaac   4380
aaggtctgca gcctgcagtg caacaaccac gcgtgcggct gggacggcgg tgactgctcc   4440
ctcaacttca atgacccctg gaagaactgc acgcagtctc tgcagtgctg gaagtacttc   4500
agtgacggcc actgtgacag ccagtgcaac tcagccggct gcctcttcga cggctttgac   4560
tgccagcgtg cggaaggcca gtgcaacccc ctgtacgacc agtactgcaa ggaccacttc   4620
agcgacgggc actgcgacca gggctgcaac agcgcggagt gcgagtggga cgggctggac   4680
tgtgcggagc atgtacccga gaggctggcg gccggcacgc tggtggtggt ggtgctgatg   4740
ccgccggagc agctgcgcaa cagctccttc cacttcctgc gggagctcag ccgcgtgctg   4800
cacaccaacg tggtcttcaa gcgtgacgca cacggccagc agatgatctt cccctactac   4860
ggccgcgagg aggagctgcg caagcacccc atcaagcgtg ccgccgaggg ctgggccgca   4920
```

-continued

```
cctgacgccc tgctgggcca ggtgaaggcc tcgctgctcc ctggtggcag cgagggtggg   4980
cggcggcgga gggagctgga ccccatggac gtccgcggct ccatcgtcta cctggagatt   5040
gacaaccggc agtgtgtgca ggcctcctcg cagtgcttcc agagtgccac cgacgtggcc   5100
gcattcctgg gagcgctcgc ctcgctgggc agcctcaaca tcccctacaa gatcgaggcc   5160
gtgcagagtg agaccgtgga gccgcccccg ccggcgcagc tgcacttcat gtacgtggcg   5220
gcggccgcct ttgtgcttct gttcttcgtg ggctgcgggg tgctgctgtc ccgcaagcgc   5280
cggcggcagc atggccagct ctggttccct gagggcttca aagtgtctga ggccagcaag   5340
aagaagcggc gggagcccct cggcgaggac tccgtgggcc tcaagcccct gaagaacgct   5400
tcagacggtg ccctcatgga cgacaaccag aatgagtggg gggacgagga cctggagacc   5460
aagaagttcc ggttcgagga gcccgtggtt ctgcctgacc tggacgacca gacagaccac   5520
cggcagtgga ctcagcagca cctggatgcc gctgacctgc gcatgtctgc catggccccc   5580
acaccgcccc agggtgaggt tgacgccgac tgcatggacg tcaatgtccg cgggcctgat   5640
ggcttcaccc cgctcatgat cgcctcctgc agcgggggcg gcctggagac gggcaacagc   5700
gaggaagagg aggacgcgcc ggccgtcatc tccgacttca tctaccaggg cgccagcctg   5760
cacaaccaga cagaccgcac gggcgagacc gccttgcacc tggccgcccg ctactcacgc   5820
tctgatgccg ccaagcgcct gctggaggcc agcgcagatg ccaacatcca ggacaacatg   5880
ggccgcaccc cgctgcatgc ggctgtgtct gccgacgcac aaggtgtctt ccagatcctg   5940
atccggaacc gagccacaga cctggatgcc cgcatgcatg atggcacgac gccactgatc   6000
ctggctgccc gcctggccgt ggagggcatg ctggaggacc tcatcaactc acacgccgac   6060
gtcaacgccg tagatgacct gggcaagtcc gccctgcact gggccgccgc cgtgaacaat   6120
gtggatgccg cagttgtgct cctgaagaac ggggctaaca aagatatgca gaacaacagg   6180
gaggagacac ccctgtttct ggccgcccgg gagggcagct acgagaccgc caaggtgctg   6240
ctggaccact ttgccaaccg ggacatcacg gatcatatgg accgcctgcc gcgcgacatc   6300
gcacaggagc gcatgcatca cgacatcgtg aggctgctgg acgagtacaa cctggtgcgc   6360
agcccgcagc tgcacggagc cccgctgggg ggcacgccca ccctgtcgcc cccgctctgc   6420
tcgcccaacg gctacctggg cagcctcaag cccggcgtgc agggcaagaa ggtccgcaag   6480
cccagcagca aaggcctggc ctgtggaagc aaggaggcca aggacctcaa ggcacggagg   6540
aagaagtccc aggacggcaa gggctgcctg ctggacagct ccggcatgct ctcgcccgtg   6600
gactccctgg agtcacccca tggctacctg tcagacgtgg cctcgccgcc actgctgccc   6660
tccccgttcc agcagtctcc gtccgtgccc ctcaaccacc tgcctgggat gcccgacacc   6720
cacctgggca tcgggcacct gaacgtggcg gccaagcccg agatggcggc gctgggtggg   6780
ggcggccggc tggcctttga gactggccca cctcgtctct cccacctgcc tgtggcctct   6840
ggcaccagca ccgtcctggg ctccagcagc ggaggggccc tgaatttcac tgtgggcggg   6900
tccaccagtt tgaatggtca atgcgagtgg ctgtcccggc tgcagagcgg catggtgccg   6960
aaccaataca accctctgcg gggggagtgtg gcaccaggcc ccctgagcac acaggccccc   7020
tccctgcagc atggcatggt aggcccgctg cacagtagcc ttgctgccag cgccctgtcc   7080
cagatgatga gctaccaggg cctgcccagc acccggctgg ccacccagcc tcacctggtg   7140
cagacccagc aggtgcagcc acaaaactta cagatgcagc agcagaacct gcagccagca   7200
aacatccagc agcagcaaag cctgcagccg ccaccaccac caccacagcc gcaccttggc   7260
gtgagctcag cagccagcgg ccacctgggc cggagcttcc tgagtggaga gccgagccag   7320
```

```
gcagacgtgc agccactggg ccccagcagc ctggcggtgc acactattct gccccaggag   7380

agccccgccc tgcccacgtc gctgccatcc tcgctggtcc cacccgtgac cgcagcccag   7440

ttcctgacgc ccccctcgca gcacagctac tcctcgcctg tggacaacac ccccagccac   7500

cagctacagg tgcctgagca ccccttcctc accccgtccc ctgagtcccc tgaccagtgg   7560

tccagctcgt ccccgcattc caacgtctcc gactggtccg agggcgtctc cagccctccc   7620

accagcatgc agtcccagat cgcccgcatt ccggaggcct tcaagtaaac ggcgcgcccc   7680

acgagacccc ggcttccttt cccaagcctt cgggcgtctg tgtgcgctct gtggatgcca   7740

gggccgacca gaggagcctt tttaaaacac atgtttttat acaaaataag aacgaggatt   7800

ttaatttttt ttagtattta tttatgtact tttattttac acagaaacac tgccttttta   7860

tttatatgta ctgttttatc tggccccagg tagaaacttt tatctattct gagaaaacaa   7920

gcaagttctg agagccaggg ttttcctacg taggatgaaa agattcttct gtgtttataa   7980

aatataaaca aagattcatg atttataaat gccatttatt tattgattcc tttttttcaaa   8040

atccaaaaag aaatgatgtt ggagaaggga agttgaacga gcatagtcca aaaagctcct   8100

ggggcgtcca ggccgcgccc tttccccgac gcccacccaa ccccaagcca gcccggccgc   8160

tccaccagca tcacctgcct gttaggagaa gctgcatcca gaggcaaacg gaggcaaagc   8220

tggctcacct tccgcacgcg gattaatttg catctgaaat aggaaacaag tgaaagcata   8280

tgggttagat gttgccatgt gttttagatg gtttcttgca agcatgcttg tgaaaatgtg   8340

ttctcggagt gtgtatgcca agagtgcacc catggtacca atcatgaatc tttgtttcag   8400

gttcagtatt atgtagttgt tcgttggtta tacaagttct tggtccctcc agaaccaccc   8460

cggccccctg cccgttcttg aaatgtaggc atcatgcatg tcaaacatga gatgtgtgga   8520

ctgtggcact tgcctgggtc acacacggag gcatcctacc cttttctggg gaaagacact   8580

gcctgggctg accccggtgg cggccccagc acctcagcct gcacagtgtc cccccaggttc  8640

cgaagaagat gctccagcaa cacagcctgg gccccagctc gcgggacccg accccccgtg   8700

ggctcccgtg ttttgtagga gacttgccag agccgggcac attgagctgt gcaacgccgt   8760

gggctgcgtc ctttggtcct gtccccgcag ccctggcagg gggcatgcgg tcgggcaggg   8820

gctggaggga ggcgggggct gcccttgggc cacccctcct agtttgggag gagcagattt   8880

ttgcaatacc aagtatagcc tatggcagaa aaaatgtctg taaatatgtt tttaaaggtg   8940

gattttgttt aaaaaatctt aatgaatgag tctgttgtgt gtcatgccag tgagggacgt   9000

cagacttggc tcagctcggg gagccttagc cgcccatgca ctggggacgc tccgctgccg   9060

tgccgcctgc actcctcagg gcagcctccc ccggctctac gggggccgcg tggtgccatc   9120

cccagggggc atgaccagat gcgtcccaag atgttgattt ttactgtgtt ttataaaata   9180

gagtgtagtt tacagaaaaa gactttaaaa gtgatctaca tgaggaactg tagatgatgt   9240

attttttca tcttttttgt taactgattt gcaataaaaa tgatactgat ggtgatctgg   9300

cttccaaaaa aaaaaaaaaa aa                                             9322
```

<210> SEQ ID NO 15
<211> LENGTH: 1089
<212> TYPE: PRT
<213> ORGANISM: Homo sapiens

<400> SEQUENCE: 15

```
Met Gly Thr Ser His Pro Ala Phe Leu Val Leu Gly Cys Leu Leu Thr
1               5                   10                  15
```

```
Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430
```

```
Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
```

```
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu  Lys Asp Trp Glu Gly  Gly Leu Asp
        995                 1000                1005

Glu Gln  Arg Leu Ser Ala Asp  Ser Gly Tyr Ile Ile  Pro Leu Pro
    1010                 1015                 1020

Asp Ile  Asp Pro Val Pro Glu  Glu Glu Asp Leu Gly  Lys Arg Asn
    1025                 1030                 1035

Arg His  Ser Ser Gln Thr Ser  Glu Glu Ser Ala Ile  Glu Thr Gly
    1040                 1045                 1050

Ser Ser  Ser Ser Thr Phe Ile  Lys Arg Glu Asp Glu  Thr Ile Glu
    1055                 1060                 1065

Asp Ile  Asp Met Met Asp Asp  Ile Gly Ile Asp Ser  Ser Asp Leu
    1070                 1075                 1080

Val Glu  Asp Ser Phe Leu
    1085
```

<210> SEQ ID NO 16
<211> LENGTH: 6574
<212> TYPE: DNA
<213> ORGANISM: Homo sapiens

<400> SEQUENCE: 16

```
aagagcaaaa agcgaaggcg caatctggac actgggagat tcggagcgca gggagtttga      60

gagaaacttt tattttgaag agaccaaggt tgaggggggg cttatttcct gacagctatt     120

tacttagagc aaatgattag ttttagaagg atggactata acattgaatc aattacaaaa     180

cgcggttttt gagcccatta ctgttggagc tacagggaga gaaacagagg aggagactgc     240

aagagatcat tggaggccgt gggcacgctc tttactccat gtgtgggaca ttcattgcgg     300

aataacatcg gaggagaagt ttcccagagc tatggggact tcccatccgg cgttcctggt     360

cttaggctgt cttctcacag ggctgagcct aatcctctgc cagctttcat taccctctat     420

ccttccaaat gaaaatgaaa aggttgtgca gctgaattca tccttttctc tgagatgctt     480

tggggagagt gaagtgagct ggcagtaccc catgtctgaa gaagagagct ccgatgtgga     540

aatcagaaat gaagaaaaca acagcggcct tttgtgacg gtcttggaag tgagcagtgc     600

ctcggcggcc cacacagggt tgtacacttg ctattacaac cacactcaga cagaagagaa     660

tgagcttgaa ggcaggcaca tttacatcta tgtgccagac ccagatgtag cctttgtacc     720
```

-continued

```
tctaggaatg acggattatt tagtcatcgt ggaggatgat gattctgcca ttataccttg    780
tcgcacaact gatcccgaga ctcctgtaac cttacacaac agtgaggggg tggtacctgc    840
ctcctacgac agcagacagg gctttaatgg gaccttcact gtagggccct atatctgtga    900
ggccaccgtc aaaggaaaga agttccagac catcccattt aatgtttatg ctttaaaagc    960
aacatcagag ctggatctag aaatggaagc tcttaaaacc gtgtataagt caggggaaac   1020
gattgtggtc acctgtgctg tttttaacaa tgaggtggtt gaccttcaat ggacttaccc   1080
tggagaagtg aaaggcaaag gcatcacaat gctggaagaa atcaaagtcc catccatcaa   1140
attggtgtac actttgacgg tccccgaggc cacggtgaaa gacagtggag attacgaatg   1200
tgctgcccgc caggctacca gggaggtcaa agaaatgaag aaagtcacta tttctgtcca   1260
tgagaaaggt ttcattgaaa tcaaacccac cttcagccag ttggaagctg tcaacctgca   1320
tgaagtcaaa cattttgttg tagaggtgcg ggcctaccca cctcccagga tatcctggct   1380
gaaaaacaat ctgactctga ttgaaaatct cactgagatc accactgatg tggaaaagat   1440
tcaggaaata aggtatcgaa gcaaattaaa gctgatccgt gctaaggaag aagacagtgg   1500
ccattatact attgtagctc aaaatgaaga tgctgtgaag agctatactt ttgaactgtt   1560
aactcaagtt ccttcatcca ttctggactt ggtcgatgat caccatggct caactggggg   1620
acagacggtg aggtgcacag ctgaaggcac gccgcttcct gatattgagt ggatgatatg   1680
caaagatatt aagaaatgta ataatgaaac ttcctggact attttggcca acaatgtctc   1740
aaacatcatc acggagatcc actcccgaga caggagtacc gtggagggcc gtgtgacttt   1800
cgccaaagtg gaggagacca tcgccgtgcg atgcctggct aagaatctcc ttggagctga   1860
gaaccgagag ctgaagctgg tggctcccac cctgcgttct gaactcacgg tggctgctgc   1920
agtcctggtg ctgttggtga ttgtgatcat ctcacttatt gtcctggttg tcatttggaa   1980
acagaaaccg aggtatgaaa ttcgctggag ggtcattgaa tcaatcagcc cagatggaca   2040
tgaatatatt tatgtggacc cgatgcagct gccttatgac tcaagatggg agtttccaag   2100
agatggacta gtgcttggtc gggtcttggg gtctggagcg tttgggaagg tggttgaagg   2160
aacagcctat ggattaagcc ggtcccaacc tgtcatgaaa gttgcagtga agatgctaaa   2220
acccacggcc agatccagtg aaaaacaagc tctcatgtct gaactgaaga taatgactca   2280
cctggggcca catttgaaca ttgtaaactt gctgggagcc tgcaccaagt caggccccat   2340
ttacatcatc acagagtatt gcttctatgg agatttggtc aactatttgc ataagaatag   2400
ggatagcttc ctgagccacc acccagagaa gccaaagaaa gagctggata tctttggatt   2460
gaaccctgct gatgaaagca cacggagcta tgttatttta tcttttgaaa acaatggtga   2520
ctacatggac atgaagcagg ctgatactac acagtatgtc cccatgctag aaaggaaaga   2580
ggtttctaaa tattccgaca tccagagatc actctatgat cgtccagcct catataagaa   2640
gaaatctatg ttagactcag aagtcaaaaa cctcctttca gatgataact cagaaggcct   2700
tactttattg gatttgttga gcttcaccta tcaagttgcc cgaggaatgg agtttttggc   2760
ttcaaaaaat tgtgtccacc gtgatctggc tgctcgcaac gtcctcctgg cacaaggaaa   2820
aattgtgaag atctgtgact ttggcctggc cagagacatc atgcatgatt cgaactatgt   2880
gtcgaaaggc agtacctttc tgcccgtgaa gtggatggct cctgagagca tctttgacaa   2940
cctctacacc acactgagtg atgtctggtc ttatggcatt ctgctctggg agatcttttc   3000
ccttggtggc accccttacc ccggcatgat ggtggattct actttctaca ataagatcaa   3060
gagtgggtac cggatggcca agcctgacca cgctaccagt gaagtctacg agatcatggt   3120
```

-continued gaaatgctgg aacagtgagc cggagaagag accctccttt taccacctga gtgagattgt 3180
ggagaatctg ctgcctggac aatataaaaa gagttatgaa aaaattcacc tggacttcct 3240
gaagagtgac catcctgctg tggcacgcat gcgtgtggac tcagacaatg catacattgg 3300
tgtcacctac aaaaacgagg aagacaagct gaaggactgg gagggtggtc tggatgagca 3360
gagactgagc gctgacagtg gctacatcat tcctctgcct gacattgacc ctgtccctga 3420
ggaggaggac ctgggcaaga ggaacagaca cagctcgcag acctctgaag agagtgccat 3480
tgagacgggt tccagcagtt ccaccttcat caagagagag gacgagacca ttgaagacat 3540
cgacatgatg gatgacatcg gcatagactc ttcagacctg gtggaagaca gcttcctgta 3600
actggcggat tcgaggggtt ccttccactt ctggggccac ctctggatcc cgttcagaaa 3660
accactttat tgcaatgcag aggttgagag gaggacttgg ttgatgttta aagagaagtt 3720
cccagccaag ggcctcgggg agcgttctaa atatgaatga atgggatatt ttgaaatgaa 3780
ctttgtcagt gttgcctctt gcaatgcctc agtagcatct cagtggtgtg tgaagtttgg 3840
agatagatgg ataagggaat aataggccac agaaggtgaa ctttgtgctt caaggacatt 3900
ggtgagagtc caacagacac aatttatact gcgacagaac ttcagcattg taattatgta 3960
aataactcta accaaggctg tgtttagatt gtattaacta tcttctttgg acttctgaag 4020
agaccactca atccatccat gtacttccct cttgaaacct gatgtcagct gctgttgaac 4080
tttttaaaga agtgcatgaa aaaccatttt tgaaccttaa aaggtactgg tactatagca 4140
ttttgctatc ttttttagtg ttaaagagat aaagaataat aattaaccaa ccttgtttaa 4200
tagatttggg tcatttagaa gcctgacaac tcattttcat attgtaatct atgtttataa 4260
tactactact gttatcagta atgctaaatg tgtaataatg taacatgatt tccctccaga 4320
gaaagcacaa tttaaaacaa tccttactaa gtaggtgatg agtttgacag tttttgacat 4380
ttatattaaa taacatgttt ctctataaag tatggtaata gctttagtga attaaattta 4440
gttgagcata gagaacaaag taaaagtagt gttgtccagg aagtcagaat ttttaactgt 4500
actgaatagg ttccccaatc catcgtatta aaaaacaatt aactgccctc tgaaataatg 4560
ggattagaaa caaacaaaac tcttaagtcc taaaagttct caatgtagag gcataaacct 4620
gtgctgaaca taacttctca tgtatattac ccaatggaaa atataatgat cagcaaaaag 4680
actggatttg cagaagtttt tttttttttt ttcttcatgc ctgatgaaag ctttggcgac 4740
cccaatatat gtatttttttg aatctatgaa cctgaaaagg gtcagaagga tgcccagaca 4800
tcagcctcct tctttcaccc cttaccccaa agagaaagag tttgaaactc gagaccataa 4860
agatattctt tagtggaggc tggatgtgca ttagcctgga tcctcagttc tcaaatgtgt 4920
gtggcagcca ggatgactag atcctgggtt tccatccttg agattctgaa gtatgaagtc 4980
tgagggaaac cagagtctgt atttttctaa actccctggc tgttctgatc ggccagtttt 5040
cggaaacact gacttaggtt tcaggaagtt gccatgggaa acaaataatt tgaactttgg 5100
aacagggttg gcattcaacc acgcaggaag cctactattt aaatccttgg cttcaggtta 5160
gtgacattta atgccatcta gctagcaatt gcgaccttaa tttaactttc cagtcttagc 5220
tgaggctgag aaagctaaag tttggttttg acaggttttc caaaagtaaa gatgctactt 5280
cccactgtat gggggagatt gaactttccc cgtctcccgt cttctgcctc ccactccata 5340
ccccgccaag gaaaggcatg tacaaaaatt atgcaattca gtgttccaag tctctgtgta 5400
accagctcag tgttttggtg gaaaaaacat tttaagtttt actgataatt tgaggttaga 5460

-continued

```
tgggaggatg aattgtcaca tctatccaca ctgtcaaaca ggttggtgtg ggttcattgg   5520

cattctttgc aatactgctt aattgctgat accatatgaa tgaaacatgg gctgtgatta   5580

ctgcaatcac tgtgctatcg gcagatgatg ctttggaaga tgcagaagca ataataaagt   5640

acttgactac ctactggtgt aatctcaatg caagccccaa ctttcttatc caactttttc   5700

atagtaagtg cgaagactga gccagattgg ccaattaaaa acgaaaacct gactaggttc   5760

tgtagagcca attagacttg aaatacgttt gtgtttctag aatcacagct caagcattct   5820

gtttatcgct cactctccct tgtacagcct tattttgttg gtgctttgca ttttgatatt   5880

gctgtgagcc ttgcatgaca tcatgaggcc ggatgaaact tctcagtcca gcagtttcca   5940

gtcctaacaa atgctcccac ctgaatttgt atatgactgc atttgtgtgt gtgtgtgtgt   6000

tttcagcaaa ttccagattt gtttcctttt ggcctcctgc aaagtctcca gaagaaaatt   6060

tgccaatctt tcctactttc tatttttatg atgacaatca aagccggcct gagaaacact   6120

atttgtgact ttttaaacga ttagtgatgt ccttaaaatg tggtctgcca atctgtacaa   6180

aatggtccta tttttgtgaa gagggacata agataaaatg atgttataca tcaatatgta   6240

tatatgtatt tctatataga cttggagaat actgccaaaa catttatgac aagctgtatc   6300

actgccttcg tttatatttt tttaactgtg ataatcccca caggcacatt aactgttgca   6360

cttttgaatg tccaaaattt atattttaga aataataaaa agaaagatac ttacatgttc   6420

ccaaaacaat ggtgtggtga atgtgtgaga aaaactaact tgatagggtc taccaataca   6480

aaatgtatta cgaatgcccc tgttcatgtt tttgttttaa aacgtgtaaa tgaagatctt   6540

tatatttcaa taaatgatat ataatttaaa gtta                               6574
```

```
<210> SEQ ID NO 17
<211> LENGTH: 1007
<212> TYPE: PRT
<213> ORGANISM: Homo sapiens

<400> SEQUENCE: 17

Met Ser Arg Arg Lys Gln Arg Lys Pro Gln Gln Leu Ile Ser Asp Cys
1               5                   10                  15

Glu Gly Pro Ser Ala Ser Glu Asn Gly Asp Ala Ser Glu Glu Asp His
            20                  25                  30

Pro Gln Val Cys Ala Lys Cys Cys Ala Gln Phe Thr Asp Pro Thr Glu
        35                  40                  45

Phe Leu Ala His Gln Asn Ala Cys Ser Thr Asp Pro Pro Val Met Val
    50                  55                  60

Ile Ile Gly Gly Gln Glu Asn Pro Asn Asn Ser Ser Ala Ser Ser Glu
65                  70                  75                  80

Pro Arg Pro Glu Gly His Asn Asn Pro Gln Val Met Asp Thr Glu His
                85                  90                  95

Ser Asn Pro Pro Asp Ser Gly Ser Ser Val Pro Thr Asp Pro Thr Trp
            100                 105                 110

Gly Pro Glu Arg Arg Gly Glu Glu Ser Pro Gly His Phe Leu Val Ala
        115                 120                 125

Ala Thr Gly Thr Ala Ala Gly Gly Gly Gly Gly Leu Ile Leu Ala Ser
    130                 135                 140

Pro Lys Leu Gly Ala Thr Pro Leu Pro Pro Glu Ser Thr Pro Ala Pro
145                 150                 155                 160

Pro Pro Pro Pro Pro Pro Pro Pro Pro Pro Gly Val Gly Ser Gly His
                165                 170                 175
```

-continued

```
Leu Asn Ile Pro Leu Ile Leu Glu Glu Leu Arg Val Leu Gln Gln Arg
            180                 185                 190

Gln Ile His Gln Met Gln Met Thr Glu Gln Ile Cys Arg Gln Val Leu
        195                 200                 205

Leu Leu Gly Ser Leu Gly Gln Thr Val Gly Ala Pro Ala Ser Pro Ser
    210                 215                 220

Glu Leu Pro Gly Thr Gly Thr Ala Ser Ser Thr Lys Pro Leu Leu Pro
225                 230                 235                 240

Leu Phe Ser Pro Ile Lys Pro Val Gln Thr Ser Lys Thr Leu Ala Ser
                245                 250                 255

Ser Ser Ser Ser Ser Ser Ser Ser Ser Gly Ala Glu Thr Pro Lys Gln
            260                 265                 270

Ala Phe Phe His Leu Tyr His Pro Leu Gly Ser Gln His Pro Phe Ser
        275                 280                 285

Ala Gly Gly Val Gly Arg Ser His Lys Pro Thr Pro Ala Pro Ser Pro
    290                 295                 300

Ala Leu Pro Gly Ser Thr Asp Gln Leu Ile Ala Ser Pro His Leu Ala
305                 310                 315                 320

Phe Pro Ser Thr Thr Gly Leu Leu Ala Ala Gln Cys Leu Gly Ala Ala
                325                 330                 335

Arg Gly Leu Glu Ala Thr Ala Ser Pro Gly Leu Leu Lys Pro Lys Asn
            340                 345                 350

Gly Ser Gly Glu Leu Ser Tyr Gly Glu Val Met Gly Pro Leu Glu Lys
        355                 360                 365

Pro Gly Gly Arg His Lys Cys Arg Phe Cys Ala Lys Val Phe Gly Ser
    370                 375                 380

Asp Ser Ala Leu Gln Ile His Leu Arg Ser His Thr Gly Glu Arg Pro
385                 390                 395                 400

Tyr Lys Cys Asn Val Cys Gly Asn Arg Phe Thr Thr Arg Gly Asn Leu
                405                 410                 415

Lys Val His Phe His Arg His Arg Glu Lys Tyr Pro His Val Gln Met
            420                 425                 430

Asn Pro His Pro Val Pro Glu His Leu Asp Tyr Val Ile Thr Ser Ser
        435                 440                 445

Gly Leu Pro Tyr Gly Met Ser Val Pro Pro Glu Lys Ala Glu Glu Glu
    450                 455                 460

Ala Ala Thr Pro Gly Gly Gly Val Glu Arg Lys Pro Leu Val Ala Ser
465                 470                 475                 480

Thr Thr Ala Leu Ser Ala Thr Glu Ser Leu Thr Leu Leu Ser Thr Ser
                485                 490                 495

Ala Gly Thr Ala Thr Ala Pro Gly Leu Pro Ala Phe Asn Lys Phe Val
            500                 505                 510

Leu Met Lys Ala Val Glu Pro Lys Asn Lys Ala Asp Glu Asn Thr Pro
        515                 520                 525

Pro Gly Ser Glu Gly Ser Ala Ile Ser Gly Val Ala Glu Ser Ser Thr
    530                 535                 540

Ala Thr Arg Met Gln Leu Ser Lys Leu Val Thr Ser Leu Pro Ser Trp
545                 550                 555                 560

Ala Leu Leu Thr Asn His Phe Lys Ser Thr Gly Ser Phe Pro Phe Pro
                565                 570                 575

Tyr Val Leu Glu Pro Leu Gly Ala Ser Pro Ser Glu Thr Ser Lys Leu
            580                 585                 590

Gln Gln Leu Val Glu Lys Ile Asp Arg Gln Gly Ala Val Ala Val Thr
```

```
        595                 600                 605

Ser Ala Ala Ser Gly Ala Pro Thr Thr Ser Ala Pro Ala Pro Ser Ser
    610                 615                 620

Ser Ala Ser Ser Gly Pro Asn Gln Cys Val Ile Cys Leu Arg Val Leu
625                 630                 635                 640

Ser Cys Pro Arg Ala Leu Arg Leu His Tyr Gly Gln His Gly Gly Glu
                645                 650                 655

Arg Pro Phe Lys Cys Lys Val Cys Gly Arg Ala Phe Ser Thr Arg Gly
            660                 665                 670

Asn Leu Arg Ala His Phe Val Gly His Lys Ala Ser Pro Ala Ala Arg
        675                 680                 685

Ala Gln Asn Ser Cys Pro Ile Cys Gln Lys Lys Phe Thr Asn Ala Val
    690                 695                 700

Thr Leu Gln Gln His Val Arg Met His Leu Gly Gly Gln Ile Pro Asn
705                 710                 715                 720

Gly Gly Thr Ala Leu Pro Glu Gly Gly Gly Ala Ala Gln Glu Asn Gly
                725                 730                 735

Ser Glu Gln Ser Thr Val Ser Gly Ala Gly Ser Phe Pro Gln Gln Gln
            740                 745                 750

Ser Gln Gln Pro Ser Pro Glu Glu Glu Leu Ser Glu Glu Glu Glu Glu
        755                 760                 765

Glu Asp Glu Glu Glu Glu Glu Asp Val Thr Asp Glu Asp Ser Leu Ala
    770                 775                 780

Gly Arg Gly Ser Glu Ser Gly Gly Glu Lys Ala Ile Ser Val Arg Gly
785                 790                 795                 800

Asp Ser Glu Glu Ala Ser Gly Ala Glu Glu Glu Val Gly Thr Val Ala
                805                 810                 815

Ala Ala Ala Thr Ala Gly Lys Glu Met Asp Ser Asn Glu Lys Thr Thr
            820                 825                 830

Gln Gln Ser Ser Leu Pro Pro Pro Pro Pro Pro Asp Ser Leu Asp Gln
        835                 840                 845

Pro Gln Pro Met Glu Gln Gly Ser Ser Gly Val Leu Gly Gly Lys Glu
    850                 855                 860

Glu Gly Gly Lys Pro Glu Arg Ser Ser Ser Pro Ala Ser Ala Leu Thr
865                 870                 875                 880

Pro Glu Gly Glu Ala Thr Ser Val Thr Leu Val Glu Glu Leu Ser Leu
                885                 890                 895

Gln Glu Ala Met Arg Lys Glu Pro Gly Glu Ser Ser Ser Arg Lys Ala
            900                 905                 910

Cys Glu Val Cys Gly Gln Ala Phe Pro Ser Gln Ala Ala Leu Glu Glu
        915                 920                 925

His Gln Lys Thr His Pro Lys Glu Gly Pro Leu Phe Thr Cys Val Phe
    930                 935                 940

Cys Arg Gln Gly Phe Leu Glu Arg Ala Thr Leu Lys Lys His Met Leu
945                 950                 955                 960

Leu Ala His His Gln Val Gln Pro Phe Ala Pro His Gly Pro Gln Asn
                965                 970                 975

Ile Ala Ala Leu Ser Leu Val Pro Gly Cys Ser Pro Ser Ile Thr Ser
            980                 985                 990

Thr Gly Leu Ser Pro Phe Pro Arg  Lys Asp Asp Pro Thr  Ile Pro
        995                 1000                1005
```

<210> SEQ ID NO 18

<211> LENGTH: 4931
<212> TYPE: DNA
<213> ORGANISM: Homo sapiens

<400> SEQUENCE: 18
gagctgcaga agcgtaggga agaagctgaa gaaaaaaagg gggcgtctcc cctttaaaga 60
cttgcaaaga ttgagagaga aagagagaga gtcaagaaca gagaatcaga gagagagaga 120
gagtctgtgt ctctgggaaa gaagaacatc tctgcttcac agtgatttgc gctgggggag 180
aggcatcaat tggcttcgga cccaaggggg agacgagacc aggtcacccc ggttaagacc 240
aagtgagcgt tgcccctccc tctcccaact ctctacccgg gaatgtctcg gcgaaagcag 300
cggaaacccc aacagttaat ctcggactgc gaaggtccca gcgcgtctga gaacggtgat 360
gctagcgagg aggatcaccc ccaagtctgt gccaagtgct gcgcacaatt cactgaccca 420
actgaattcc tcgcccacca gaacgcatgt tctactgacc ctcctgtaat ggtgataatt 480
gggggccagg agaaccccaa caactcttcg gcctcctctg aaccccggcc tgagggtcac 540
aataatcctc aggtcatgga cacagagcat agcaaccccc cagattctgg gtcctccgtg 600
cccacggatc ccacctgggg cccagagagg agaggagagg agtctccagg gcatttcctg 660
gtcgctgcca caggtacagc ggctggggga ggcgggggcc tgatcttggc cagtcccaag 720
ctgggagcaa ccccattacc tccagaatcg acccctgcac cccctcctcc tccaccaccc 780
cctccgcccc caggggtagg cagtggccac ttgaatatcc ccctgatctt ggaagagcta 840
cgggtgctgc agcagcggca gatccatcag atgcagatga ctgagcaaat ctgcaggcag 900
gtgctgttgc ttggctcctt aggccagacg gtgggtgccc ctgccagtcc ctcagagcta 960
cctgggacag ggactgcctc ttccaccaag cccctactac ccctcttcag ccccatcaag 1020
cctgtccaaa ccagcaagac actggcatct tcctcctcct cctcctcttc ctcttcaggg 1080
gcagaaacgc ccaagcaggc cttcttccac ctttaccacc cactggggtc acagcatcct 1140
ttctctgctg gaggggttgg gcgaagccac aaacccaccc ctgccccttc cccagccttg 1200
ccaggcagca cagatcagct gattgcctcg cctcatctgg cattcccaag caccacggga 1260
ctactggcag cacagtgtct tggggcagcc cgaggccttg aggccactgc ctccccaggg 1320
ctcctgaagc caaagaatgg aagtggtgag ctgagctacg gagaagtgat gggtcccttg 1380
gagaagcctg gtggaaggca caaatgccgc ttctgtgcca aagtatttgg cagtgacagt 1440
gccctgcaga tccaccttcg ttcccacacg ggtgagaggc cctataagtg caatgtctgt 1500
ggaaaccgtt ttaccacccg tggcaacctc aaagtgcatt tccaccggca tcgtgagaag 1560
tacccacatg tgcagatgaa cccacaccca gtaccagagc acctagacta tgtcattacc 1620
agcagtggct tgccttatgg tatgtccgtg ccaccagaga aggccgagga ggaggcagcc 1680
actccaggtg gaggggttga gcgcaagcct ctggtggcct ccacaacagc actcagtgcc 1740
acagagagcc tgactctgct ctccaccagt gcaggcacag ccacggctcc aggactccct 1800
gctttcaata agtttgtgct catgaaagca gtggaaccca agaataaagc tgatgaaaac 1860
acccccccag ggagtgaggg ctcagccatc agtggagtgg cagaaagtag cacggcaact 1920
cgcatgcaac taagtaagtt ggtgacttca ctaccaagct gggcactgct taccaaccac 1980
ttcaagtcca ctggcagctt ccccttcccc tatgtgctag agcccttggg ggcctcaccc 2040
tctgagacat caaagctgca gcaactggta gaaaagattg accggcaagg agctgtggcg 2100
gtgacctcag ctgcctcagg agcccccacc acctctgccc ctgcaccttc atcctcagcc 2160
tcttctggac ctaaccagtg tgtcatctgt ctccgagtgc ttagctgtcc tcgggcccta 2220

-continued

```
cgccttcatt atggccaaca tggaggtgag aggcccttca aatgcaaagt gtgtggcaga   2280
gccttctcca ccaggggtaa tctgcgtgca catttcgtgg gccacaaggc cagtccagct   2340
gcccgggcac agaattcctg ccccatctgc cagaagaagt tcaccaatgc tgtcactctg   2400
cagcagcatg tccggatgca cctgggggc cagatcccca acggtggtac tgcactccct   2460
gaaggtggag gagctgctca ggagaatggc tccgagcaat ctacagtctc cggggcaggg   2520
agtttccccc agcagcagtc ccagcagcca tcaccggaag aggagttgtc tgaggaggag   2580
gaagaggagg atgaggaaga agaggaagat gtgactgatg aagattccct ggcagggaga   2640
ggctcagaga gtggaggtga gaaggcaata tcagtgagag gtgattcaga agaggcatct   2700
ggggcagagg aggaggtggg gacagtggcg gcagcagcca cagctgggaa ggagatggac   2760
agtaatgaga aaactactca acagtcttct ttgccaccac caccaccacc tgacagcctg   2820
gatcagcctc agccaatgga gcagggaagc agtggtgttt taggaggcaa ggaagagggg   2880
ggcaaaccgg agagaagctc aagtccggca tcagcactca ccccagaagg ggaagccacc   2940
agcgtgacct tggtagagga gctgagcctg caggaggcaa tgagaaagga gccaggagag   3000
agcagcagca gaaaggcctg cgaagtgtgt ggccaggcct ttccctccca ggcagctctg   3060
gaggagcatc agaagaccca ccccaaggag gggccgctct tcacttgtgt tttctgcagg   3120
cagggctttc ttgagcgggc taccctcaag aagcatatgc tcctggcaca ccaccaggta   3180
cagccctttg ccccccatgg ccctcagaat attgctgctc tttctctagt ccctggctgt   3240
tcgccttcca tcacctccac agggctctcc cccttttcccc gaaaagatga ccccacgatc   3300
ccatgagcct gtttttctgt acctgctgct ctttgtccca cagagcagaa acagcttcac   3360
aaaaggacct cccagagtta tgagccctga ttttgtcttt ttctctaagt tcttaacatg   3420
ttatgtccct agtggctttt ctgtagtccc tgagcttgga aattactgtg cttacaaggg   3480
gatggccccc taaggaattt ttcttccctc ctcattcttt gtacctgagg aacatagatt   3540
ctctgcagct ttctcaaggg gaaccctctc cagcttccct ggtgtgaccc ttcttccccc   3600
tcctctctcc tctccctttc cctttggtag gtgcacctga gcacctacat ttggcattgc   3660
agcctagcca aaaagggctg gcagctgtct ctggagggcc cagtgccact cctctggggt   3720
gacctttctg ctcagctggt gggtatgggt cccctatctt tctagaacca gtatgtggca   3780
ttcctgtcaa atggcctgcc catgaagccc tggaattcca gctccacctc cactaccact   3840
ccaagcctgg ccccaccagt gctgtttggc ctaggaactg tggctgggaa ggtgcctcca   3900
acaatgggat ccagggaagc caaggagaag acagcccccc tcctatttca gcctcctgca   3960
cccaaggcag tgcctgagaa gcccatcata gacaagaagt agcaaactgt acattccttc   4020
ttcctccccc tgctccagaa ggtgccggta ctgaagatgc tccagtaatt ggtgacccaa   4080
ccctaggaag tagggagaaa tgaaggaagg gcataggaaa attttcccag taaatcccct   4140
gatggtcaca ttaaggtaaa ggttttggct ggtcagtgtg ccaagacctc tccagcttct   4200
cattcatgat gacctctcaa agttgggaaa caagctgatt tcttgccaag aggtctccca   4260
ggagatattt gggaaatgtg aagttcgtat ctttaaggag catttttggt cagcatggtt   4320
gatgaactaa tgatgagaga gttaaggaat gttgctagaa catagggctt gctggtacct   4380
atgtgactaa gaaagggaca tgatgtaagg gaaaaggcct caaattcttg tgaatgtgga   4440
cattctcgtt aatattcttt tgggctaata gtgacatagt gtgcagaggt gtaccaggga   4500
tcatggggga tttcctagca ctagtatgct tctagtttta gataactccc tcctttattc   4560
```

-continued

```
cctggcccct tgtattttcc ttatcttcct ctttcaagac ccctacccat tttgcctatc   4620

cgtaggctgg ggcttgtgtc tttgtcattg tctggttctt aagagtccca gctccaggtg   4680

gcgtcctccc tgcctctccg tcttgtaatg agttgtagta tttactctta acataggatc   4740

atttggaaca ggagttctga ggaggagaga gtgagggttt tgctattgac tgacttgaac   4800

gatggcttct cctcaagctg taggctccag agcttcctaa cctagtaaaa tgtcaagaac   4860

agacgggaga tattagtgtc tttccctcta tcattaaagg tgttttaacc aaaaaaaaaa   4920

aaaaaaaaaa a                                                        4931
```

<210> SEQ ID NO 19
<211> LENGTH: 3616
<212> TYPE: PRT
<213> ORGANISM: Homo sapiens

<400> SEQUENCE: 19

```
Met Glu Thr Cys Asp Ser Pro Pro Ile Ser Arg Gln Glu Asn Gly Gln
1               5                   10                  15

Ser Thr Ser Lys Leu Cys Gly Thr Thr Gln Leu Asp Asn Glu Val Pro
            20                  25                  30

Glu Lys Val Ala Gly Met Glu Pro Asp Arg Glu Asn Ser Ser Thr Asp
        35                  40                  45

Asp Asn Leu Lys Thr Asp Glu Arg Lys Ser Glu Ala Leu Leu Gly Phe
    50                  55                  60

Ser Val Glu Asn Ala Ala Ala Thr Gln Val Thr Ser Ala Lys Glu Ile
65                  70                  75                  80

Pro Cys Asn Glu Cys Ala Thr Ser Phe Pro Ser Leu Gln Lys Tyr Met
                85                  90                  95

Glu His His Cys Pro Asn Ala Arg Leu Pro Val Leu Lys Asp Asp Asn
            100                 105                 110

Glu Ser Glu Ile Ser Glu Leu Glu Asp Ser Asp Val Glu Asn Leu Thr
        115                 120                 125

Gly Glu Ile Val Tyr Gln Pro Asp Gly Ser Ala Tyr Ile Ile Glu Asp
    130                 135                 140

Ser Lys Glu Ser Gly Gln Asn Ala Gln Thr Gly Ala Asn Ser Lys Leu
145                 150                 155                 160

Phe Ser Thr Ala Met Phe Leu Asp Ser Leu Ala Ser Ala Gly Glu Lys
                165                 170                 175

Ser Asp Gln Ser Ala Ser Ala Pro Met Ser Phe Tyr Pro Gln Ile Ile
            180                 185                 190

Asn Thr Phe His Ile Ala Ser Ser Leu Gly Lys Pro Phe Thr Ala Asp
        195                 200                 205

Gln Ala Phe Pro Asn Thr Ser Ala Leu Ala Gly Val Gly Pro Val Leu
    210                 215                 220

His Ser Phe Arg Val Tyr Asp Leu Arg His Lys Arg Glu Lys Asp Tyr
225                 230                 235                 240

Leu Thr Ser Asp Gly Ser Ala Lys Asn Ser Cys Val Ser Lys Asp Val
                245                 250                 255

Pro Asn Asn Val Asp Leu Ser Lys Phe Asp Gly Cys Val Ser Asp Gly
            260                 265                 270

Lys Arg Lys Pro Val Leu Met Cys Phe Leu Cys Lys Leu Ser Phe Gly
        275                 280                 285

Tyr Ile Arg Ser Phe Val Thr His Ala Val His Asp His Arg Met Thr
    290                 295                 300
```

-continued

```
Leu Asn Asp Glu Glu Gln Lys Leu Leu Ser Asn Lys Cys Val Ser Ala
305                 310                 315                 320

Ile Ile Gln Gly Ile Gly Lys Asp Lys Glu Pro Leu Ile Ser Phe Leu
                325                 330                 335

Glu Pro Lys Lys Ser Thr Ser Val Tyr Pro His Phe Ser Thr Thr Asn
            340                 345                 350

Leu Ile Gly Pro Asp Pro Thr Phe Arg Gly Leu Trp Ser Ala Phe His
        355                 360                 365

Val Glu Asn Gly Asp Ser Leu Pro Ala Gly Phe Ala Phe Leu Lys Gly
    370                 375                 380

Ser Ala Ser Thr Ser Ser Ser Ala Glu Gln Pro Leu Gly Ile Thr Gln
385                 390                 395                 400

Met Pro Lys Ala Glu Val Asn Leu Gly Gly Leu Ser Ser Leu Val Val
                405                 410                 415

Asn Thr Pro Ile Thr Ser Val Ser Leu Ser His Ser Ser Ser Glu Ser
            420                 425                 430

Ser Lys Met Ser Glu Ser Lys Asp Gln Glu Asn Asn Cys Glu Arg Pro
        435                 440                 445

Lys Glu Ser Asn Val Leu His Pro Asn Gly Glu Cys Pro Val Lys Ser
    450                 455                 460

Glu Pro Thr Glu Pro Gly Asp Glu Asp Glu Glu Asp Ala Tyr Ser Asn
465                 470                 475                 480

Glu Leu Asp Asp Glu Glu Val Leu Gly Glu Leu Thr Asp Ser Ile Gly
                485                 490                 495

Asn Lys Asp Phe Pro Leu Leu Asn Gln Ser Ile Ser Pro Leu Ser Ser
            500                 505                 510

Ser Val Leu Lys Phe Ile Glu Lys Gly Thr Ser Ser Ser Ser Ala Thr
        515                 520                 525

Val Ser Asp Asp Thr Glu Lys Lys Lys Gln Thr Ala Ala Val Arg Ala
    530                 535                 540

Ser Gly Ser Val Ala Ser Asn Tyr Gly Ile Ser Gly Lys Asp Phe Ala
545                 550                 555                 560

Asp Ala Ser Ala Ser Lys Asp Ser Ala Thr Ala Ala His Pro Ser Glu
                565                 570                 575

Ile Ala Arg Gly Asp Glu Asp Ser Ser Ala Thr Pro His Gln His Gly
            580                 585                 590

Phe Thr Pro Ser Thr Pro Gly Thr Pro Gly Pro Gly Gly Asp Gly Ser
        595                 600                 605

Pro Gly Ser Gly Ile Glu Cys Pro Lys Cys Asp Thr Val Leu Gly Ser
    610                 615                 620

Ser Arg Ser Leu Gly Gly His Met Thr Met Met His Ser Arg Asn Ser
625                 630                 635                 640

Cys Lys Thr Leu Lys Cys Pro Lys Cys Asn Trp His Tyr Lys Tyr Gln
                645                 650                 655

Gln Thr Leu Glu Ala His Met Lys Glu Lys His Pro Glu Pro Gly Gly
            660                 665                 670

Ser Cys Val Tyr Cys Lys Thr Gly Gln Pro His Pro Arg Leu Ala Arg
        675                 680                 685

Gly Glu Ser Tyr Thr Cys Gly Tyr Lys Pro Phe Arg Cys Glu Val Cys
    690                 695                 700

Asn Tyr Ser Thr Thr Thr Lys Gly Asn Leu Ser Ile His Met Gln Ser
705                 710                 715                 720

Asp Lys His Leu Asn Asn Val Gln Asn Leu Gln Asn Gly Asn Gly Glu
```

```
                725                 730                 735

Gln Val Phe Gly His Ser Ala Pro Ala Pro Asn Thr Ser Leu Ser Gly
            740                 745                 750

Cys Gly Thr Pro Ser Pro Ser Lys Pro Lys Gln Lys Pro Thr Trp Arg
        755                 760                 765

Cys Glu Val Cys Asp Tyr Glu Thr Asn Val Ala Arg Asn Leu Arg Ile
    770                 775                 780

His Met Thr Ser Glu Lys His Met His Asn Met Met Leu Leu Gln Gln
785                 790                 795                 800

Asn Met Lys Gln Ile Gln His Asn Leu His Leu Gly Leu Ala Pro Ala
                805                 810                 815

Glu Ala Glu Leu Tyr Gln Tyr Tyr Leu Ala Gln Asn Ile Gly Leu Thr
            820                 825                 830

Gly Met Lys Leu Glu Asn Pro Ala Asp Pro Gln Leu Met Ile Asn Pro
        835                 840                 845

Phe Gln Leu Asp Pro Ala Thr Ala Ala Ala Leu Ala Pro Gly Leu Val
    850                 855                 860

Asn Asn Glu Leu Pro Pro Glu Ile Arg Leu Ala Ser Gly Gln Leu Met
865                 870                 875                 880

Gly Asp Asp Leu Ser Leu Leu Thr Ala Gly Glu Leu Ser Pro Tyr Ile
                885                 890                 895

Ser Asp Pro Ala Leu Lys Leu Phe Gln Cys Ala Val Cys Asn Lys Phe
            900                 905                 910

Thr Ser Asp Ser Leu Glu Ala Leu Ser Val His Val Ser Ser Glu Arg
        915                 920                 925

Ser Leu Pro Glu Glu Glu Trp Arg Ala Val Ile Gly Asp Ile Tyr Gln
    930                 935                 940

Cys Lys Leu Cys Asn Tyr Asn Thr Gln Leu Lys Ala Asn Phe Gln Leu
945                 950                 955                 960

His Cys Lys Thr Asp Lys His Met Gln Lys Tyr Gln Leu Val Ala His
                965                 970                 975

Ile Lys Glu Gly Gly Lys Ser Asn Glu Trp Arg Leu Lys Cys Ile Ala
            980                 985                 990

Ile Gly Asn Pro Val His Leu Lys  Cys Asn Ala Cys Asp  Tyr Tyr Thr
        995                 1000                1005

Asn Ser  Val Asp Lys Leu Arg  Leu His Thr Thr Asn  His Arg His
    1010                 1015                 1020

Glu Ala  Ala Leu Lys Leu Tyr  Lys His Leu Gln Lys  Gln Glu Gly
    1025                 1030                 1035

Ala Val  Asn Pro Glu Ser Cys  Tyr Tyr Tyr Cys Ala  Val Cys Asp
    1040                 1045                 1050

Tyr Thr  Thr Lys Val Lys Leu  Asn Leu Val Gln His  Val Arg Ser
    1055                 1060                 1065

Val Lys  His Gln Gln Thr Glu  Gly Leu Arg Lys Leu  Gln Leu His
    1070                 1075                 1080

Gln Gln  Gly Leu Ala Pro Glu  Glu Asp Asn Leu Ser  Glu Ile Phe
    1085                 1090                 1095

Phe Val  Lys Asp Cys Pro Pro  Asn Glu Leu Glu Thr  Ala Ser Leu
    1100                 1105                 1110

Gly Ala  Arg Thr Cys Asp Asp  Asp Leu Thr Glu Gln  Gln Leu Arg
    1115                 1120                 1125

Ser Thr  Ser Glu Glu Gln Ser  Glu Glu Ala Glu Gly  Ala Ile Lys
    1130                 1135                 1140
```

```
Pro Thr  Ala Val Ala Glu Asp  Asp Glu Lys Asp Thr  Ser Glu Arg
    1145                 1150                 1155

Asp Asn  Ser Glu Gly Lys Asn  Ser Asn Lys Asp Ser  Gly Ile Ile
    1160                 1165                 1170

Thr Pro  Glu Lys Glu Leu Lys  Val Ser Val Ala Gly  Gly Thr Gln
    1175                 1180                 1185

Pro Leu  Leu Leu Ala Lys Glu  Glu Asp Val Ala Thr  Lys Arg Ser
    1190                 1195                 1200

Lys Pro  Thr Glu Asp Asn Lys  Phe Cys His Glu Gln  Phe Tyr Gln
    1205                 1210                 1215

Cys Pro  Tyr Cys Asn Tyr Asn  Ser Arg Asp Gln Ser  Arg Ile Gln
    1220                 1225                 1230

Met His  Val Leu Ser Gln His  Ser Val Gln Pro Val  Ile Cys Cys
    1235                 1240                 1245

Pro Leu  Cys Gln Asp Val Leu  Ser Asn Lys Met His  Leu Gln Leu
    1250                 1255                 1260

His Leu  Thr His Leu His Ser  Val Ser Pro Asp Cys  Val Glu Lys
    1265                 1270                 1275

Leu Leu  Met Thr Val Pro Val  Pro Asp Val Met Met  Pro Asn Ser
    1280                 1285                 1290

Met Leu  Leu Pro Ala Ala Ala  Ser Glu Lys Ser Glu  Arg Asp Thr
    1295                 1300                 1305

Pro Ala  Ala Val Thr Ala Glu  Gly Ser Gly Lys Tyr  Ser Gly Glu
    1310                 1315                 1320

Ser Pro  Met Asp Asp Lys Ser  Met Ala Gly Leu Glu  Asp Ser Lys
    1325                 1330                 1335

Ala Asn  Val Glu Val Lys Asn  Glu Glu Gln Lys Pro  Thr Lys Glu
    1340                 1345                 1350

Pro Leu  Glu Val Ser Glu Trp  Asn Lys Asn Ser Ser  Lys Asp Val
    1355                 1360                 1365

Lys Ile  Pro Asp Thr Leu Gln  Asp Gln Leu Asn Glu  Gln Gln Lys
    1370                 1375                 1380

Arg Gln  Pro Leu Ser Val Ser  Asp Arg His Val Tyr  Lys Tyr Arg
    1385                 1390                 1395

Cys Asn  His Cys Ser Leu Ala  Phe Lys Thr Met Gln  Lys Leu Gln
    1400                 1405                 1410

Ile His  Ser Gln Tyr His Ala  Ile Arg Ala Ala Thr  Met Cys Asn
    1415                 1420                 1425

Leu Cys  Gln Arg Ser Phe Arg  Thr Phe Gln Ala Leu  Lys Lys His
    1430                 1435                 1440

Leu Glu  Ala Gly His Pro Glu  Leu Ser Glu Ala Glu  Leu Gln Gln
    1445                 1450                 1455

Leu Tyr  Ala Ser Leu Pro Val  Asn Gly Glu Leu Trp  Ala Glu Ser
    1460                 1465                 1470

Glu Thr  Met Ser Gln Asp Asp  His Gly Leu Glu Gln  Glu Met Glu
    1475                 1480                 1485

Arg Glu  Tyr Glu Val Asp His  Glu Gly Lys Ala Ser  Pro Val Gly
    1490                 1495                 1500

Ser Asp  Ser Ser Ser Ile Pro  Asp Asp Met Gly Ser  Glu Pro Lys
    1505                 1510                 1515

Arg Thr  Leu Pro Phe Arg Lys  Gly Pro Asn Phe Thr  Met Glu Lys
    1520                 1525                 1530
```

-continued

```
Phe Leu  Asp Pro Ser Arg Pro  Tyr Lys Cys Thr Val  Cys Lys Glu
    1535                 1540                 1545

Ser Phe  Thr Gln Lys Asn Ile  Leu Leu Val His Tyr  Asn Ser Val
    1550                 1555                 1560

Ser His  Leu His Lys Leu Lys  Lys Val Leu Gln Glu  Ala Ser Ser
    1565                 1570                 1575

Pro Val  Pro Gln Glu Thr Asn  Ser Asn Thr Asp Asn  Lys Pro Tyr
    1580                 1585                 1590

Lys Cys  Ser Ile Cys Asn Val  Ala Tyr Ser Gln Ser  Ser Thr Leu
    1595                 1600                 1605

Glu Ile  His Met Arg Ser Val  Leu His Gln Thr Lys  Ala Arg Ala
    1610                 1615                 1620

Ala Lys  Leu Glu Pro Ser Gly  His Val Ala Gly Gly  His Ser Ile
    1625                 1630                 1635

Ala Ala  Asn Val Asn Ser Pro  Gly Gln Gly Met Leu  Asp Ser Met
    1640                 1645                 1650

Ser Leu  Ala Ala Val Asn Ser  Lys Asp Thr His Leu  Asp Ala Lys
    1655                 1660                 1665

Glu Leu  Asn Lys Lys Gln Thr  Pro Asp Leu Ile Ser  Ala Gln Pro
    1670                 1675                 1680

Ala His  His Pro Pro Gln Ser  Pro Ala Gln Ile Gln  Met Gln Leu
    1685                 1690                 1695

Gln His  Glu Leu Gln Gln Gln  Ala Ala Phe Phe Gln  Pro Gln Phe
    1700                 1705                 1710

Leu Asn  Pro Ala Phe Leu Pro  His Phe Pro Met Thr  Pro Glu Ala
    1715                 1720                 1725

Leu Leu  Gln Phe Gln Gln Pro  Gln Phe Leu Phe Pro  Phe Tyr Ile
    1730                 1735                 1740

Pro Gly  Thr Glu Phe Ser Leu  Gly Pro Asp Leu Gly  Leu Pro Gly
    1745                 1750                 1755

Ser Ala  Thr Phe Gly Met Pro  Gly Met Thr Gly Met  Ala Gly Ser
    1760                 1765                 1770

Leu Leu  Glu Asp Leu Lys Gln  Gln Ile Gln Thr Gln  His His Val
    1775                 1780                 1785

Gly Gln  Thr Gln Leu Gln Ile  Leu Gln Gln Gln Ala  Gln Gln Tyr
    1790                 1795                 1800

Gln Ala  Thr Gln Pro Gln Leu  Gln Pro Gln Lys Gln  Gln Gln Gln
    1805                 1810                 1815

Pro Pro  Pro Pro Gln Gln Gln  Gln Gln Gln Gln Ala  Ser Lys Leu
    1820                 1825                 1830

Leu Lys  Gln Glu Gln Ser Asn  Ile Val Ser Ala Asp  Cys Gln Ile
    1835                 1840                 1845

Met Lys  Asp Val Pro Ser Tyr  Lys Glu Ala Glu Asp  Ile Ser Glu
    1850                 1855                 1860

Lys Pro  Glu Lys Pro Lys Gln  Glu Phe Ile Ser Glu  Gly Glu Gly
    1865                 1870                 1875

Leu Lys  Glu Gly Lys Asp Thr  Lys Lys Gln Lys Ser  Leu Glu Pro
    1880                 1885                 1890

Ser Ile  Pro Pro Pro Arg Ile  Ala Ser Gly Ala Arg  Gly Asn Ala
    1895                 1900                 1905

Ala Lys  Ala Leu Leu Glu Asn  Phe Gly Phe Glu Leu  Val Ile Gln
    1910                 1915                 1920

Tyr Asn  Glu Asn Arg Gln Lys  Val Gln Lys Lys Gly  Lys Ser Gly
```

```
    1925                1930                1935

Glu Gly  Glu Asn Thr Asp Lys  Leu Glu Cys Gly Thr  Cys Gly Lys
    1940                1945                1950

Leu Phe  Ser Asn Val Leu Ile  Leu Lys Ser His Gln  Glu His Val
    1955                1960                1965

His Gly  Gln Phe Phe Pro Tyr  Ala Ala Leu Glu Lys  Phe Ala Arg
    1970                1975                1980

Gln Tyr  Arg Glu Ala Tyr Asp  Lys Leu Tyr Pro Ile  Ser Pro Ser
    1985                1990                1995

Ser Pro  Glu Thr Pro Pro Pro  Pro Pro Pro Pro Pro  Pro Leu Pro
    2000                2005                2010

Pro Ala  Pro Pro Gln Pro Ser  Ser Met Gly Pro Val  Lys Ile Pro
    2015                2020                2025

Asn Thr  Val Ser Thr Pro Leu  Gln Ala Pro Pro Pro  Thr Pro Pro
    2030                2035                2040

Pro Pro  Pro Pro Pro Pro Pro  Pro Pro Pro Pro Pro  Pro Pro Pro
    2045                2050                2055

Pro Pro  Pro Ser Ala Pro Pro  Gln Val Gln Leu Pro  Val Ser Leu
    2060                2065                2070

Asp Leu  Pro Leu Phe Pro Ser  Ile Met Met Gln Pro  Val Gln His
    2075                2080                2085

Pro Ala  Leu Pro Pro Gln Leu  Ala Leu Gln Leu Pro  Gln Met Asp
    2090                2095                2100

Ala Leu  Ser Ala Asp Leu Thr  Gln Leu Cys Gln Gln  Gln Leu Gly
    2105                2110                2115

Leu Asp  Pro Asn Phe Leu Arg  His Ser Gln Phe Lys  Arg Pro Arg
    2120                2125                2130

Thr Arg  Ile Thr Asp Asp Gln  Leu Lys Ile Leu Arg  Ala Tyr Phe
    2135                2140                2145

Asp Ile  Asn Asn Ser Pro Ser  Glu Glu Gln Ile Gln  Glu Met Ala
    2150                2155                2160

Glu Lys  Ser Gly Leu Ser Gln  Lys Val Ile Lys His  Trp Phe Arg
    2165                2170                2175

Asn Thr  Leu Phe Lys Glu Arg  Gln Arg Asn Lys Asp  Ser Pro Tyr
    2180                2185                2190

Asn Phe  Ser Asn Pro Pro Ile  Thr Val Leu Glu Asp  Ile Arg Ile
    2195                2200                2205

Asp Pro  Gln Pro Thr Ser Leu  Glu His Tyr Lys Ser  Asp Ala Ser
    2210                2215                2220

Phe Ser  Lys Arg Ser Ser Arg  Thr Arg Phe Thr Asp  Tyr Gln Leu
    2225                2230                2235

Arg Val  Leu Gln Asp Phe Phe  Asp Thr Asn Ala Tyr  Pro Lys Asp
    2240                2245                2250

Asp Glu  Ile Glu Gln Leu Ser  Thr Val Leu Asn Leu  Pro Thr Arg
    2255                2260                2265

Val Ile  Val Val Trp Phe Gln  Asn Ala Arg Gln Lys  Ala Arg Lys
    2270                2275                2280

Ser Tyr  Glu Asn Gln Ala Glu  Thr Lys Asp Asn Glu  Lys Arg Glu
    2285                2290                2295

Leu Thr  Asn Glu Arg Tyr Ile  Arg Thr Ser Asn Met  Gln Tyr Gln
    2300                2305                2310

Cys Lys  Lys Cys Asn Val Val  Phe Pro Arg Ile Phe  Asp Leu Ile
    2315                2320                2325
```

```
Thr His Gln Lys Lys Gln Cys Tyr Lys Asp Glu Asp Asp Asp Ala
    2330                2335                2340

Gln Asp Glu Ser Gln Thr Glu Asp Ser Met Asp Ala Thr Asp Gln
    2345                2350                2355

Val Val Tyr Lys His Cys Thr Val Ser Gly Gln Thr Asp Ala Ala
    2360                2365                2370

Lys Asn Ala Ala Ala Pro Ala Ala Ser Ser Gly Ser Gly Thr Ser
    2375                2380                2385

Thr Pro Leu Ile Pro Ser Pro Lys Pro Glu Pro Glu Lys Thr Ser
    2390                2395                2400

Pro Lys Pro Glu Tyr Pro Ala Glu Lys Pro Lys Gln Ser Asp Pro
    2405                2410                2415

Ser Pro Pro Ser Gln Gly Thr Lys Pro Ala Leu Pro Leu Ala Ser
    2420                2425                2430

Thr Ser Ser Asp Pro Pro Gln Ala Ser Thr Ala Gln Pro Gln Pro
    2435                2440                2445

Gln Pro Gln Pro Pro Lys Gln Pro Gln Leu Ile Gly Arg Pro Pro
    2450                2455                2460

Ser Ala Ser Gln Thr Pro Val Pro Ser Ser Pro Leu Gln Ile Ser
    2465                2470                2475

Met Thr Ser Leu Gln Asn Ser Leu Pro Pro Gln Leu Leu Gln Tyr
    2480                2485                2490

Gln Cys Asp Gln Cys Thr Val Ala Phe Pro Thr Leu Glu Leu Trp
    2495                2500                2505

Gln Glu His Gln His Met His Phe Leu Ala Ala Gln Asn Gln Phe
    2510                2515                2520

Leu His Ser Pro Phe Leu Glu Arg Pro Met Asp Met Pro Tyr Met
    2525                2530                2535

Ile Phe Asp Pro Asn Asn Pro Leu Met Thr Gly Gln Leu Leu Gly
    2540                2545                2550

Ser Ser Leu Thr Gln Met Pro Pro Gln Ala Ser Ser Ser His Thr
    2555                2560                2565

Thr Ala Pro Thr Thr Val Ala Ala Ser Leu Lys Arg Lys Leu Asp
    2570                2575                2580

Asp Lys Glu Asp Asn Asn Cys Ser Glu Lys Glu Gly Gly Asn Ser
    2585                2590                2595

Gly Glu Asp Gln His Arg Asp Lys Arg Leu Arg Thr Thr Ile Thr
    2600                2605                2610

Pro Glu Gln Leu Glu Ile Leu Tyr Glu Lys Tyr Leu Leu Asp Ser
    2615                2620                2625

Asn Pro Thr Arg Lys Met Leu Asp His Ile Ala Arg Glu Val Gly
    2630                2635                2640

Leu Lys Lys Arg Val Val Gln Val Trp Phe Gln Asn Thr Arg Ala
    2645                2650                2655

Arg Glu Arg Lys Gly Gln Phe Arg Ala Val Gly Pro Ala Gln Ser
    2660                2665                2670

His Lys Arg Cys Pro Phe Cys Arg Ala Leu Phe Lys Ala Lys Ser
    2675                2680                2685

Ala Leu Glu Ser His Ile Arg Ser Arg His Trp Asn Glu Gly Lys
    2690                2695                2700

Gln Ala Gly Tyr Ser Leu Pro Pro Ser Pro Leu Ile Ser Thr Glu
    2705                2710                2715
```

Asp Gly Gly Glu Ser Pro Gln Lys Tyr Ile Tyr Phe Asp Tyr Pro
2720 2725 2730

Ser Leu Pro Leu Thr Lys Ile Asp Leu Ser Ser Glu Asn Glu Leu
2735 2740 2745

Ala Ser Thr Val Ser Thr Pro Val Ser Lys Thr Ala Glu Leu Ser
2750 2755 2760

Pro Lys Asn Leu Leu Ser Pro Ser Ser Phe Lys Ala Glu Cys Ser
2765 2770 2775

Glu Asp Val Glu Asn Leu Asn Ala Pro Pro Ala Glu Ala Gly Tyr
2780 2785 2790

Asp Gln Asn Lys Thr Asp Phe Asp Glu Thr Ser Ser Ile Asn Thr
2795 2800 2805

Ala Ile Ser Asp Ala Thr Thr Gly Asp Glu Gly Asn Thr Glu Met
2810 2815 2820

Glu Ser Thr Thr Gly Ser Ser Gly Asp Val Lys Pro Ala Leu Ser
2825 2830 2835

Pro Lys Glu Pro Lys Thr Leu Asp Thr Leu Pro Lys Pro Ala Thr
2840 2845 2850

Thr Pro Thr Thr Glu Val Cys Asp Asp Lys Phe Leu Phe Ser Leu
2855 2860 2865

Thr Ser Pro Ser Ile His Phe Asn Asp Lys Asp Gly Asp His Asp
2870 2875 2880

Gln Ser Phe Tyr Ile Thr Asp Asp Pro Asp Asp Asn Ala Asp Arg
2885 2890 2895

Ser Glu Thr Ser Ser Ile Ala Asp Pro Ser Ser Pro Asn Pro Phe
2900 2905 2910

Gly Ser Ser Asn Pro Phe Lys Ser Lys Ser Asn Asp Arg Pro Gly
2915 2920 2925

His Lys Arg Phe Arg Thr Gln Met Ser Asn Leu Gln Leu Lys Val
2930 2935 2940

Leu Lys Ala Cys Phe Ser Asp Tyr Arg Thr Pro Thr Met Gln Glu
2945 2950 2955

Cys Glu Met Leu Gly Asn Glu Ile Gly Leu Pro Lys Arg Val Val
2960 2965 2970

Gln Val Trp Phe Gln Asn Ala Arg Ala Lys Glu Lys Lys Phe Lys
2975 2980 2985

Ile Asn Ile Gly Lys Pro Phe Met Ile Asn Gln Gly Gly Thr Glu
2990 2995 3000

Gly Thr Lys Pro Glu Cys Thr Leu Cys Gly Val Lys Tyr Ser Ala
3005 3010 3015

Arg Leu Ser Ile Arg Asp His Ile Phe Ser Lys Gln His Ile Ser
3020 3025 3030

Lys Val Arg Glu Thr Val Gly Ser Gln Leu Asp Arg Glu Lys Asp
3035 3040 3045

Tyr Leu Ala Pro Thr Thr Val Arg Gln Leu Met Ala Gln Gln Glu
3050 3055 3060

Leu Asp Arg Ile Lys Lys Ala Ser Asp Val Leu Gly Leu Thr Val
3065 3070 3075

Gln Gln Pro Gly Met Met Asp Ser Ser Ser Leu His Gly Ile Ser
3080 3085 3090

Leu Pro Thr Ala Tyr Pro Gly Leu Pro Gly Leu Pro Pro Val Leu
3095 3100 3105

Leu Pro Gly Met Asn Gly Pro Ser Ser Leu Pro Gly Phe Pro Gln 3110 3115 3120

Asn Ser Asn Thr Leu Thr Pro Pro Gly Ala Gly Met Leu Gly Phe
3125 3130 3135

Pro Thr Ser Ala Thr Ser Ser Pro Ala Leu Ser Leu Ser Ser Ala
3140 3145 3150

Pro Thr Lys Pro Leu Leu Gln Thr Pro Pro Pro Pro Pro Pro Pro
3155 3160 3165

Pro Pro Pro Pro Pro Ser Ser Ser Leu Ser Gly Gln Gln Thr Glu
3170 3175 3180

Gln Gln Asn Lys Glu Ser Glu Lys Lys Gln Thr Lys Pro Asn Lys
3185 3190 3195

Val Lys Lys Ile Lys Glu Glu Glu Leu Glu Ala Thr Lys Pro Glu
3200 3205 3210

Lys His Pro Lys Lys Glu Glu Lys Ile Ser Ser Ala Leu Ser Val
3215 3220 3225

Leu Gly Lys Val Val Gly Glu Thr His Val Asp Pro Ile Gln Leu
3230 3235 3240

Gln Ala Leu Gln Asn Ala Ile Ala Gly Asp Pro Ala Ser Phe Ile
3245 3250 3255

Gly Gly Gln Phe Leu Pro Tyr Phe Ile Pro Gly Phe Ala Ser Tyr
3260 3265 3270

Phe Thr Pro Gln Leu Pro Gly Thr Val Gln Gly Gly Tyr Phe Pro
3275 3280 3285

Pro Val Cys Gly Met Glu Ser Leu Phe Pro Tyr Gly Pro Thr Met
3290 3295 3300

Pro Gln Thr Leu Ala Gly Leu Ser Pro Gly Ala Leu Leu Gln Gln
3305 3310 3315

Tyr Gln Gln Tyr Gln Gln Asn Leu Gln Glu Ser Leu Gln Lys Gln
3320 3325 3330

Gln Lys Gln Gln Gln Glu Gln Gln Gln Lys Pro Val Gln Ala Lys
3335 3340 3345

Thr Ser Lys Val Glu Ser Asp Gln Pro Gln Asn Ser Asn Asp Ala
3350 3355 3360

Ser Glu Thr Lys Glu Asp Lys Ser Thr Ala Thr Glu Ser Thr Lys
3365 3370 3375

Glu Glu Pro Gln Leu Glu Ser Lys Ser Ala Asp Phe Ser Asp Thr
3380 3385 3390

Tyr Val Val Pro Phe Val Lys Tyr Glu Phe Ile Cys Arg Lys Cys
3395 3400 3405

Gln Met Met Phe Thr Asp Glu Asp Ala Ala Val Asn His Gln Lys
3410 3415 3420

Ser Phe Cys Tyr Phe Gly Gln Pro Leu Ile Asp Pro Gln Glu Thr
3425 3430 3435

Val Leu Arg Val Pro Val Ser Lys Tyr Gln Cys Leu Ala Cys Asp
3440 3445 3450

Val Ala Ile Ser Gly Asn Glu Ala Leu Ser Gln His Leu Gln Ser
3455 3460 3465

Ser Leu His Lys Glu Lys Thr Ile Lys Gln Ala Met Arg Asn Ala
3470 3475 3480

Lys Glu His Val Arg Leu Leu Pro His Ser Val Cys Ser Pro Asn
3485 3490 3495

Pro Asn Thr Thr Ser Thr Ser Gln Ser Ala Ala Ser Ser Asn Asn
3500 3505 3510

```
Thr Tyr  Pro His Leu Ser Cys  Phe Ser Met Lys Ser  Trp Pro Asn
    3515                 3520                 3525

Ile Leu  Phe Gln Ala Ser Ala  Arg Arg Ala Ala Ser  Pro Pro Ser
    3530                 3535                 3540

Ser Pro  Pro Ser Leu Ser Leu  Pro Ser Thr Val Thr  Ser Ser Leu
    3545                 3550                 3555

Cys Ser  Thr Ser Gly Val Gln  Thr Ser Leu Pro Thr  Glu Ser Cys
    3560                 3565                 3570

Ser Asp  Glu Ser Asp Ser Glu  Leu Ser Gln Lys Leu  Glu Asp Leu
    3575                 3580                 3585

Asp Asn  Ser Leu Glu Val Lys  Ala Lys Pro Ala Ser  Gly Leu Asp
    3590                 3595                 3600

Gly Asn  Phe Asn Ser Ile Arg  Met Asp Met Phe Ser  Val
    3605                 3610                 3615
```

<210> SEQ ID NO 20
<211> LENGTH: 13975
<212> TYPE: DNA
<213> ORGANISM: Homo sapiens

<400> SEQUENCE: 20

```
attttttaa acagggctaa aacgataata attagcagaa taaagacata tcggattttc      60

atttcctttc ctccttttcc caacccttc acaaccaaac agcgagaccg cggtcggcac     120

atgctttaac tcctcccgga cccccgagga ccgctccatg ccccccactt tctgctccag     180

cgtttttatt ttcacccaat aaagttcgag gattattttt tattttttt gtttttttaa     240

tgaaccctct cgttttactt ggatgtgatc agctgtaagt aaaataaaag caaaacaaaa     300

aagaggcgaa gatcgagtag gaactgcagg ggaaatggaa agtccctgac aggctggatg     360

aaatgagatc cccatgtagc aattgccatg gaaacctgtg actcccctcc tatctcaagg     420

caggaaaatg ggcagagcac atcaaagcta tgtggaacga cacaacttga taatgaggtg     480

ccagagaaag ttgcagggat ggagcctgac agggaaaaca gctccacaga tgacaacctg     540

aaaacggatg agcgcaaaag tgaagccttg ctgggtttca gcgttgagaa tgcagctgcc     600

actcaggtta cctcagcaaa ggagataccc tgcaacgaat gtgccacttc ttttcccagt     660

ttacagaaat acatggaaca ccactgccct aatgcccgcc ttcctgtcct gaaggatgac     720

aacgagagcg agatcagcga gttagaggac agtgacgtgg aaaatctaac aggggagatc     780

gtttaccagc ctgatgggtc agcatatata attgaggact ccaaagaaag tgggcagaat     840

gcacagactg gggcaaatag caaactcttt tctacagcga tgttcctgga ctccctggca     900

tctgctggag agaagagtga tcagtctgct tctgcaccta tgtcgttcta cccacagatc     960

atcaacactt ttcatatcgc ttcatccctc gggaaaccat ttacagccga tcaggctttc    1020

ccaaatacct cagcattagc aggagttggt cctgtgttgc acagtttccg tgtctatgat    1080

ctccgacaca agagagagaa agactatcta accagtgatg gctcagccaa aaactcctgt    1140

gtgtccaaag atgtccctaa caatgtggac ttgtccaaat tcgatggttg tgttagcgat    1200

gggaaaagga aacctgtttt aatgtgtttc ttgtgcaagt tgtcttttgg ttatatcagg    1260

tcatttgtaa cccatgctgt gcatgatcat cggatgaccc tcaatgacga ggagcagaag    1320

ctcctcagta ataaatgcgt ctccgccata atacagggga ttggcaaaga caaagaacct    1380

cttataagct ttctggaacc aaaaaaatcc acttctgttt atccccattt ttctactaca    1440

aacctcatag gacccgatcc aaccttccgc ggtttatgga gcgcttttca tgttgaaaat    1500
```

```
ggtgactctt tgccggctgg ctttgccttc ttaaaaggaa gcgcgagcac ctcgagctca   1560
gcagagcagc cgctggggat tacccaaatg ccaaaggctg aagtgaatct ggggggggctg  1620
tctagtttag tagtgaacac cccaattacc tctgtctccc tcagccactc atcgtctgag   1680
tctagcaaga tgtcagagag caaagaccaa gagaacaact gtgaaaggcc aaaagaaagc   1740
aacgttttac acccaaacgg ggagtgccct gtcaaaagtg aacccactga accgggagat   1800
gaggatgaag aagatgcgta ctccaatgaa cttgatgacg aggaagtatt aggtgaactc   1860
accgatagta ttggtaacaa agatttccct ctcttaaacc aaagcatttc tcctttatca   1920
tccagtgtgc taaaatttat tgaaaagggt acctcgtcct cctcggcgac tgtttctgat   1980
gacacagaaa agaaaaaaca gactgctgct gttagggcca gtggcagtgt tgctagtaac   2040
tatggcatca gtggcaagga ctttgcagac gcaagtgcca gtaaagacag tgccacagct   2100
gctcatccaa gtgaaatagc ccggggagac gaagacagtt cagccactcc tcaccagcat   2160
ggctttaccc cgagtactcc tggcacacca gggcctggag gagacggctc accgggcagt   2220
ggcatcgagt gtccaaagtg cgacactgtg ttggggtctt cgaggtctct tggtggtcat   2280
atgactatga tgcactcgag gaactcatgc aaaaccctca aatgtcctaa atgtaactgg   2340
cactacaaat atcagcagac cctggaggcc catatgaagg agaaacaccc tgagccgggt   2400
ggctcttgtg tttattgtaa gactggacag cctcacccca ggcttgcccg gggtgagagt   2460
tacacgtgtg gctataaacc cttccgttgt gaggtttgta actactctac cactaccaaa   2520
ggcaacctca gtattcatat gcagtcggac aagcacctga acaatgttca gaatctccaa   2580
aatggcaatg gtgagcaggt gtttggccac tctgccccag cccccaacac cagcctcagt   2640
ggctgcggaa caccctctcc gtccaaaccc aaacagaaac ccacctggcg gtgtgaagtt   2700
tgtgattatg aaaccaatgt cgccaggaac ctccgaattc atatgaccag cgaaaagcac   2760
atgcataata tgatgctttt gcagcagaac atgaagcaga tccagcataa tctgcacttg   2820
ggcctcgccc cggcggaagc agagctttat cagtactacc tagcccagaa cataggcctg   2880
accggaatga agctggaaaa ccctgccgac cctcagctga tgatcaatcc attccagctg   2940
gatccagcga cagcagcggc tttggcacca gggctcgtaa ataatgagct gccgcctgaa   3000
atccggcttg ccagtggtca gctaatgggt gatgacctgt ccctccttac tgcaggagag   3060
ctgtcacctt atatcagtga cccagcgctg aagctattcc agtgtgctgt ttgcaacaaa   3120
ttcacctctg acagcctgga ggccctaagt gtgcatgtga gcagtgagcg ctctctccct   3180
gaagaggaat ggagggcagt aattggagat atctaccagt gcaagctctg caactacaac   3240
actcagctca aagccaactt ccagctacac tgcaagactg ataaacatat gcagaaatat   3300
caactggtgg ctcacattaa agaaggggc aaaagcaatg agtggaggtt gaagtgtatt    3360
gccattggca accctgttca cctaaaatgt aacgcctgtg actattacac caacagtgtg   3420
gataaattac gcttgcatac caccaatcac aggcacgagg cggccctgaa gctctacaag   3480
cacttgcaga agcaagaggg tgcagtgaat cccgaatcct gctattacta ctgtgccgtg   3540
tgtgattaca ccaccaaggt caagttgaat ctggtacaac atgtccgttc ggtgaagcat   3600
cagcagactg agggcctacg gaagctccag ctccaccagc aaggcctggc accagaggag   3660
gacaacctca gtgagatctt ttttgttaaa gattgcccac caaatgagct tgaaactgcc   3720
tcattgggag ccaggacttg tgatgatgat cttacagagc agcagttgag atcgacctca   3780
gaagaacaaa gtgaggaggc agaaggagct attaagccta cagcagtggc cgaggacgat   3840
```

-continued

```
gaaaaagaca caagtgagag agacaatagt gaaggcaaaa actctaataa agactctggg   3900
ataatcacac cagagaagga actaaaagtt agtgtggcag gggtacccca gccactcctg   3960
ctggcaaaag aagaggatgt tgcaacaaaa aggtcaaaac ctacagagga caataaattc   4020
tgtcatgaac agttctatca atgtccttat tgtaactaca atagtaggga ccaaagtcgt   4080
atccagatgc acgtcctatc acagcactcg gtgcagccgg tcatctgctg tcctctctgt   4140
caggacgtcc tcagcaacaa aatgcatctc caactgcatc tgacgcattt gcacagtgtg   4200
tctccagact gtgtggagaa gctgcttatg acagtgcctg tccctgatgt gatgatgcca   4260
aacagtatgc tactgccagc agctgcctct gagaaatcag agcgggacac acctgcagcc   4320
gtgacagctg aggggtctgg gaaatattca ggtgaaagtc caatggatga caaaagcatg   4380
gcaggtctcg aggattcaaa ggctaatgtg gaagtaaaga atgaggagca gaaaccgact   4440
aaagaaccct tggaagtctc agaatggaat aaaaatagca gtaaggatgt gaaaatcccc   4500
gacacactgc aagatcaatt aaatgaacag caaaaaaggc aaccgctctc tgtttctgac   4560
cgtcatgtct acaagtatcg ctgtaaccat tgtagcttgg ctttcaaaac tatgcagaag   4620
cttcagatac attcccagta tcatgcaatt cgggctgcga caatgtgtaa cctctgccag   4680
cgcagtttcc gtacattcca ggctttaaaa aaacacttgg aagcaggcca ccctgaactg   4740
agtgaagctg aacttcaaca gctatatgcc tccttgcccg tgaatggaga actgtgggca   4800
gagagcgaaa ctatgtccca ggatgaccat ggcctagagc aggaaatgga gagagagtat   4860
gaggtggacc acgaagggaa agcaagtcct gtaggaagtg atagtagctc tattccagat   4920
gacatgggct ctgaaccaaa gcggacctta cctttttagaa aagggcccaa ttttacgatg   4980
gaaaaattcc ttgatccatc tcgtccatat aaatgtacag tgtgtaaaga gtcattcacc   5040
caaaagaaca ttctcttggt ccactataat tcagtttctc acttgcataa gctgaaaaaa   5100
gttttgcagg aagcctccag tcctgtccca caagaaacca acagcaacac agataacaaa   5160
ccctacaagt gcagcatctg caatgttgca tacagccaaa gctcaacatt ggaaatccac   5220
atgaggtctg tgctccacca gacaaaggct agggctgcaa agctggagcc cagtggtcat   5280
gtggctggtg ggcacagcat tgcagcaaat gtcaacagcc ctggccaggg gatgttagat   5340
tccatgagtt tagcagctgt aaacagcaaa gatacccatt tagatgccaa agaattaaat   5400
aaaaagcaaa ctcctgattt aatctctgct caacctgcac atcacccacc acagtcacca   5460
gcacaaattc agatgcaact acagcacgaa ttacaacagc aagccgcatt ctttcagcct   5520
cagtttctaa acccagcctt tttgcctcat tttcctatga ccccagaagc actgctgcag   5580
tttcagcagc ctcagtttct ctttccattt tatatacctg ggacggagtt cagcttgggg   5640
ccagatttgg gcttgccagg ctctgccaca tttgggatgc ctggcatgac aggaatggct   5700
ggctccttgc ttgaagacct aaagcagcag attcaaaccc aacatcacgt tggtcaaact   5760
caactccaga tactacagca acaagcacaa caataccaag ccacacagcc ccagctgcag   5820
cctcaaaaac aacagcagca gccaccacct ccacagcagc agcagcaaca gcaggcaagc   5880
aaattattga aacaagagca aagtaacata gtgagtgcag actgccaaat catgaaggat   5940
gtgccatctt ataaggaggc agaagatatt tctgaaaagc cagaaaaacc aaagcaggaa   6000
tttataagtg aaggtgaagg actcaaagaa ggcaaagaca caaagaagca aaaatccttg   6060
gaaccatcca tcccaccacc ccgaatagct tcaggggcca gaggaaatgc tgccaaagcg   6120
ttattggaaa actttggttt tgaactggtc attcagtata acgaaaacag gcagaaggta   6180
cagaagaagg gcaaaagtgg tgaaggcgaa aacactgaca aactagaatg tggaacatgt   6240
```

```
ggtaaattgt tttccaatgt tcttatttta aagagtcacc aagaacatgt acatgggcaa   6300
tttttccat atgcagcgct agaaaaattt gctcgtcaat acagggaggc ctatgacaag   6360
ctttatccaa tttctccatc ttctccagaa acgccgcccc cgccacctcc tcctcctccc   6420
ttgcctccgg ctcctccaca gccttcttct atgggtcctg taaagatccc caacacggtt   6480
tctactcctc tgcaagctcc accacccact cctcccccac caccaccacc tcctcctcct   6540
cctcctcctc cccccccacc tcctccacct tctgctcctc cacaggtcca actgccggtt   6600
tctctggacc tgccgctctt tccttccatt atgatgcaac ctgtgcaaca ccctgcgctt   6660
cctccccagc ttgccctgca gctgccacag atggacgcac tctctgcaga cctcacccaa   6720
ctttgccagc agcagctcgg attagatccc aacttcttaa gacattctca gttcaaacgc   6780
ccacggacaa gaattacaga tgatcagcta aaaatcctga gggcttattt tgacattaat   6840
aattctccaa gtgaagaaca gatccaggaa atggcagaga aatctggcct ctcccaaaaa   6900
gttatcaaac actggtttag aaatacgctt tttaaggaac gacagagaaa taaagattca   6960
ccatacaact tcagtaaccc tcctataacg gttttagaag atatcagaat tgatccacag   7020
cccacctctt tagaacatta caaatctgat gcatcattca gtaaaaggtc ttctagaacg   7080
agatttactg actaccagct tagggttctg caagactttt ttgacacaaa cgcttaccca   7140
aaagatgatg aaatagaaca actctccact gttctcaatc tgcctacccg ggttattgtt   7200
gtatggttcc agaatgctcg tcagaaagca cgaaagagtt atgagaatca agcagaaaca   7260
aaagataatg aaaaaagaga actcactaat gaacggtaca ttcgaacaag caacatgcag   7320
taccagtgta aaaagtgcaa tgtggttttc cccaggatct ttgacttgat tacgcatcag   7380
aaaaagcagt gttacaagga tgaagatgat gatgcccaag atgaaagcca aacagaagac   7440
tccatggatg ccactgatca agtggtatac aagcattgca cagtgtctgg ccaaacggat   7500
gcagctaaaa acgctgctgc ccctgcagca agttctggct ctgggaccag cacccccctg   7560
attccatcac ccaaaccaga acctgagaag acttctccaa aacctgaata tcccgcagaa   7620
aagccaaagc agagtgaccc ctctccccct tctcaaggca ccaaaccagc cctgccatta   7680
gcatcgactt cctcggaccc accacaggca tccacagccc agccacagcc acagccacag   7740
ccaccaaaac aaccccaact tatcggaaga cctccctcgg cctctcaaac accggtccct   7800
tccagtccac tgcaaatttc catgacgtct ctccagaaca gtctacctcc acagttacta   7860
caataccaat gtgatcagtg tacagttgcc ttcccaactc tggaactctg gcaggaacac   7920
cagcacatgc acttccttgc tgctcaaaac caattccttc actctccgtt cttggaaagg   7980
cccatggaca tgccctacat gatatttgac cccaacaatc cgctgatgac tggacaactg   8040
ctgggcagtt ccctcactca aatgcccct caggccagtt cctcccacac cacagccccc   8100
acaacggttg ctgcttccct aaaaaggaaa ctagacgata aagaagataa taattgcagt   8160
gaaaaagaag gagggaatag cggtgaagac caacaccgag ataaacgctt gagaaccacg   8220
atcaccccgg aacagctgga aatactctat gaaaaatact tgctggattc caatcctacc   8280
agaaaaatgc ttgatcatat tgcccgcgaa gtcgggctga aaaaaagggt cgtgcaagtc   8340
tggttccaga atacacgagc gcgggagagg aaaggccagt tccgggcggt gggtccagca   8400
cagtctcata aacggtgtcc gttttgccga gccctgttta aagcaaagtc ggccttagaa   8460
agccacattc gctctcggca ctggaatgaa ggaaagcagg caggttacag cttgccacca   8520
agccctttaa tatccaccga agatgggga gaaagcccac agaaatacat ctattttgat   8580
```

-continued

```
tacccatctt tgccattaac taaaattgat ctatcaagtg agaatgaatt ggcttctaca   8640
gtgtcaacac ctgttagtaa aacagcagag ctgtcaccga agaatctttt aagcccttct   8700
tcttttaaag cagagtgttc tgaggatgta gagaatttaa atgcccctcc tgctgaggct   8760
gggtatgatc aaaataaaac cgattttgat gagacttcat cgattaatac ggcaatcagt   8820
gacgccacca ccggagacga gggaaacact gaaatggaaa gcaccacagg aagttccgga   8880
gatgtgaaac cggctttgtc tcccaaagag ccaaaaactc tggatactct gccaaaacct   8940
gcaaccacac ctaccacgga ggtctgcgat gacaaatttc tcttttctct cacaagccca   9000
tccatccatt tcaatgacaa agatggcgac cacgaccaaa gcttttacat cacagatgac   9060
ccggatgaca acgccgaccg cagcgaaacg tccagcatag cggacccgag ctccccaaat   9120
ccattcggat ccagcaatcc ctttaaatcc aaaagtaatg atcggccggg tcacaagcgt   9180
tttcgaacgc aaatgagcaa tcttcaactc aaggttctca aggcttgctt tagtgactac   9240
cgaactccaa ccatgcaaga atgtgaaatg ttagggaatg agattggtct gcccaaacgc   9300
gtagtccagg tgtggttcca aaatgcaagg gcaaaggaaa agaaatttaa aattaacata   9360
gggaagcctt tcatgatcaa tcaaggcgga acggaaggca ccaaaccaga gtgtaccctc   9420
tgcggggtga agtactctgc ccgcttgtcc atcagagatc acatttctc caaacagcac    9480
atttcaaaag tgagggagac cgttggcagt cagctcgatc gggagaaaga ttacttggct   9540
ccgaccacgg ttcggcagct gatggcacag caagaacttg atcgtataaa gaaagcttca   9600
gacgtgctgg gcttgacggt acagcagcca ggcatgatgg acagcagttc tctccacggc   9660
atcagcctgc caacagccta ccccggactc cccggccttc ctccagtcct tctccccgga   9720
atgaacggtc catcctcctt gccgggattt ccacaaaatt caaacacttt aacacctccc   9780
ggtgcaggca tgcttgggtt tcctacttca gctacttcgt ctcctgccct gtctctcagc   9840
agtgccccca ccaaaccttt gctgcagact ccaccacctc caccacctcc tcctcctcct   9900
cctccttcat cctctctgtc aggacagcag accgagcaac agaacaaaga atctgagaaa   9960
aagcaaacta agccaaacaa ggtgaaaaaa atcaaagagg aggaattaga ggccaccaaa  10020
cccgaaaaac accccaaaaa agaggaaaaa atctcatctg ctctttcagt gttgggcaaa  10080
gttgtaggtg aaacacatgt cgatcctatt cagttgcagg cattacagaa tgcaattgct  10140
ggtgacccag cttcctttat aggcggacag ttcttgccat actttatccc tgggtttgct  10200
tcttatttta cacctcagct ccctggaaca gtgcaggggg gatacttccc acctgtctgt  10260
ggcatggaga gcctctttcc ttatggccct acaatgcccc agacactggc aggtctgtcc  10320
ccaggtgcac tgttgcagca gtaccaacag tatcagcaga acctgcagga gtccctgcaa  10380
aagcagcaaa agcaacagca agaacagcag cagaaaccag ttcaggcaaa gacatccaaa  10440
gtagaaagtg accagccgca aaactccaac gatgcttcag aaacaaagga agacaaaagt  10500
actgctacag aaagcacaaa agaagaaccc cagttagaat ccaaaagtgc agacttttca  10560
gacacttacg ttgttccatt cgtcaagtat gagtttatat gcagaaagtg ccagatgatg  10620
tttactgatg aagacgccgc agtaaatcat caaaagtcct tctgttattt cggtcagcct  10680
ttgattgacc cacaagagac agtgcttcgt gtcccagtca gcaaatatca gtgtcttgcc  10740
tgtgatgtgg ctatcagtgg gaatgaagca cttagccaac acctccagtc aagcttgcac  10800
aaagagaaaa caatcaaaca agcaatgaga aatgccaaag agcatgttag attattacct  10860
cactcagtct gctcccctaa tcctaacacc acatctacct cgcagtctgc agcttcttct  10920
aataacacct atcctcatct ttcttgcttc tccatgaagt cctggcctaa tatccttttc  10980
```

caagcgtctg ccaggagagc tgcttctccc ccttcttctc ctccttccct ttccttgcct 11040
tcaacggtta cctcaagttt gtgcagcacc tcaggggttc aaacctcact acccacagaa 11100
agttgttcag atgagtctga cagtgagctg agccagaagc tagaagactt agataattct 11160
ttggaagtga aggctaagcc tgcttctggc ctagatggta atttcaatag catccgaatg 11220
gatatgttca gtgtgtagga gtgaagacag gatcccgtgc ttaaaaaaat aaaaaataaa 11280
aaaataaaaa aaaaataaga ctttaactgc agttccaaag cttctctaac ccaaaaatta 11340
cagtaccaaa tgattgactc aggattgttt ttcccatatt gatatgctgg caatatagga 11400
tggtatgtaa tggacagaac tgatgcagat ggttgaatgc gcttgtacta tatgctaaaa 11460
tatggaaaag gaaaaaaaaa tctcacaagt tcttttggaa cttgtttcaa gccaaaaact 11520
ctcaagaaag caaattgcac ctcagctgga ttgatttcca aatgctagca tgtactgtat 11580
gggaggatga tccagatgtt tcaaagagaa tttctcttag tttagttagg tgtaattcag 11640
tagctttaaa ttctcaggtc agaacataac atttctcatt tgttaaaagc agcaagaagc 11700
ctggtaaaac tgtgactttt ccccaaacgt caatctttat tagaaagcat tttctaggtg 11760
tgtttagtgt acaaagagac tttataaccc ttactggaca acacacagat ccttgagctc 11820
acgctgcagg atagtacagt tttaccgcag agggaatctg gaacagtgga atcatgtgtc 11880
tgccctgtgt attgcagttt gtattgccac aagctatatt tataccagtg tcacccttttt 11940
cttgtagaat atactaataa tctgtgccaa ctctaccttc tcacttttac ctctgacgtc 12000
attctttttt tctgaaagag gtaataattc tagttttgat agactctgag gattatgtga 12060
acaggacatt tttcatttgt gaatttaatg ctatactgtc aaggtacttg cttgtgtctg 12120
aactctagtg cacttatgat tttgtagacc atgtgaaatt taataagata cctttttttt 12180
cctttctttg tgtgtagtgc agcaacagtt tggtctgcat ttgttagaag tttaactcct 12240
aacaacccaa agacctattt aacaattggt gcataaatga aagtagtact gtatacttga 12300
aactgtttaa gtacaagttg aacaaaaatt atgaaaaggt atatttgctt ctcgggaaag 12360
caaagaagct gctttaaaaa ataaaaaggg gactaaaaat ttgttttgta taaagaggtt 12420
agccctgcgc acgtaggact gaattcagtg atatccctat acactgccat ttagtggata 12480
ggttattgta cttccattca tactctgggc acttgtgttg tattgttctg ttacatactt 12540
tttttaacct gttttgtttt atcatatatg cattaaaagt attatcttta tcaacatttg 12600
ctgctactgt gttaacattt ttgttttgct tgccatgaat ttcaacttcc accacccagt 12660
gaattgattt ataaattgct atgctttgct gtttttctgt tgctgtggaa cttaaagaat 12720
gtgaaagctg tcaaagggta ttttacgaat cacttttgtg tttgatatag taaaacaatg 12780
tgattcattc caaagtaaca gaaggttatt tgtaagaaag ttaaaggctt gtgaacaaag 12840
aaagctaagc tgttgtacat atttgtagtt ggctgtgcat ggtacaaatt tattaatatg 12900
aagaaatgca aaatgtattg cttttgatat ttctcttccg agatgaacaa gtagcatgta 12960
atgcaactgt ttgacagttt aactcaagtc atgcttcaaa ctgttttaat gatcaaatca 13020
agacacattt cattttacat tttattattg tacagttttt gtttcggatg atgatcacag 13080
caatctttat tctatacatt ttatgtgaac ttttttaatg tctttaattt ggattttttt 13140
ttttttagt attttaacat ttattttaat cctgaagaca cttttttgat tgtgtttcgt 13200
aagagacaac atggcctcct aaggtgcaat cctgccgcta tagtgagcta atgtcctgaa 13260
tccaaaggct tcagaaaatt gcttttgcct ttttcatgaa tgttaagcag cagcattgtg 13320

-continued

```
agatcgatct gtcctggcag ttaacacgat gtgcaacagt gtgttagcat ggaacagaac  13380

gcttttcaca aaacaaagga ctgttttaca aatgattatt ccgacagtgt gtcgacataa  13440

acttttacaa ctgcacagca gccaaaaaaa gaaaaaaaaa agaaaaaaaa ctttaactgg  13500

atggacgttg ttagggtgag aaataaaagg acagcctcca aaggttgaga atgagaattg  13560

tttttcctg gatatcaaag ggattatcac agcgcaatca ttgtctacac aacatgtact  13620

ctcaacgcct gggttacata ggaaatgcac cctgaggttt taataaaagc ccctatggct  13680

ataactttaa ataaactaaa ccaaaaatgt tattgatgtt ttatatatag agagtagtct  13740

cattagtttt tgttactgta atgtttgaag tctcaaatgc accgtattac ggtaaataac  13800

atggttttga aaactttttt ttattttgtc acagacctgt tgtcatagtt gaaatgatgt  13860

ttattgtaga tggtatttga acttattctt ctggaaatag ttcatcaagt atgtttgttg  13920

ctcattgtga tacattaaaa actgtatcta catatttaaa aaaaaaaaaa aaaaa       13975
```

<210> SEQ ID NO 21
<211> LENGTH: 317
<212> TYPE: PRT
<213> ORGANISM: Homo sapiens

<400> SEQUENCE: 21

```
Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
```

```
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315
```

<210> SEQ ID NO 22
<211> LENGTH: 2520
<212> TYPE: DNA
<213> ORGANISM: Homo sapiens

<400> SEQUENCE: 22

```
ggatggttgt ctattaactt gttcaaaaaa gtatcaggag ttgtcaaggc agagaagaga     60

gtgtttgcaa aaggggaaa gtagtttgct gcctctttaa gactaggact gagagaaaga    120

agaggagaga gaaagaaagg gagagaagtt tgagccccag gcttaagcct ttccaaaaaa    180

taataataac aatcatcggc ggcggcagga tcggccagag gaggagggaa gcgctttttt    240

tgatcctgat tccagtttgc ctctctcttt ttttccccca aattattctt cgcctgattt    300

tcctcgcgga gccctgcgct cccgacaccc ccgcccgcct cccctcctcc tctccccccg    360

cccgcgggcc ccccaaagtc ccggccgggc cgagggtcgg cggccgccgg cgggccgggc    420

ccgcgcacag cgcccgcatg tacaacatga tggagacgga gctgaagccg ccgggcccgc    480

agcaaacttc gggggggcggc ggcggcaact ccaccgcggc ggcggccggc ggcaaccaga    540

aaaacagccc ggaccgcgtc aagcggccca tgaatgcctt catggtgtgg tcccgcgggc    600

agcggcgcaa gatggcccag gagaacccca agatgcacaa ctcggagatc agcaagcgcc    660

tgggcgccga gtggaaactt ttgtcggaga cggagaagcg gccgttcatc gacgaggcta    720

agcggctgcg agcgctgcac atgaaggagc acccggatta taaataccgg ccccggcgga    780

aaaccaagac gctcatgaag aaggataagt acacgctgcc cggcgggctg ctggcccccg    840

gcggcaatag catggcgagc ggggtcgggg tgggcgccgg cctgggcgcg ggcgtgaacc    900

agcgcatgga cagttacgcg cacatgaacg gctggagcaa cggcagctac agcatgatgc    960

aggaccagct gggctacccg cagcacccgg gcctcaatgc gcacggcgca gcgcagatgc   1020

agcccatgca ccgctacgac gtgagcgccc tgcagtacaa ctccatgacc agctcgcaga   1080

cctacatgaa cggctcgccc acctacagca tgtcctactc gcagcagggc acccctggca   1140

tggctcttgg ctccatgggt tcggtggtca agtccgaggc cagctccagc ccccctgtgg   1200

ttacctcttc ctcccactcc agggcgccct gccaggccgg ggacctccgg gacatgatca   1260

gcatgtatct ccccggcgcc gaggtgccgg aacccgccgc ccccagcaga cttcacatgt   1320

cccagcacta ccagagcggc ccggtgcccg gcacggccat taacggcaca ctgcccctct   1380

cacacatgtg agggccggac agcgaactgg agggggggaga aattttcaaa gaaaaacgag   1440

ggaaatggga ggggtgcaaa agaggagagt aagaaacagc atggagaaaa cccggtacgc   1500

tcaaaaagaa aaaggaaaaa aaaaaatccc atcacccaca gcaaatgaca gctgcaaaag   1560

agaacaccaa tcccatccac actcacgcaa aaaccgcgat gccgacaaga aaacttttat   1620

gagagagatc ctggacttct ttttggggga ctatttttgt acagagaaaa cctggggagg   1680

gtggggaggg cgggggaatg gaccttgtat agatctggag gaaagaaagc tacgaaaaac   1740

tttttaaaag ttctagtggt acggtaggag ctttgcagga agtttgcaaa agtctttacc   1800
```

-continued

```
aataatattt agagctagtc tccaagcgac gaaaaaaatg ttttaatatt tgcaagcaac   1860

ttttgtacag tatttatcga gataaacatg gcaatcaaaa tgtccattgt ttataagctg   1920

agaatttgcc aatatttttc aaggagaggc ttcttgctga attttgattc tgcagctgaa   1980

atttaggaca gttgcaaacg tgaaaagaag aaaattattc aaatttggac attttaattg   2040

tttaaaaatt gtacaaaagg aaaaaattag aataagtact ggcgaaccat ctctgtggtc   2100

ttgtttaaaa agggcaaaag ttttagactg tactaaattt tataacttac tgttaaaagc   2160

aaaaatggcc atgcaggttg acaccgttgg taatttataa tagcttttgt tcgatcccaa   2220

ctttccattt tgttcagata aaaaaaacca tgaaattact gtgtttgaaa tatttttctta   2280

tggtttgtaa tatttctgta aatttattgt gatattttaa ggttttcccc cctttatttt   2340

ccgtagttgt attttaaaag attcggctct gtattatttg aatcagtctg ccgagaatcc   2400

atgtatatat ttgaactaat atcatcctta taacaggtac attttcaact taagttttta   2460

ctccattatg cacagtttga gataaataaa tttttgaaat atggacactg aaaaaaaaaa   2520
```

<210> SEQ ID NO 23
<211> LENGTH: 323
<212> TYPE: PRT
<213> ORGANISM: Homo sapiens

<400> SEQUENCE: 23

```
Met Asp Ser Asp Ala Ser Leu Val Ser Ser Arg Pro Ser Ser Pro Glu
1               5                   10                  15

Pro Asp Asp Leu Phe Leu Pro Ala Arg Ser Lys Gly Ser Ser Gly Ser
            20                  25                  30

Ala Phe Thr Gly Gly Thr Val Ser Ser Ser Thr Pro Ser Asp Cys Pro
        35                  40                  45

Pro Glu Leu Ser Ala Glu Leu Arg Gly Ala Met Gly Ser Ala Gly Ala
    50                  55                  60

His Pro Gly Asp Lys Leu Gly Gly Ser Gly Phe Lys Ser Ser Ser Ser
65                  70                  75                  80

Ser Thr Ser Ser Ser Thr Ser Ser Ala Ala Ala Ser Ser Thr Lys Lys
                85                  90                  95

Asp Lys Lys Gln Met Thr Glu Pro Glu Leu Gln Gln Leu Arg Leu Lys
            100                 105                 110

Ile Asn Ser Arg Glu Arg Lys Arg Met His Asp Leu Asn Ile Ala Met
        115                 120                 125

Asp Gly Leu Arg Glu Val Met Pro Tyr Ala His Gly Pro Ser Val Arg
    130                 135                 140

Lys Leu Ser Lys Ile Ala Thr Leu Leu Leu Ala Arg Asn Tyr Ile Leu
145                 150                 155                 160

Met Leu Thr Asn Ser Leu Glu Glu Met Lys Arg Leu Val Ser Glu Ile
                165                 170                 175

Tyr Gly Gly His His Ala Gly Phe His Pro Ser Ala Cys Gly Gly Leu
            180                 185                 190

Ala His Ser Ala Pro Leu Pro Ala Ala Thr Ala His Pro Ala Ala Ala
        195                 200                 205

Ala His Ala Ala His His Pro Ala Val His His Pro Ile Leu Pro Pro
    210                 215                 220

Ala Ala Ala Ala Ala Ala Ala Ala Ala Ala Ala Ala Ala Val Ser Ser
225                 230                 235                 240

Ala Ser Leu Pro Gly Ser Gly Leu Pro Ser Val Gly Ser Ile Arg Pro
                245                 250                 255
```

```
Pro His Gly Leu Leu Lys Ser Pro Ser Ala Ala Ala Ala Ala Pro Leu
            260                 265                 270

Gly Gly Gly Gly Gly Gly Ser Gly Ala Ser Gly Gly Phe Gln His Trp
        275                 280                 285

Gly Gly Met Pro Cys Pro Cys Ser Met Cys Gln Val Pro Pro Pro His
    290                 295                 300

His His Val Ser Ala Met Gly Ala Gly Ser Leu Pro Arg Leu Thr Ser
305                 310                 315                 320

Asp Ala Lys


<210> SEQ ID NO 24
<211> LENGTH: 2521
<212> TYPE: DNA
<213> ORGANISM: Homo sapiens

<400> SEQUENCE: 24

aaaaaccggc cgagccccta aaggtgcgga tgcttattat agatcgacgc gacaccagcg     60

cccggtgcca ggttctcccc tgaggctttt cggagcgagc tcctcaaatc gcatccagat    120

tttcgggtcc gagggaagga ggaccctgcg aaagctgcga cgactatctt cccctggggc    180

catggactcg gacgccagcc tggtgtccag ccgcccgtcg tcgccagagc ccgatgacct    240

ttttctgccg gcccggagta agggcagcag cggcagcgcc ttcactgggg gcaccgtgtc    300

ctcgtccacc ccgagtgact gcccgccgga gctgagcgcc gagctgcgcg gcgctatggg    360

ctctgcgggc gcgcatcctg ggacaagct aggaggcagt ggcttcaagt catcctcgtc     420

cagcacctcg tcgtctacgt cgtcggcggc tgcgtcgtcc accaagaagg acaagaagca    480

aatgacagag ccggagctgc agcagctgcg tctcaagatc aacagccgcg agcgcaagcg    540

catgcacgac ctcaacatcg ccatggatgg cctccgcgag gtcatgccgt acgcacacgg    600

cccttcggtg cgcaagcttt ccaagatcgc cacgctgctg ctggcgcgca actacatcct    660

catgctcacc aactcgctgg aggagatgaa gcgactggtg agcgagatct acgggggcca    720

ccacgctggc ttccacccgt cggcctgcgg cggcctggcg cactccgcgc ccctgcccgc    780

cgccaccgcg cacccggcag cagcagcgca cgccgcacat caccccgcgg tgcaccaccc    840

catcctgccg cccgccgccg cagcggctgc tgccgccgct gcagccgcgg ctgtgtccag    900

cgcctctctg cccggatccg ggctgccgtc ggtcggctcc atccgtccac cgcacggcct    960

actcaagtct ccgtctgctg ccgcggccgc cccgctgggg ggcgggggcg gcggcagtgg   1020

ggcgagcggg ggcttccagc actggggcgg catgccctgc ccctgcagca tgtgccaggt   1080

gccgccgccg caccaccacg tgtcggctat gggcgccggc agcctgccgc gcctcacctc   1140

cgacgccaag tgagccgact ggcgccggcg cgttctggcg acaggggagc caggggccgc   1200

ggggaagcga ggactggcct gcgctgggct cgggagctct gtcgcgagga ggggcgcagg   1260

accatggact gggggtgggg catggtgggg attccagcat ctgcgaaccc aagcaatggg   1320

ggcgcccaca gagcagtggg gagtgagggg atgttctctc cgggacctga tcgagcgctg   1380

tctggcttta acctgagctg gtccagtaga catcgtttta tgaaaaggta ccgctgtgtg   1440

cattcctcac tagaactcat ccgacccccg acccccacct ccgggaaaag attctaaaaa   1500

cttctttccc tgagagcgtg gcctgacttg cagactcggc ttgggcagca cttcgggggg   1560

ggagggggtg ttatgggagg gggacacatt ggggccttgc tcctcttcct cctttcttgg   1620

cgggtgggag actccgggta gccgcactgc agaagcaaca gcccgaccgc gccctccagg   1680
```

-continued

```
gtcgtccctg gcccaaggcc aggggccaca agttagttgg aagccggcgt tcggtatcag   1740

aagcgctgat ggtcatatcc aatctcaata tctgggtcaa tccacaccct cttagaactg   1800

tggccgttcc tccctgtctc tcgttgattt gggagaatat ggttttctaa taaatctgtg   1860

gatgttcctt cttcaacagt atgagcaagt ttatagacat tcagagtaga accacttgtg   1920

gattggaata acccaaaact gccgatttca ggggcgggtg cattgtagtt attattttaa   1980

aatagaaact accccaccga ctcatctttc cttctctaag cacaaagtga tttggttatt   2040

ttggtacctg agaacgtaac agaattaaaa ggcagttgct gtggaaacag tttgggttat   2100

ttgggggttc tgttggcttt ttaaaatttt ctttttttgga tgtgtaaatt tatcaatgat   2160

gaggtaagtg cgcaatgcta agctgtttgc tcacgtgact gccagcccca tcggagtcta   2220

agccggcttt cctctatttt ggtttatttt tgccacgttt aacacaaatg gtaaactcct   2280

ccacgtgctt cctgcgttcc gtgcaagccg cctcggcgct gcctgcgttg caaactgggc   2340

tttgtagcgt ctgccgtgta acacccttcc tctgatcgca ccgcccctcg cagagagtgt   2400

atcatctgtt ttatttttgt aaaaacaaag tgctaaataa tatttattac ttgtttggtt   2460

gcaaaaacgg aataaatgac tgagtgttga gattttaaat aaaatttaaa gtaaaaaaaa   2520

a                                                                   2521


<210> SEQ ID NO 25
<211> LENGTH: 443
<212> TYPE: PRT
<213> ORGANISM: Homo sapiens

<400> SEQUENCE: 25

Met Ala Thr Ala Ala Ser Asn His Tyr Ser Leu Leu Thr Ser Ser Ala
1               5                   10                  15

Ser Ile Val His Ala Glu Pro Pro Gly Gly Met Gln Gln Gly Ala Gly
            20                  25                  30

Gly Tyr Arg Glu Ala Gln Ser Leu Val Gln Gly Asp Tyr Gly Ala Leu
        35                  40                  45

Gln Ser Asn Gly His Pro Leu Ser His Ala His Gln Trp Ile Thr Ala
    50                  55                  60

Leu Ser His Gly Gly Gly Gly Gly Gly Gly Gly Gly Gly Gly Gly Gly
65                  70                  75                  80

Gly Gly Gly Gly Gly Gly Gly Gly Asp Gly Ser Pro Trp Ser Thr Ser
                85                  90                  95

Pro Leu Gly Gln Pro Asp Ile Lys Pro Ser Val Val Val Gln Gln Gly
            100                 105                 110

Gly Arg Gly Asp Glu Leu His Gly Pro Gly Ala Leu Gln Gln Gln His
        115                 120                 125

Gln Gln Gln Gln Gln Gln Gln Gln Gln Gln Gln Gln Gln Gln Gln Gln
    130                 135                 140

Gln Gln Gln Gln Gln Arg Pro Pro His Leu Val His His Ala Ala Asn
145                 150                 155                 160

His His Pro Gly Pro Gly Ala Trp Arg Ser Ala Ala Ala Ala Ala His
                165                 170                 175

Leu Pro Pro Ser Met Gly Ala Ser Asn Gly Gly Leu Leu Tyr Ser Gln
            180                 185                 190

Pro Ser Phe Thr Val Asn Gly Met Leu Gly Ala Gly Gly Gln Pro Ala
        195                 200                 205

Gly Leu His His His Gly Leu Arg Asp Ala His Asp Glu Pro His His
    210                 215                 220
```

```
Ala Asp His His Pro His Pro His Ser His Pro His Gln Gln Pro Pro
225                 230                 235                 240

Pro Pro Pro Pro Pro Gln Gly Pro Pro Gly His Pro Gly Ala His His
                245                 250                 255

Asp Pro His Ser Asp Glu Asp Thr Pro Thr Ser Asp Asp Leu Glu Gln
            260                 265                 270

Phe Ala Lys Gln Phe Lys Gln Arg Arg Ile Lys Leu Gly Phe Thr Gln
        275                 280                 285

Ala Asp Val Gly Leu Ala Leu Gly Thr Leu Tyr Gly Asn Val Phe Ser
    290                 295                 300

Gln Thr Thr Ile Cys Arg Phe Glu Ala Leu Gln Leu Ser Phe Lys Asn
305                 310                 315                 320

Met Cys Lys Leu Lys Pro Leu Leu Asn Lys Trp Leu Glu Glu Ala Asp
                325                 330                 335

Ser Ser Ser Gly Ser Pro Thr Ser Ile Asp Lys Ile Ala Ala Gln Gly
            340                 345                 350

Arg Lys Arg Lys Lys Arg Thr Ser Ile Glu Val Ser Val Lys Gly Ala
        355                 360                 365

Leu Glu Ser His Phe Leu Lys Cys Pro Lys Pro Ser Ala Gln Glu Ile
    370                 375                 380

Thr Ser Leu Ala Asp Ser Leu Gln Leu Glu Lys Glu Val Val Arg Val
385                 390                 395                 400

Trp Phe Cys Asn Arg Arg Gln Lys Glu Lys Arg Met Thr Pro Pro Gly
                405                 410                 415

Gly Thr Leu Pro Gly Ala Glu Asp Val Tyr Gly Gly Ser Arg Asp Thr
            420                 425                 430

Pro Pro His His Gly Val Gln Thr Pro Val Gln
        435                 440
```

<210> SEQ ID NO 26
<211> LENGTH: 4108
<212> TYPE: DNA
<213> ORGANISM: Homo sapiens

<400> SEQUENCE: 26

```
agtaatagca ggagcagcaa cagaaggcgt cggagcgggc gtcggagctg cccgctgtgg      60

gagagagagg agacagaaag agcgagcgag gagagggagc ccgaggcgaa aaagtaactg     120

tcaaatgcgc ggctccttta accggagcgc tcagtccggc tccgagagtc atggcgaccg     180

cagcgtctaa ccactacagc ctgctcacct ccagcgcctc catcgtgcac gccgagccgc     240

ccggcggcat gcagcagggc gcgggggggct accgcgaagc gcagagcctg gtgcagggcg    300

actacggcgc tctgcagagc aacggacacc cgctcagcca cgctcaccag tggatcaccg     360

cgctgtccca cggcggcggc ggcgggggcg gtggcggcgg cggggggggc gggggcggcg     420

gcgggggcgg cggcgacggc tccccgtggt ccaccagccc cctgggccag ccggacatca     480

agccctcggt ggtggtgcag cagggcggcc gcggagacga gctgcacggg ccaggcgccc     540

tgcagcagca gcatcagcag cagcaacagc aacagcagca gcaacagcag caacagcagc     600

agcagcagca gcaacagcgg ccgccgcatc tggtgcacca cgccgctaac caccacccgg     660

gacccggggc atggcggagc gcggcggctg cagcgcacct cccaccctcc atgggagcgt     720

ccaacggcgg cttgctctac tcgcagccca gcttcacggt gaacggcatg ctgggcgccg     780

gcgggcagcc ggccggtctg caccaccacg gcctgcggga cgcgcacgac gagccacacc     840
```

-continued

```
atgccgacca ccacccgcac ccgcactcgc acccacacca gcagccgccg cccccgccgc    900
ccccgcaggg tccgcctggc cacccaggcg cgcaccacga cccgcactcg gacgaggaca    960
cgccgacctc ggacgacctg gagcagttcg ccaagcagtt caagcagcgg cggatcaaac   1020
tgggatttac ccaagcggac gtggggctgg ctctgggcac cctgtatggc aacgtgttct   1080
cgcagaccac catctgcagg tttgaggccc tgcagctgag cttcaagaac atgtgcaagc   1140
tgaagccttt gttgaacaag tggttggagg aggcggactc gtcctcgggc agccccacga   1200
gcatagacaa gatcgcagcg caagggcgca agcggaaaaa gcggacctcc atcgaggtga   1260
gcgtcaaggg ggctctggag agccatttcc tcaaatgccc caagccctcg gcccaggaga   1320
tcacctccct cgcggacagc ttacagctgg agaaggaggt ggtgagagtt tggttttgta   1380
acaggagaca gaaagagaaa aggatgaccc ctcccggagg gactctgccg ggcgccgagg   1440
atgtgtacgg ggggagtagg gacactccac cacaccacgg ggtgcagacg cccgtccagt   1500
gaactcgagc tgggggaggg gcagagcgcg gggctccccc tccccttcgg tccttggccc   1560
tttcccggcc ctcttgttcc ctctctaact tctgattgtt cttttatttt taattattat   1620
ttccccgtcc cttaaaaaga caaaaaaaat aaggcaaaag gaaagcaact aagacactgg   1680
actatccttt aaaggtagca ggtgtaatga tgtgttttga cctttgcagg cgagtaacca   1740
ggcaatggag tggagtgtct cctggagaga gtgaggagag tgtgtgatag ctagaaagag   1800
agagagacag agagatggca agcactgaga taaatacctg gcaaaactaa ataaattacc   1860
aaaaaggaaa aaaaatccac caaaccatga taaacacaaa atgcagcttc ctgatgctta   1920
gagttggcac atgctgctgt gtttatttat tgtggattcc catcaggaaa gaggaaaaaa   1980
tacacatgtt ctttcatata ggcaaaattt aaccacataa atttgcactg caagaaaatt   2040
gaagtttacg tgaacaaatt catgagcata ttttctcttt ctccccaccg ttaatttggg   2100
agttgccgtt ttgggggatt ttgttttgct ttgctttatt catcggagag agttgaagcc   2160
agctcttggc cactctccat ttctaatgtt cttgtgttgc cccttcttcg tactgtttgt   2220
gaactttggt taccttcaca ttccccttac gagggtgtaa catctatttg ttcctcttac   2280
caaagcaaaa ggattggctt catacaaaat agacaattct ctgatttcag gaaatgtgca   2340
tggtctaccc gctttatcga aggcaagaat ccggtttgga atataaaaat aagcattggt   2400
tgttcttacc agccacaaag taaacttcat tttcaggcag tgtttctggg ggaggttatg   2460
gagggaagaa aaaagaaaaa tcgatagtga gtgactgatt gcttcatttt atcaggcggg   2520
cccattgtga aagagctcag gggaaatgtg gaggttaaat atatttccag agttgtccag   2580
cagaaagaaa gtggcacttt gaagagaact agggaagtac atatcttcag atatccctat   2640
atagttctct accttcagtt ttagtaacaa ttatgaagaa ttatttgtgc tgacagcagc   2700
agttaaactt tgtttctcta atagcttttt ttttacataa aaaaagaccc aggaacttaa   2760
tagtgtatgc ataagactgt gttttttagc acacagatac ccacagcata cactgacgat   2820
ctccacgcag tagacaggtt ttgtcttcac tagctcattt gtttatcaag tcatatttag   2880
ggtcccacac cctcttttcc tgtaatttat tgcagaatac accactttga cttggacagc   2940
tttctgcccc ctctttcact aaggaaggca aatgaagtga aaaaaaaaaa tgccattttc   3000
aatccttcct ttctcccctt tgttaatagt tttaagtgaa tttttgacct tatcttaatg   3060
gaaaacggtt aactccaaac acaaaagact ctactggaaa gtgtaggtga aaaaacttgt   3120
aactgtattg aaaataaata ccattaaact gtgatcagtt aaaatttaaa agaaaaatca   3180
gcacaaaagg gcgctaaaag ggaaaacact ttttattaat cttaaaagtt tgggggtttt   3240
```

```
tttccagtta ggtattagat aaatttttat tttaaaaaat gaaagtctca ctaccataaa   3300

attatggttc agcatcagat tagcattgca ctcagtagtc tttaaggttt taggaaatat   3360

gctttatatt gtcttttcaa acacctgtga ttgtttcatt ttccatgttt ttgcaagata   3420

aatggtgact tataatgggc atatttattt gcctgtattt catttccccc aatgaatgtc   3480

acaaggagat gggcacggag ctgcttcggg tgcatcacgc tgctcgttcc tgaggtatgg   3540

gaactggcct ttagtgaagc tatccagagc agggcaaata gccactggta aagggaggaa   3600

atgaatttcc agatacttat taccaagtag gtaaggtcag aagctggagt tcagagaatg   3660

tgtctacagc ttctctgact cttataggtt tactaagatg aaagttacca ctgaacctta   3720

ccactatgta tatatgttta atatctgtct tttgaaatgc agaaatagtt taaatgtttc   3780

tttgtctatt tttcttttt tttaatgcta cccagggaaa tattttcata tcatttttaa   3840

gtggcctgcc tcaatgtata tttatttctt ttgaaacaaa aaggttctgg aaactgtttt   3900

tctgtagctt taaatgaata ggtgagcaaa atctatatgg gatgtaattt ttttgttcag   3960

tctcttaaaa aatactttgt tttggtacat ttggttgtgc ttgtggggaa aataaaaacg   4020

cagagatcct tatatattta tgttaaagta atattttatt atctacataa aacagaaatg   4080

cacaataaaa aaaaaaaaaa aaaaaaaa                                      4108
```

<210> SEQ ID NO 27
<211> LENGTH: 852
<212> TYPE: PRT
<213> ORGANISM: Homo sapiens

<400> SEQUENCE: 27

```
Met Leu Ser Gly Lys Lys Ala Ala Ala Ala Ala Ala Ala Ala Ala Ala
1               5                   10                  15

Ala Ala Thr Gly Thr Glu Ala Gly Pro Gly Thr Ala Gly Gly Ser Glu
            20                  25                  30

Asn Gly Ser Glu Val Ala Ala Gln Pro Ala Gly Leu Ser Gly Pro Ala
        35                  40                  45

Glu Val Gly Pro Gly Ala Val Gly Glu Arg Thr Pro Arg Lys Lys Glu
    50                  55                  60

Pro Pro Arg Ala Ser Pro Pro Gly Gly Leu Ala Glu Pro Pro Gly Ser
65                  70                  75                  80

Ala Gly Pro Gln Ala Gly Pro Thr Val Val Pro Gly Ser Ala Thr Pro
                85                  90                  95

Met Glu Thr Gly Ile Ala Glu Thr Pro Glu Gly Arg Arg Thr Ser Arg
            100                 105                 110

Arg Lys Arg Ala Lys Val Glu Tyr Arg Glu Met Asp Glu Ser Leu Ala
        115                 120                 125

Asn Leu Ser Glu Asp Glu Tyr Tyr Ser Glu Glu Glu Arg Asn Ala Lys
    130                 135                 140

Ala Glu Lys Glu Lys Lys Leu Pro Pro Pro Pro Pro Gln Ala Pro Pro
145                 150                 155                 160

Glu Glu Glu Asn Glu Ser Glu Pro Glu Glu Pro Ser Gly Val Glu Gly
                165                 170                 175

Ala Ala Phe Gln Ser Arg Leu Pro His Asp Arg Met Thr Ser Gln Glu
            180                 185                 190

Ala Ala Cys Phe Pro Asp Ile Ile Ser Gly Pro Gln Gln Thr Gln Lys
        195                 200                 205

Val Phe Leu Phe Ile Arg Asn Arg Thr Leu Gln Leu Trp Leu Asp Asn
```

```
    210                 215                 220

Pro Lys Ile Gln Leu Thr Phe Glu Ala Thr Leu Gln Gln Leu Glu Ala
225                 230                 235                 240

Pro Tyr Asn Ser Asp Thr Val Leu Val His Arg Val His Ser Tyr Leu
                245                 250                 255

Glu Arg His Gly Leu Ile Asn Phe Gly Ile Tyr Lys Arg Ile Lys Pro
            260                 265                 270

Leu Pro Thr Lys Lys Thr Gly Lys Val Ile Ile Ile Gly Ser Gly Val
        275                 280                 285

Ser Gly Leu Ala Ala Ala Arg Gln Leu Gln Ser Phe Gly Met Asp Val
    290                 295                 300

Thr Leu Leu Glu Ala Arg Asp Arg Val Gly Gly Arg Val Ala Thr Phe
305                 310                 315                 320

Arg Lys Gly Asn Tyr Val Ala Asp Leu Gly Ala Met Val Val Thr Gly
                325                 330                 335

Leu Gly Gly Asn Pro Met Ala Val Val Ser Lys Gln Val Asn Met Glu
            340                 345                 350

Leu Ala Lys Ile Lys Gln Lys Cys Pro Leu Tyr Glu Ala Asn Gly Gln
        355                 360                 365

Ala Val Pro Lys Glu Lys Asp Glu Met Val Glu Gln Glu Phe Asn Arg
    370                 375                 380

Leu Leu Glu Ala Thr Ser Tyr Leu Ser His Gln Leu Asp Phe Asn Val
385                 390                 395                 400

Leu Asn Asn Lys Pro Val Ser Leu Gly Gln Ala Leu Glu Val Val Ile
                405                 410                 415

Gln Leu Gln Glu Lys His Val Lys Asp Glu Gln Ile Glu His Trp Lys
            420                 425                 430

Lys Ile Val Lys Thr Gln Glu Glu Leu Lys Glu Leu Leu Asn Lys Met
        435                 440                 445

Val Asn Leu Lys Glu Lys Ile Lys Glu Leu His Gln Gln Tyr Lys Glu
    450                 455                 460

Ala Ser Glu Val Lys Pro Pro Arg Asp Ile Thr Ala Glu Phe Leu Val
465                 470                 475                 480

Lys Ser Lys His Arg Asp Leu Thr Ala Leu Cys Lys Glu Tyr Asp Glu
                485                 490                 495

Leu Ala Glu Thr Gln Gly Lys Leu Glu Glu Lys Leu Gln Glu Leu Glu
            500                 505                 510

Ala Asn Pro Pro Ser Asp Val Tyr Leu Ser Ser Arg Asp Arg Gln Ile
        515                 520                 525

Leu Asp Trp His Phe Ala Asn Leu Glu Phe Ala Asn Ala Thr Pro Leu
    530                 535                 540

Ser Thr Leu Ser Leu Lys His Trp Asp Gln Asp Asp Asp Phe Glu Phe
545                 550                 555                 560

Thr Gly Ser His Leu Thr Val Arg Asn Gly Tyr Ser Cys Val Pro Val
                565                 570                 575

Ala Leu Ala Glu Gly Leu Asp Ile Lys Leu Asn Thr Ala Val Arg Gln
            580                 585                 590

Val Arg Tyr Thr Ala Ser Gly Cys Glu Val Ile Ala Val Asn Thr Arg
        595                 600                 605

Ser Thr Ser Gln Thr Phe Ile Tyr Lys Cys Asp Ala Val Leu Cys Thr
    610                 615                 620

Leu Pro Leu Gly Val Leu Lys Gln Gln Pro Pro Ala Val Gln Phe Val
625                 630                 635                 640
```

Pro Pro Leu Pro Glu Trp Lys Thr Ser Ala Val Gln Arg Met Gly Phe
645 650 655

Gly Asn Leu Asn Lys Val Val Leu Cys Phe Asp Arg Val Phe Trp Asp
660 665 670

Pro Ser Val Asn Leu Phe Gly His Val Gly Ser Thr Thr Ala Ser Arg
675 680 685

Gly Glu Leu Phe Leu Phe Trp Asn Leu Tyr Lys Ala Pro Ile Leu Leu
690 695 700

Ala Leu Val Ala Gly Glu Ala Ala Gly Ile Met Glu Asn Ile Ser Asp
705 710 715 720

Asp Val Ile Val Gly Arg Cys Leu Ala Ile Leu Lys Gly Ile Phe Gly
725 730 735

Ser Ser Ala Val Pro Gln Pro Lys Glu Thr Val Val Ser Arg Trp Arg
740 745 750

Ala Asp Pro Trp Ala Arg Gly Ser Tyr Ser Tyr Val Ala Ala Gly Ser
755 760 765

Ser Gly Asn Asp Tyr Asp Leu Met Ala Gln Pro Ile Thr Pro Gly Pro
770 775 780

Ser Ile Pro Gly Ala Pro Gln Pro Ile Pro Arg Leu Phe Phe Ala Gly
785 790 795 800

Glu His Thr Ile Arg Asn Tyr Pro Ala Thr Val His Gly Ala Leu Leu
805 810 815

Ser Gly Leu Arg Glu Ala Gly Arg Ile Ala Asp Gln Phe Leu Gly Ala
820 825 830

Met Tyr Thr Leu Pro Arg Gln Ala Thr Pro Gly Val Pro Ala Gln Gln
835 840 845

Ser Pro Ser Met
850

<210> SEQ ID NO 28
<211> LENGTH: 3053
<212> TYPE: DNA
<213> ORGANISM: Homo sapiens

<400> SEQUENCE: 28
ggcgcggcgg gagcgcgctt ggcgcgtgcg tacgcgacgg cggttggcgg cgcgcgggca 60
gcgtgaagcg aggcgaggca aggcttttcg gacccacgga gcgacagagc gagcggcccc 120
tacggccgtc ggcggcccgg cggcccgaga tgttatctgg gaagaaggcg gcagccgcgg 180
cggcggcggc tgcagcggca gcaaccggga cggaggctgg ccctgggaca gcaggcggct 240
ccgagaacgg gtctgaggtg gccgcgcagc ccgcgggcct gtcgggccca gccgaggtcg 300
ggccgggggc ggtgggggag cgcacacccc gcaagaaaga gcctccgcgg gcctcgcccc 360
ccgggggcct ggcggaaccg ccggggtccg cagggcctca ggccggccct actgtcgtgc 420
ctgggtctgc gacccccatg gaaactggaa tagcagagac tccggagggg cgtcggacca 480
gccggcgcaa gcgggcgaag gtagagtaca gagagatgga tgaaagcttg gccaacctct 540
cagaagatga gtattattca gaagaagaga gaaatgccaa agcagagaag gaaaagaagc 600
ttcccccacc acccccctcaa gccccacctg aggaagaaaa tgaaagtgag cctgaagaac 660
catcgggtgt ggagggcgca gctttccaga gccgacttcc tcatgaccgg atgacttctc 720
aagaagcagc ctgttttcca gatattatca gtggaccaca acagacccag aaggtttttc 780
ttttcattag aaaccgcaca ctgcagttgt ggttggataa tccaaagatt cagctgacat 840

-continued

```
ttgaggctac tctccaacaa ttagaagcac cttataacag tgatactgtg cttgtccacc    900
gagttcacag ttatttagag cgtcatggtc ttatcaactt cggcatctat aagaggataa    960
aacccctacc aactaaaaag acaggaaagg taattattat aggctctggg gtctcaggct   1020
tggcagcagc tcgacagtta caaagttttg gaatggatgt cacacttttg gaagccaggg   1080
atcgtgtggg tggacgagtt gccacatttc gcaaaggaaa ctatgtagct gatcttggag   1140
ccatggtggt aacaggtctt ggagggaatc ctatggctgt ggtcagcaaa caagtaaata   1200
tggaactggc caagatcaag caaaaatgcc cactttatga agccaacgga caagctgttc   1260
ctaaagagaa agatgaaatg gtagagcaag agtttaaccg gttgctagaa gctacatctt   1320
accttagtca tcaactagac ttcaatgtcc tcaataataa gcctgtgtcc cttggccagg   1380
cattggaagt tgtcattcag ttacaagaga agcatgtcaa agatgagcag attgaacatt   1440
ggaagaagat agtgaaaact caggaagaat tgaaagaact tcttaataag atggtaaatt   1500
tgaaagagaa aattaaagaa ctccatcagc aatacaaaga agcatctgaa gtaaagccac   1560
ccagagatat tactgccgag ttcttagtga aaagcaaaca cagggatctg accgccctat   1620
gcaaggaata tgatgaatta gctgaaacac aaggaaagct agaagaaaaa cttcaggagt   1680
tggaagcgaa tcccccaagt gatgtatatc tctcatcaag agacagacaa atacttgatt   1740
ggcattttgc aaatcttgaa tttgctaatg ccacacctct ctcaactctc tcccttaagc   1800
actgggatca ggatgatgac tttgagttca ctggcagcca cctgacagta aggaatggct   1860
actcgtgtgt gcctgtggct ttagcagaag gcctagacat taaactgaat acagcagtgc   1920
gacaggttcg ctacacggct tcaggatgtg aagtgatagc tgtgaatacc cgctccacga   1980
gtcaaacctt tatttataaa tgcgacgcag ttctctgtac ccttcccctg ggtgtgctga   2040
agcagcagcc accagccgtt cagtttgtgc cacctctccc tgagtggaaa acatctgcag   2100
tccaaaggat gggatttggc aaccttaaca aggtggtgtt gtgttttgat cgggtgttct   2160
gggatccaag tgtcaatttg ttcgggcatg ttggcagtac gactgccagc aggggtgagc   2220
tcttcctctt ctggaacctc tataaagctc caatactgtt ggcactagtg gcaggagaag   2280
ctgctggtat catggaaaac ataagtgacg atgtgattgt tggccgatgc ctggccattc   2340
tcaaagggat ttttggtagc agtgcagtac ctcagcccaa agaaactgtg gtgtctcgtt   2400
ggcgtgctga tccctgggct cggggctctt attcctatgt tgctgcagga tcatctggaa   2460
atgactatga tttaatggct cagccaatca ctcctggccc ctcgattcca ggtgccccac   2520
agccgattcc acgactcttc tttgcgggag aacatacgat ccgtaactac ccagccacag   2580
tgcatggtgc tctgctgagt gggctgcgag aagcgggaag aattgcagac cagtttttgg   2640
gggccatgta tacgctgcct cgccaggcca caccaggtgt tcctgcacag cagtccccaa   2700
gcatgtgaga cagatgcatt ctaagggaag aggcccatgt gcctgtttct gccatgtaag   2760
gaaggctctt ctagcaatac tagatcccac tgagaaaatc caccctggca tctgggctcc   2820
tgatcagctg atggagctcc tgatttgaca aaggagcttg cctcctttga atgacctaga   2880
gcacagggag gaacttgtcc attagtttgg aattgtgttc ttcgtaaaga ctgaggcaag   2940
caagtgctgt gaaataacat catcttagtc ccttggtgtg tggggttttt gttttttttt   3000
tatattttga gaataaaact tcatataaaa ttggcaaaaa aaaaaaaaaa aaa          3053
```

<210> SEQ ID NO 29
<211> LENGTH: 876
<212> TYPE: PRT
<213> ORGANISM: Homo sapiens

<400> SEQUENCE: 29

```
Met Leu Ser Gly Lys Lys Ala Ala Ala Ala Ala Ala Ala Ala Ala Ala
1               5                   10                  15

Ala Ala Thr Gly Thr Glu Ala Gly Pro Gly Thr Ala Gly Gly Ser Glu
            20                  25                  30

Asn Gly Ser Glu Val Ala Ala Gln Pro Ala Gly Leu Ser Gly Pro Ala
        35                  40                  45

Glu Val Gly Pro Gly Ala Val Gly Glu Arg Thr Pro Arg Lys Lys Glu
    50                  55                  60

Pro Pro Arg Ala Ser Pro Pro Gly Gly Leu Ala Glu Pro Pro Gly Ser
65                  70                  75                  80

Ala Gly Pro Gln Ala Gly Pro Thr Val Val Pro Gly Ser Ala Thr Pro
                85                  90                  95

Met Glu Thr Gly Ile Ala Glu Thr Pro Glu Gly Arg Arg Thr Ser Arg
            100                 105                 110

Arg Lys Arg Ala Lys Val Glu Tyr Arg Glu Met Asp Glu Ser Leu Ala
        115                 120                 125

Asn Leu Ser Glu Asp Glu Tyr Tyr Ser Glu Glu Glu Arg Asn Ala Lys
    130                 135                 140

Ala Glu Lys Glu Lys Lys Leu Pro Pro Pro Pro Pro Gln Ala Pro Pro
145                 150                 155                 160

Glu Glu Glu Asn Glu Ser Glu Pro Glu Glu Pro Ser Gly Gln Ala Gly
                165                 170                 175

Gly Leu Gln Asp Asp Ser Ser Gly Gly Tyr Gly Asp Gly Gln Ala Ser
            180                 185                 190

Gly Val Glu Gly Ala Ala Phe Gln Ser Arg Leu Pro His Asp Arg Met
        195                 200                 205

Thr Ser Gln Glu Ala Ala Cys Phe Pro Asp Ile Ile Ser Gly Pro Gln
    210                 215                 220

Gln Thr Gln Lys Val Phe Leu Phe Ile Arg Asn Arg Thr Leu Gln Leu
225                 230                 235                 240

Trp Leu Asp Asn Pro Lys Ile Gln Leu Thr Phe Glu Ala Thr Leu Gln
                245                 250                 255

Gln Leu Glu Ala Pro Tyr Asn Ser Asp Thr Val Leu Val His Arg Val
            260                 265                 270

His Ser Tyr Leu Glu Arg His Gly Leu Ile Asn Phe Gly Ile Tyr Lys
        275                 280                 285

Arg Ile Lys Pro Leu Pro Thr Lys Lys Thr Gly Lys Val Ile Ile Ile
    290                 295                 300

Gly Ser Gly Val Ser Gly Leu Ala Ala Ala Arg Gln Leu Gln Ser Phe
305                 310                 315                 320

Gly Met Asp Val Thr Leu Leu Glu Ala Arg Asp Arg Val Gly Gly Arg
                325                 330                 335

Val Ala Thr Phe Arg Lys Gly Asn Tyr Val Ala Asp Leu Gly Ala Met
            340                 345                 350

Val Val Thr Gly Leu Gly Gly Asn Pro Met Ala Val Val Ser Lys Gln
        355                 360                 365

Val Asn Met Glu Leu Ala Lys Ile Lys Gln Lys Cys Pro Leu Tyr Glu
    370                 375                 380

Ala Asn Gly Gln Ala Asp Thr Val Lys Val Pro Lys Glu Lys Asp Glu
385                 390                 395                 400

Met Val Glu Gln Glu Phe Asn Arg Leu Leu Glu Ala Thr Ser Tyr Leu
```

-continued

```
                405                 410                 415

Ser His Gln Leu Asp Phe Asn Val Leu Asn Asn Lys Pro Val Ser Leu
            420                 425                 430

Gly Gln Ala Leu Glu Val Val Ile Gln Leu Gln Glu Lys His Val Lys
        435                 440                 445

Asp Glu Gln Ile Glu His Trp Lys Lys Ile Val Lys Thr Gln Glu Glu
    450                 455                 460

Leu Lys Glu Leu Leu Asn Lys Met Val Asn Leu Lys Glu Lys Ile Lys
465                 470                 475                 480

Glu Leu His Gln Gln Tyr Lys Glu Ala Ser Glu Val Lys Pro Pro Arg
                485                 490                 495

Asp Ile Thr Ala Glu Phe Leu Val Lys Ser Lys His Arg Asp Leu Thr
            500                 505                 510

Ala Leu Cys Lys Glu Tyr Asp Glu Leu Ala Glu Thr Gln Gly Lys Leu
        515                 520                 525

Glu Glu Lys Leu Gln Glu Leu Glu Ala Asn Pro Pro Ser Asp Val Tyr
    530                 535                 540

Leu Ser Ser Arg Asp Arg Gln Ile Leu Asp Trp His Phe Ala Asn Leu
545                 550                 555                 560

Glu Phe Ala Asn Ala Thr Pro Leu Ser Thr Leu Ser Leu Lys His Trp
                565                 570                 575

Asp Gln Asp Asp Asp Phe Glu Phe Thr Gly Ser His Leu Thr Val Arg
            580                 585                 590

Asn Gly Tyr Ser Cys Val Pro Val Ala Leu Ala Glu Gly Leu Asp Ile
        595                 600                 605

Lys Leu Asn Thr Ala Val Arg Gln Val Arg Tyr Thr Ala Ser Gly Cys
    610                 615                 620

Glu Val Ile Ala Val Asn Thr Arg Ser Thr Ser Gln Thr Phe Ile Tyr
625                 630                 635                 640

Lys Cys Asp Ala Val Leu Cys Thr Leu Pro Leu Gly Val Leu Lys Gln
                645                 650                 655

Gln Pro Pro Ala Val Gln Phe Val Pro Pro Leu Pro Glu Trp Lys Thr
            660                 665                 670

Ser Ala Val Gln Arg Met Gly Phe Gly Asn Leu Asn Lys Val Val Leu
        675                 680                 685

Cys Phe Asp Arg Val Phe Trp Asp Pro Ser Val Asn Leu Phe Gly His
    690                 695                 700

Val Gly Ser Thr Thr Ala Ser Arg Gly Glu Leu Phe Leu Phe Trp Asn
705                 710                 715                 720

Leu Tyr Lys Ala Pro Ile Leu Leu Ala Leu Val Ala Gly Glu Ala Ala
                725                 730                 735

Gly Ile Met Glu Asn Ile Ser Asp Asp Val Ile Val Gly Arg Cys Leu
            740                 745                 750

Ala Ile Leu Lys Gly Ile Phe Gly Ser Ser Ala Val Pro Gln Pro Lys
        755                 760                 765

Glu Thr Val Val Ser Arg Trp Arg Ala Asp Pro Trp Ala Arg Gly Ser
    770                 775                 780

Tyr Ser Tyr Val Ala Ala Gly Ser Ser Gly Asn Asp Tyr Asp Leu Met
785                 790                 795                 800

Ala Gln Pro Ile Thr Pro Gly Pro Ser Ile Pro Gly Ala Pro Gln Pro
                805                 810                 815

Ile Pro Arg Leu Phe Phe Ala Gly Glu His Thr Ile Arg Asn Tyr Pro
            820                 825                 830
```

Ala Thr Val His Gly Ala Leu Leu Ser Gly Leu Arg Glu Ala Gly Arg
835 840 845

Ile Ala Asp Gln Phe Leu Gly Ala Met Tyr Thr Leu Pro Arg Gln Ala
850 855 860

Thr Pro Gly Val Pro Ala Gln Gln Ser Pro Ser Met
865 870 875

<210> SEQ ID NO 30
<211> LENGTH: 3125
<212> TYPE: DNA
<213> ORGANISM: Homo sapiens

<400> SEQUENCE: 30
ggcgcggcgg gagcgcgctt ggcgcgtgcg tacgcgacgg cggttggcgg cgcgcgggca 60
gcgtgaagcg aggcgaggca aggcttttcg gacccacgga gcgacagagc gagcggcccc 120
tacggccgtc ggcggcccgg cggcccgaga tgttatctgg gaagaaggcg gcagccgcgg 180
cggcggcggc tgcagcggca gcaaccggga cggaggctgg ccctgggaca gcaggcggct 240
ccgagaacgg gtctgaggtg gccgcgcagc ccgcgggcct gtcgggccca gccgaggtcg 300
ggccgggggc ggtgggggag cgcacacccc gcaagaaaga gcctccgcgg gcctcgcccc 360
ccgggggcct ggcggaaccg ccggggtccg cagggcctca ggccggccct actgtcgtgc 420
ctgggtctgc gacccccatg gaaactggaa tagcagagac tccggagggg cgtcggacca 480
gccggcgcaa gcgggcgaag gtagagtaca gagagatgga tgaaagcttg gccaacctct 540
cagaagatga gtattattca gaagaagaga gaaatgccaa agcagagaag gaaaagaagc 600
ttcccccacc acccccctcaa gccccacctg aggaagaaaa tgaaagtgag cctgaagaac 660
catcggggca agcaggagga cttcaagacg acagttctgg agggtatgga gacggccaag 720
catcaggtgt ggagggcgca gctttccaga gccgacttcc tcatgaccgg atgacttctc 780
aagaagcagc ctgttttcca gatattatca gtggaccaca acagacccag aaggtttttc 840
ttttcattag aaaccgcaca ctgcagttgt ggttggataa tccaaagatt cagctgacat 900
ttgaggctac tctccaacaa ttagaagcac cttataacag tgatactgtg cttgtccacc 960
gagttcacag ttatttagag cgtcatggtc ttatcaactt cggcatctat aagaggataa 1020
aacccctacc aactaaaaag acaggaaagg taattattat aggctctggg gtctcaggct 1080
tggcagcagc tcgacagtta caaagttttg gaatggatgt cacacttttg gaagccaggg 1140
atcgtgtggg tggacgagtt gccacatttc gcaaaggaaa ctatgtagct gatcttggag 1200
ccatggtggt aacaggtctt ggagggaatc ctatggctgt ggtcagcaaa caagtaaata 1260
tggaactggc caagatcaag caaaaatgcc cactttatga agccaacgga caagctgaca 1320
ctgtcaaggt tcctaaagag aaagatgaaa tggtagagca agagtttaac cggttgctag 1380
aagctacatc ttaccttagt catcaactag acttcaatgt cctcaataat aagcctgtgt 1440
cccttggcca ggcattggaa gttgtcattc agttacaaga gaagcatgtc aaagatgagc 1500
agattgaaca ttggaagaag atagtgaaaa ctcaggaaga attgaaagaa cttcttaata 1560
agatggtaaa tttgaaagag aaaattaaag aactccatca gcaatacaaa gaagcatctg 1620
aagtaaagcc acccagagat attactgccg agttcttagt gaaaagcaaa cacagggatc 1680
tgaccgccct atgcaaggaa tatgatgaat tagctgaaac acaaggaaag ctagaagaaa 1740
aacttcagga gttggaagcg aatcccccaa gtgatgtata tctctcatca agagacagac 1800
aaatacttga ttggcatttt gcaaatcttg aatttgctaa tgccacacct ctctcaactc 1860

```
tctcccttaa gcactgggat caggatgatg actttgagtt cactggcagc cacctgacag   1920

taaggaatgg ctactcgtgt gtgcctgtgg ctttagcaga aggcctagac attaaactga   1980

atacagcagt gcgacaggtt cgctacacgg cttcaggatg tgaagtgata gctgtgaata   2040

cccgctccac gagtcaaacc tttatttata aatgcgacgc agttctctgt acccttcccc   2100

tgggtgtgct gaagcagcag ccaccagccg ttcagtttgt gccacctctc cctgagtgga   2160

aaacatctgc agtccaaagg atgggatttg gcaaccttaa caaggtggtg ttgtgttttg   2220

atcgggtgtt ctgggatcca agtgtcaatt tgttcgggca tgttggcagt acgactgcca   2280

gcaggggtga gctcttcctc ttctggaacc tctataaagc tccaatactg ttggcactag   2340

tggcaggaga agctgctggt atcatggaaa acataagtga cgatgtgatt gttggccgat   2400

gcctggccat tctcaaaggg atttttggta gcagtgcagt acctcagccc aaagaaactg   2460

tggtgtctcg ttggcgtgct gatccctggg ctcggggctc ttattcctat gttgctgcag   2520

gatcatctgg aaatgactat gatttaatgg ctcagccaat cactcctggc ccctcgattc   2580

caggtgcccc acagccgatt ccacgactct tctttgcggg agaacatacg atccgtaact   2640

acccagccac agtgcatggt gctctgctga gtgggctgcg agaagcggga agaattgcag   2700

accagttttt gggggccatg tatacgctgc ctcgccaggc cacaccaggt gttcctgcac   2760

agcagtcccc aagcatgtga gacagatgca ttctaaggga agaggcccat gtgcctgttt   2820

ctgccatgta aggaaggctc ttctagcaat actagatccc actgagaaaa tccaccctgg   2880

catctgggct cctgatcagc tgatggagct cctgatttga caaaggagct tgcctccttt   2940

gaatgaccta gagcacaggg aggaacttgt ccattagttt ggaattgtgt tcttcgtaaa   3000

gactgaggca agcaagtgct gtgaaataac atcatcttag tcccttggtg tgtggggttt   3060

ttgttttttt tttatatttt gagaataaaa cttcatataa aattggcaaa aaaaaaaaaa   3120

aaaaa                                                               3125


<210> SEQ ID NO 31
<211> LENGTH: 523
<212> TYPE: PRT
<213> ORGANISM: Homo sapiens

<400> SEQUENCE: 31

Met Pro Ser Val Met Glu Lys Pro Ser Ala Gly Ser Gly Ile Leu Ser
1               5                   10                  15

Arg Ser Arg Ala Lys Thr Val Pro Asn Gly Gly Gln Pro His Ser Glu
            20                  25                  30

Asp Asp Ser Ser Glu Glu Glu His Ser His Asp Ser Met Ile Arg Val
        35                  40                  45

Gly Thr Asn Tyr Gln Ala Val Ile Pro Glu Cys Lys Pro Glu Ser Pro
    50                  55                  60

Ala Arg Tyr Ser Asn Lys Glu Leu Lys Gly Met Leu Val Trp Ser Pro
65                  70                  75                  80

Asn His Cys Val Ser Asp Ala Lys Leu Asp Lys Tyr Ile Ala Met Ala
                85                  90                  95

Lys Glu Lys His Gly Tyr Asn Ile Glu Gln Ala Leu Gly Met Leu Leu
            100                 105                 110

Trp His Lys His Asp Val Glu Lys Ser Leu Ala Asp Leu Ala Asn Phe
        115                 120                 125

Thr Pro Phe Pro Asp Glu Trp Thr Val Glu Asp Lys Val Leu Phe Glu
    130                 135                 140
```

```
Gln Ala Phe Gly Phe His Gly Lys Cys Phe Gln Arg Ile Gln Gln Met
145                 150                 155                 160

Leu Pro Asp Lys Leu Ile Pro Ser Leu Val Lys Tyr Tyr Tyr Ser Trp
                165                 170                 175

Lys Lys Thr Arg Ser Arg Thr Ser Val Met Asp Arg Gln Ala Arg Arg
            180                 185                 190

Leu Gly Gly Arg Lys Asp Lys Glu Asp Ser Asp Glu Leu Glu Glu Gly
        195                 200                 205

Arg Gly Gly Val Ser Glu Gly Glu Pro Asp Pro Ala Asp Pro Lys Arg
    210                 215                 220

Glu Pro Leu Pro Ser Arg Pro Leu Asn Ala Arg Pro Gly Pro Gly Lys
225                 230                 235                 240

Lys Glu Val Gln Val Ser Gln Tyr Arg His His Pro Leu Arg Thr Arg
                245                 250                 255

Arg Arg Pro Pro Lys Gly Met Tyr Leu Ser Pro Glu Gly Leu Thr Ala
            260                 265                 270

Val Ser Gly Ser Pro Asp Leu Ala Asn Leu Thr Leu Arg Gly Leu Asp
        275                 280                 285

Ser Gln Leu Ile Ser Leu Lys Arg Gln Val Gln Ser Met Lys Gln Thr
    290                 295                 300

Asn Ser Ser Leu Arg Gln Ala Leu Glu Gly Gly Ile Asp Pro Leu Arg
305                 310                 315                 320

Pro Pro Glu Ala Asn Thr Lys Phe Asn Ser Arg Trp Thr Thr Asp Glu
                325                 330                 335

Gln Leu Leu Ala Val Gln Ala Ile Arg Arg Tyr Gly Lys Asp Phe Gly
            340                 345                 350

Ala Ile Ala Glu Val Ile Gly Asn Lys Thr Leu Thr Gln Val Lys Thr
        355                 360                 365

Phe Phe Val Ser Tyr Arg Arg Arg Phe Asn Leu Glu Glu Val Leu Gln
    370                 375                 380

Glu Trp Glu Ala Glu Gln Asp Gly Ala Pro Gly Ala Pro Val Pro Met
385                 390                 395                 400

Glu Glu Ala Arg Arg Gly Ala Pro Leu Pro Ala Pro Ala Leu Glu Glu
                405                 410                 415

Asp Asp Glu Val Gln Ile Thr Ser Val Ser Thr Ser Val Pro Arg Ser
            420                 425                 430

Val Pro Pro Ala Pro Pro Pro Pro Pro Pro Pro Thr Ser Leu Ser Gln
        435                 440                 445

Pro Pro Pro Leu Leu Arg Pro Pro Leu Pro Thr Ala Pro Thr Leu Leu
    450                 455                 460

Arg Gln Pro Pro Pro Leu Gln Gln Gly Arg Phe Leu Gln Pro Arg Leu
465                 470                 475                 480

Ala Pro Asn Gln Pro Pro Pro Pro Leu Ile Arg Pro Ala Leu Ala Ala
                485                 490                 495

Pro Arg His Ser Ala Arg Pro Gly Pro Gln Pro Pro Pro Thr Leu Ile
            500                 505                 510

Gly Thr Pro Leu Glu Pro Pro Ala Pro Ser Leu
        515                 520
```

<210> SEQ ID NO 32
<211> LENGTH: 2621
<212> TYPE: DNA
<213> ORGANISM: Homo sapiens

<400> SEQUENCE: 32

```
gcgcccagcc gctgaacggc gtgggcaggt gggcggtggg gttccagggc gccccgagga     60
caggggggccc cgacttcagg ggaaccccaa ccctgagggg cgtacatagt aatcacgccc    120
cagccgcacc ggaccttgcg ctcatccctt gcgtccccca cttctgcaca aacttttctg    180
acgccctggc tcgtgggggt cgtggagagc gctggggcta ccaggtgggc tcccaccccg    240
ccggacccta gccacgctga cctcctgcct ctcctaacct cagtggcgac ctctccaggc    300
cgggccgggc tcggcactcg gagcgagtgc ggcaaccact gtcgctctcc gaaggctcct    360
gcgccccccg gggcagctgg gcggggtaat gccctcagtg atggagaagc cgagcgcggg    420
ctctgggatc ctgtcccgta gccgggccaa gacggtgccc aacggcggac agccccactc    480
ggaggatgac agcagcgagg aggagcactc gcacgacagc atgatccgcg ttggaaccaa    540
ttaccaggcc gtaattccgg agtgcaagcc tgagagcccc gcacgctaca gcaacaagga    600
gctgaagggg atgctggtgt ggtcacccaa ccactgtgtg tcagatgcca agcttgacaa    660
gtacattgcg atggccaagg agaagcatgg ctacaacatt gagcaggcgc tgggcatgct    720
tctgtggcat aagcacgatg tggagaagtc gctggccgac ctggccaact tcaccccatt    780
ccctgacgag tggacagtag aggacaaggt gctgtttgaa caggcctttg gcttccatgg    840
caaatgcttc cagcggatcc agcagatgct gcctgacaag ttgattccca gcctggtgaa    900
atactactac tcttggaaga agacccgcag ccgaactagt gtgatggaca gacaggcccg    960
gcggctgggg ggccgcaagg acaaagaaga cagtgatgag ctcgaagagg gtcgaggagg   1020
cgtgagtgag ggagagcccg atcctgcaga tcccaagaga gagcctctac cctctcggcc   1080
cctgaatgca cgcccaggcc ctgggaaaaa ggaggtccag gtgtctcagt accgccacca   1140
tcccttgcga acccggcgtc gcccacccaa gggcatgtac ctgagccctg aaggcctcac   1200
ggcagtgtca ggaagcccgg accttgccaa cctcacgctc cgaggtcttg actctcagct   1260
catctccctc aagcgccagg tacagagcat gaagcagacg aacagcagcc tgcgccaagc   1320
cctggagggc ggtattgatc cactacgccc cccggaggcc aacaccaagt tcaactcccg   1380
ctggaccaca gatgagcagc ttttggctgt tcaagccatc cgtaggtatg gcaaagactt   1440
tggggctatt gcagaggtga ttgggaacaa gactctgacc caggtgaaga ctttctttgt   1500
gagctaccgg cgccgcttca atctggagga ggtgctgcag gaatgggagg ctgagcagga   1560
tggggcccct ggagccccag tccccatgga ggaggctagg agaggggctc cattgccagc   1620
cccagcccta gaggaagatg atgaggtcca gattacatcg gtctccacgt ccgtgccccg   1680
atcagtgccc cctgcgccac cacccctcc acctcccacc tcgctgtccc agccaccccc   1740
gctgctgagg ccacctttgc ccacggctcc cactctgctc cgacagccac ccccactgca   1800
gcagggccgc ttcctccagc cccggctggc ccccaaccag cccccaccgc ctctcatccg   1860
ccccgctctg gctgcccccc gccacagcgc ccgccctggc cctcagcccc cacccaccct   1920
gattggaacc cctctggagc cccagcacc ctcactctga gccctgacgt cctccaccaa   1980
ccacgggctc caggacccct ttgctggcca tccccaggca tctctggtgt cactgaggac   2040
agaagggact agggctctgg cggggtcttt gtaagaccag agtttcggac agcccagccc   2100
cgccctttgg gttctgcatg tgttcctggc agctgggcct gtctcctggg gccatggccg   2160
ggctcagggg cctttgagct ggcctgaggg cactttcgct tcctggccgg tactggaatg   2220
gctgtgtcct agtctgctgg ggcttggcct ctgggtcctg ccctttgtgt gtccggggta   2280
gtgaccttag cgtggagtgg ggagagggca gttgggtgtg ctggctgttc tcattcctct   2340
```

ttcccttctt ttagcaataa gtctggggtg aggtggggag ggaggctgca ggggggggagg 2400 tgggcagagg ggccttacag cagcagaggc tggaagagaa gctctgtctt caggggccag 2460
ctgggaaatg ctaaggagct gagggtgccc accaagccca ccttccagaa acttggagaa 2520
atgggggttg ggaacttatg cagacatgga tttatttttc aacatttttt aaaaattaaa 2580
aaaaataaaa tctaagctta ctgaaaaaaa aaaaaaaaaa a 2621

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
gttgttcctg aaggttactg 20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
gctggtgcaa caacattgct 20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
gcacggcgtg gactacttga 20

<210> SEQ ID NO 36
<211> LENGTH: 20
<212> TYPE: DNA
<213> ORGANISM: Artificial Sequence
<220> FEATURE:
<223> OTHER INFORMATION: Sythetic oligonucleotide

<400> SEQUENCE: 36
gctgcaccgt gttcatgccc 20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
gagctggacg gcgacgtaaa 20

<210> SEQ ID NO 38
<211> LENGTH: 20
<212> TYPE: DNA
<213> ORGANISM: Artificial Sequence
<220> FEATURE:
<223> OTHER INFORMATION: Sythentic oligonucleotide

<400> SEQUENCE: 38
accaacttgc ccaggttcaa 20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
gttcaagagc agcctaggca 20

<210> SEQ ID NO 40
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 40
cagcagatct ttttgcacaa gc 22

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 41
tgcccaaagt tacaagagcc a 21

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
atgaacacgg tgcagctgta 20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
agggccagct ggtactgata 20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
gttcctgctt ccttcccctc 20

<210> SEQ ID NO 45
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 45

tgcacagtcc ccgcattaat                                              20


<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46

cagggttcga ttccgtagag                                              20


<210> SEQ ID NO 47
<211> LENGTH: 20
<212> TYPE: DNA
<213> ORGANISM: Artificial Sequence
<220> FEATURE:
<223> OTHER INFORMATION: Sythetic oligonucleotide

<400> SEQUENCE: 47

cctccagtgg atcctcgtta                                              20


<210> SEQ ID NO 48
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 48

caccccagca aaccatatta tgc                                          23


<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49

cacacagcca tgcagggatt                                              20


<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50

tggatacgtg gcgtaaaatg                                              20


<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
```

-continued

```
cgagcagact ggcatctgta                                                20


<210> SEQ ID NO 52
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 52

gtgctcacgc tcggagaaa                                                 19


<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 53

gtgggaaaca gctcgaatgg t                                              21


<210> SEQ ID NO 54
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 54

caggtctcgt gccaatcaaa a                                              21


<210> SEQ ID NO 55
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 55

gctgttgctg gtgtgtattc t                                              21
```

COMPOSITIONS AND METHODS FOR TREATING DRUG-TOLERANT GLIOBLASTOMA

CROSS REFERENCE TO RELATED APPLICATIONS

This application is the U.S. national phase application, pursuant to 35 U.S.C. § 371, of PCT international application Ser. No.: PCT/US2016/024083, filed Mar. 24, 2016, designating the United States and published in English, which claims the benefit of and priority to U.S. Provisional Application Ser. No. 62/266,544, filed Dec. 11, 2015, the contents of which are incorporated herein by reference.

STATEMENT OF RIGHTS TO INVENTIONS MADE UNDER FEDERALLY SPONSORED RESEARCH

This invention was made with government support under grant no. R25NS065743 awarded by the National Institutes of Health (NIH). The government has certain rights in the invention.

BACKGROUND OF THE INVENTION

Glioblastoma (GBM) is the most common malignant brain tumor in adults and is associated with poor prognosis despite aggressive treatment. Transcriptional profiling studies have revealed biologically relevant GBM subtypes associated with survival and response to therapy, as well as specific dysregulated cellular pathways. Recent studies have documented the presence of one or more sub-populations of GBM cells with tumor-propagating capacity. These cells are believed to play a major role in tumor recurrence and resistance to therapy. Unfortunately, the epigenetic determinants that contribute to this therapeutic resistance have remained elusive. Compositions and methods for identifying subpopulations of tumor propagating cells and reducing their survival and proliferation are urgently required.

SUMMARY OF THE INVENTION

As described below, the present invention features compositions and methods for the diagnosis and treatment of glioblastoma, particularly tumor propagating cells within the glioblastoma.

In one aspect, the invention provides a method of increasing cell death in a glioblastoma stem cell involving contacting a glioblastoma stem cell with a platelet-derived growth factor receptor alpha inhibitor and one or more of a histone lysine demethylase inhibitor and a Notch inhibitor.

In another aspect, the invention provides a method of treating a subject having glioblastoma involving administering to the subject a platelet-derived growth factor receptor alpha inhibitor and one or more of a histone lysine demethylase inhibitor and a Notch inhibitor.

In another aspect, the invention provides a pharmaceutical composition containing a platelet-derived growth factor receptor alpha inhibitor and one or more of a histone lysine demethylase inhibitor and a Notch inhibitor.

In various embodiments of any aspect delineated herein, the inhibitor of platelet-derived growth factor receptor alpha is dasatinib, crenolanib, or combination thereof.

In various embodiments of any aspect delineated herein, the inhibitor of histone lysine demethylase is KDM5-C70, GSKJ4, or combination thereof. In various aspects, the histone lysine demethylase is KDM6A, KDM6B, or combination thereof.

In various embodiments of any aspect delineated herein, the Notch inhibitor is Compound E. In various aspects, Notch comprises Notch1 intracellular domain (N1ICD).

In various embodiments of any aspect delineated herein, the glioblastoma stem cell, including, e.g., in a glioblastoma, is identified as having increased expression of one or more of SALL2, FABP7, DLX2, ZFHX4, HEY1, HES5, and FABP7.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "DLX2 polypeptide" is meant a polypeptide or fragment thereof having at least about 85% amino acid identity to NCBI Accession No. NP_004396 and having DNA binding activity.

By "DLX2 nucleic acid molecule" is meant a polynucleotide encoding a DLX2 polypeptide. An exemplary DLX2 nucleic acid molecule sequence is provided at NCBI Accession No. NM_004405.

By "FABP7 polypeptide" is meant a polypeptide or fragment thereof having at least about 85% amino acid identity to NCBI Accession No. NP_001437 and having binding activity fatty acids and hydrophobic ligands.

By "FABP7 nucleic acid molecule" is meant a polynucleotide encoding a FABP7 polypeptide. An exemplary FABP7 nucleic acid molecule sequence is provided at NCBI Accession No. NM_001446.

By "HES5 polypeptide" is meant a polypeptide or fragment thereof having at least about 85% amino acid identity to NCBI Accession No. NP_001010926 and having DNA binding and Notch receptor binding activity.

By "HES5 nucleic acid molecule" is meant a polynucleotide encoding an HES5 polypeptide. An exemplary HES5 nucleic acid molecule sequence is provided at NCBI Accession No. NM_001010926.

By "HEY1 polypeptide" is meant a polypeptide or fragment thereof having at least about 85% amino acid identity to NCBI Accession No. NP_001035798 and having DNA binding activity.

By "HEY1 nucleic acid molecule" is meant a polynucleotide encoding a HEY1 polypeptide. An exemplary HEY1 nucleic acid molecule sequence is provided at NCBI Accession No. NM_001040708.

By "KDM6A polypeptide" is meant a polypeptide or fragment thereof having at least about 85% amino acid identity to NCBI Accession No. NP_001278344 and having histone lysine demethylase activity.

By "KDM6A nucleic acid molecule" is meant a polynucleotide encoding a KDM6A polypeptide. An exemplary KDM6A nucleic acid molecule sequence is provided at NCBI Accession No. NM_001291415.

By "KDM6B polypeptide" is meant a polypeptide or fragment thereof having at least about 85% amino acid identity to NCBI Accession No. NP_001073893 and having histone lysine demethylase activity.

By "KDM6B nucleic acid molecule" is meant a polynucleotide encoding a KDM6B polypeptide. An exemplary KDM6B nucleic acid molecule sequence is provided at NCBI Accession No. NM_001080424.

By "Notch polypeptide" is meant a polypeptide or fragment thereof having at least about 85% amino acid identity to NCBI Accession No. NP_060087 and having Notch pathway signaling activity.

By "Notch nucleic acid molecule" is meant a polynucleotide encoding a Notch polypeptide. An exemplary Notch nucleic acid molecule sequence is provided at NCBI Accession No. NM_017617.

By "Notch intracellular domain (ICD) polypeptide" is meant a polypeptide or fragment thereof having at least about 85% amino acid identity to amino acids 1754-2555 of NCBI Accession No. NP_060087 and having transcriptional activation activity.

By "PDGFRA polypeptide" is meant a polypeptide or fragment thereof having at least about 85% amino acid identity to NCBI Accession No. NP_006197 and having platelet-derived growth factor binding activity.

By "PDGFRA nucleic acid molecule" is meant a polynucleotide encoding a Platelet-derived growth factor receptor, alpha polypeptide. An exemplary PDGFA nucleic acid molecule sequence is provided at NCBI Accession No. NM_006206.

By "SALL2 polypeptide" is meant a polypeptide or fragment thereof having at least about 85% amino acid identity to NCBI Accession No. NP_005398 and having DNA binding activity.

By "SALL2 nucleic acid molecule" is meant a polynucleotide encoding an SALL2 polypeptide. An exemplary SALL2 nucleic acid molecule sequence is provided at NCBI Accession No. NM_005407.

By "ZFHX4 polypeptide" is meant a polypeptide or fragment thereof having at least about 85% amino acid identity to NCBI Accession No. NP_078997 and having DNA binding activity.

By "ZFHX4 nucleic acid molecule" is meant a polynucleotide encoding a ZFHX4 polypeptide. An exemplary ZFHX4 nucleic acid molecule sequence is provided at NCBI Accession No. NM_024721.

By "SOX2 polypeptide" is meant a polypeptide or fragment thereof having at least about 85% amino acid identity to NCBI Accession No. NP_003097 and having DNA binding activity. By "SOX2 nucleic acid molecule" is meant a polynucleotide encoding a SOX2 polypeptide. An exemplary SOX2 nucleic acid molecule sequence is provided at NCBI Accession No. NM_003106.

By "OLIG2 polypeptide" is meant a polypeptide or fragment thereof having at least about 85% amino acid identity to NCBI Accession No. NP_005797 and having DNA binding activity.

By "OLIG2 nucleic acid molecule" is meant a polynucleotide encoding an OLIG2 polypeptide. An exemplary OLIG2 nucleic acid molecule sequence is provided at NCBI Accession No. NM_005806.

By "POU3F2 polypeptide" is meant a polypeptide or fragment thereof having at least about 85% amino acid identity to NCBI Accession No. NP_005595 and having DNA binding activity. Alternative names for POU3F2 are Brn2 and Oct7.

By "POU3F2 nucleic acid molecule" is meant a polynucleotide encoding an POU3F2 polypeptide. An exemplary POU3F2 nucleic acid molecule sequence is provided at NCBI Accession No. NM_005604.

By "LSD1 polypeptide" is meant a polypeptide or fragment thereof having at least about 85% amino acid identity to NCBI Accession No. NP_055828 or NP_001009999 and having histone methyltransferase activity. LSD1 is also known as KDM1A.

By "LSD1 nucleic acid molecule" is meant a polynucleotide encoding an LSD1 polypeptide. An exemplary LSD1 nucleic acid molecule sequence is provided at NCBI Accession No. NM_015013 or NM_001009999.

By "RCOR2 polypeptide" is meant a polypeptide or fragment thereof having at least about 85% amino acid identity to NCBI Accession No. NP_775858 and having transcriptional repressor activity.

By "RCOR2 nucleic acid molecule" is meant a polynucleotide encoding an RCOR2 polypeptide. An exemplary RCOR2 nucleic acid molecule sequence is provided at NCBI Accession No. NM_173587.

As used herein the term "dasatinib" is a compound having the molecular formula $C_{22}H_{26}CLN_7O_2S$ (CAS number 302962-49-8) and platelet-derived growth factor receptor inhibitory activity. The structure of dasatinib is provided below.

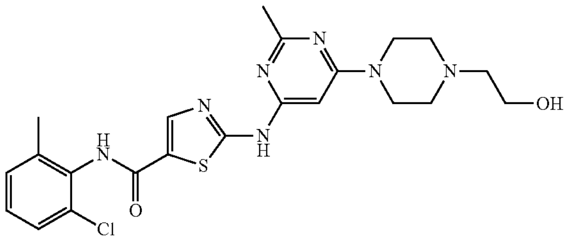 [SMILES: Cc1nc(Nc2ncc(C(=O)Nc3c(C)cccc3Cl)s2)cc(N2CCN(CCO)CC2)n1]

As used herein the term "crenolanib" is a compound having the molecular formula $C_{26}H_{29}N_5O_2$ (CAS number 670220-88-9) and platelet-derived growth factor receptor inhibitory activity. The structure of crenolanib is provided below.

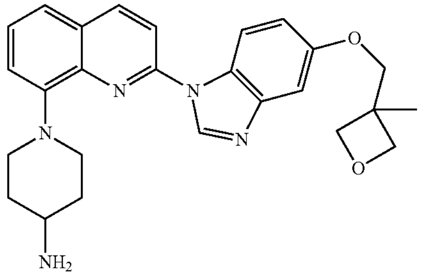 [SMILES: CC1(COc2ccc3c(c2)ncn3-c2ccc3cccc(N4CCC(N)CC4)c3n2)COC1]

As used herein the term "KDM5-C70" is a compound having the molecular formula $C_{17}H_{28}N_4O_3$ and histone lysine demethylase inhibitory activity. The structure of KDM5-C70 is provided below.

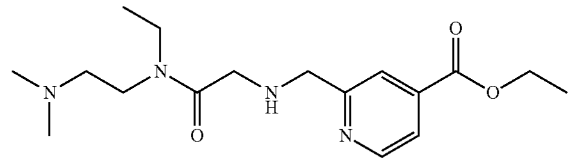 [SMILES: CCOC(=O)c1ccnc(CNCC(=O)N(CC)CCN(C)C)c1]

As used herein the term "GSKJ4" is a compound having the molecular formula $C_{24}H_{27}N_5O_2$ (CAS number 1373423-53-0) and histone lysine demethylase inhibitory activity. The structure of GSKJ4 is provided below.

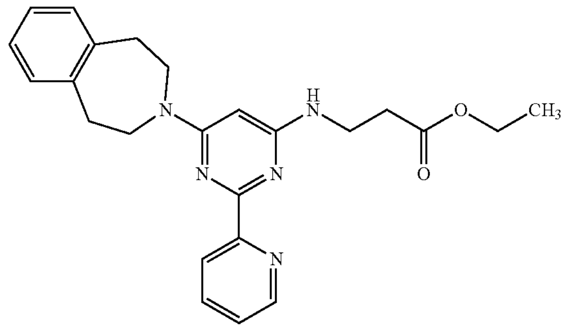 [SMILES: CCOC(=O)CCNc1cc(N2CCc3ccccc3CC2)nc(-c2ccccn2)n1]

As used herein the term "Compound E" is a compound having the molecular formula $C_{27}H_{24}F_2N_4O_3$ (CAS number 209986-17-4) and Notch inhibitory activity. The structure of Compound E is provided below.

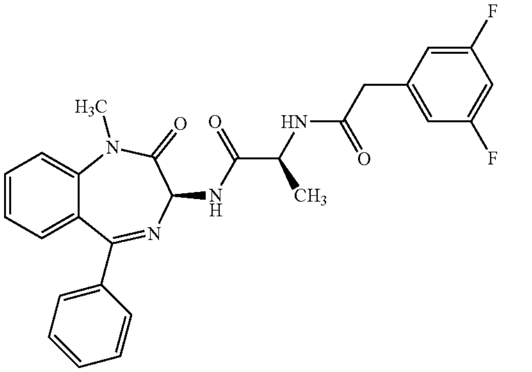 [SMILES: C[C@H](NC(=O)Cc1cc(F)cc(F)c1)C(=O)N[C@H]1N=C(c2ccccc2)c2ccccc2N(C)C1=O]

A "biomarker" or "marker" as used herein generally refers to a protein, nucleic acid molecule, clinical indicator, or other analyte that is associated with a disease. In one embodiment, a marker of glioblastoma is differentially present in a biological sample obtained from a subject having or at risk of developing glioblastoma relative to a reference. A marker is differentially present if the mean or median level of the biomarker present in the sample is statistically different from the level present in a reference. A reference level may be, for example, the level present in a sample obtained from a healthy control subject or the level obtained from the subject at an earlier timepoint, i.e., prior to treatment. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. The differential presence of a marker of the invention in a subject sample can be useful in characterizing the subject as having or at risk of developing glioblastoma, for determining the prognosis of the subject, for evaluating therapeutic efficacy, or for selecting a treatment regimen.

Select exemplary sequences delineated herein are shown in FIG. 16.

By "agent" is meant any small molecule chemical compound, antibody, nucleic acid molecule, or polypeptide, or fragments thereof.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism.

By "capture reagent" is meant a reagent that specifically binds a nucleic acid molecule or polypeptide to select or isolate the nucleic acid molecule or polypeptide.

By "clinical aggressiveness" is meant the severity of the neoplasia. Aggressive neoplasias are more likely to metastasize than less aggressive neoplasias. While conservative methods of treatment are appropriate for less aggressive neoplasias, more aggressive neoplasias require more aggressive therapeutic regimens.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

By "Molecular profile" is meant a characterization of the expression or expression level of two or more markers (e.g., polypeptides or polynucleotides).

By "neoplasia" is meant any disease that is caused by or results in inappropriately high levels of cell division, inappropriately low levels of apoptosis, or both. Glioblastoma is one example of a neoplasia or cancer. Other examples of cancers include, without limitation, prostate cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

By "reference" is meant a standard of comparison. For example, the LSD1, RCOR2, POU3F2, SOX2, SALL2 and/or OLIG2 polypeptide or polynucleotide level present in a patient sample may be compared to the level of said polypeptide or polynucleotide present in a corresponding healthy cell or tissue or in a neoplastic cell or tissue that lacks a propensity to metastasize. In one embodiment, the standard of comparison is the level of LSD1, RCOR2, POU3F2, SOX2, SALL2 and/or OLIG2 polypeptide or polynucleotide level present in a glioblastoma cell that is not capable of unlimited self-renewal and/or tumor propagation.

By "periodic" is meant at regular intervals. Periodic patient monitoring includes, for example, a schedule of tests that are administered daily, bi-weekly, bi-monthly, monthly, bi-annually, or annually.

By "severity of neoplasia" is meant the degree of pathology. The severity of a neoplasia increases, for example, as the stage or grade of the neoplasia increases.

By "Marker profile" is meant a characterization of the expression or expression level of two or more polypeptides or polynucleotides.

The term "glioblastoma" refers to both primary brain tumors, as well as metastases of the primary brain tumors that may have settled anywhere in the body.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "reference" is meant a standard of comparison. For example, the marker level(s) present in a patient sample may be compared to the level of the marker in a corresponding healthy cell or tissue or in a diseased cell or tissue (e.g., a cell or tissue derived from a subject having glioblastoma). In particular embodiments, the LSD1, RCOR2, POU3F2, SOX2, SALL2 and/or OLIG2 polypeptide or polynucleotide level polypeptide level present in a patient sample may be compared to the level of said polypeptide present in a corresponding sample obtained at an earlier time point (i.e., prior to treatment), to a healthy cell or tissue or a neoplastic cell or tissue that lacks a propensity to metastasize. As used herein, the term "sample" includes a biologic sample such as any tissue, cell, fluid, or other material derived from an organism.

By "specifically binds" is meant a compound (e.g., antibody) that recognizes and binds a molecule (e.g., polypeptide), but which does not substantially recognize and bind other molecules in a sample, for example, a biological sample.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF THE DRAWINGS

FIG. 1A is a line graph showing cell cycle meta-signature z-scores (y-axis) for ordered individual cells (x-axis) for three primary tumors (MGH26, MGH28, MGH30) and two GSC lines (GSC6, GSC8). Lower panel depicts heatmap of cell cycle meta-signature z-scores (values greater than 2 were mapped to 2). A higher fraction of cells in GSC lines display robust cell cycle expression in comparison to primary tumor specimens. FIG. 1B shows dose-response curves for 4 day dasatinib treatment. PDGFRA amplified GSC8 displayed selective sensitivity ($IC_{50}$~10 nM) in comparison to MYC-amplified GSC4 and EGFR-dependent GSC26. Error bars represent s.e.m. across three replicates. Representative example of two biological replicates is shown. FIG. 1C depicts immunoblots showing levels of phosphorylated PDGFRα, Akt, and Erk1/2 upon dasatinib treatment for 3 hours (3 h), 12 days (12 d), and >8 weeks (Per) in GSC8. Dasatinib treatment significantly reduced levels of phosphorylated proteins. Representative example of two biological replicates is shown. FIG. 1D is a stacked barplot showing the fraction of cells viable, in G0/G1, and in S/G2/M (y-axis), respectively, for GSC8 treated with dasatinib (1 μM) at various timepoints (x-axis). Washout refers to removal of dasatinib for >8 weeks. Error bars represent s.d. across at least three biological replicates. FIG. 1E depicts flow cytometry scatterplots for EdU incorporation (x-axis) and Ki67 (y-axis). Dasatinib treatment (4 d, 1 μM) induced cell cycle arrest and G0 induction. Representative example of three biological replicates is shown. FIG. 1F is a stacked barplot summarizing flow cytometry data for Ki67 and EdU incorporation in GSC8 naïve and GSC8 treated with dasatinib (4 d, 1 μM). Error bars represent s.d. across three biological replicates. FIG. 1G is a stacked barplot summarizing flow cytometry data for Ki67 and EdU incorporation after EdU pulse (2 h) and subsequent treatments. Dasatinib treated cells maintained similar relative levels of $EdU^+$ cells, which lose Ki67 positivity. Error bars represent s.d. across three biological replicates. FIG. 1H depicts barplots showing the relative amount of cells (%, y-axis) after 4 day drug treatments at various doses (x-axis) in comparison to DMSO controls. $GSC8^{Per}$ tolerated higher concentrations of PDGFR inhibitors (dasatinib, crenolanib) in comparison to GSC8 naïve. Error bars represent s.e.m. across six replicates. Representative example of two biological replicates is shown. FIG. 1I is a barplot showing dasatinib $IC_{50}$ values (y-axis) for GSC8 naïve, $GSC8^{Per}$, and at different time points following dasatinib removal. Washout of dasatinib from $GSC8^{Per}$ cultures led to resensitization to dasatinib-mediated growth arrest. Error bars represent s.d. of three biological replicates from separately derived $GSC8^{Per}$ lines. FIG. 1J is a schematic illustrating formation of slow-cycling, drug-tolerant persisters.

FIG. 2A depicts dose-response curves for 4 day PD0325901, buparlisib, MK2206, and temozolomide (TMZ) treatment in GSC8, GSC26, and GSC4. Error bars represent s.e.m. across three replicates. One of two biological replicates shown. FIG. 2B depicts dose-response curves for 4 day crenolanib treatment in GSC8 and GSC4. GSC8 is preferentially sensitive to crenolanib. Error bars represent s.e.m. across three replicates. One of two biological replicates shown. FIG. 2C depicts dose-response curve for 4 day palbociclib treatment are shown. Error bars represent s.e.m. across three replicates. One of two biological replicates shown.

FIG. 3A depicts flow cytometry scatterplots for levels of EdU incorporation (y-axis) and DNA content (x-axis) are shown for GSC8 naïve, GSC8$^{12d}$, and GSC8$^{Per}$. Populations were gated on viable cells using Live/Dead fixable far red dead cell stain kit. One of three to eight biological replicates shown. FIG. 3B is a table summarizing the percentage of viable cells that are in S, G2, or M at various timepoints of dasatinib treatment. FIG. 3C depicts flow cytometry scatterplots for levels of Ki67 (y-axis) and EdU incorporation (y-axis) after EdU pulse labeling (2 h). EdU levels decreased after 4 days of vehicle treatment but were largely retained following 4 days of dasatinib treatment. A large fraction of EdU$^{+}$ become Ki67$^{-}$ after drug treatment. Populations were gated on viable cells using Zombie aqua. One of three biological replicates shown. FIG. 3D depicts flow cytometry scatterplots for levels of EdU incorporation (y-axis) and DNA content (x-axis) for GSC8 treated with PD0325901 or palbociclib for 4 days or >8 weeks (Per). GSC8 PD0325901$^{Per}$ and GSC8 palbociclib$^{Per}$ lines partially recover proliferation in contrast to acute 4 day drug treatment. One of two biological replicates shown.

FIG. 4A depicts immunoblots showing levels of PDGFRα and α-tubulin in GSC8 cells treated with dasatinib. No substantial decrease of PDGFRα was observed with drug treatment. FIG. 4B is a flow cytometry histogram showing cell counts (y-axis) versus levels of PDGFRα (x-axis) in GSC8 naïve, GSC8$^{Per}$, GSC87, and an unstained control. This data shows high PDGFRα positivity in GSC8 naïve, GSC8 treated with dasatinib for 4 days, and GSC8$^{Per}$. Populations were gated on viable cells using FxCycle violet (DAPI), and ~1% of unstained control were considered PDGFRα positive. Representative example of two biological replicates is shown. FIG. 4C is a scatterplot showing mean read count (x-axis) versus fold-change in read counts (y-axis) for ChIP-input-derived sequencing data within annotated genes across conditions, illustrating results of DESeq2 (Love et al., 2014). Using an adjusted p-value cutoff of 0.05, no genes compared between GSC8 naïve and GSC8$^{12d}$, and only two genes compared between GSC8 naïve and GSC8$^{Per}$, were identified as significantly altered (purple dots). However, closer examination of the genes (LOC100130075 and LINC00426) revealed that the pseudo gene LOC100130075 localized within a MDM2 amplification, while an aberrant CNV state of the lincRNA LINC00426 was not apparent upon visual inspection of ChIP-seq binding profiles. This analysis revealed little to no potential de novo CNVs acquired in GSC persisters.

FIG. 5A is a heatmap showing expression profiles of the 4,084 most variably expressed genes across GSC8 naïve, GSC8$^{12d}$, and GSC8$^{Per}$ as determined by RNA-seq. K-means clustering was performed to distinguish sets of genes with coherent patterns of expression across the time course of dasatinib treatment. Data was generated from three biological replicates of separately derived GSC8$^{12d}$ and GSC8$^{Per}$ cultures. Color represents z-scores of gene expression across conditions. FIG. 5B depicts gene set enrichment analysis (GSEA) (Subramanian et al., 2005) showing relative enrichment of a cell cycle meta-signature (upper panel), gene sets related to quiescence in mouse neural stem cells (middle panel), and Sox2-positive medulloblastoma cells (lower panel) across naïve and GSC8 persister states. The cell cycle gene signature was negatively enriched, while the quiescence gene signatures were positively enriched upon dasatinib treatment. FIG. 5C is a barplot showing the fraction of cells (y-axis) positive for CD133 or CD15 by flow cytometry. GSC8$^{Per}$ display increased positivity for CD133 and CD15 in comparison to GSC8 naïve. Gates were determined using an unstained control, where ~2% of cells were considered positive. Error bars represent s.d. across three biological replicates. FIG. 5D depicts barplots showing the expression levels (y-axis) of SOX2, PROM1, and CDKN2A in GSC8 naïve, GSC8$^{12d}$, GSC8$^{Per}$, and normal human brain (GTEx) (GTEx Consortium, 2013). SOX2 and PROM1 expression in GSC8 naïve was considerably higher in comparison to normal brain obtained from GTEx and was further upregulated in GSC8$^{Per}$. By contrast, expression of CDKN2A, which is frequently deleted in GBM, was detected to lesser extent in GSC8 relative to normal brain. Error bars represent s.e.m.

FIGS. 6A and 6B show that GSC persisters were depleted of cell cycle gene signatures and enriched for stemness markers. FIG. 6A is a table showing representative gene signatures (Gene ontology, MSigDB C2 collection) enriched in differentially expressed gene clusters from FIG. 5A. Clusters 1-3 were enriched in signatures related to cell cycle, proliferation, and metabolism, while clusters 4-6 were enriched in signatures related to transcriptional regulation and neurodevelopment. FIG. 6B depicts flow cytometry contour plot for levels of CD133 (x-axis) and CD15 (y-axis). Dasatinib treatment in GSC8 resulted in significantly increased positivity for CD133 and CD15. Gates were determined using an unstained control, where ~2% of cells were considered positive. Representative example of three biological replicates is shown.

FIG. 7A is a heatmap showing normalized H3K27ac ChIP-seq signal for GSC8 naïve, GSC8$^{12d}$, and GSC8$^{Per}$ across different genomic intervals (rows). K-means clustering of rows identified groups of H3K27ac regions that are shared (I), naïve-enriched (II-III), GSC8$^{12d}$-enriched (IV-V), and GSC8$^{Per}$-enriched (VI-VII). Color corresponds to normalized ChIP signal. FIGS. 7B-7E are heatmaps showing mean expression of gene sets derived from RNA-seq data clusters 1-6 in FIG. 5A and N1ICD GSC8$^{Per}$ target genes (rows) across single tumor cells (columns) in two EGFR-amplified tumors (MGH30, MGH26). This analysis revealed distinct subpopulations of tumor cells enriched for proliferative (scoring high for clusters 1-3) and stemness signatures (scoring high for clusters 4-6) derived from the persister model. Furthermore, cells that score highly for N1ICD target genes correlated more strongly with stem-like tumor cells. Colors correspond to z-scores calculated across individual cells.

FIG. 8A depicts immunoblots showing levels of chromatin regulators in GSC8 upon dasatinib treatment. Levels of KDM5B and KDM6B increased while EZH2 was reduced. Representative example of two biological replicates is shown. FIG. 8B depicts ChIP-seq profile plots showing average ChIP-seq signal for H3K4me3 (y-axis) centered around cell cycle promoters (x-axis). The x-axis shows flanking regions of ±3 kb and the y-axis shows average signal in reads per million. Cell cycle genes were obtained from (Whitfield et al., 2002).

FIG. 9A depicts barplots showing fold-change in gene expression (y-axis) for various KDMs upon drug treatments by qRT-PCR. 48 hr drug treatments (dasatinib, PD0325901) led to up-regulation of numerous KDMs in GSC8. Error bars represent s.e.m. across three technical replicates. One of two biological replicates is shown. FIG. 9B depicts boxplots showing H3K4me3 peak width (y-axis) after various drug treatments. H3K4me3 peak width increases upon KDM5-C70 treatment (4 d, 2.5 μM) but not with GSKJ4 treatment (4 d, 1.5 μM). The y-axis indicates genomic length in kb. FIG. 9C depicts ChIP-seq profiles showing ChIP-seq signal (y-axis) for H3K4me3 surrounding the RRM2 promoter. KDM5-C70 treatment leads to partial rescue in H3K4me3 levels upon dasatinib treatment. The y-axis represents reads per million mapped reads. FIG. 9D depicts dose-response curves for 4 day KDM5-C70 treatment in GSC8 naïve, GSC8$^{12d}$, and GSC8$^{Per}$. KDM5-C70 had subtle effects on proliferation. Error bars represent s.e.m. across three replicates. One of two biological replicates shown. FIG. 9E depicts dasatinib dose-response curves for 4 day treatment in GSC8 naïve simultaneously treated with KDM5-C70 (2.5 μM, purple line) or vehicle (0.15% v/v DMSO, gray line). No significant effect was observed. Error bars represent s.e.m. across three replicates. One of two biological replicates shown. FIG. 9F depicts ChIP-seq profile plots showing H3K27me3 ChIP-seq signal (y-axis) across H3K27me3 peaks of GSC8 naïve (grey), GSC8$^{12d}$ (blue), GSC8$^{Per}$ (red), and GSC8 PD0325901$^{Per}$ (green). The x-axis represents size scaled genomic location, and the y-axis shows average signal in reads per million. For this analysis, union peaks over all displayed samples with minimum size of 10 kb were considered. FIG. 9G. depicts ChIP-seq profile plots showing H3K27me3 ChIP-seq signal (y-axis) across of H3K27me3 peaks of GSC8 naïve (grey), GSC8 treated with dasatinib for 4 days (orange), GSC8$^{12d}$ (blue), and GSC8$^{Per}$ (red). The x-axis represents size scaled genomic location, and the y-axis shows average signal in reads per million mapped reads. For this analysis, union peaks over all displayed samples with a minimum size of 10 kb were considered. FIG. 9H depicts ChIP-seq profile plots showing H3K4me3 ChIP-seq signal (y-axis) centered around all H3K4me3 peaks in GSC8 naïve (grey), GSC8$^{12d}$ (blue), GSC8 treated with GSKJ4 for 8 days (green), and GSC8$^{12d}$ treated with GSKJ4 for 8 days starting after 4 days of dasatinib treatment (orange). The x-axis shows flanking regions of ±3 kb, and the y-axis shows average signal in reads per million. For this analysis, union peaks over all displayed samples were considered.

FIG. 10A depicts DNA agarose (1%) gel images showing SURVEYOR analysis for sgRNAs used in the study for GSC8 naïve, GSC8$^{Per}$, GSC4, and GSC87. Efficient editing at genomic loci of interest was demonstrated. Experiment performed once. FIG. 10B depicts line graphs showing cell growth as relative Cell-titer Glo (CTG) values normalized to day zero ($T_0$) (y-axis) over a time course (x-axis) following CRISPR-Cas9 mediated knockout of respective genes. CRISPR-Cas9 mediated knockout of KDM6A/B depleted emergence of GSC8 persisters. Error bars represent s.e.m. across four replicates. One of two biological replicates shown. FIG. 10C depicts dose-response curves for 4 day GSKJ4 treatment. GSC8 PD0325901$^{Per}$ were preferentially sensitive to GSKJ4 in comparison to GSC8 naïve. Error bars represent s.e.m. across three replicates. One of two biological replicates shown. FIG. 10D depicts dose-response curves for 4 day GSKJ5 treatment in GSC8 naïve, GSC8$^{12d}$, GSC8$^{Per}$, and GSC8 PD0325901$^{Per}$. Negligible differential effects on cell proliferation were observed. Error bars represent s.e.m. across three replicates. One of two biological replicates shown. FIG. 10E is a barplot showing the fraction of cells (y-axis) positive for EdU, and CD133 in untreated GSC8 and GSC87. Error bars represent s.d. across three biological replicates. FIG. 10F is a flow cytometry histogram showing cell counts (y-axis) versus levels of PDGFRα (x-axis) in GSC8 naïve, GSC87, and GSC4. This data showed high PDGFRα positivity in GSC8 naïve and GSC87. Populations were gated on viable cells using FxCycle violet.

FIG. 11A depicts line graphs showing cell growth as relative Cell-titer Glo (CTG) values normalized to day zero ($T_0$) (y-axis) over a time course (x-axis) following CRISPR-Cas9 mediated knockout of respective genes. CRISPR-Cas9 mediated knockout of KDM6A and KDM6B only modestly affected the proliferation of GSC8 naïve (left panel) but significantly impaired proliferation of GSC8 das$^{Per}$ (right panel). Error bars represent s.e.m. across three replicates. Representative example of three biological replicates is shown. FIG. 11B depict dose-response curves for 4 day GSKJ4 treatment. GSC8 das$^{12d}$ and GSC8 das$^{Per}$ were preferentially sensitive to GSKJ4 in comparison to GSC8 naïve. Error bars represent s.e.m. across three replicates. Representative example of three biological replicates is shown. FIG. 11C is a heatmap showing mean expression of cell cycle genes and gene sets derived from RNA-seq data clusters 1-6 from FIG. 5A. GSC4 and GSC87 demonstrated inherently variable expression levels of cell cycle as well as 'naive' and 'persister' signatures. Color represents z-scores calculated across GSC culture models and conditions. FIG. 11D depicts line graphs showing cell growth as relative Cell-titer Glo (CTG) values normalized to day zero ($T_0$) (y-axis) over a time course (x-axis) following CRISPR-Cas9 mediated knockout of respective genes. CRISPR-Cas9 mediated knockout of KDM6B preferentially affected the proliferation of GSC87 (right panel), which displayed 'persister-like' characteristics. Error bars represent s.e.m. across three replicates. Representative example of two biological replicates is shown.

FIG. 12A is a schematic illustrating a proposed model, whereby EZH2 loss and KDM6A/B upregulation facilitate H3K27 remodeling and subsequent activation of stemness programs. FIG. 12B depicts heatmaps showing average normalized ChIP-seq signal for H3K27ac (left panel) and H3K27me3 (right panel) for groups of genomic intervals derived from clustering analysis in FIG. 7A. H3K27ac and H3K27me3 signals were calculated within 1 kb and 20 kb windows centered around H3K27ac peaks, respectively. Color corresponds to normalized ChIP signal. FIG. 12C is a scatterplot showing changes in expression (y-axis) and intragenic H3K27me3 levels (x-axis) for genes associated with H3K27ac peaks in cluster VI/VII in FIG. 7A that contain at least one H3K27me3 peak in GSC naive, $GSC8^{12d}$ or $GSC8^{Per}$. The y-axis represents log 2 fold-change in gene expression comparing $GSC8^{Per}$ to GSC8 naïve. The x-axis represents log 2 fold-change of intragenic H3K27me3 levels comparing $GSC8^{Per}$ to GSC8 naïve. FIG. 12D depicts ChIP-seq profiles showing ChIP-seq signal (y-axis) for H3K27ac and H3K27me3 at genomic loci of HEY1, FABP7, HES5, and SALL2. The y-axis shows average signal in reads per million.

FIG. 13A is a heatmap showing average expression of genes implicated in Notch signaling {Kopan:2009ic} for GSC8 naïve, $GSC8^{12d}$, and $GSC8^{Per}$. Color represents z-scores of average gene expression values within each condition. FIG. 13B depicts immunoblots showing levels of N1ICD and RBPJ in GSC8 naïve and GSC8 treated with dasatinib for 3 h, 12 d, and >8 weeks (Per). Representative example of two biological replicates is shown. FIG. 13C depict dose-response curves for 12 day Compound E treatment. $GSC8^{Per}$ were preferentially sensitive in comparison to GSC8 naïve. Error bars represent s.e.m. across four replicates. Representative example of three biological replicates is shown. FIG. 13D depicts ChIP-seq profile plots showing ChIP-seq signal (y-axis) of N1ICD (left panel) and RBPJ (right panel) across identified peaks for each respective factor. The x-axis shows flanking regions of ±1 kb and the y-axis shows average signal in reads per million. FIG. 13E depicts ChIP-seq profiles showing ChIP-seq signal (y-axis) of N1ICD, RBPJ, H3K27ac and H3K27me3 at the HEY1 locus. The y-axis shows average signal in reads per million. FIG. 13F is a scatterplot showing changes in expression (y-axis) and intragenic H3K27me3 levels (x-axis) of genes associated with an N1ICD peak in $GSC8^{Per}$ that contain at least one H3K27me3 peak in GSC naïve, $GSC8^{12d}$ or $GSC8^{Per}$. The y-axis represents log 2 fold-change in gene expression comparing $GSC8^{Per}$ to GSC8 naïve. The x-axis represents log 2 fold-change of intragenic H3K27me3 levels comparing $GSC8^{Per}$ to GSC8 naïve.

FIG. 14A is a consensus RBPJ motif logo detected in N1ICD and RBPJ ChIP-seq peaks in $GSC8^{Per}$. Corresponding p-values are shown. FIG. 14B depicts ChIP-seq profiles showing ChIP-seq signal (y-axis) for Notch1 ICD, RBPJ, H3K27ac and H3K27me3 at genomic loci of the canonical Notch targets HES4, HES5 and HES1. The y-axis represents reads per million.

FIG. 16 provides exemplary sequences of DLX2, FABP7, HES5, HEY1, KDM6A, KDM6B, Notch, PDGFRA, spalt-like transcription factor 2 (SALL2), ZFHX4, human sex determining region Y-box 2 (SOX2), oligodendrocyte transcription factor 2 (OLIG2), POU class 3 homeobox 2 (POU3F2), lysine-specific demethylase 1 (LSD1), RE1-silencing transcription factor corepressor 2 (RCOR2) polypeptides and nucleic acid molecules.

DETAILED DESCRIPTION OF THE INVENTION

Figure 1:
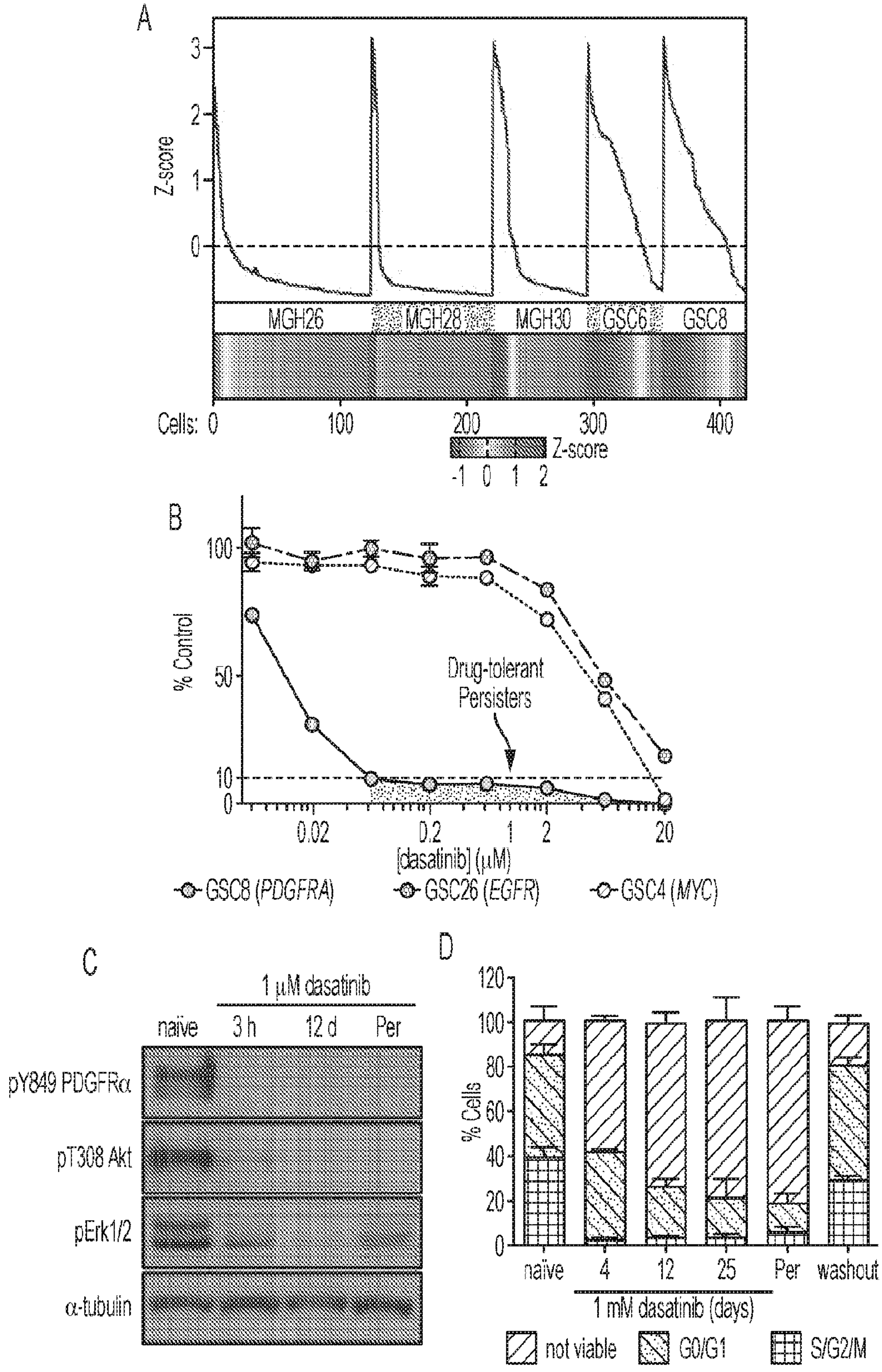
FIGS. 1A-1J show that PDGFR inhibition prompted emergence of slow-cycling drug-tolerant persisters.
Figure 1:
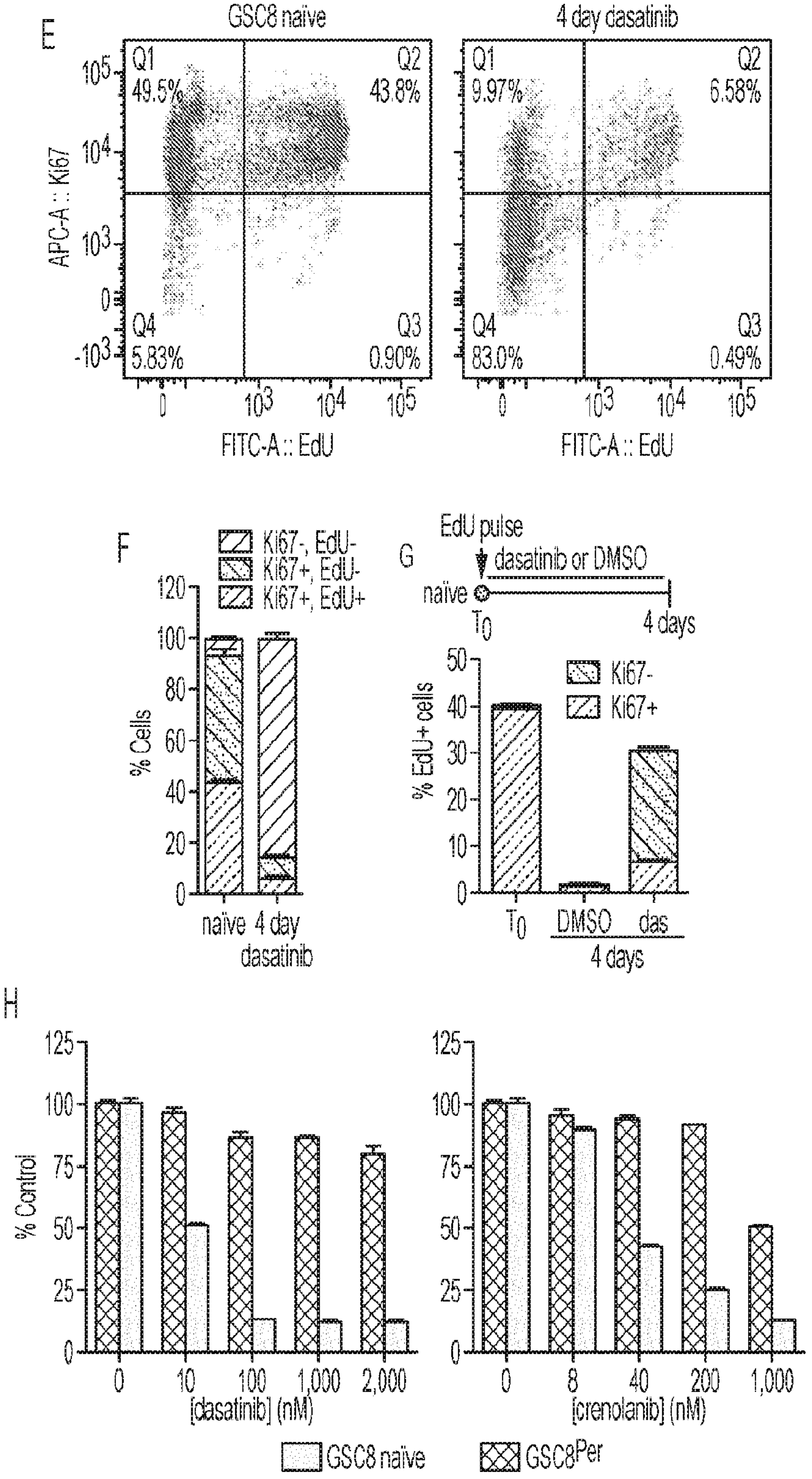

The invention features compositions and methods that are useful for the diagnosis, treatment and prevention of neoplasias (e.g., glioblastoma), as well as for characterizing a neoplasia (e.g., glioblastoma) to determine subject diagnosis, prognosis and/or to aid in treatment selection. The invention further provides compositions and methods for monitoring a patient identified as having a neoplasia (e.g., glioblastoma).

The present invention is based at least in part on several discoveries described herein. Evidence is provided that GSCs can adopt, and transition between, proliferative and slow-cycling states. Dynamic inter-conversion between these states was modeled using the phenotype of reversible drug tolerance in an RTK-dependent GSC line. Inhibition of RTK signaling resulted in rapid emergence of slow-cycling cells insensitive to RTK inhibitors and heavily depleted for cell cycle gene expression programs. These persister cells ($GSC^{Per}$) expressed increased levels of NSC markers and recapitulated key transcriptional features of stem-like GBM cells in vivo, including over-expression of histone lysine demethylases (KDMs). $GSC^{Per}$ demonstrated widespread redistribution of histone H3 lysine 27 trimethylation (H3K27me3) that is dependent on the H3K27 demethylases KDM6A and KDM6B. Moreover, it was found that KDM6A/B were important for the $GSC^{Per}$ state, but dispensable for the proliferative (naïve) GSC state. H3K27 demethylation in $GSC^{Per}$ is accompanied by activation of master regulators involved in neurodevelopment and glioma, including Notch signaling effectors and targets that were important for persistent stem cell states. These studies highlight key roles for chromatin remodeling and developmental plasticity in GBM biology, and have the potential to inform strategies for overcoming therapeutic resistance by targeting epigenetic and developmental pathways.

The present invention is based, at least in part, on the discovery that pluripotent stem cell transcription factors, POU3F2, SOX2, SALL2, and OLIG2, are expressed by glioblastoma tumor-initiating cells; and that one or more of POU3F2, SOX2, SALL2, and OLIG2 may be used to characterize the glioblastoma to inform treatment selection and subject prognosis. In other embodiments, the combination of POU3F2, SOX2, SALL2, and OLIG2 are characterized to inform treatment selection and subject prognosis. As reported in more detail below, cis-regulatory elements were surveyed in three matched pairs of tumor-propagating gliomaspheres TPCs and differentiated glioblastoma cells DGCs established from three human tumors to generate an epigenetic signature of tumor-initiating GBM cells. Specifically, histone H3 lysine 27 acetylation (H3K27ac) was specifically mapped, which marks promoters and enhancers that are "active" in a given cell state. Glioblastoma tumor-initiating cells achieve pluripotency by reprogramming and expressing the combination of markers POU3F2, SOX2, SALL2, and OLIG2 stem cell transcription factors. Accordingly, the invention provides diagnostic compositions that are useful in identifying subjects as having or having a propensity to develop a glioblastoma carcinoma, to develop a recurrence of glioblastoma, and/or to develop metastatic glioblastoma, as well as methods of using these compositions to identify a subject's prognosis, select a treatment regimen, and monitor the subject before, during or after treatment.

As described herein, GSCs can evade targeted therapies by reversibly transitioning to a slow-cycling state reminiscent of quiescent neural stem cells. These persister GSCs up-regulate primitive developmental programs, and are sustained by Notch signaling. The transition from proliferative to persister states is accompanied by widespread redistribution of repressive histone methylation. Accordingly, persister GSCs up-regulate and depend on the corresponding histone demethylases KDM6A/B. Importantly, persister-like cells are present in primary glioblastomas prior to treatment, and may thus contribute to tumor relapse. These findings illustrate how cancer cells may hijack native developmental programs for deranged proliferation, adaptation, and tolerance. They also indicate potential strategies for eliminating refractory tumor cells by targeting epigenetic and developmental pathways.

Glioblastoma

Glioblastoma (GBM) is the most common malignant brain tumor in adults and remains incurable despite aggressive treatment. Genome sequencing and transcriptional profiling studies have highlighted a large number of genetic events and identified multiple biologically relevant GBM subtypes, representing a significant challenge for targeted therapy. In addition, there is strong evidence that differentiation status significantly impacts GBM cell properties, with stem-like cells likely driving tumor propagation and therapeutic resistance. The transcription factor ASCL1 was recently identified as an important regulator of Wnt signaling in GBM stemlike cells. Although putative stem-like populations in GBM can be enriched using cell surface markers such as CD133, SSEA-1, CD44, and integrin alpha 6, the consistency of the various markers and the extent to which genetic heterogeneity contributes to observed phenotypic differences remains controversial. A TF code for GBM stem-like cells, analogous to those identified in iPS reprogramming and direct lineage conversion experiments, could thus provide important insights into the epigenetic circuitry underlying GBM pathogenesis.

Transcription Factors and Epigenetic State of Induced Tumor-Propagating Gliomaspheres (TPCs)

In mammalian development, stem and progenitor cells differentiate hierarchically to give rise to germ layers, lineages and specialized cell types. These cell fate decisions are dictated and sustained by master regulator transcription factors (TFs), chromatin regulators and associated cellular networks. It is now well established that developmental decisions can be overridden by artificial induction of combinations of 'core' TFs that yield induced pluripotent stem (iPS) cells or direct lineage conversion. These TFs bind and activate cis-regulatory elements that modulate transcription, and thereby direct cell type-specific gene expression programs.

Increasing evidence suggests that certain malignant tumors also depend on a cellular hierarchy, with privileged sub-populations driving tumor propagation and growth. Moreover, oncogenic transformation frequently involves re-acquisition of developmental programs, with parallels to artificial nuclear reprogramming. Consistently, many master regulator TFs have been implicated in tumorigenesis as oncogenes and partners in fusion proteins. For example, the pluripotency and neurodevelopmental factor Sox2 is an important driver of stem-like populations in multiple malignancies. Thus, in addition to their developmental functions, certain TFs may play critical roles in directing cellular hierarchies and phenotypes within tumors, with important clinical consequences. Studies of leukemia pioneered the concept that triggering cellular differentiation can abolish certain malignant programs and override genetic alterations. Similarly, iPS reprogramming experiments have shown that artificially changing cancer cell identity profoundly alters their properties. Recent studies have established analogous hierarchies in certain solid tumors, including glioblastoma, and thus point to the importance of understanding the epigenetic identities and susceptibilities of such aggressive subpopulations. These findings suggest that epigenetic circuits superimposed upon genetic mutations determine key features of cancer cells. Nonetheless, these malignant programs are poorly understood in most malignancies.

As described herein, functional genomics and cellular reprogramming were combined to reconstruct the transcriptional circuitry that governs the developmental hierarchy in human GBM. A core set of four neurodevelopmental TFs (POU3F2, SOX2, SALL2 and OLIG2) important for GBM propagation were identified. These TFs coordinately bind and activate TPC-specific cis-regulatory elements, and are sufficient to fully reprogram differentiated GBM cells to 'induced' TPCs that faithfully recapitulate the epigenetic landscape and phenotype of their native counterparts. Importantly, this TF code was used to identify sub-populations of candidate tumor propagating cells within primary human GBM tumors.

The in vivo relevance of the core TF network is supported by (i) the direct identification of stem-like cells within primary GBM tumors that coordinately express all four factors; (ii) chromatin maps for primary tumors that confirm the activity of large numbers of TPC-specific regulatory elements; and (iii) the requirement of all four factors for in vivo tumorigenicity in xenotransplanted mice. Given their demonstrated functionality, it is proposed that the core TFs have specific advantages for identifying aggressive cellular subsets relative to conventional surface markers that have been defined empirically and remain controversial.

Genome-wide binding maps and transcriptional profiles revealed downstream gene targets of the four TFs, including two key subunits of a transcriptional co-repressor complex: RCOR2 and the histone demethylase LSD1. Surprisingly, RCOR2 was able to substitute for OLIG2 in the reprogramming cocktail, thus validating the regulatory model. Tumor propagating GBM cells, but not their differentiated counterparts, were exquisitely sensitive to LSD1 suppression by shRNA knockdown or chemical inhibition. This selectivity is consistent with prior studies showing efficacy of LSD1 inhibitors against MLL-AF9 leukemia stem cells. These findings indicate that epigenetic therapies have the potential to target aggressive sub-populations and represent novel opportunities in GBM management.

As described herein, it is shown that cancer stem cells can evade RTK inhibition and other anti-proliferative therapies by regressing to a slow-cycling state reminiscent of quiescent neural stem cells. Specifically, it was found that patient-derived, multipotent GBM stem cells can inter-convert between a proliferative RTK-dependent state and a dormant, refractory Notch-dependent state. These alternate states directly parallel important stages of normal neural development, which are involved in the maintenance and expansion of neural stem cells.

An expanding body of literature supports a cancer stem cell model in GBM, wherein tumor propagation is mediated by multipotent cells at the apex of a differentiation hierarchy. GBM stem cells are thought to resist current therapies and thus underlie inevitable relapse. Consistently, single-cell expression profiles of primary GBMs revealed a dormant subpopulation of tumor cells with transcriptional signatures analogous to the slow-cycling GSC persister model. This supports the clinical significance of this study, and emphasizes the urgent need for alternative therapeutic strategies to eliminate this refractory tumor compartment.

The stringency and directionality of cancer stem cell hierarchies remains a critical question in the field. Differentiation of GSC models is largely unidirectional, at least in vitro, but may be reversed by induction of neurodevelopmental TFs (Suvà et al., 2014). The observation that GSCs may further dedifferentiate to an even more primitive developmental state raises further questions regarding how tumor cells circumvent checkpoints that normally restrict developmental transitions. Chromatin structure is widely implicated in cell fate restriction, and may thus be highly relevant to the control of epigenetic transitions in cancer. Numerous KDMs are up-regulated in slow-cycling GSC persisters and stem-like cells in vivo. The persisters exhibit widespread redistribution of the repressive chromatin modification H3K27me3 and a specific dependency on the corresponding demethylases, KDM6A/B. In addition to drug treatment, KDMs are induced by other stressors, including cell cycle arrest (Agger et al., 2009; Ene et al., 2012), DNA damage (Williams et al., 2014), hypoxia (Xia et al., 2009), and inflammation (De Santa et al., 2007). Such endogenous stressors may drive the KDM up-regulation that we detect in primary GBMs, thereby establishing persister-like cells in patients before drug treatment. Without being bound by theory, it is hypothesized that the ensuing histone demethylation promotes epigenetic plasticity, which allows activation of alternative cis-regulatory elements and pathways to support survival and adaptation to stressful tumor microenvironments (Johnstone and Baylin, 2010; Chaffer et al., 2013).

One such alternative pathway activated is Notch signaling, which is known to activate critical developmental programs implicated in neural stem cells and GSCs (Fan et al., 2010; Wang et al., 2010; Cenciarelli et al., 2014; Saito et al., 2014). Notch signaling becomes activated in $GSC^{Per}$, and appears to drive the expression of master regulators of neurodevelopment and stem cell quiescence. In fact, the bi-directional epigenetic switch between RTK- and Notch-dependent states in $GSC^{Per}$ shows a striking resemblance to the antagonism between these two signaling pathways in neural stem cells (Aguirre et al., 2010; Lim and Alvarez-Buylla, 2014; Mizutani et al., 2007). The findings described herein may therefore contextualize proliferative heterogeneity within the tumor hierarchy, which parallels a conserved developmental mechanism. Importantly, the Notch-dependency of this dormant and refractory cancer stem cell state indicates the potential of combining Notch antagonists with conventional or targeted therapies.

In summary, a reversible epigenetic transition was discovered that enables cancer stem cells to toggle between proliferative and slow-cycling states, which enables GBM tumors to propagate, adapt, and persist in the face of environmental and therapeutic pressures. The underlying regulatory programs closely parallel pathways in neural stem cell biology, thus illustrating how cancer cells may exploit native developmental programs for deranged proliferation, adaptation, and tolerance. Further understanding such hijacked developmental programs, and approaches for their modulation, have the potential to provide effective therapeutic strategies that address malignant hierarchies and dormant cancer cells in GBM and other tumors.

Biomarkers

In particular embodiments, a biomarker (e.g., LSD1, RCOR2, POU3F2, SOX2, SALL2 or OLIG2) is a biomolecule that is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for characterizing a disease. Levels of LSD1, RCOR2, POU3F2, SOX2, SALL2 or OLIG2 are typically increased in a subpopulation of tumor propagating glioblastoma cells.

Types of Biological Samples

The level of SALL2, FABP7, DLX2, ZFHX4, HEY1, HES5, LSD1, RCOR2, POU3F2, SOX2, and/or OLIG2 protein or polynucleotide is measured in different types of biologic samples. In one embodiment, the level of SALL2, FABP7, DLX2, ZFHX4, HEY1, HES5, LSD1, RCOR2, POU3F2, SOX2, and/or OLIG2 proteins or polynucleotides is measured in different types of biologic samples. In another embodiment, the level of SALL2, FABP7, DLX2, ZFHX4, HEY1, HES5, LSD1, RCOR2, POU3F2, SOX2, and/or OLIG2 proteins or polynucleotides is measured in different types of biologic samples. In one embodiment, the biologic sample is a tissue sample that includes cells of a tissue or organ (e.g., glioblastoma cells). Glioblastoma tissue is obtained, for example, from a biopsy of the tumor. In another embodiment, the biologic sample is a biologic fluid sample. Biological fluid samples include cerebrospinal fluid blood, blood serum, plasma, urine, and saliva, or any other biological fluid useful in the methods of the invention.

Diagnostic Assays

The present invention provides a number of diagnostic assays that are useful for the identification or characterization of glioblastoma, or a propensity to develop such a condition. In one embodiment, glioblastoma is characterized by quantifying the level of one or more of the following markers: POU3F2, SOX2, SALL2, and/or OLIG2. In certain embodiments, LSD1 and RCOR2 are markers used in combination with POU3F2, SOX2, SALL2, and/or OLIG2. In another embodiment, glioblastoma is characterized by quantifying the level of one or more of the following markers: POU3F2, SOX2, SALL2, and/or OLIG2. In yet another embodiment, glioblastoma is characterized by quantifying the level of the following markers: POU3F2, SOX2, SALL2, and/or OLIG2. While the examples provided below describe specific methods of detecting levels of these markers, the skilled artisan appreciates that the invention is not limited to such methods. Marker levels are quantifiable by any standard method, such methods include, but are not limited to real-time PCR, Southern blot, PCR, mass spectroscopy, and/or antibody binding.

The examples describe primers used in the invention for amplification of markers of the invention. The primers of the invention embrace oligonucleotides of sufficient length and appropriate sequence so as to provide specific amplification. While exemplary primers are provided herein, it is understood that any primer that hybridizes with the marker sequences of the invention are useful in the methods of the invention for detecting marker levels.

The level of any two or more of the markers described herein defines the marker profile of a glioblastoma. The level of marker is compared to a reference. In one embodiment, the reference is the level of marker present in a control sample obtained from a patient that does not have glioblastoma. In another embodiment, the reference is a baseline level of marker present in a biologic sample derived from a patient prior to, during, or after treatment for a neoplasia. In yet another embodiment, the reference is a standardized curve. The level of any one or more of the markers described herein (e.g., the combination of POU3F2, SOX2, SALL2, and/or OLIG2) is used, alone or in combination with other standard methods, to characterize the neoplasia.

Detection of Biomarkers

The biomarkers of this invention can be detected by any suitable method. The methods described herein can be used individually or in combination for a more accurate detection of the biomarkers (e.g., mass spectrometry, immunoassay, and the like).

Detection by Immunoassay

In particular embodiments, the biomarkers of the invention (e.g., POU3F2, SOX2, SALL2, and/or OLIG2) are measured by immunoassay. Immunoassay typically utilizes an antibody (or other agent that specifically binds the marker) to detect the presence or level of a biomarker in a sample. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, Western blot, sandwich immunoassays including ELISA and other enzyme immunoassays, fluorescence-based immunoassays, chemiluminescence. Nephelometry is an assay done in liquid phase, in which antibodies are in solution. Binding of the antigen to the antibody results in changes in absorbance, which is measured. Other forms of immunoassay include magnetic immunoassay, radioimmunoassay, and real-time immunoquantitative PCR (iqPCR).

Immunoassays can be carried out on solid substrates (e.g., chips, beads, microfluidic platforms, membranes) or on any other forms that supports binding of the antibody to the marker and subsequent detection. A single marker may be detected at a time or a multiplex format may be used. Multiplex immunoanalysis may involve planar microarrays (protein chips) and bead-based microarrays (suspension arrays).

In a SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

Detection by Biochip

In aspects of the invention, a sample is analyzed by means of a biochip (also known as a microarray). The polypeptides and nucleic acid molecules of the invention are useful as hybridizable array elements in a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28: e3. i-e3. vii, 2000), MacBeath et al., (Science 289:1760-1763, 2000), Zhu et al. (Nature Genet. 26:283-289), and in U.S. Pat. No. 6,436,665, hereby incorporated by reference.

Detection by Protein Biochip

In aspects of the invention, a sample is analyzed by means of a protein biochip (also known as a protein microarray). Such biochips are useful in high-throughput low-cost screens to identify alterations in the expression or post-translation modification of a polypeptide of the invention, or a fragment thereof. In embodiments, a protein biochip of the invention binds a biomarker (e.g., POU3F2, SOX2, SALL2, and/or OLIG2) present in a subject sample and detects an alteration in the level of the biomarker. Typically, a protein biochip features a protein, or fragment thereof, bound to a solid support. Suitable solid supports include membranes (e.g., membranes composed of nitrocellulose, paper, or other material), polymer-based films (e.g., polystyrene), beads, or glass slides. For some applications, proteins (e.g., antibodies that bind a marker of the invention) are spotted on a substrate using any convenient method known to the skilled artisan (e.g., by hand or by inkjet printer).

In embodiments, the protein biochip is hybridized with a detectable probe. Such probes can be polypeptide, nucleic acid molecules, antibodies, or small molecules. For some applications, polypeptide and nucleic acid molecule probes are derived from a biological sample taken from a patient, such as a bodily fluid (such as cerebrospinal fluid, blood, blood serum, plasma, saliva, urine, ascites, cyst fluid, and the like); a homogenized tissue sample (e.g., a tissue sample obtained by biopsy); or a cell isolated from a patient sample. Probes can also include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

Many protein biochips are described in the art. These include, for example, protein biochips produced by Ciphergen Biosystems, Inc. (Fremont, CA), Zyomyx (Hayward, CA), Packard BioScience Company (Meriden, CT), Phylos (Lexington, MA), Invitrogen (Carlsbad, CA), Biacore (Uppsala, Sweden) and Procognia (Berkshire, UK). Examples of such protein biochips are described in the following patents or published patent applications: U.S. Pat. Nos. 6,225,047; 6,537,749; 6,329,209; and 5,242,828; PCT International Publication Nos. WO 00/56934; WO 03/048768; and WO 99/51773.

Detection by Nucleic Acid Biochip

In aspects of the invention, a sample is analyzed by means of a nucleic acid biochip (also known as a nucleic acid microarray). To produce a nucleic acid biochip, oligonucleotides may be synthesized or bound to the surface of a substrate using a chemical coupling procedure and an ink jet application apparatus, as described in PCT application WO95/251116 (Baldeschweiler et al.). Alternatively, a gridded array may be used to arrange and link cDNA fragments or oligonucleotides to the surface of a substrate using a vacuum system, thermal, UV, mechanical or chemical bonding procedure. Exemplary nucleic acid molecules useful in the invention include polynucleotides encoding SALL2, FABP7, DLX2, ZFHX4, HEY1, HES5, LSD1, RCOR2, POU3F2, SOX2, and/or OLIG2 proteins, and fragments thereof.

A nucleic acid molecule (e.g. RNA or DNA) derived from a biological sample may be used to produce a hybridization probe as described herein. The biological samples are generally derived from a patient, e.g., as a bodily fluid (such as blood, blood serum, plasma, saliva, urine, ascites, cyst fluid, and the like); a homogenized tissue sample (e.g., a tissue sample obtained by biopsy); or a cell isolated from a patient sample. For some applications, cultured cells or other tissue preparations may be used. The mRNA is isolated according to standard methods, and cDNA is produced and used as a template to make complementary RNA suitable for hybridization. Such methods are well known in the art. The RNA is amplified in the presence of fluorescent nucleotides, and the labeled probes are then incubated with the microarray to allow the probe sequence to hybridize to complementary oligonucleotides bound to the biochip.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., of at least about 37° C., or of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In embodiments, hybridization will occur at 37° C. in 500 mM NaCl, 50 mM trisodium citrate, 1% SDS, 35% formamide, and 100 μg/ml denatured salmon sperm DNA (ssDNA). In other embodiments, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., of at least about 42° C., or of at least about 68° C. In embodiments, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In other embodiments, wash steps will occur at 68 C in 15 mM NaCl, 1.5 mM trisodium citrate, and 0.1% SDS. Additional variations on these conditions will be readily apparent to those skilled in the art.

Detection system for measuring the absence, presence, and amount of hybridization for all of the distinct nucleic acid sequences are well known in the art. For example, simultaneous detection is described in Heller et al., Proc. Natl. Acad. Sci. 94:2150-2155, 1997. In embodiments, a scanner is used to determine the levels and patterns of fluorescence.

Detection by Mass Spectrometry

In aspects of the invention, the biomarkers of this invention (e.g., POU3F2, SOX2, SALL2, and/or OLIG2) are detected by mass spectrometry (MS). Mass spectrometry is a well known tool for analyzing chemical compounds that employs a mass spectrometer to detect gas phase ions. Mass spectrometers are well known in the art and include, but are not limited to, time-of-flight, magnetic sector, quadrupole filter, ion trap, ion cyclotron resonance, electrostatic sector analyzer and hybrids of these. The method may be performed in an automated (Villanueva, et al., *Nature Protocols* (2006) 1(2):880-891) or semi-automated format. This can be accomplished, for example with the mass spectrometer operably linked to a liquid chromatography device (LC-MS/MS or LC-MS) or gas chromatography device (GC-MS or GC-MS/MS). Methods for performing mass spectrometry are well known and have been disclosed, for example, in US Patent Application Publication Nos: 20050023454; 20050035286; U.S. Pat. No. 5,800,979 and the references disclosed therein.

Laser Desorption/Ionization

In embodiments, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analysis of proteins by LDI can take the form of MALDI or of SELDI. The analysis of proteins by LDI can take the form of MALDI or of SELDI.

Laser desorption/ionization in a single time of flight instrument typically is performed in linear extraction mode. Tandem mass spectrometers can employ orthogonal extraction modes.

Matrix-Assisted Laser Desorption/Ionization (MALDI) and Electrospray Ionization (ESI)

In embodiments, the mass spectrometric technique for use in the invention is matrix-assisted laser desorption/ionization (MALDI) or electrospray ionization (ESI). In related embodiments, the procedure is MALDI with time of flight (TOF) analysis, known as MALDI-TOF MS. This involves forming a matrix on a membrane with an agent that absorbs the incident light strongly at the particular wavelength employed. The sample is excited by UV or IR laser light into the vapor phase in the MALDI mass spectrometer. Ions are generated by the vaporization and form an ion plume. The ions are accelerated in an electric field and separated according to their time of travel along a given distance, giving a mass/charge (m/z) reading which is very accurate and sensitive. MALDI spectrometers are well known in the art and are commercially available from, for example, PerSeptive Biosystems, Inc. (Framingham, Mass., USA).

Magnetic-based serum processing can be combined with traditional MALDI-TOF. Through this approach, improved peptide capture is achieved prior to matrix mixture and deposition of the sample on MALDI target plates. Accordingly, in embodiments, methods of peptide capture are enhanced through the use of derivatized magnetic bead based sample processing.

MALDI-TOF MS allows scanning of the fragments of many proteins at once. Thus, many proteins can be run simultaneously on a polyacrylamide gel, subjected to a method of the invention to produce an array of spots on a collecting membrane, and the array may be analyzed. Subsequently, automated output of the results is provided by using an server (e.g., ExPASy) to generate the data in a form suitable for computers.

Other techniques for improving the mass accuracy and sensitivity of the MALDI-TOF MS can be used to analyze the fragments of protein obtained on a collection membrane. These include, but are not limited to, the use of delayed ion extraction, energy reflectors, ion-trap modules, and the like. In addition, post source decay and MS-MS analysis are useful to provide further structural analysis. With ESI, the sample is in the liquid phase and the analysis can be by ion-trap, TOF, single quadrupole, multi-quadrupole mass spectrometers, and the like. The use of such devices (other than a single quadrupole) allows MS-MS or $MS^n$ analysis to be performed. Tandem mass spectrometry allows multiple reactions to be monitored at the same time.

Capillary infusion may be employed to introduce the marker to a desired mass spectrometer implementation, for instance, because it can efficiently introduce small quantities of a sample into a mass spectrometer without destroying the vacuum. Capillary columns are routinely used to interface the ionization source of a mass spectrometer with other separation techniques including, but not limited to, gas chromatography (GC) and liquid chromatography (LC). GC and LC can serve to separate a solution into its different components prior to mass analysis. Such techniques are readily combined with mass spectrometry. One variation of the technique is the coupling of high performance liquid chromatography (HPLC) to a mass spectrometer for integrated sample separation/and mass spectrometer analysis.

Quadrupole mass analyzers may also be employed as needed to practice the invention. Fourier-transform ion cyclotron resonance (FTMS) can also be used for some invention embodiments. It offers high resolution and the ability of tandem mass spectrometry experiments. FTMS is based on the principle of a charged particle orbiting in the presence of a magnetic field. Coupled to ESI and MALDI, FTMS offers high accuracy with errors as low as 0.001%.

Surface-Enhanced Laser Desorption/Ionization (SELDI)

In embodiments, the mass spectrometric technique for use in the invention is "Surface Enhanced Laser Desorption and Ionization" or "SELDI," as described, for example, in U.S. Pat. No. 5,719,060 and No. 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe.

SELDI has also been called "affinity capture mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen comprise surfaces having chromatographic or biospecific adsorbents attached thereto at addressable locations. Ciphergen's ProteinChip® arrays include NP20 (hydrophilic); H4 and H50 (hydrophobic); SAX-2, Q-10 and (anion exchange); WCX-2 and CM-10 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (IMAC 3 and IMAC 30) or O-methacryloyl-N,N-bis-carboxymethyl tyrosine functionalities (IMAC 50) that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); U.S. Pat. No. 6,897,072 (Rich et al., "Probes for a Gas Phase Ion Spectrometer," May 24, 2005); U.S. Pat. No. 6,555,813 (Beecher et al., "Sample Holder with Hydrophobic Coating for Gas Phase Mass Spectrometer," Apr. 29, 2003); U.S. Patent Publication No. U.S. 2003-0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Patent Application Publication No. US 2003/-0218130 A1 (Boschetti et al., "Biochips With Surfaces Coated With Polysaccharide-Based Hydrogels," Apr. 14, 2003) and U.S. Pat. No. 7,045,366 (Huang et al., "Photocrosslinked Hydrogel Blend Surface Coatings" May 16, 2006).

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In yet another method, one can capture the biomarkers with a solid-phase bound immuno-adsorbent that has antibodies that bind the biomarkers. After washing the adsorbent to remove unbound material, the biomarkers are eluted from the solid phase and detected by applying to a SELDI biochip that binds the biomarkers and analyzing by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Subject Monitoring

The disease state or treatment of a subject having glioblastoma, or a propensity to develop such a condition can be monitored using the methods and compositions of the invention. In one embodiment, the expression of markers present in a bodily fluid, such as cerebrospinal fluid, blood, blood serum, plasma, urine, and saliva, is monitored. Such monitoring may be useful, for example, in assessing the efficacy of a particular drug in a subject or in assessing disease progression. Therapeutics that decrease the expression of a marker of the invention (e.g., SALL2, FABP7, DLX2, ZFHX4, HEY1, HES5, LSD1, RCOR2, POU3F2, SOX2, and/or OLIG2) are taken as particularly useful in the invention.

The diagnostic methods of the invention are also useful for monitoring the course of a glioblastoma in a patient or for assessing the efficacy of a therapeutic regimen. In one embodiment, the diagnostic methods of the invention are used periodically to monitor the polynucleotide or polypeptide levels of one or more of SALL2, FABP7, DLX2, ZFHX4, HEY1, HES5, LSD1, RCOR2, POU3F2, SOX2, and/or OLIG2. In one example, the neoplasia is characterized using a diagnostic assay of the invention prior to administering therapy. This assay provides a baseline that describes the level of one or more markers of the neoplasia prior to treatment. Additional diagnostic assays are administered during the course of therapy to monitor the efficacy of a selected therapeutic regimen. A therapy is identified as efficacious when a diagnostic assay of the invention detects a decrease in marker levels relative to the baseline level of marker prior to treatment.

Selection of a Treatment Method

After a subject is diagnosed as having glioblastoma a method of treatment is selected. In glioblastoma, for example, a number of standard treatment regimens are available. The marker profile of the neoplasia is used in selecting a treatment method. In one embodiment, less aggressive neoplasias have lower levels of SALL2, FABP7, DLX2, ZFHX4, HEY1, HES5, LSD1, RCOR2, POU3F2, SOX2, and/or OLIG2 than more aggressive neoplasias. Marker profiles (e.g., glioblastomas that fail to express or express lower levels of POU3F2, SOX2, SALL2, and/or OLIG2) that correlate with good clinical outcomes are identified as less aggressive neoplasias.

Less aggressive neoplasias are likely to be susceptible to conservative treatment methods. More aggressive neoplasias are identified as having increased levels of SALL2, FABP7, DLX2, ZFHX4, HEY1, HES5, LSD1, RCOR2, POU3F2, SOX2, and/or OLIG2 relative to corresponding control cells. Such neoplasias are less susceptible to conservative treatment methods and are likely to recur. When methods of the invention indicate that a neoplasia is very aggressive, an aggressive method of treatment should be selected. Aggressive therapeutic regimens typically include one or more of the following therapies: surgical resection, radiation therapy, or chemotherapy.

In particular embodiments, the invention provides agents that target RCOR2 and/or LSD1, and reduce their interaction, or reduce their biological activity. In one embodiment, the invention provides for the use of S2101:

S2101

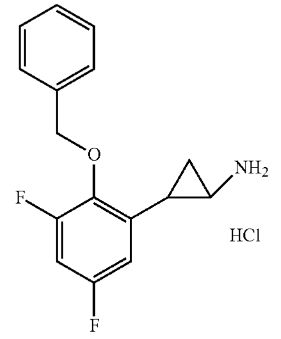

In another embodiment, the RCOR2 and/or LSD1 inhibitors can be any RCOR2 and/or LSD1 inhibitors known in the art. Non limiting examples are pargyline, TCP, RN-1, CAS 927019-63-4, and CBB1007, incorporated herein by reference.

In yet another embodiment, the invention provides methods for treating glioblastoma featuring fusion proteins comprising a natural transcription activator-like effector (TALE) fused to a transcriptional repressor domain (Cong et al., Nature Comm. 3: 968-974, 2012, incorporated herein by reference).

Inhibitory Nucleic Acids

Inhibitory nucleic acid molecules are those oligonucleotides that inhibit the expression or activity of a SALL2, FABP7, DLX2, ZFHX4, HEY1, HES5, LSD1, RCOR2, POU3F2, SOX2, and/or OLIG2 polypeptide. Such oligonucleotides include single and double stranded nucleic acid molecules (e.g., DNA, RNA, and analogs thereof) that bind a nucleic acid molecule that encodes SALL2, FABP7, DLX2, ZFHX4, HEY1, HES5, LSD1, RCOR2, POU3F2, SOX2, and/or OLIG2 polypeptide (e.g., antisense molecules, siRNA, shRNA) as well as nucleic acid molecules that bind directly to a SALL2, FABP7, DLX2, ZFHX4, HEY1, HES5, LSD1, RCOR2, POU3F2, SOX2, and/or OLIG2 polypeptide or polynucleotide to modulate its biological activity (e.g., aptamers).

Ribozymes

Catalytic RNA molecules or ribozymes that include an antisense SALL2, FABP7, DLX2, ZFHX4, HEY1, HES5, LSD1, RCOR2, POU3F2, SOX2, and/or OLIG2 sequence of the present invention can be used to inhibit expression of a SALL2, FABP7, DLX2, ZFHX4, HEY1, HES5, LSD1, RCOR2, POU3F2, SOX2, and/or OLIG2 nucleic acid molecule in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an siRNA approach in mammals was demonstrated in vivo by McCaffrey et al. (Nature 418: 38-39.2002).

Given the sequence of a target gene, siRNAs may be designed to inactivate that gene. Such siRNAs, for example, could be administered directly to an affected tissue, or administered systemically. The nucleic acid sequence of a SALL2, FABP7, DLX2, ZFHX4, HEY1, HES5, LSD1, RCOR2, POU3F2, SOX2, and/or OLIG2 gene can be used to design small interfering RNAs (siRNAs). The 21 to 25 nucleotide siRNAs may be used, for example, as therapeutics to treat a vascular disease or disorder.

The inhibitory nucleic acid molecules of the present invention may be employed as double-stranded RNAs for RNA interference (RNAi)-mediated knock-down of SALL2, FABP7, DLX2, ZFHX4, HEY1, HES5, LSD1, RCOR2, POU3F2, SOX2, and/or OLIG2 expression. In one embodiment, SALL2, FABP7, DLX2, ZFHX4, HEY1, HES5, LSD1, RCOR2, POU3F2, SOX2, and/or OLIG2 expression is reduced in glioblastoma cell. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the invention, double-stranded RNA (dsRNA) molecule is made that includes between eight and nineteen consecutive nucleobases of a nucleobase oligomer of the invention. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

Delivery of Nucleobase Oligomers

Naked inhibitory nucleic acid molecules, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Therapy

Therapy may be provided wherever cancer therapy is performed: at home, the doctor's office, a clinic, a hospital's outpatient department, or a hospital. In one embodiment, the invention provides for the use of S2101 as a therapy.

Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

Depending on the type of cancer and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place. Cancer growth is uncontrolled and progressive, and occurs under conditions that would not elicit, or would cause cessation of, multiplication of normal cells.

A nucleobase oligomer of the invention, or other negative regulator of SALL2, FABP7, DLX2, ZFHX4, HEY1, HES5, LSD1, RCOR2, POU3F2, SOX2, and/or OLIG2, may be administered within a pharmaceutically-acceptable diluent, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for delivering an agent that disrupts the activity of SALL2, FABP7, DLX2, ZFHX4, HEY1, HES5, LSD1, RCOR2, POU3F2, SOX2, and/or OLIG2 polypeptides or polynucleotides include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a disease or condition. The preferred dosage of a nucleobase oligomer of the invention is likely to depend on such variables as the type and extent of the disorder, the overall health status of the particular patient, the formulation of the compound excipients, and its route of administration.

As described above, if desired, treatment with a nucleobase oligomer of the invention may be combined with therapies for the treatment of proliferative disease (e.g., radiotherapy, surgery, or chemotherapy).

For any of the methods of application described above, a nucleobase oligomer of the invention is desirably administered intravenously or is applied to the site of the needed apoptosis event (e.g., by injection).

Polynucleotide Therapy

Polynucleotide therapy is another therapeutic approach in which a nucleic acid encoding a SALL2, FABP7, DLX2, ZFHX4, HEY1, HES5, LSD1, RCOR2, POU3F2, SOX2, and/or OLIG2 inhibitory nucleic acid molecule is introduced into cells. The transgene is delivered to cells in a form in which it can be taken up and expressed in an effective amount to inhibit neoplasia progression.

Transducing retroviral, adenoviral, or human immunodeficiency viral (HIV) vectors are used for somatic cell gene therapy because of their high efficiency of infection and stable integration and expression (see, for example, Cayouette et al., Hum. Gene Ther., 8:423-430, 1997; Kido et al., Curr. Eye Res. 15:833-844, 1996; Bloomer et al., J. Virol. 71:6641-6649, 1997; Naldini et al., Science 272:263-267, 1996; Miyoshi et al., Proc. Natl. Acad. Sci. USA, 94:10319-10323, 1997). For example, SALL2, FABP7, DLX2, ZFHX4, HEY1, HES5, LSD1, RCOR2, POU3F2, SOX2, and/or OLIG2 inhibitory nucleic acid molecules, or portions thereof, can be cloned into a retroviral vector and driven from its endogenous promoter, from the retroviral long terminal repeat, or from a promoter specific for the target cell type of interest (such as epithelial carcinoma cells). Other viral vectors that can be used include, but are not limited to, adenovirus, adeno-associated virus, vaccinia virus, bovine papilloma virus, vesicular stomatitus virus, or a herpes virus such as Epstein-Barr Virus.

Gene transfer can be achieved using non-viral means requiring infection in vitro. This would include calcium phosphate, DEAE-dextran, electroporation, and protoplast fusion. Liposomes may also be potentially beneficial for delivery of DNA into a cell. Although these methods are available, many of these are of lower efficiency.

Tumor Propagating Cells

The invention provides for the recombinant expression of SALL2, FABP7, DLX2, ZFHX4, HEY1, HES5, LSD1, RCOR2, POU3F2, SOX2, and/or OLIG2 in a cell of the invention. Such expression induces the cell to become a tumor propagating cell (TPC). Such cells are useful in screening methods for therapeutic agents useful in the treatment of glioblastoma.

Recombinant Polypeptide Expression

The invention provides recombinant POU3F2, SOX2, SALL2 and/or OLIG2 proteins useful for inducing tumor propagating cells. The transcription factor reprograms the cell and alters its transcriptional and/or translational profile, i.e., alters the set of mRNAs and/or polypeptides expressed by the cell. In one working embodiment, a transcription factor protein of the invention is POU3F2, SOX2, SALL2 and/or OLIG2. When this protein is expressed in a differentiated glioblastoma cell or other neural cell it reprograms the cell to become self-renewing and capable of tumor initiating. Recombinant polypeptides of the invention are produced using virtually any method known to the skilled artisan. Typically, recombinant polypeptides are produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. The method of transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Screening

Accordingly, the invention provides methods for identifying agents (e.g., polypeptides, polynucleotides, such as inhibitory nucleic acid molecules, and small compounds) useful for the diagnosis, treatment or prevention of glioblastoma. Screens for the identification of such agents employ glioblastoma stem cells identified according to the methods of the invention. The use of such cells, which express increased levels of SALL2, FABP7, DLX2, ZFHX4, HEY1, HES5, LSD1, RCOR2, POU3F2, SOX2, and/or OLIG2 is particularly advantageous for the identification of agents that reduce the survival of this aggressive subpopulation of glioblastoma cells. Agents identified as reducing the survival, reducing the proliferation, or increasing cell death in SALL2, FABP7, DLX2, ZFHX4, HEY1, HES5, LSD1, RCOR2, POU3F2, SOX2, and/or OLIG2 expressing cell are particularly useful.

Methods of observing changes in SALL2, FABP7, DLX2, ZFHX4, HEY1, HES5, LSD1, RCOR2, POU3F2, SOX2, and/or OLIG2 biological activity are exploited in high throughput assays for the purpose of identifying compounds that modulate SALL2, FABP7, DLX2, ZFHX4, HEY1, HES5, LSD1, RCOR2, POU3F2, SOX2, and/or OLIG2 biological activity, e.g., transcriptional regulation or protein-nucleic acid interactions. In particular embodiments, a reduction in cell survival or an increase in cell death is used as a read-out for efficacy.

Any number of methods are available for carrying out screening assays to identify new candidate compounds that decrease the expression of an POU3F2, SOX2, SALL2, and/or OLIG2 nucleic acid molecule. In one example, candidate compounds are added at varying concentrations to the culture medium of cultured cells expressing one of the nucleic acid sequences of the invention. Gene expression is then measured, for example, by microarray analysis, Northern blot analysis (Ausubel et al., supra), or RT-PCR, using any appropriate fragment prepared from the nucleic acid molecule as a hybridization probe. The level of gene expression in the presence of the candidate compound is compared to the level measured in a control culture medium lacking the candidate molecule. A compound which reduces the expression of a SALL2, FABP7, DLX2, ZFHX4, HEY1, HES5, LSD1, RCOR2, POU3F2, SOX2, and/or OLIG2 gene, or a functional equivalent thereof, is considered useful in the invention; such a molecule may be used, for example, as a therapeutic to treat a neoplasia in a human patient.

In another example, the effect of candidate compounds may be measured at the level of polypeptide production using the same general approach and standard immunological techniques, such as Western blotting or immunoprecipitation with an antibody specific for a polypeptide encoded by an SALL2, FABP7, DLX2, ZFHX4, HEY1, HES5, LSD1, RCOR2, POU3F2, SOX2, and/or OLIG2 gene. For example, immunoassays may be used to detect or monitor the expression of at least one of the polypeptides of the invention in an organism. Polyclonal or monoclonal antibodies (produced as described above) that are capable of binding to such a polypeptide may be used in any standard immunoassay format (e.g., ELISA, Western blot, or RIA assay) to measure the level of the polypeptide. In some embodiments, a compound that promotes an increase in the expression or biological activity of the polypeptide is considered particularly useful. Again, such a molecule may be used, for example, as a therapeutic to delay, ameliorate, or treat a neoplasia in a human patient.

In yet another working example, candidate compounds may be screened for those that specifically bind to a polypeptide encoded by an SALL2, FABP7, DLX2, ZFHX4, HEY1, HES5, LSD1, RCOR2, POU3F2, SOX2, and/or OLIG2 gene. The efficacy of such a candidate compound is dependent upon its ability to interact with such a polypeptide or a functional equivalent thereof. Such an interaction can be readily assayed using any number of standard binding techniques and functional assays (e.g., those described in Ausubel et al., supra). In one embodiment, a candidate compound may be tested in vitro for its ability to specifically bind a polypeptide of the invention. In another embodiment, a candidate compound is tested for its ability to inhibit the biological activity of a polypeptide described herein, such as a SALL2, FABP7, DLX2, ZFHX4, HEY1, HES5, LSD1, RCOR2, POU3F2, SOX2, and/or OLIG2 polypeptide. The biological activity of an SALL2, FABP7, DLX2, ZFHX4, HEY1, HES5, LSD1, RCOR2, POU3F2, SOX2, and/or OLIG2 polypeptide may be assayed using any standard method, for example, a matrigel cell invasion or cell migration assay.

In another working example, a nucleic acid described herein (e.g., an SALL2, FABP7, DLX2, ZFHX4, HEY1, HES5, LSD1, RCOR2, POU3F2, SOX2, and/or OLIG2 nucleic acid) is expressed as a transcriptional or translational fusion with a detectable reporter, and expressed in an isolated cell (e.g., mammalian) under the control of a heterologous promoter, such as an inducible promoter. The cell expressing the fusion protein is then contacted with a candidate compound, and the expression of the detectable reporter in that cell is compared to the expression of the detectable reporter in an untreated control cell. A candidate compound that alters the expression of the detectable reporter is a compound that is useful for the treatment of a neoplasia. Preferably, the compound decreases the expression of the reporter.

In another example, a candidate compound that binds to a polypeptide encoded by an POU3F2, SOX2, SALL2, and/or OLIG2 gene may be identified using a chromatography-based technique. For example, a recombinant polypeptide of the invention may be purified by standard techniques from cells engineered to express the polypeptide (e.g., those described above) and may be immobilized on a column. A solution of candidate compounds is then passed through the column, and a compound specific for the SALL2, FABP7, DLX2, ZFHX4, HEY1, HES5, LSD1, RCOR2, POU3F2, SOX2, and/or OLIG2 polypeptide is identified on the basis of its ability to bind to the polypeptide and be immobilized on the column. To isolate the compound, the column is washed to remove non-specifically bound molecules, and the compound of interest is then released from the column and collected. Similar methods may be used to isolate a compound bound to a polypeptide microarray. Compounds isolated by this method (or any other appropriate method) may, if desired, be further purified (e.g., by high performance liquid chromatography). In addition, these candidate compounds may be tested for their ability to increase the activity of an SALL2, FABP7, DLX2, ZFHX4, HEY1, HES5, LSD1, RCOR2, POU3F2, SOX2, and/or OLIG2 polypeptide (e.g., as described herein). Compounds isolated by this approach may also be used, for example, as therapeutics to treat a neoplasia in a human patient. Compounds that are identified as binding to a polypeptide of the invention with an affinity constant less than or equal to 10 mM are considered particularly useful in the invention. Alternatively, any in vivo protein interaction detection system, for example, any two-hybrid assay may be utilized.

Potential antagonists include organic molecules, peptides, peptide mimetics, polypeptides, nucleic acids, and antibodies that bind to a nucleic acid sequence or polypeptide of the invention (e.g., an SALL2, FABP7, DLX2, ZFHX4, HEY1, HES5, LSD1, RCOR2, POU3F2, SOX2, and/or OLIG2 polypeptide or nucleic acid molecule).

Each of the DNA sequences listed herein may also be used in the discovery and development of a therapeutic compound for the treatment of neoplasia. The encoded protein, upon expression, can be used as a target for the screening of drugs. Additionally, the DNA sequences encoding the amino terminal regions of the encoded protein or Shine-Delgarno or other translation facilitating sequences of the respective mRNA can be used to construct sequences that promote the expression of the coding sequence of interest. Such sequences may be isolated by standard techniques (Ausubel et al., supra).

Optionally, compounds identified in any of the above-described assays may be confirmed as useful in an assay for compounds that modulate the propensity of a neoplasia to metastasize.

Small molecules of the invention preferably have a molecular weight below 2,000 daltons, more preferably between 300 and 1,000 daltons, and most preferably between 400 and 700 daltons. It is preferred that these small molecules are organic molecules.

Test Extracts and Agents

In general, agents that modulate (e.g., inhibit) SALL2, FABP7, DLX2, ZFHX4, HEY1, HES5, LSD1, RCOR2, POU3F2, SOX2, and/or OLIG2 expression, biological activity, or POU3F2, SOX2, SALL2, and/or OLIG2-dependent signaling are identified from large libraries of both natural products, synthetic (or semi-synthetic) extracts or chemical libraries, according to methods known in the art. Preferably, these compounds decrease POU3F2, SOX2, SALL2, and/or OLIG2 expression or biological activity.

Those skilled in the art will understand that the precise source of test extracts or compounds is not critical to the screening procedure(s) of the invention. Accordingly, virtually any number of chemical extracts or compounds can be screened using the exemplary methods described herein.

Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from, for example, Brandon Associates (Merrimack, N.H.), Aldrich Chemical (Milwaukee, Wis.), and Talon Cheminformatics (Acton, Ont.)

Alternatively, libraries of natural compounds in the form of bacterial, fungal, plant, and animal extracts are commercially available from a number of sources, including, but not limited to, Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art (e.g., by combinatorial chemistry methods or standard extraction and fractionation methods). Furthermore, if desired, any library or compound may be readily modified using standard chemical, physical, or biochemical methods.

Assays for Measuring Cell Viability

Agents useful in the methods of the invention include those that inhibit any one or more of SALL2, FABP7, DLX2, ZFHX4, HEY1, HES5, LSD1, RCOR2, POU3F2, SOX2, and/or OLIG2. Such agents are identified by inducing cell death and/or reducing cell survival, i.e., viability.

Assays for measuring cell viability are known in the art, and are described, for example, by Crouch et al. (J. Immunol. Meth. 160, 81-8); Kangas et al. (Med. Biol. 62, 338-43, 1984); Lundin et al., (Meth. Enzymol. 133, 27-42, 1986); Petty et al. (Comparison of J. Biolum. Chemilum. 10, 29-34,.1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett. 1: 611, 1991; Cory et al., Cancer Comm. 3, 207-12, 1991; Paull J. Heterocyclic Chem. 25, 911, 1988). Assays for cell viability are also available commercially. These assays include but are not limited to CELLTITER-GLO® Luminescent Cell Viability Assay (Promega), which uses luciferase technology to detect ATP and quantify the health or number of cells in culture, and the CELLTITER-GLO® Luminescent Cell Viability Assay, which is a lactate dehydrogenase (LDH) cytotoxicity assay (Promega).

Candidate compounds that induce or increase neoplastic cell death (e.g., increase apoptosis, reduce cell survival) are also useful as anti-neoplasm therapeutics. Assays for measuring cell apoptosis are known to the skilled artisan. Apoptotic cells are characterized by characteristic morphological changes, including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, APO-ONE® Homogeneous Caspase-3/7 Assay, FragEL TUNEL kit (ONCOGENE RESEARCH PRODUCTS, San Diego, CA), the ApoBrdU DNA Fragmentation Assay (BIOVISION, Mountain View, CA), and the Quick Apoptotic DNA Ladder Detection Kit (BIOVISION, Mountain View, CA).

Neoplastic cells have a propensity to metastasize, or spread, from their locus of origination to distant points throughout the body. Assays for metastatic potential or invasiveness are known to the skilled artisan. Such assays include in vitro assays for loss of contact inhibition (Kim et al., Proc Natl Acad Sci USA. 101:16251-6, 2004), increased soft agar colony formation in vitro (Zhong et al., Int J Oncol. 24(6):1573-9, 2004), pulmonary metastasis models (Datta et al., In Vivo, 16:451-7, 2002) and Matrigel-based cell invasion assays (Hagemann et al. *Carcinogenesis.* 25: 1543-1549, 2004). In vivo screening methods for cell invasiveness are also known in the art, and include, for example, tumorigenicity screening in athymic nude mice. A commonly used in vitro assay to evaluate metastasis is the Matrigel-Based Cell Invasion Assay (BD Bioscience, Franklin Lakes, NJ).

If desired, candidate compounds selected using any of the screening methods described herein are tested for their efficacy using animal models of neoplasia. In one embodiment, mice are injected with neoplastic human cells. The mice containing the neoplastic cells are then injected (e.g., intraperitoneally) with vehicle (PBS) or candidate compound daily for a period of time to be empirically determined. Mice are then euthanized and the neoplastic tissues are collected and analyzed for SALL2, FABP7, DLX2, ZFHX4, HEY1, HES5, LSD1, RCOR2, POU3F2, SOX2, and/or OLIG2 mRNA or protein levels using methods described herein. Compounds that decrease SALL2, FABP7, DLX2, ZFHX4, HEY1, HES5, LSD1, RCOR2, POU3F2, SOX2, and/or OLIG2 mRNA or protein expression relative to control levels are expected to be efficacious for the treatment of a neoplasm in a subject (e.g., a human patient). In another embodiment, the effect of a candidate compound on tumor load is analyzed in mice injected with a human neoplastic cell. The neoplastic cell is allowed to grow to form a mass. The mice are then treated with a candidate compound or vehicle (PBS) daily for a period of time to be empirically determined. Mice are euthanized and the neoplastic tissue is collected. The mass of the neoplastic tissue in mice treated with the selected candidate compounds is compared to the mass of neoplastic tissue present in corresponding control mice.

Kits

The invention provides kits for the treatment or prevention of glioblastoma. In one embodiment, the kit includes a therapeutic or prophylactic composition containing an effective amount of an inhibitory nucleic acid molecule that disrupts the expression of an SALL2, FABP7, DLX2, ZFHX4, HEY1, HES5, LSD1, RCOR2, POU3F2, SOX2, and/or OLIG2 polynucleotide or polypeptide in unit dosage form. In another embodiment, the kit includes a therapeutic or prophylactic composition containing an effective amount of S2101 in unit dosage form.

In some embodiments, the kit comprises a sterile container which contains a therapeutic or prophylactic cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an inhibitory nucleic acid molecule of the invention is provided together with instructions for administering the inhibitory nucleic acid molecule or small compound (e.g., S2101) to a subject having or at risk of developing glioblastoma. The instructions will generally include information about the use of the composition for the treatment or prevention of glioblastoma. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. Sustained Inhibition of Kinase Signaling Enriches for Slow-Cycling GSCs Glioblastoma stem cells (GSCs) maintained in serum-free neurosphere culture conditions share features with neural stem cells (NSCs), including multipotency, and effectively initiate tumors in xenotransplantation assays (Singh et al., 2003; Singh et al., 2004; Galli et al., 2004; Lee et al., 2006; Bao et al., 2006; Wakimoto et al., 2009; Chen et al., 2010; Lathia et al., 2015). To investigate proliferative programs in GSCs, single-cell transcriptomes of primary glioblastoma (GBM) cells were compared to in vitro GSCs (patient-derived models GSC6 and GSC8) (Wakimoto et al., 2009; Suvà et al., 2014; Patel et al., 2014). In primary tumors, only a fraction of cells display proliferative markers (2-20% $Ki67^+$) (Louis et al., 2007; Tamura et al., 2013) or express cell cycle signatures (Patel et al., 2014). Moreover, when developmental and cell cycle signatures were compared across single cells from human tumors, it was found that stem-like GBM cells were depleted of proliferative signatures (Patel et al., 2014). This contrasts with the large majority of in vitro GSCs with such proliferative signatures, per single-cell RNA-seq (FIG. 1A). Although different GSC lines exhibit variable levels of proliferation (Wakimoto et al., 2009), this represents a potential important distinction between in vitro and in vivo cancer stem cell models. Therefore, it was considered whether proliferative GSCs could be induced to an in vivo-like non-proliferative state, thus allowing the study of regulatory programs that sustain these alternate epigenetic states.

Figure 2:
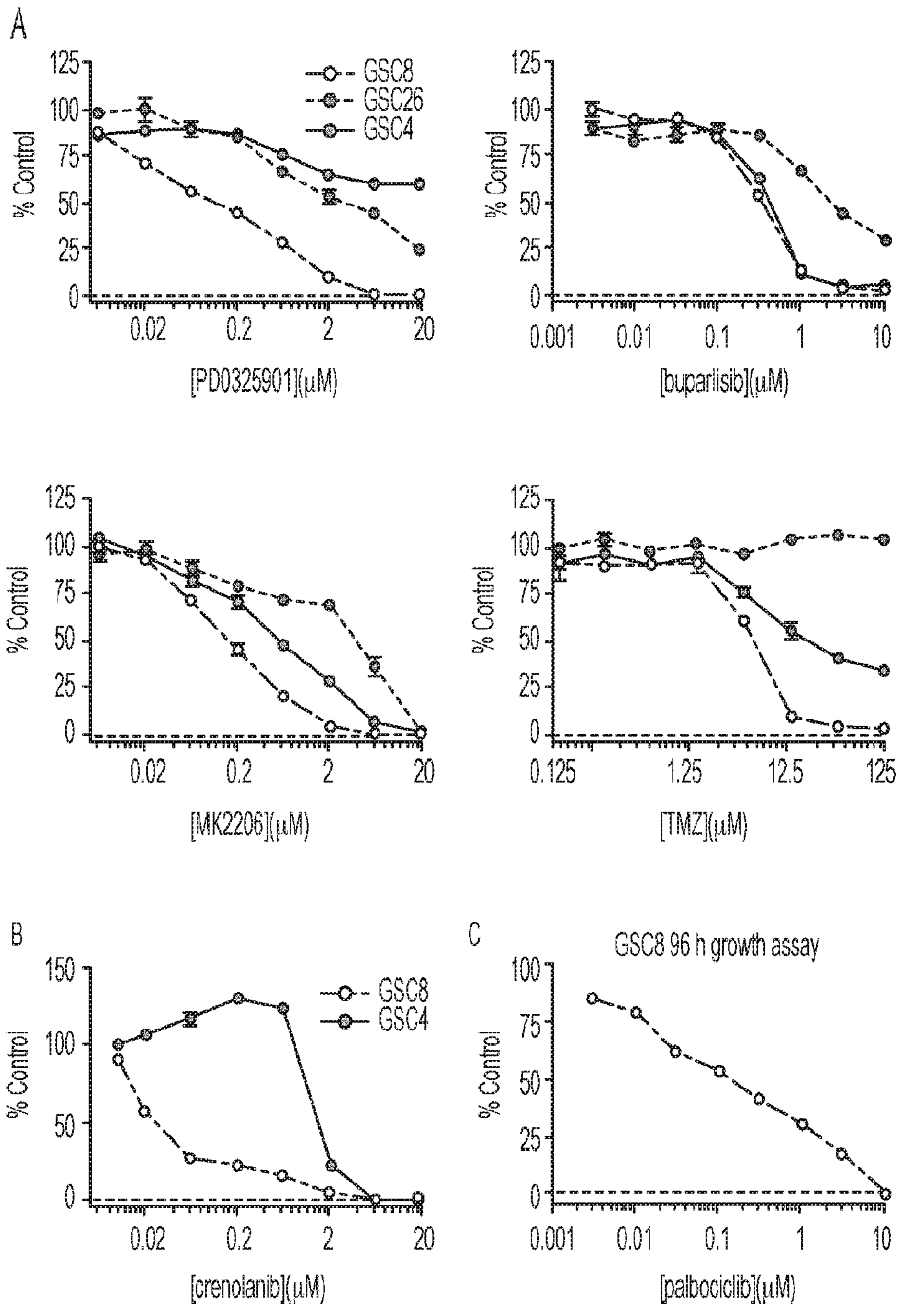
FIGS. 2A-2C depict dose-response curves for drug treatments in GSC in vitro models.

A panel of GSC lines were tested for sensitivity to small molecule inhibitors of oncogenic signaling pathways (FIG. 2A). It was found that cell line GSC8, which is PDGFRA amplified, was highly sensitive to dasatinib ($IC_{50}$~10 nM, FIG. 1B), a PDGFRα/Src inhibitor currently being evaluated in GBM clinical trials (Franceschi et al., 2012). In agreement with PDGFRα being the relevant target of dasatinib in this model, GSC8 was also sensitive to crenolanib, a PDGFRα inhibitor that does not appreciably inhibit Src (FIG. 2B). Dasatinib treatment reduced phosphorylation of PDGFRα (pY849), as well as downstream signaling targets Akt (pT308) and Erk1/2 (pT202/pY204, pT185/pY187) (FIG. 1C). GSC8 is also differentially sensitive to the MEK inhibitor PD0325901 (FIG. 2A). Without being bound to theory, this indicates that growth inhibition afforded by PDGFRα inhibition operates through downstream Mitogen-activated protein kinase (MAPK) signaling.

Figure 3:
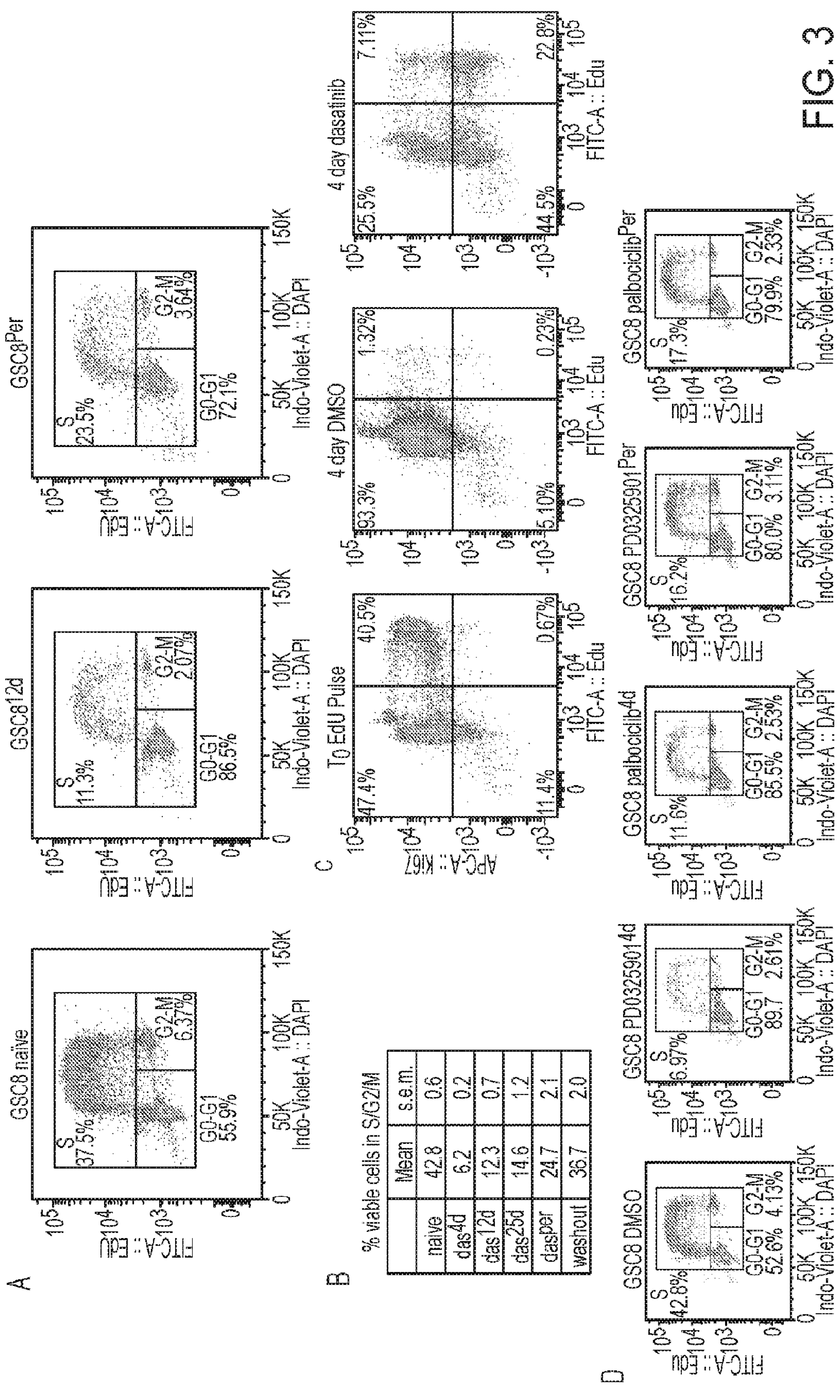
FIGS. 3A-3D depicts cell cycle analysis and EdU labeling of GSC persisters.

Despite the dramatic effects of dasatinib, sustained exposure consistently yielded a persistent subpopulation that tolerates higher drug concentrations (FIG. 1B). Cell cycle analysis of dasatinib-treated GSCs (1 μM, ~100 times the $IC_{50}$ dose) at different time points demonstrated that the fraction of viable cells in cycle acutely drops and then slowly recovers (FIGS. 1D, 3A, and 3B). Consistently, Ki67 levels were strongly reduced after 4 days of dasatinib treatment, (17% vs 93% $Ki67^+$ in naïve) (FIGS. 1E and 1F). Furthermore, initial EdU pulse labeling followed by 4 day dasatinib treatment demonstrated that proliferative cells survived and actively transitioned to a $Ki67^-$ state. Without being bound to theory, this indicated a dynamic response as opposed to selection of a pre-existing slow-cycling population (FIGS. 1G and 3C). These data demonstrate that while many cells acutely die upon exposure to dasatinib, a subset undergoes rapid cell cycle arrest and then recovers the ability to slowly expand despite the presence of the inhibitor. These drug persistent cells are termed $GSC8^{Per}$. Notably, GSC8 persister lines could also be derived with inhibitors of downstream kinases, including MEK and CDK4/6 (FIGS. 2C and 3D).

Figure 4:
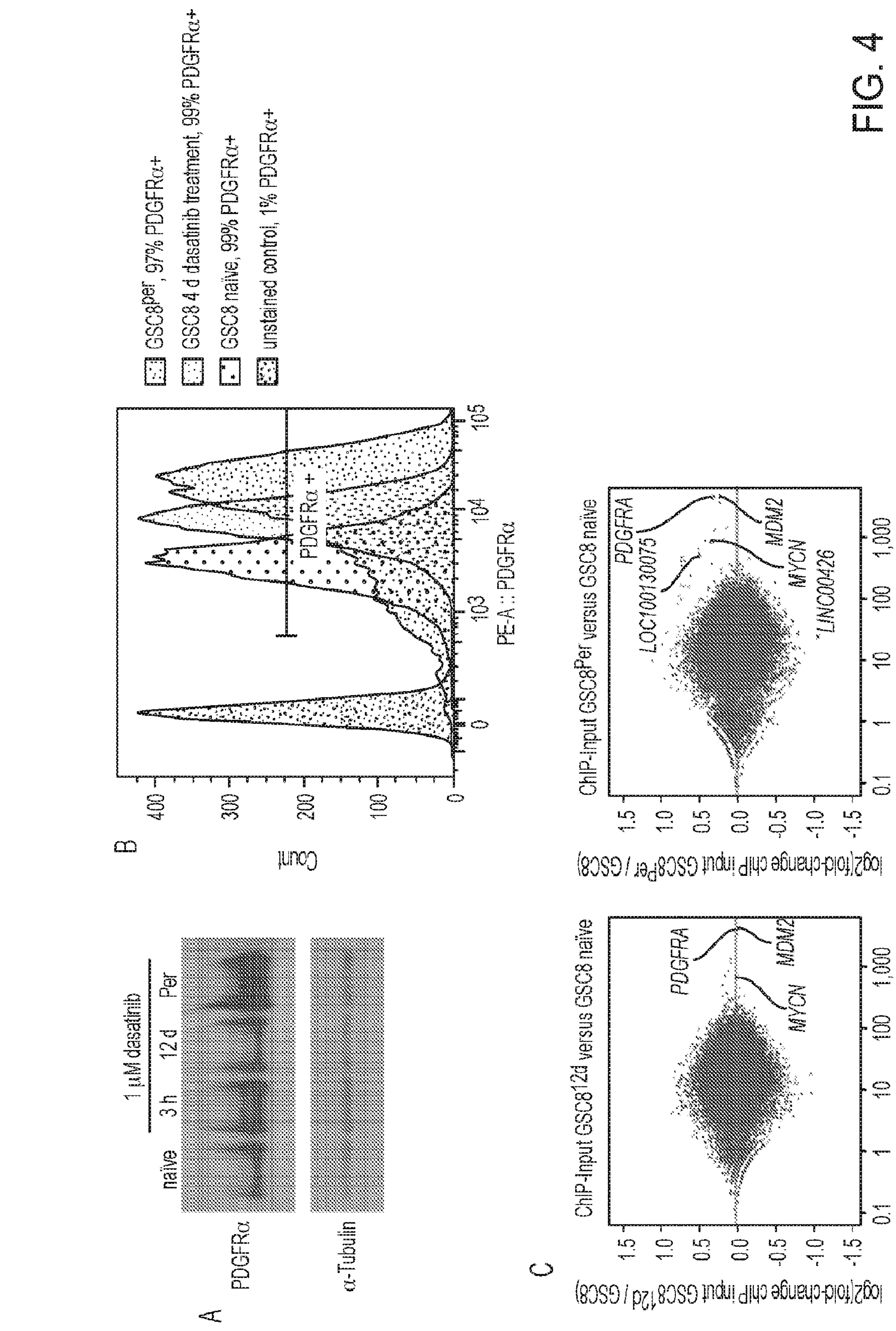
FIGS. 4A-4C show levels of PDGFRα and ChIP input in GSC persisters.

Populations of $GSC8^{Per}$ cultured in dasatinib for at least 8 weeks were isolated. These cells were relatively insensitive to dasatinib and crenolanib (FIG. 1H), and still lacked PDGFRα pY849 autophosphorylation (FIG. 1C). Without being bound to theory, this indicated that no second site mutation of PDGFRα was conferring dasatinib resistance. It was considered if other genetic mechanisms might underlie drug-tolerance in GSC8 persisters. A recent study demonstrated that drug-tolerance to EGFR inhibitors might be mediated by loss of $EGFR^+$ extrachromosomal DNA and subsequent EGFR expression levels (Nathanson et al., 2014). In GSC8 persisters, however, total expression levels of PDGFRα remained relatively constant or increased (FIGS. 4A and 4B). Moreover, low-coverage whole genome sequencing data (ChIP-seq input) did not reveal any significant changes in copy number variations at PDGFRA or other loci (FIG. 4C). Lastly and most importantly, the $GSC8^{Per}$ state was reversible, as removal of dasatinib permitted full recovery of growth and cell viability (FIG. 1D), as well as rapid re-sensitization to acute drug-induced arrest even after >4 months of chronic dasatinib treatment (FIG. 1I). Without being bound to theory, the rapidity and reversibility of acquired resistance strongly indicated that epigenetic rather than genetic changes underlied the drug-tolerant phenotype, as demonstrated in other cancer models (Sharma et al., 2010; Koppikar et al., 2013; Knoechel et al., 2014; Sun et al., 2014; Ravindran Menon et al., 2015; Fong et al., 2015).

Figure 5:
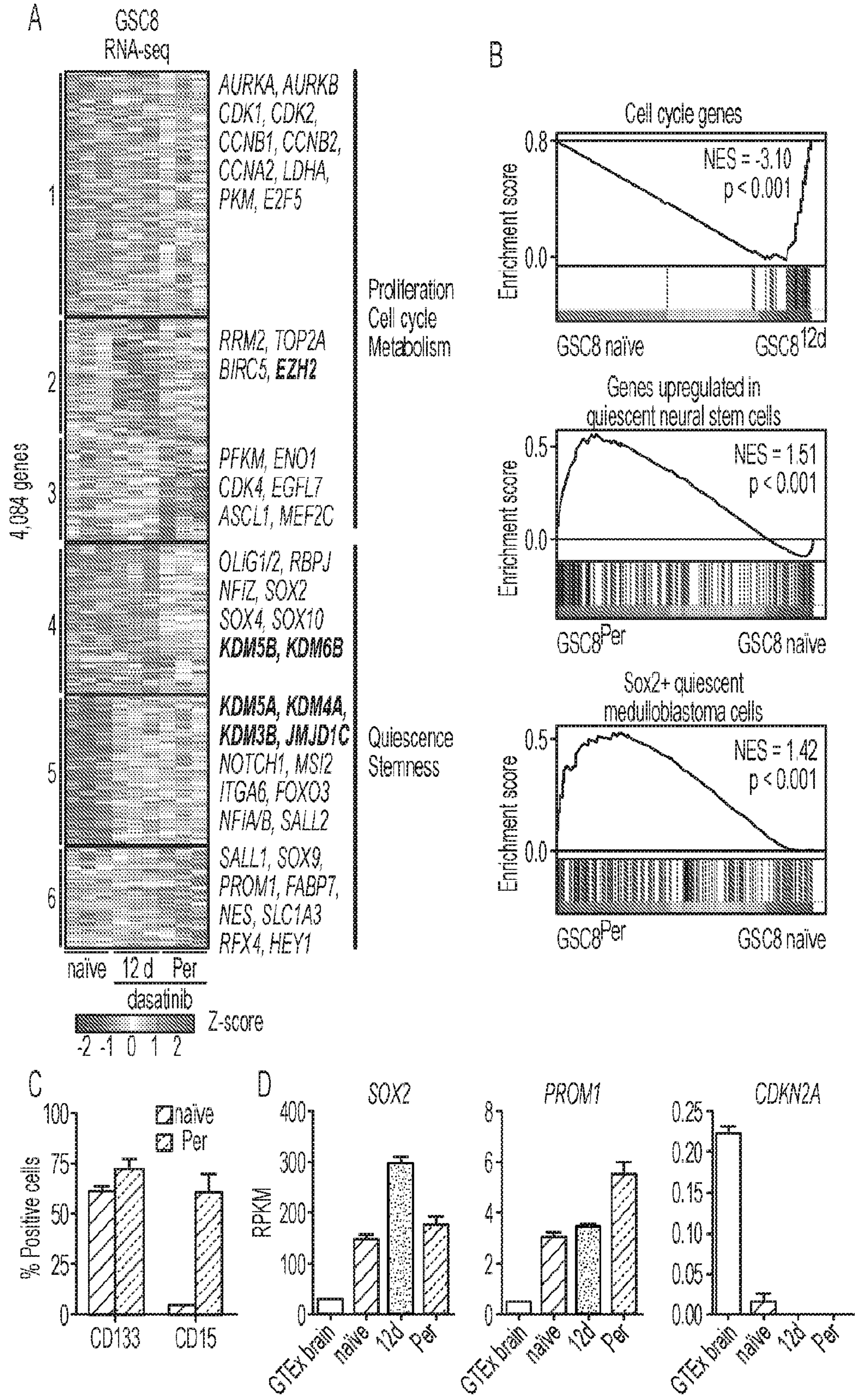
FIGS. 5A-5D show that transcriptional programs related to slow proliferation and stemness are enriched in GSC8 persisters.

Example 2. Persister GSCs Express Primitive Neurodevelopmental and Quiescence Markers To investigate regulatory circuits in persister GSCs, $GSC8^{Per}$, expanded for at least 8 weeks in dasatinib, were compared to actively cycling naïve GSCs and short-treatment GSCs ($GSC8^{12d}$) at maximal cell cycle arrest (FIG. 1J). First, gene expression was profiled in these populations by RNA-seq. Clustering of the 4,084 genes with highest variability across these states revealed gene sets with coherent expression changes (FIG. 5A; Appendix A: Supplementary Tables 1 and 2). Genes depleted in $GSC8^{12d}$ (clusters 1-3) and $GSC8^{Per}$ (clusters 1 and 3) were related to cell cycle and proliferation, consistent with the reduced proliferation of these populations (FIGS. 5A, 5B, and 6A). Genes upregulated in GSC persisters were enriched for signatures derived from quiescent neural stem cells (Martynoga et al., 2013) and quiescent, stem-like medulloblastoma cells (FIG. 5B) (Vanner et al., 2014). $GSC8^{Per}$ cells also have relatively high expression of stemness factors previously linked to GSCs (FIG. 5A, clusters 4-6). These include master TFs with established roles in neurodevelopment and GSC maintenance, such as SOX2, SOX4, OLIG2, and SALL2 (Ligon et al., 2007; Gangemi et al., 2009; Ikushima et al., 2009; Mehta et al., 2011; Suvà et al., 2014), as well as several regulators implicated in stem-like tumor cells in vivo, including NFIA/B, SOX9, and RFX4 (Patel et al., 2014). The persisters also displayed increased classical stemness markers, including PROM1 (CD133) and SSEA-1 (CD15) (Singh et al., 2004; Son et al., 2009) (FIGS. 5C and 6B). Without being bound to theory, the observation that many of these markers are already expressed in naïve GSC8 but are further induced in $GSC8^{Per}$ (FIG. 5D), indicated that while both populations reflect stem-like states, the persisters may adopt a more primitive phenotype.

Figure 7:
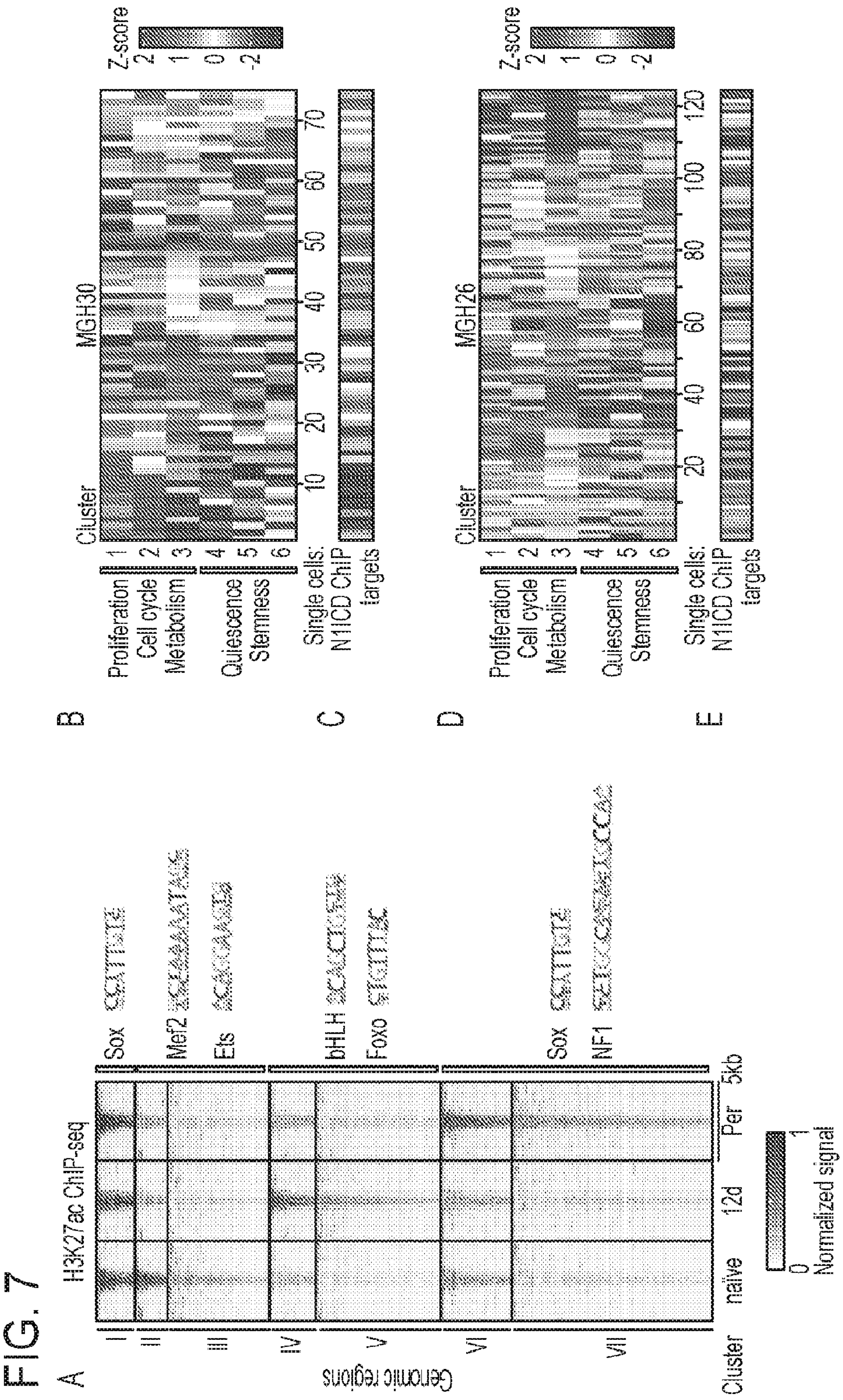
FIGS. 7A-7E show that GSC$^{Per}$ resemble slow-cycling, stem-like primary tumor cells.

To identify gene regulatory circuits that distinguish these alternate states, cis-regulatory elements were charted in GSC8 naïve, $GSC8^{12d}$, and $GSC8^{Per}$ by mapping histone H3 lysine 27 acetylation (H3K27ac), a marker of active promoters and enhancers (Creyghton et al., 2010; Ernst et al., 2011, Rada-Iglesias et al., 2012). Clustering algorithms were used to distinguish sets of shared or differentially-regulated elements, which were scanned for over-represented transcription factor (TF) sequence motifs (FIG. 7A). The patterns of differential TF activity predicted by this analysis were largely concordant with the TF expression patterns derived by RNA-seq (FIG. 5A). GSC8 naïve-specific elements (FIG. 7A, cluster II and III) were enriched for MEF2 motifs, consistent with high expression of MEF2C and its dimerization partner ASCL1 in the naïve state (FIG. 5A, cluster 3) (Black et al., 1996). These regulators have been previously implicated in proliferative stem cell populations (Castro et al., 2011, Rheinbay et al., 2013). $GSC8^{12d}$-specific elements (FIG. 7A, cluster IV and V) were enriched for Foxo motifs, in line with FOXO3 upregulation (FIG. 5A, cluster 5) and its nuclear translocation upon Akt inactivation (Brunet et al., 2004) (FIG. 1C). $GSC8^{Per}$-specific elements (FIG. 7A, cluster VI and VII) were enriched for SOX and NFI motifs, consistent with increased expression of several members of these TF families in $GSC8^{Per}$. Thus, concordant transcriptional and epigenetic differences distinguished the respective GSC states, and implicated neurodevelopmental TFs and quiescent stem cell programs in persister GSCs.

Example 3. $GSC^{Per}$ Resemble Slow-Cycling, Stem-Like Tumor Subpopulations

Next expression data for these in vitro GSCs were integrated with primary GBM tumor-derived single cell RNA-seq data (Patel et al., 2014). Single tumor cells were scored for the gene signatures derived by comparing the three GSC states (FIG. 5A), and clustered accordingly. Signatures for proliferation, cell cycle, and metabolism were tightly co-expressed in a small subset of tumor cells (FIGS. 7B and 7D), consistent with relatively low Ki67 positivity in GBM (Louis et al., 2007; Patel et al., 2014). Signatures for quiescence and stemness programs scored in a distinct subset of tumor cells (FIGS. 7B and 7D). Without being bound to theory, the anti-correlation between proliferative and stemness signatures indicated that stem-like cells in vivo are relatively dormant. Notably, the relative enrichments of these signatures across individual tumor cells roughly paralleled the progressive changes in the persister model. Without being bound to theory, these data indicate that slow-cycling $GSC^{Per}$ cells recapitulate aspects of stem-like primary tumor cells, and thus support the physiologic relevance of the persister model.

Example 4. Redistribution of Histone Methylation by KDMs in $GSC^{Per}$

Figure 8:
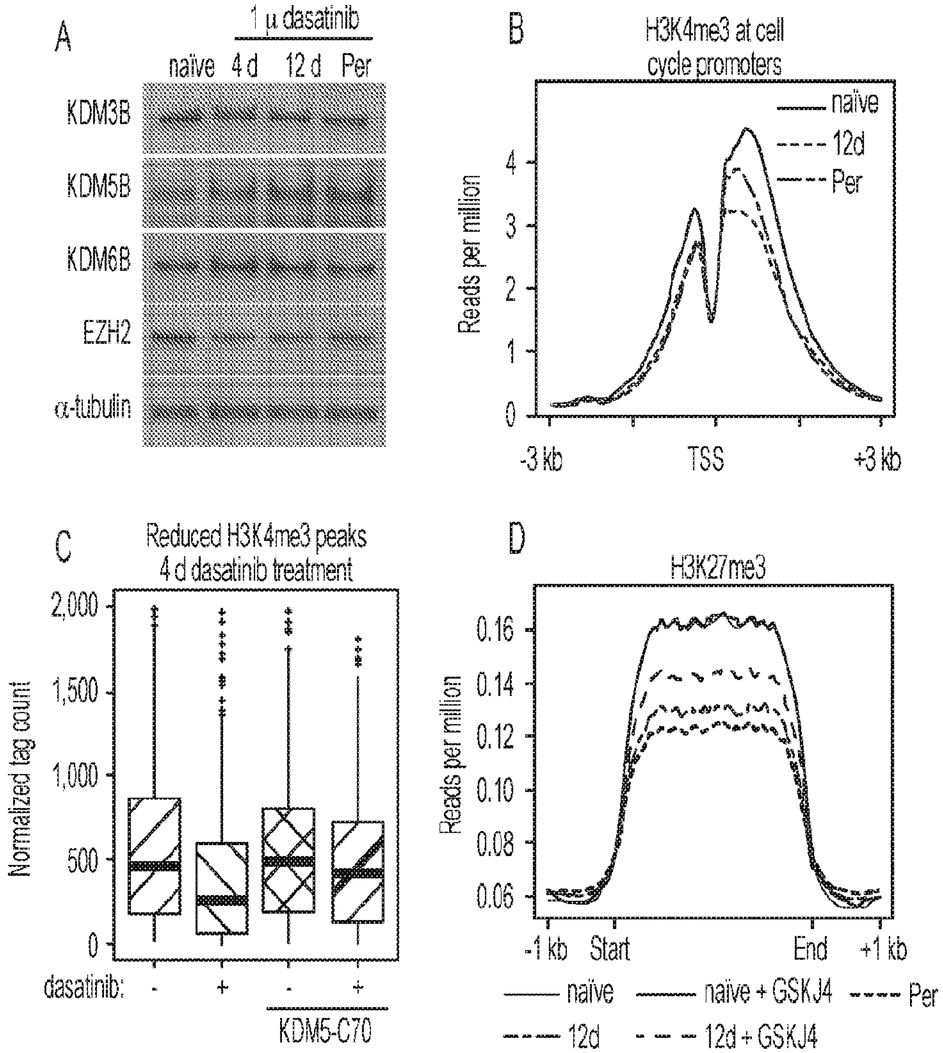
FIGS. 8A and 8B show that KDM induction was associated with widespread histone methylation redistribution.
FIG. 8C depicts boxplots showing normalized H3K4me3 ChIP-seq read counts (y-axis) within the top 500 most reduced differential H3K4me3 peaks following 4 day treatment of dasatanib, whereas KDM5-C70 significantly attenuated H3K4me3 reduction ($p<10^{-16}$, Mann-Whitney Test).
FIG. 8D depicts ChIP-seq profile plots showing H3K27me3 ChIP-seq signal (y-axis) across all H3K27me3 domains (>10 kb in length) in GSC8 naïve (grey), GSC8$^{12d}$ (blue), GSC8$^{Per}$ (red), GSC8 treated with GSKJ4 (8 d, 1.5 μM, purple), and GSC8$^{12d}$ treated with GSKJ4 (8 d, 1.5 μM, orange) starting after 4 days of initial dasatinib treatment. The x-axis represents size scaled H3K27me3 domains, with ±1 kb flanking regions, and the y-axis shows average signal in reads per million.
FIG. 8E depicts ChIP-seq binding profiles showing ChIP-seq signal (y-axis) for H3K4me3, H3K27ac, and H3K27me3 surrounding the SOX2 locus. The y-axis shows average signal in reads per million.
Figure 8:
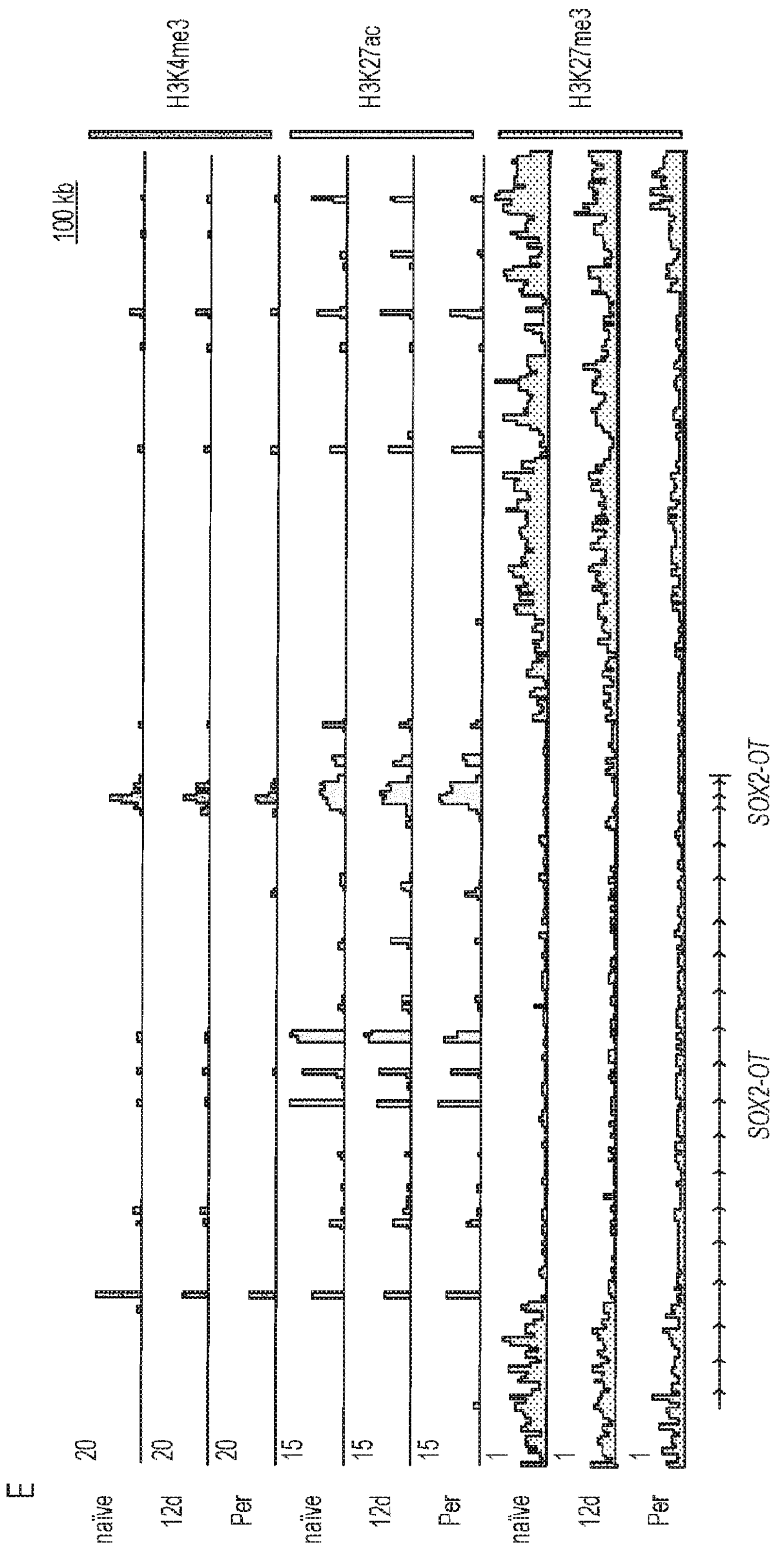
Figure 9:
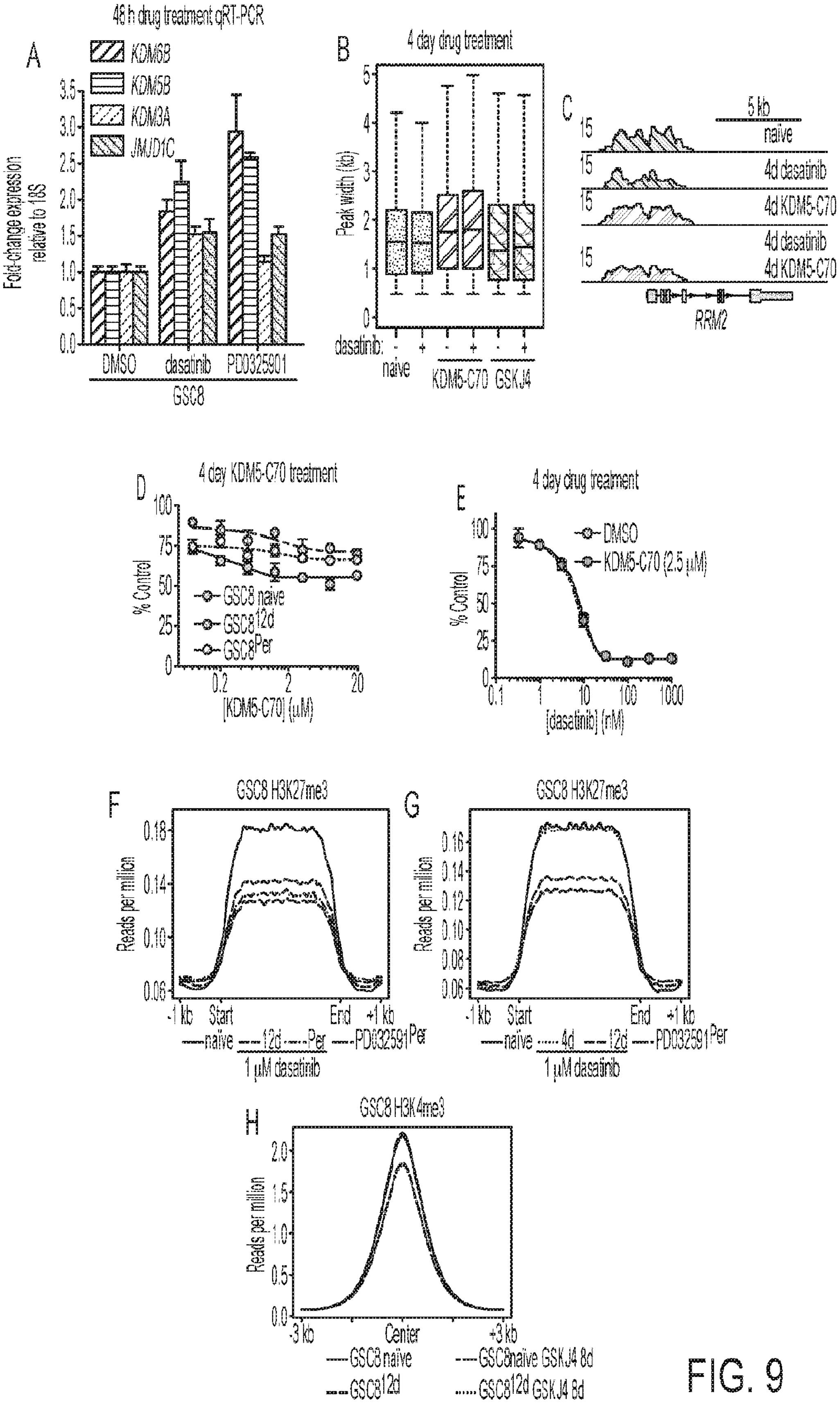
FIGS. 9A-9H shows effects of small molecule inhibitors on KDM expression and histone methylation modifications.

In addition to cell cycle, stemness, and TF genes, the expression of numerous chromatin regulators was altered in GSC persisters (FIG. 5A). In particular, several histone lysine demethylases (KDMs) were up-regulated, including enzymes that catalyze the removal of H3K4 (KDM5A, KDM5B), H3K9 and/or H3K36 (KDM3B, KDM4A), or H3K27 methylation (KDM6B) (FIGS. 5A and 8A). KDM induction was also observed upon treatment of GSC8 with MEK inhibitor PD0325901 (FIG. 9A). Importantly, KDM up-regulation was also evident in non-cycling GBM cells in vivo (Patel et al., 2014). Prior studies have implicated altered chromatin states and active remodeling in quiescence (Baxter et al., 2004; Lien et al., 2011; Liu et al., 2013; McKnight et al., 2015). Moreover, H3K4 demethylases have been shown to play important roles in slow-cycling drug-tolerant lung and melanoma cell lines (Sharma et al., 2010; Roesch et al., 2010; Roesch et al., 2013). Therefore, it was considered whether KDMs were important in GSC persistence.

Prompted by these prior studies, H3K4 methylation and potential roles for the corresponding demethylases KDM5A and KDM5B in GSCs were studied. Consistent with prior studies (Chicas et al., 2012), it was found that H3K4me3 at cell cycle-associated promoters was reduced by short-term dasatinib treatment, and remained depleted in $GSC8^{Per}$ (FIG. 8B). To investigate the functional significance of this alteration, a recently described small molecule KDM5 inhibitor, KDM5-C70 (Labelle et al., 2014; WO2014053491; incorporated herein by reference) was utilized. Treatment of naïve GSCs with 2.5 μM KDM5-C70 caused H3K4me3 peaks to expand, as expected from prior KDM5 knock-down studies (FIG. 9B) (Kidder et al., 2014; Benayoun et al., 2014). Moreover, KDM5-C70 partially rescued the H3K4me3 reduction associated with dasatinib treatment (FIGS. 8C and 9C). Without being bound to theory, these observations indicated that KDM5 enzymes contributed to the H3K4me3 redistribution, and that KDM5-C70 effectively inhibited this activity. However, KDM5 inhibition did not significantly impede the formation or proliferation of GSC8 persisters (FIGS. 9D and 9E). This prompted the consideration of potential roles of other KDMs.

The H3K27 demethylase KDM6B was up-regulated in GSC persisters, while the H3K27 methyltranferase EZH2 was down-regulated (FIGS. 5A and 8A). KDM6A, another H3K27 demethylase, was also upregulated in GSC persisters, albeit to a lesser extent (Appendix A: Supplementary Tables 1 and 2). Therefore, H3K27me3 was mapped in GSC8 naïve, $GSC8^{12d}$, and $GSC8^{Per}$ by ChIP-seq. It was found that H3K27me3 peaks were strongly reduced in $GSC8^{12d}$ and $GSC8^{Per}$ (FIGS. 8D, 8E, and 9G), consistent with a global redistribution of this repressive mark. A similar pattern was observed upon treatment with MEK inhibitor PD0325901 (FIG. 9F). To assess whether H3K27me3 redistribution is mediated by KDM6A/B, GSCs were treated with a small molecule KDM6A/B inhibitor, 'GSKJ4' (Kruidenier et al., 2013) (FIG. 8D). Treatment of naïve GSC8 with 1.5 μM GSKJ4 had negligible effects on the pre-existing H3K27me3 landscape (FIG. 8D). However, GSKJ4 rescued the dramatic H3K27me3 loss associated with dasatinib treatment (FIG. 8D). GSKJ4 treatment did not significantly increase H3K4me3 in these models, which supports its selectivity for KDM6A/B at the doses used in the study (Heinemann et al., 2014) (FIGS. 9B and 9H). Without being bound to theory, these findings raise the possibility that widespread H3K27me3 demethylation by KDM6A/B contributes to the persister GSC phenotype.

Example 5. KDM6 Demethylases are Important for GSC Persisters

The KDM6-dependent redistribution of H3K27me3 in $GSC8^{Per}$, together with the up-regulation of KDM6A and KDM6B, led to a hypothesis that GSC persisters was dependent on these enzymes. Therefore, KDM6A and KDM6B were separately knocked out in GSC8 naïve and $GSC8^{Per}$ using CRISPR-Cas9 genome editing (Ran et al., 2013). Short-guide RNAs (sgRNAs) targeting the catalytic Jumonji-C domain of each demethylase were specifically utilized. This was prompted by a recent study that established the efficacy of such a targeted strategy for inactivating chromatin modulatory proteins (Shi et al., 2015).

Figure 10:
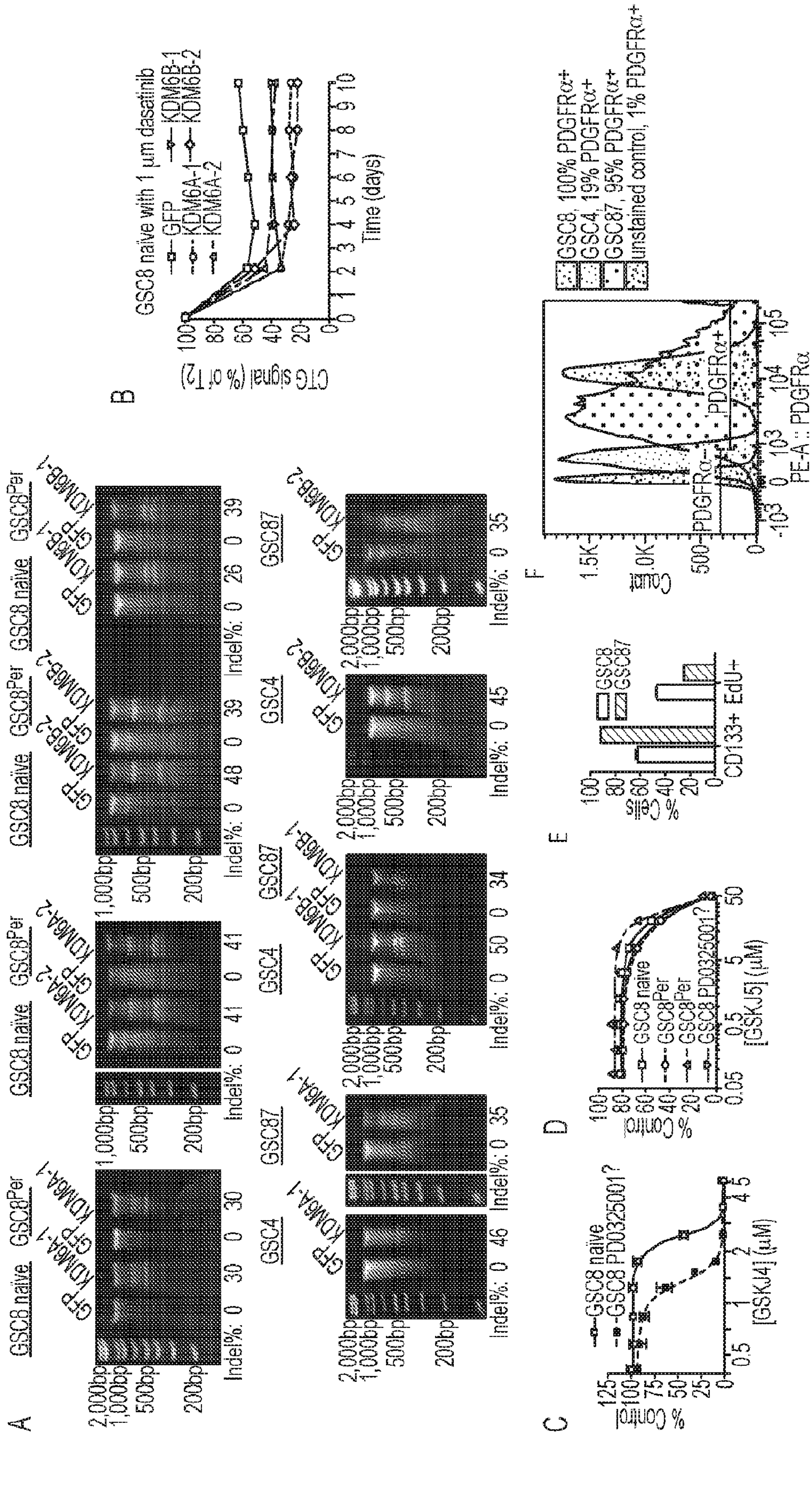
FIGS. 10A-10F depict results of KDM6A and KDM6B CRISPR-Cas9 and small molecule studies.
Figure 11:
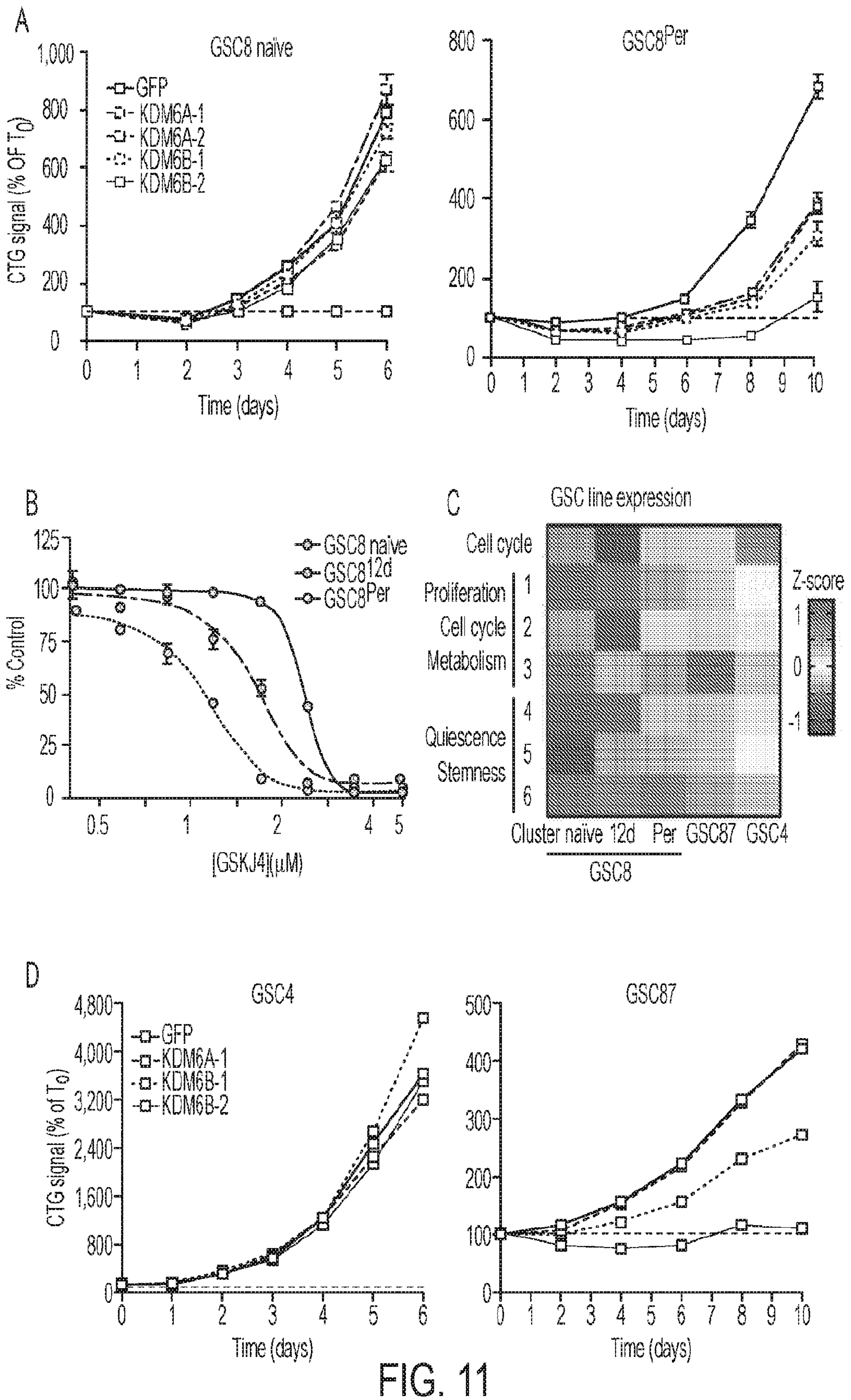
FIGS. 11A-11D show that KDM6A/B were important for GSC$^{Per}$.

Successful genome editing was confirmed by SURVEYOR analysis (FIG. 10A). Growth of GSC8 naïve cells was minimally affected by KDM6A and KDM6B knockout. In contrast, $GSC8^{Per}$ cells were highly sensitive to knockout of either demethylase (FIG. 11A). $GSC8^{Per}$ growth reduction afforded by KDM6B knockout was most pronounced, consistent with prior studies establishing a role of KDM6B in cancer cell proliferation (Ntziachristos et al., 2014; Hashizume et al., 2014). Moreover, GSC8 naïve cells lacking KDM6A or KDM6B ineffectively formed persisters upon dasatinib treatment (FIG. 10B). Consistent with these genetic data, the KDM6A/B inhibitor GSKJ4 significantly compromised viability of $GSC8^{12d}$ and $GSC8^{Per}$ at doses well tolerated by naïve GSC8 (FIG. 11B). Likewise, GSC8 persisters derived from sustained MEK inhibition were also preferentially sensitive to GSKJ4 (FIG. 10C). In contrast, GSC persisters displayed no preferential sensitivity to GSKJ5, an inactive isomer of GSKJ4 (FIG. 10D) (Kruidenier et al., 2013).

To further explore this KDM6 dependency, the study was expanded to other GSC models. The proliferative rates of patient-derived GSCs were highly variable. GSC4 is a MYC-amplified line that rapidly proliferates, while GSC87 is a PDGFRA-amplified line that is baseline slow-cycling (FIGS. 10E and 10F). RNA-seq data for these lines revealed that GSC4 expressed a proliferative gene signature akin to naïve GSC8 cells, while GSC87 expressed a persister-like gene signature (FIG. 11C; Appendix A: Supplementary Tables 1 and 2). Furthermore, GSC87 exhibited relatively low levels of EdU incorporation and higher CD133 positivity (FIG. 10E). Remarkably, it was found that knockout of either KDM6A or KDM6B had negligible effects on the highly proliferative GSC4 model, but KDM6B knockout significantly impaired the slow-cycling GSC87 model (FIG. 11D). These data support specific and important roles for KDM6 demethylases in slow-cycling, persister-like GSCs.

Figure 12:
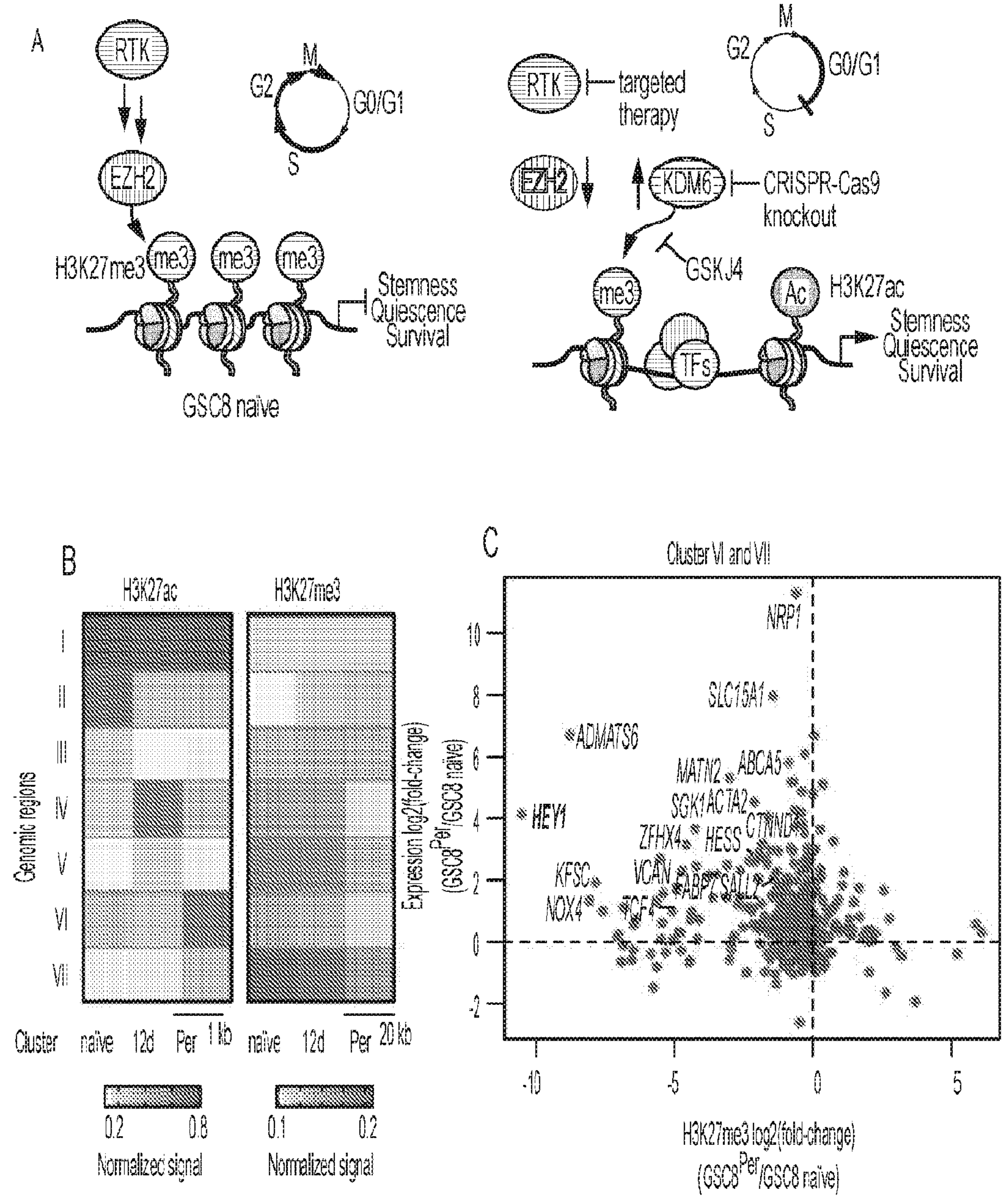
FIGS. 12A-12D show that H3K27me3 redistribution facilitated re-activation of neurodevelopmental genes.
Figure 12:
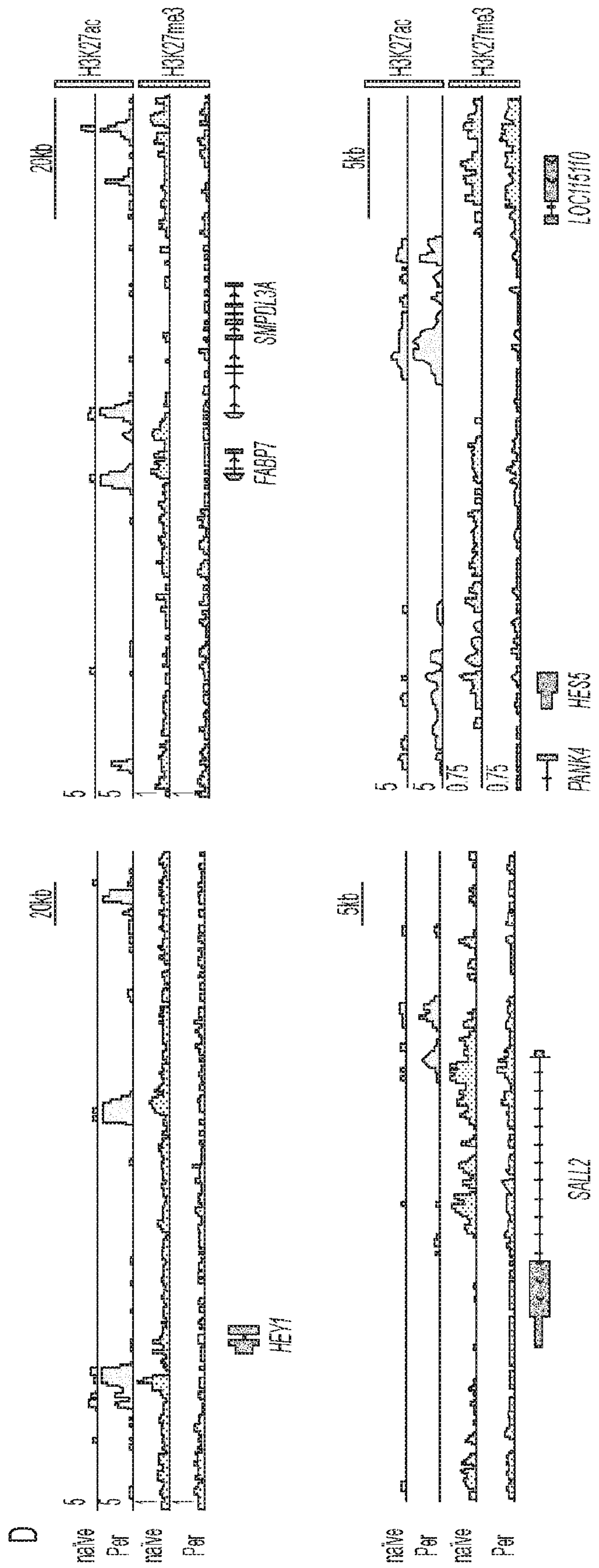

Example 6. Chromatin Landscape Alterations Facilitate Activation of Neurodevelopmental Programs The mechanisms by which KDM6 enzymes and widespread H3K27me3 demethylation facilitate the persister state were considered. It was hypothesized that redistribution of this repressive modification may be linked to reactivation of cis-regulatory elements that direct the increased stemness and quiescence programs in persister GSCs (FIG. 12A). In support of this model, it was found that H3K27me3 became strongly depleted over genomic regions surrounding H3K27ac-marked cis-regulatory elements that were selectively activated in $GSC8^{12d}$ and/or $GSC8^{Per}$ cells (FIG. 12B). The relationship between H3K27me3 depletion and expression of genes near these differential H3K27ac peaks was also examined (FIG. 12C). It was found that expression of these specific genes was significantly increased in $GSC8^{Per}$. These activated genes included master regulators with established roles in neural development, neural stem cells, and gliomagenesis, such as SALL2, FABP7, DLX2, and ZFHX4 (Chen et al., 2010; Suvà et al., 2014; Park et al., 2014; Chudnovsky et al., 2014). They also included key targets of Notch signaling, such as HEY1, HES5, and FABP7 (Anthony et al., 2005). Chromatin profiles for each of these loci revealed coincident H3K27me3 loss and H3K27ac gain over putative enhancer elements (FIG. 12D). Without being bound by theory, these data indicate that KDM6 were required to reduce H3K27me3 levels and thereby help sustain activation of regulatory elements that drive developmental genes and programs vital for the persister GSC state.

Figure 13:
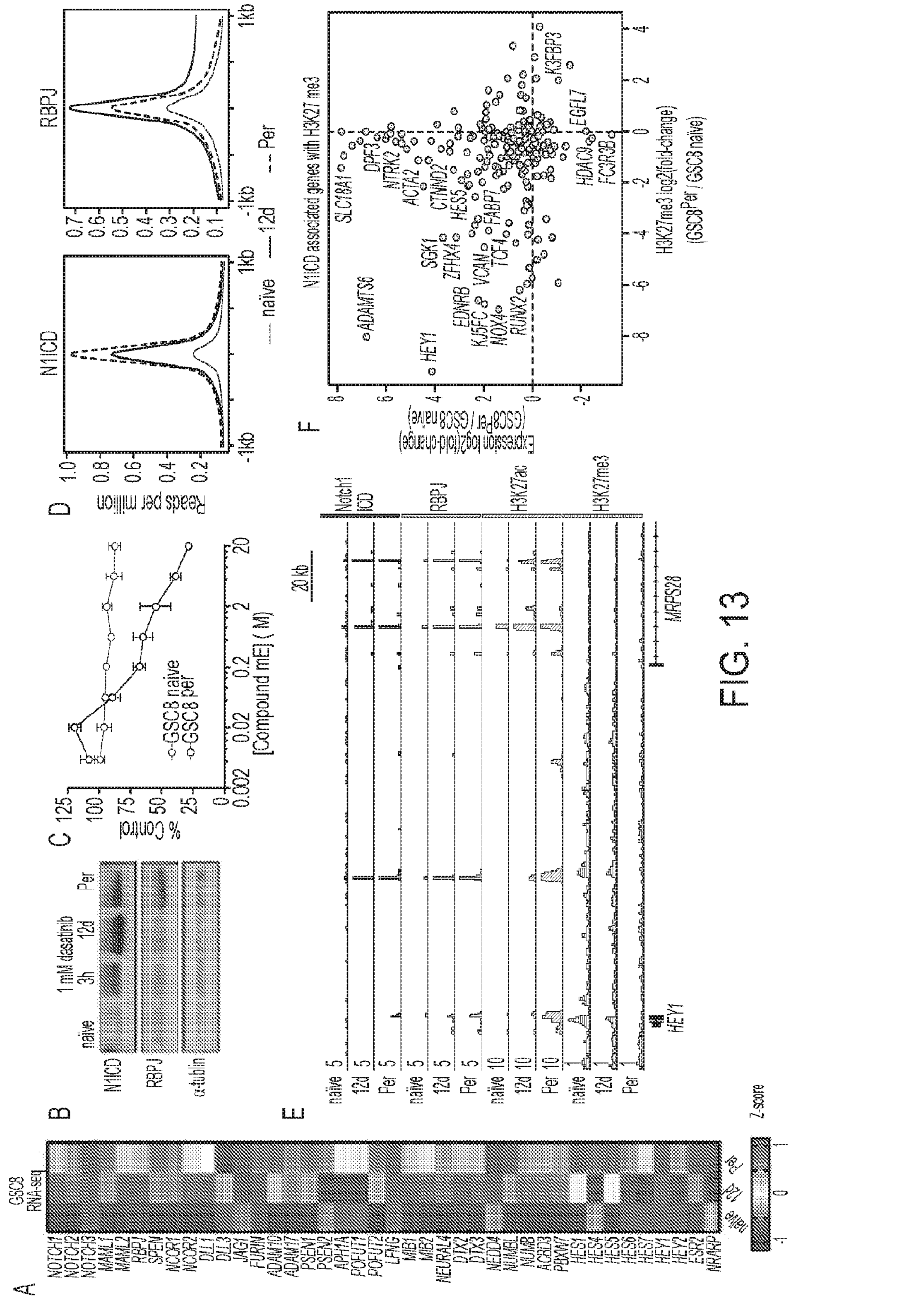
FIGS. 13A-13F show that Notch signaling was activated in $GSC^{Per}$.

Example 7. $GSC^{Per}$ Undergo an Epigenetic Switch From an RTK- to a Notch-Dependent State The erasure of repressive H3K27me3 and re-activation of H3K27ac-marked elements was particularly pronounced among documented Notch target genes. For example, reactivation of several regulatory elements in the HEY1 locus was observed (FIGS. 12C and 12D). HEY1 encodes a TF that drives GBM growth and has been associated with poor survival (Hulleman et al., 2009). Further analysis indicated that multiple Notch pathway genes were upregulated in $GSC8^{Per}$ (FIG. 13A). These include Notch-activating ligands (e.g., DLL1), Notch receptors (e.g., NOTCH1, NOTCH2, NOTCH3), canonical downstream targets (e.g., HES and HEY TFs, FABP7 (Anthony et al., 2005)) as well as other pathway components (e.g. DTX3 and DTX4).

Furthermore, high levels we detected of the Notch1 intracellular domain (N1ICD), the cleaved product of Notch1 activation, and the associated transcription factor RBPJ in GSC8 persisters (FIG. 13B). Importantly, GSC8$^{Per}$ growth was significantly reduced by a Notch inhibitor (γ-secretase) at relevant doses, but had little effect on naïve GSC8 (FIG. 13C). Without being bound to theory, these observations indicated that activation of Notch signaling allowed GSCs to transition to an RTK-independent epigenetic state.

Figure 14:
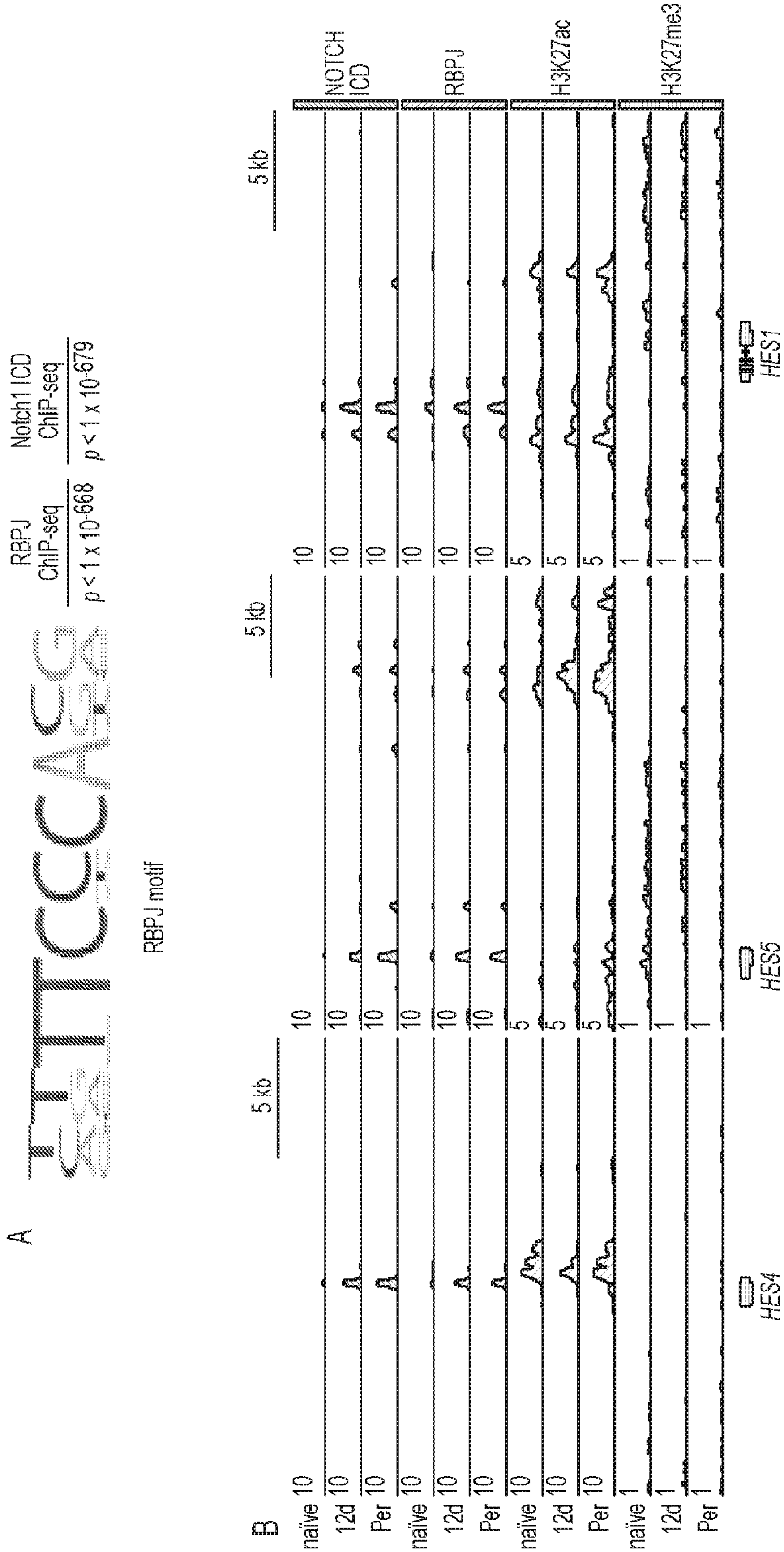
FIGS. 14A and 14B shows Notch1 ICD (N1ICD) and RBPJ binding in GSC persisters.
Figure 15:
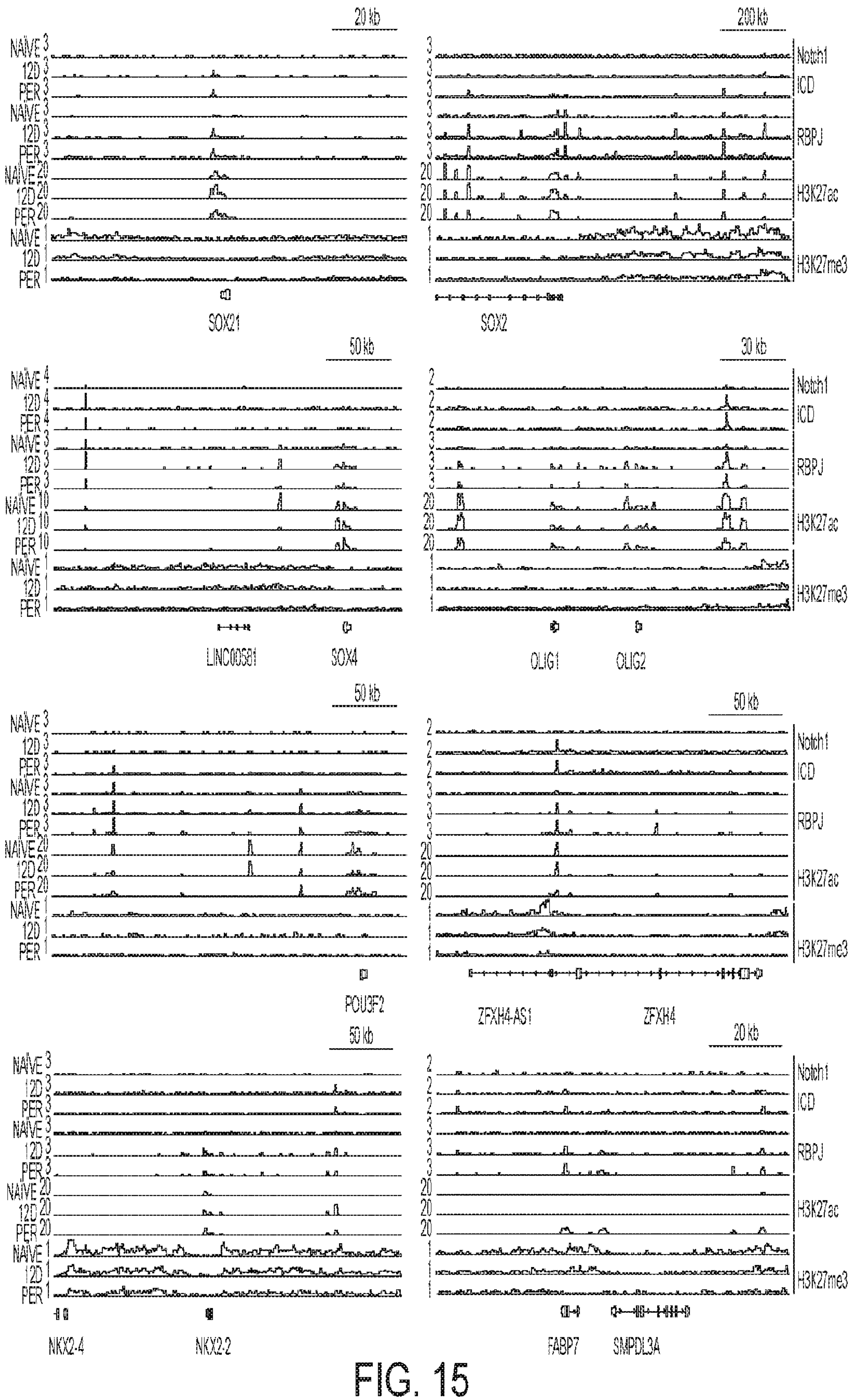
FIG. 15 shows that N1ICD and RBPJ bind nearby GSC master regulator genes. ChIP-seq profiles show ChIP-seq signal (y-axis) of Notch1 ICD (N1ICD), RBPJ, H3K27ac and H3K27me3 at genomic loci of different developmental regulators. The y-axis represents reads per million.

To understand how Notch signaling might facilitate establishment of GSC persisters, N1ICD and RBPJ by ChIP-seq were mapped. As expected, DNA sequences underlying N1ICD and RBPJ binding sites were highly enriched for RBPJ recognition motifs (FIG. 14A). Widespread gain of N1ICD and RBPJ binding sites were observed in both GSC8$^{12d}$ and GSC8$^{Per}$ (FIG. 13D). N1ICD was strongly recruited to many canonical Notch targets (e.g., HES1, HES4, HES5, HEM, several of which exhibited marked reductions in H3K27me3 levels and increases in mRNA transcript levels (FIGS. 13E and 14B). A clear example was again the HEY1 locus, where N1ICD and RBPJ first bind to distal enhancer elements in GSC8$^{12d}$ and later localize to the HEY1 promoter in GSC8$^{Per}$ (FIG. 13E). These binding patterns were accompanied by loss of H3K27me3, gain of H3K27ac, and strong upregulation of HEY1 (17-fold). Consistent with this specific example, many N1ICD-associated genes marked by H3K27me3 experienced demethylation and concomitant up-regulation in GSC8$^{Per}$ (FIG. 13F). Additionally, N1ICD binding also occurred near many neurodevelopmental master regulators, including SOX TFs as well as OLIG1/2 (FIG. 15). Without being bound to theory, these N1ICD binding patterns indicated an important role for Notch signaling in the re-activation and maintenance of primitive stem cell and quiescence programs in GSC persisters.

Lastly, it was considered whether exclusivity between proliferating and Notch-dependent states was also evident in primary tumors by single cell RNA-seq. Single tumor cells from two EGFR-amplified tumors (MGH26, MGH30) were scored for expression of N1ICD-target genes. Remarkably, individual tumor cells with higher expression of these putative Notch targets were also enriched for stemness and quiescence signatures, but were depleted for proliferative gene programs (FIGS. 7C and 7E). These data provide further support for the in vivo relevance of the alternate proliferative and slow-cycling epigenetic states that we have modeled, and for a specific role for Notch signaling in sustaining a dormant RTK-independent compartment in primary GBM tumors.

The results described herein were obtained using the following materials and methods.

Cell Culture

Patient-derived GSC culture lines were maintained in Neurobasal medium (Life Technologies) supplemented with N2/B27, penicillin/streptomycin (Life Technologies), GlutaMAX (Life Technologies), recombinant human EGF (20 ng/mL, R & D systems), and recombinant human FGF2 (20 ng/mL, R & D systems). For drug persister cultures, fresh compound and media were replenished every 4-6 days. For downstream studies (e.g., ChIP, immunoblot, gene expression), viable cells were enriched using Lympholyte (Cedarlane) to viability levels comparable to untreated cultures.

Chemical Reagents

Compounds were stored at −20 or −80° C. in 100% DMSO. Vehicle represents 0.1% DMSO unless otherwise specified. Sources: dasatinib, crenolanib, PD0325901, palbociclib, MK-2206, temozolomide, buparlisib, dacomitinib (Selleck Chemicals); GSKJ4, GSKJ5 (Tocris Bioscience); KDM5-C70 (Xcess Biosciences); Compound E (Enzo Life Sciences).

Cell Growth Assays

Freshly dissociated single cell suspensions were plated (96-well) in triplicate or quadruplicate at 1,000 to 10,000 cells/well for testing. For 4 day growth assays, CELLTITER-GLO® Luminescent Cell Viability Assay (Promega) was added to wells and end point luminescence was measured (BioTek Synergy HT Platereader). For 12 day assays, 1× compound in media was added at day 4 and all wells were replated with fresh media and compound at day 8 before viability was measured at day 12. For each inhibitor, n=3 replicates were used for each concentration and was repeated in two to four independent experiments.

Immunoblotting

Immunoblotting was performed according to standard procedures using the following antibodies: EZH2 (Cell Signaling Technology (CST), 5246), KDM6B (Abcam, ab38113), KDM5B (CST, 3273), KDM3B (A300-883A), cleaved Notch1 (Val1744) (CST, 4147), RBPJ (Abcam, ab25949), Erk1/2 p44/p42 (Millipore, 05-1152), phospho-Erk1/2 (Thr202/Tyr204, Thr185/Tyr187) (Millipore, 05-797R), pan-Akt (CST, 4691), phospho-Akt (Ser473) (CST, 4060), phospho-PDGF Receptor α (Tyr849)/PDGF Receptor β (Tyr857) (CST, 3170), PDGF Receptor α (CST, 5241), β-Actin (Sigma-Aldrich, A5060), α-tubulin (Abcam, ab4074; CST, 3873).

CRISPR-Cas9 Experiments

CRISPR sgRNA sequences were designed according to Doench et al. (Doench et al., 2014), selected to target the demethylase catalytic domain (Shi et al., 2015), and subcloned into lentiCRISPR v1. sgRNA targeting sequences are included at Table 1.

TABLE 1 sgRNA Sequences Used for CRISPR-Cas9 Genome Editing

| Oligo Name | Target Sequence | Strand | Transcript | Amino Acid Cut position | Percent Peptide | Annotation | sgRNA Score |
|---|---|---|---|---|---|---|---|
| KDM6A-1 | GTTGTTCCTGAAGGTTACTG | sense | ENST00000377967 | 1173 | 83.73 | CDS | 0.75372173 |
| KDM6A-2 | GCTGGTGCAACAACATTGCT | sense | ENST00000377967 | 1238 | 88.37 | CDS | 0.50574068 |
| KDM6B-1 | GCACGGCGTGGACTACTTGA | sense | ENST00000448097 | 1433 | 87.22 | CDS | 0.5861893 |

TABLE 1-continued sgRNA Sequences Used for CRISPR-Cas9 Genome Editing

| Oligo Name | Target Sequence | Strand | Transcript | Amino Acid Cut position | Percent Peptide | Annotation | sgRNA Score |
|---|---|---|---|---|---|---|---|
| KDM6B-2 | GCTGCACCGTGTTCATGCCC | antisense | ENST00000448097 | 1372 | 83.51 | CDS | 0.46988206 |
| GFP control | GAGCTGGACGGCGACGTAAA | | | | | | |

Lentiviruses were produced using standard protocols. Briefly, CRISPR plasmids were cotransfected with GAG/POL and VSVG plasmids into 293T packaging cells using FuGENE HD (Promega) to produce virus. Viral supernatant was collected 72 hr after transfection and concentrated using Lenti-X Concentrator (Clontech) following the manufacturer's instructions. Approximately $1.25\times10^6$ adherently attached GSC cells (5 μg/mL Engelbreth-Holm-Swarm laminin, Sigma) (Pollard et al., 2009) were infected with concentrated virus for 24 hr, and were selected 48 hr after infection with puromycin (GSC4, GSC8: 1 μg/mL, GSC87: 2 μg/mL, Life Technologies) for 4 days. After 4-5 days of recovery, cells were dissociated and plated (96-well) in triplicate or quadruplicate at 2,500 to 5,000 cells/well. Growth was normalized to cells plated on day zero using an ATP standard curve measured at each time point. Each experiment was repeated in two to four independent experiments. Efficiency of genome editing was assessed by PCR amplification (PCR SuperMix, Life Technologies) of 50 ng of genomic DNA using primer sets surrounding the sgRNA-targeted region (~800 to 1,000 bp), followed by subjection of the resultant PCR products to SURVEYOR analysis according to the manufacturer's protocol (Integrated DNA Technologies, 706020). PCR primers for SURVEYOR analysis are listed at Table 2.

TABLE 2

SURVEYOR primer sequences

| sgRNA | Fwd Primer | Rev Primer |
|---|---|---|
| KDM6A-1 | ACCAACTTGCCCAGGTTCAA | GTTCAAGAGCAGCCTAGGCA |
| KDM6A-2 | CAGCAGATCTTTTTGCACAAGC | TGCCCAAAGTTACAAGAGCCA |
| KDM6B-1 | ATGAACACGGTGCAGCTGTA | AGGGCCAGCTGGTACTGATA |
| KDM6B-2 | GTTCCTGCTTCCTTCCCCTC | TGCACAGTCCCCGCATTAAT |

Flow Cytometric Analysis

For cell cycle analysis, ~$1\times10^6$ viable dissociated cells were plated and treated with 1 μM EdU for 2 hr. Cells were then washed with PBS, incubated with Zombie Aqua viability dye (Biolegend) or Live/Dead fixable far red dead cell stain kit (Life Technologies) for 20 min, washed with PBS, and then fixed with ice-cold 70% ethanol. Staining for EdU was performed using the Click-iT EdU Flow Cytometry Assay kit (Life Technologies) according to the manufacturer's protocol. DNA content was visualized using FxCycle Violet (Life Technologies). Ki67 (clone B56, BD Biosciences) was stained for 30 min at ambient temperature. For surface marker analysis, cells were washed with PBS and stained with antibodies against CD15 (VIMC6, Miltenyi Biotec), CD133/1 (AC133, Miltenyi Biotec), or PDGFRα (16A1, BioLegend) for 30 min at 4° C. All experiments were performed with at least two biological replicates, with the exception of PDGFRα staining in GSC4 and GSC87.

Real-Time Quantitative RT-PCR and RNA-Seq Library Preparation

Whole RNA was extracted from 1-$3\times10^6$ cells using the QIAGEN RNeasy kit according to the manufacturer's protocol. For qRT-PCR, total RNA was reverse-transcribed into cDNA (High Capacity cDNA Reverse Transcriptase Kit, Applied Biosystems) and qRT-PCR amplification was performed using fast SYBR Green Master Mix (Life Technologies) with specific PCR primers for genes of interest and 18S as an endogenous control. Relative quantification for each target was performed using the comparative Ct method (Applied Biosystems). For RNA-seq library preparation, Poly(A)$^+$ RNA was enriched using magnetic oligo(dT)-beads (Life Technologies) and libraries were prepared as previously described (Gifford et al., 2013). Sequences for qRT-PCR primers used are listed at Table 3.

TABLE 3 qRT-PCR primer sequences

| Primer | Sequence |
|---|---|
| 18S-Fwd | cagggttcgattccgtagag |
| 18S-Rev | cctccagtggatcctcgtta |
| KDM6B-Fwd | caccccagcaaaccatattatgc |
| KDM6B-Rev | cacacagccatgcagggatt |
| KDM5B-Fwd | tggatacgtggcgtaaaatg |
| KDM5B-Rev | cgagcagactggcatctgta |
| KDM3A-Fwd | gtgctcacgctcggagaaa |
| KDM3A-Rev | gtgggaaacagctcgaatggt |
| JMJD1C-Fwd | caggtctcgtgccaatcaaaa |
| JMJD1C-Rev | gctgttgctggtgtgtattct |

Chromatin Immunoprecipitation (ChIP)-Sequencing

Chromatin Immunoprecipitation (ChIP) was performed as previously described (Suvà et al., 2014). Briefly, formaldehyde-fixed cells were lysed and sheared (Branson S220) on wet ice. The sheared chromatin was cleared and incubated overnight at 4° C. with the following antibodies: H3K4me3

(Millipore, 07-473, Lot 2207275), H3K27me3 (Millipore, 07-449, lot 2382150), H3K27ac (Active Motif, 39133 lot 25812006), RBPJ (Abcam, ab25949, lot GR169397-1), and cleaved Notch1 (CST, 4147, lot #4). Antibody-chromatin complexes were immunoprecipitated with protein G magnetic Dynal beads (Life Technologies), washed, eluted, reverse crosslinked, and treated with RNAse A followed by proteinase K. ChIP DNA was purified using Ampure XP beads (Beckmann Coulter) and then used to prepare sequencing libraries for sequencing with the Next-Seq Illumina genome analyzer.

RNA-Sequence Data Processing

Paired-end reads were aligned to UCSC transcriptome (hg19) using Bowtie (Langmead et al., 2009) (version 0.12.7) with the following parameters: --chunkmbs 512 -q --phred33-quals -n 0-125 -I 1 -X 2000 -p 6 -a -m 15. Gene expression, quantified as transcript per million (TPM), was estimated using RSEM (2011) with the following parameters: --fragment-length-max 1000 --estimate-rspd --paired-end.

Differential Gene Expression Analysis

All data processing was performed using R version ≥3.1.0 (R Core Team, 2014;) and BioConductor (Gentleman et al., 2004; All heatmaps were generated using the R package ggplot2 (Wickham 2009). To identify variable genes across the time course of drug treatment, triplicate RNA-seq data sets were generated for each time point and processed as outlined above. The resulting TPM values were employed for differential gene expression analysis using the R package EBSeq (Leng et al., 2015). To identify variable genes the following pairwise comparisons were performed: GSC8 naïve versus $GSC8^{12d}$, GSC8 naïve versus $GSC8^{Per}$, $GSC8^{12d}$ versus $GSC8^{Per}$. All genes with a posterior probability of differential expression (PPDE) greater than 0.5 in at least one of the comparisons were considered as variable genes. A table of all genes and significantly differentially expressed genes is provided at Appendix A: Supplementary Tables 1 and 2. GSEA version 2.1 (Subramanian et al., 2005) was carried out using signal-to-noise on log 2+1 transformed transcript per million (TPM) values as the metric; genes with mean TPM less than 10 under all given conditions were excluded from analysis.

Expression Analysis of Primary GBM-Derived Single-Cell RNA Data

For the single-cell gene expression analysis, previously published single-cell RNA-seq datasets (Patel et al., 2014) derived from primary GBM tumors were used. To remove low quality data for each tumor, all cells with less than 3,000 detectable genes were excluded and all genes with a mean TPM less than 10 were excluded. To assess the cell cycle state the cell cycle signature derived in a previous study (see (Patel et al., 2014) for details) was used. To score single-cells for individual signatures (e.g. cell cycle or persister signatures) computed mean TPM values were computed for the corresponding signature gene sets and resulting values were transformed into standard scores (z-scores).

Chromatin Immunoprecipitation Sequencing (ChIP-Seq) Data Analysis

Reads were aligned to hg19 using BWA (Li and Durbin, 2009) and identical ChIP-seq sequence reads were collapsed to avoid PCR duplicates. In order to avoid possible saturation biases, reads were downsampled to approximately similar numbers (~20 million reads). Peaks were called using HOMER v4.6 (Heinz et al., 2010) using matched inputs with the following parameters: H3K4me3, -histone -tagThreshold 30; H3K27ac, -histone -tagThreshold 50; H3K27me3, -histone -size 3000 -minDist 2500 -F 1.5 -L 0 -FDR 0.1; Notch1 ICD, -factor; and RBPJ, -factor. TF motif enrichment analysis was performed using HOMER v4.6 on 1 kb windows centered on previously called H3K27ac, Notch1 ICD, and RBPJ peaks (parameters: -size given -mask). Quantification of the H3K27me3 ChIP-seq signals, using fore- and background normalization, was essentially performed as outlined in (Zhu et al., 2013) with few modifications. To exclude genomic regions with potential copy number aberrations, read counts derived from whole cell extracts ChIP-seq within 5 kb genomic windows were quantified. Read counts were performed using interval overlap functions of the R package Genomic Ranges (Lawrence et al., 2013). To compute normalization constants, all genomic windows with read counts equal to 0 or greater than 3 standard deviations from the mean were excluded from the analysis. For a given H3K27me3 ChIP-seq data set, the background constant was estimated as the median of the read count distribution within 5 kb windows overlapping the 5% most highly expressed genes, as active genes are considered to be devoid of repressive chromatin modifications. The foreground signal was estimated as the median of the read count distribution within 5 kb windows centered around each called peak and subtracting the background signal. To quantify H3K27me3 signal within 5 kb regions of interest, the background signal was subtracted from the corresponding read count and the resulting value divided by the foreground signal. Values smaller or larger than 0 or 1 were mapped to 0 or 1, respectively. The fore- and background normalization of H3K27ac was performed analogously but with the following modifications. To account for the narrower signal, all operations were performed using 1 kb windows. For a given H3K27ac ChIP-seq data set, the background signal was estimated as the median of the read count distribution within all 1 kb windows across the genome but not overlapping with a called peak. To account for greater dynamic range, the foreground signal was estimated as the 0.95-quantile of the read count distribution within 1 kb windows centered around each called peak and subtracting the background constant. To estimate the H3K27ac signal within a 1 kb region of interest, the background constant was subtracted from the corresponding read count and the resulting value was divided by the foreground constant. Values smaller or larger than 0 or 1 were mapped to 0 or 1, respectively. In order to quantify ChIP-seq intensities within genomic regions of different sizes (e.g. genes), the obtained normalization constants were scaled accordingly. Differential peak calling was performed using HOMER v4.6. To determine most significantly changed peaks, the results were ranked by significance and the top 500 peaks were considered. Association of peaks with neighboring genes was performed using the R package ChIPpeakAnno (Zhu et al., 2010).

Chromatin Immunoprecipitation Sequencing (ChIP-Seq) Binding Profiles

ChIP-seq profile plots were generated using ngs.plot (Shen et al., 2014). To assess H3K27me3 levels across broad domains, H3K27me3 metaprofiles were generated over the union of peaks, called in each of the corresponding GSC8 persister conditions, and having a minimum size of 10 kb.

Accession Numbers

Data accompanying this paper are available through GEO under accession number GSE74557, which is incorporated herein by reference.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents, publications, and accession numbers mentioned in this specification are herein incorporated by reference to the same extent as if each independent patent, publication, and accession number was specifically and individually indicated to be incorporated by reference.

The following references are cited herein:

Agger, K., Cloos, P. A. C., Rudkjaer, L., Williams, K., Andersen, G., Christensen, J., and Helin, K. (2009). The H3K27me3 demethylase JMJD3 contributes to the activation of the INK4A-ARF locus in response to oncogene- and stress-induced senescence. Genes Dev. 23, 1171-1176.

Aguirre, A., Rubio, M. E., and Gallo, V. (2010). Notch and EGFR pathway interaction regulates neural stem cell number and self-renewal. Nature 467, 323-327.

Anthony, T. E., Mason, H. A., Gridley, T., Fishell, G., and Heintz, N. (2005). Brain lipid-binding protein is a direct target of Notch signaling in radial glial cells. Genes Dev. 19, 1028-1033.

Bao, S., Wu, Q., McLendon, R. E., Hao, Y., Shi, Q., Hjelmeland, A. B., Dewhirst, M. W., Bigner, D. D., and Rich, J. N. (2006). Glioma stem cells promote radioresistance by preferential activation of the DNA damage response. Nature 444, 756-760.

Baxter, J., Sauer, S., Peters, A., John, R., Williams, R., Caparros, M.-L., Arney, K., Otte, A., Jenuwein, T., Merkenschlager, M., et al. (2004). Histone hypomethylation is an indicator of epigenetic plasticity in quiescent lymphocytes. Embo J. 23, 4462-4472.

Benayoun, B. A., Pollina, E. A., Ucar, D., Mahmoudi, S., Karra, K., Wong, E. D., Devarajan, K., Daugherty, A. C., Kundaje, A. B., Mancini, E., et al. (2014). H3K4me3 breadth is linked to cell identity and transcriptional consistency. Cell 158, 673-688.

Black, B. L., Ligon, K. L., Zhang, Y., and Olson, E. N. (1996). Cooperative transcriptional activation by the neurogenic basic helix-loop-helix protein MASH1 and members of the myocyte enhancer factor-2 (MEF2) family. Journal of Biological Chemistry 271, 26659-26663.

Brennan, C. W., Verhaak, R. G. W., McKenna, A., Campos, B., Noushmehr, H., Salama, S. R., Zheng, S., Chakravarty, D., Sanborn, J. Z., Berman, S. H., et al. (2013). The somatic genomic landscape of glioblastoma. Cell 155, 462-477.

Brunet, A., Sweeney, L. B., Sturgill, J. F., Chua, K. F., Greer, P. L., Lin, Y., Tran, H., Ross, S. E., Mostoslaysky, R., Cohen, H. Y., et al. (2004). Stress-dependent regulation of FOXO transcription factors by the SIRT1 deacetylase. Science 303, 2011-2015.

Castro, D. S., Martynoga, B., Parras, C., Ramesh, V., Pacary, E., Johnston, C., Drechsel, D., Lebel-Potter, M., Garcia, L. G., Hunt, C., et al. (2011). A novel function of the proneural factor Ascl1 in progenitor proliferation identified by genome-wide characterization of its targets. Genes Dev. 25, 930-945.

Cenciarelli, C., Marei, H. E. S., Zonfrillo, M., Pierimarchi, P., Paldino, E., Casalbore, P., Felsani, A., Vescovi, A. L., Maira, G., and Mangiola, A. (2014). PDGF receptor alpha inhibition induces apoptosis in glioblastoma cancer stem cells refractory to anti-Notch and anti-EGFR treatment. Mol. Cancer 13, 247.

Chaffer, C. L., Marjanovic, N. D., Lee, T., Bell, G., Kleer, C. G., Reinhardt, F., D'Alessio, A. C., Young, R. A., and Weinberg, R. A. (2013). Poised Chromatin at the ZEB1 Promoter Enables Breast Cancer Cell Plasticity and Enhances Tumorigenicity. Cell 154, 61-74.

Chen, J., Li, Y., Yu, T.-S., McKay, R. M., Burns, D. K., Kerrie, S. G., and Parada, L. F. (2012). A restricted cell population propagates glioblastoma growth after chemotherapy. Nature 488, 522-526.

Chen, R., Nishimura, M. C., Bumbaca, S. M., Kharbanda, S., Forrest, W. F., Kasman, I. M., Greve, J. M., Soriano, R. H., Gilmour, L. L., Rivers, C. S., et al. (2010). A hierarchy of self-renewing tumor-initiating cell types in glioblastoma. Cancer Cell 17, 362-375.

Chicas, A., Kapoor, A., Wang, X., Aksoy, O., Evertts, A. G., Zhang, M. Q., Garcia, B. A., Bernstein, E., and Lowe, S. W. (2012). H3K4 demethylation by Jarid1a and Jarid1b contributes to retinoblastoma-mediated gene silencing during cellular senescence. Proc Natl Acad Sci USA 109, 8971-8976.

Chudnovsky, Y., Kim, D., Zheng, S., Whyte, W. A., Bansal, M., Bray, M.-A., Gopal, S., Theisen, M. A., Bilodeau, S., Thiru, P., et al. (2014). ZFHX4 Interacts with the NuRD Core Member CHD4 and Regulates the Glioblastoma Tumor-Initiating Cell State. Cell Rep 6, 313-324.

Codega, P., Silva-Vargas, V., Paul, A., Maldonado-Soto, A. R., DeLeo, A. M., Pastrana, E., and Doetsch, F. (2014). Prospective identification and purification of quiescent adult neural stem cells from their in vivo niche. Neuron 82, 545-559.

Creyghton, M. P., Cheng, A. W., Welstead, G. G., Kooistra, T., Carey, B. W., Steine, E. J., Hanna, J., Lodato, M. A., Frampton, G. M., Sharp, P. A., et al. (2010). Histone H3K27ac separates active from poised enhancers and predicts developmental state. Proc Natl Acad Sci USA 107, 21931-21936.

De Santa, F., Totaro, M. G., Prosperini, E., Notarbartolo, S., Testa, G., and Natoli, G. (2007). The histone H3 lysine-27 demethylase Jmjd3 links inflammation to inhibition of polycomb-mediated gene silencing. Cell 130, 1083-1094.

Doench, J. G., Hartenian, E., Graham, D. B., Tothova, Z., Hegde, M., Smith, I., Sullender, M., Ebert, B. L., Xavier, R. J., and Root, D. E. (2014). Rational design of highly active sgRNAs for CRISPR-Cas9-mediated gene inactivation. Nat Biotechnol 32, 1262-1267.

Doetsch, F., Caillé, I., Lim, D. A., Garcia-Verdugo, J. M., and Alvarez-Buylla, A. (1999). Subventricular Zone Astrocytes Are Neural Stem Cells in the Adult Mammalian Brain. Cell 97, 703-716.

Easwaran, H., Tsai, H.-C., and Baylin, S. B. (2014). Cancer Epigenetics: Tumor Heterogeneity, Plasticity of Stem-like States, and Drug Resistance. Mol. Cell 54, 716-727.

Eder, K., and Kalman, B (2014). Molecular heterogeneity of glioblastoma and its clinical relevance. Pathol. Oncol. Res. 20, 777-787.

Ene, C. I., Edwards, L., Riddick, G., Baysan, M., Woolard, K., Kotliarova, S., Lai, C., Belova, G., Cam, M., Walling, J., et al. (2012). Histone demethylase Jumonji D3 (JMJD3) as a tumor suppressor by regulating p53 protein nuclear stabilization. PLoS ONE 7, e51407.

Ernst, J., Kheradpour, P., Mikkelsen, T. S., Shoresh, N., Ward, L. D., Epstein, C. B., Zhang, X., Wang, L., Issner, R., Coyne, M., et al. (2011). Mapping and analysis of chromatin state dynamics in nine human cell types. Nature 473, 43-49.
Fan, X., Khaki, L., Zhu, T. S., Soules, M. E., Talsma, C. E., Gul, N., Koh, C., Zhang, J., Li, Y.-M., Maciaczyk, J., et al. (2010). NOTCH pathway blockade depletes CD133-positive glioblastoma cells and inhibits growth of tumor neurospheres and xenografts. Stem Cells 28, 5-16.
Fong, C. Y., Gilan, O., Lam, E. Y. N., Rubin, A. F., Ftouni, S., Tyler, D., Stanley, K., Sinha, D., Yeh, P., Morison, J., et al. (2015). BET inhibitor resistance emerges from leukaemia stem cells. Nature 525, 538-542.
Franceschi, E., Stupp, R., van den Bent, M. J., van Herpen, C., Laigle Donadey, F., Gorlia, T., Hegi, M., Lhermitte, B., Strauss, L. C., Allgeier, A., et al. (2012). EORTC 26083 phase I/II trial of dasatinib in combination with CCNU in patients with recurrent glioblastoma. Neuro-Oncology 14, 1503-1510.
Galli, R., Binda, E., Orfanelli, U., Cipelletti, B., Gritti, A., De Vitis, S., Fiocco, R., Foroni, C., DiMeco, F., and Vescovi, A. (2004). Isolation and characterization of tumorigenic, stem-like neural precursors from human glioblastoma. Cancer Research 64, 7011-7021.
Gangemi, R. M. R., Griffero, F., Marubbi, D., Perera, M., Capra, M. C., Malatesta, P., Ravetti, G. L., Zona, G. L., Daga, A., and Corte, G. (2009). SOX2 Silencing in Glioblastoma Tumor-Initiating Cells Causes Stop of Proliferation and Loss of Tumorigenicity. Stem Cells 27, 40-48.
Gentleman, R. C., Carey, V. J., Bates, D. M., Bolstad, B., Dealing, M., Dudoit, S., Ellis, B., Gautier, L., Ge, Y., Gentry, J., et al. (2004). Bioconductor: open software development for computational biology and bioinformatics. Genome Biol. 5, R80.
Gifford, C. A., Ziller, M. J., Gu, H., Trapnell, C., Donaghey, J., Tsankov, A., Shalek, A. K., Kelley, D. R., Shishkin, A. A., Issner, R., et al. (2013). Transcriptional and Epigenetic Dynamics during Specification of Human Embryonic Stem Cells. Cell 153, 1149-1163.
Grasbon-Frodl, E. M., Kreth, F. W., Ruiter, M., Schnell, O., Bise, K., Felsberg, J., Reifenberger, G., Tonn, J.-C., and Kretzschmar, H. A. (2007). Intratumoral homogeneity of MGMT promoter hypermethylation as demonstrated in serial stereotactic specimens from anaplastic astrocytomas and glioblastomas. Int. J. Cancer 121, 2458-2464.
GTEx Consortium (2013). The Genotype-Tissue Expression (GTEx) project. Nat Genet 45, 580-585.
Hashizume, R., Andor, N., Ihara, Y., Lerner, R., Gan, H., Chen, X., Fang, D., Huang, X., Tom, M. W., Ngo, V., et al. (2014). Pharmacologic inhibition of histone demethylation as a therapy for pediatric brainstem glioma. Nat Med 20, 1394-1396.
Heinemann, B., Nielsen, J. M., Hudlebusch, H. R., Lees, M. J., Larsen, D. V., Boesen, T., Labelle, M., Gerlach, L.-O., Birk, P., and Helin, K. (2014). Inhibition of demethylases by GSK-J1/J4. Nature 514, E1-E2.
Heinz, S., Benner, C., Spann, N., Bertolino, E., Lin, Y. C., Laslo, P., Cheng, J. X., Murre, C., Singh, H., and Glass, C. K. (2010). Simple Combinations of Lineage-Determining Transcription Factors Prime cis-Regulatory Elements Required for Macrophage and B Cell Identities. Mol. Cell 38, 576-589.
Hulleman, E., Quarto, M., Vernell, R., Masserdotti, G., Colli, E., Kros, J. M., Levi, D., Gaetani, P., Tunici, P., Finocchiaro, G., et al. (2009). A role for the transcription factor HEY1 in glioblastoma. J. Cell. Mol. Med. 13, 136-146.
Ikushima, H., Todo, T., Ino, Y., Takahashi, M., Miyazawa, K., and Miyazono, K. (2009). Autocrine TGF-beta signaling maintains tumorigenicity of glioma-initiating cells through Sry-related HMG-box factors. Cell Stem Cell 5, 504-514.
Johnstone, S. E., and Baylin, S. B. (2010). Stress and the epigenetic landscape: a link to the pathobiology of human diseases? Nat Rev Genet 11, 806-812.
Jordan, C. T., Guzman, M. L., and Noble, M. (2006). Cancer stem cells. N. Engl. J. Med. 355, 1253-1261.
Kidder, B. L., Hu, G., and Zhao, K. (2014). KDM5B focuses H3K4 methylation near promoters and enhancers during embryonic stem cell self-renewal and differentiation. Genome Biol. 15, R32.
Knoechel, B., Roderick, J. E., Williamson, K. E., Zhu, J., Lohr, J. G., Cotton, M. J., Gillespie, S. M., Fernandez, D., Ku, M., Wang, H., et al. (2014). An epigenetic mechanism of resistance to targeted therapy in T cell acute lymphoblastic leukemia. Nat Genet.
Koppikar, P., Bhagwat, N., Kilpivaara, O., Manshouri, T., Adli, M., Hricik, T., Liu, F., Saunders, L. M., Mullally, A., Abdel-Wahab, O., et al. (2013). Heterodimeric JAK-STAT activation as a mechanism of persistence to JAK2 inhibitor therapy. Nature 489, 155-159.
Kreso, A., O'Brien, C. A., van Galen, P., Gan, O. I., Notta, F., Brown, A. M. K., Ng, K., Ma, J., Wienholds, E., Dunant, C., et al. (2013). Variable clonal repopulation dynamics influence chemotherapy response in colorectal cancer. Science 339, 543-548.
Kruidenier, L., Chung, C.-W., Cheng, Z., Liddle, J., Che, K., Joberty, G., Bantscheff, M., Bountra, C., Bridges, A., Diallo, H., et al. (2013). A selective jumonji H3K27 demethylase inhibitor modulates the proinflammatory macrophage response. Nature 488, 404-408.
Labelle, M., Boesen, T., Mehrotra, M., Khan, Q., and Ullah, F. April 2014. Inhibitors of histone demethylases. International Patent, WO2014/053491.
Langmead, B., Trapnell, C., Pop, M., and Salzberg, S. L. (2009). Ultrafast and memory-efficient alignment of short DNA sequences to the human genome. Genome Biol. 10, R25.
Lathia, J. D., Mack, S. C., Mulkearns-Hubert, E. E., Valentim, C. L. L., and Rich, J. N. (2015). Cancer stem cells in glioblastoma. Genes Dev. 29, 1203-1217.
Lawrence, M., Huber, W., Pagès, H., Aboyoun, P., Carlson, M., Gentleman, R, Morgan, M. T., and Carey, V. J. (2013). Software for computing and annotating genomic ranges. PLoS Comput. Biol. 9, e1003118.
Lee, J., Kotliarova, S., Kotliarov, Y., Li, A., Su, Q., Donin, N. M., Pastorino, S., Purow, B. W., Christopher, N., Zhang, W., et al. (2006). Tumor stem cells derived from glioblastomas cultured in bFGF and EGF more closely mirror the phenotype and genotype of primary tumors than do serum-cultured cell lines. Ccell 9, 391-403.
Leng, N., Li, Y., McIntosh, B. E., Nguyen, B. K., Duffin, B., Tian, S., Thomson, J. A., Dewey, C. N., Stewart, R., and Kendziorski, C. (2015). EBSeq-HMM: a Bayesian approach for identifying gene-expression changes in ordered RNA-seq experiments. Bioinformatics 31, 2614-2622.
Li, H., and Durbin, R. (2009). Fast and accurate short read alignment with Burrows-Wheeler transform. Bioinformatics 25, 1754-1760.
Lien, W.-H., Guo, X., Polak, L., Lawton, L. N., Young, R. A., Zheng, D., and Fuchs, E. (2011). Genome-wide Maps of Histone Modifications Unwind In  Vivo Chromatin States of the Hair Follicle Lineage. Stem Cell 9, 219-232.

Ligon, K. L., Huillard, E., Mehta, S., Kesari, S., Liu, H., Alberta, J. A., Bachoo, R. M., Kane, M., Louis, D. N., DePinho, R. A., et al. (2007). Olig2-regulated lineage-restricted pathway controls replication competence in neural stem cells and malignant glioma. Neuron 53, 503-517.

Lim, D. A., and Alvarez-Buylla, A. (2014). Adult neural stem cells stake their ground. Trends in Neurosciences 37, 563-571.

Liu, L., Cheung, T. H., Charville, G. W., Hurgo, B. M. C., Leavitt, T., Shih, J., Brunet, A., and Rando, T. A. (2013). Chromatin modifications as determinants of muscle stem cell quiescence and chronological aging. Cell Rep 4, 189-204.

Louis, D. N., and International Agency for Research on Cancer. (2007). WHO classification of tumours of the central nervous system, 4th edn (Lyon: International Agency for Research on Cancer).

Love, M. I., Huber, W., and Anders, S. (2014). Moderated estimation of fold change and dispersion for RNA-seq data with DESeq2. Genome Biol. 15, 550.

Martynoga, B., Mateo, J. L., Zhou, B., Andersen, J., Achimastou, A., Urban, N., van den Berg, D., Georgopoulou, D., Hadjur, S., Wittbrodt, J., et al. (2013). Epigenomic enhancer annotation reveals a key role for NFIX in neural stem cell quiescence. Genes Dev. 27, 1769-1786.

McKnight, J. N., Boerma, J. W., Breeden, L. L., and Tsukiyama, T. (2015). Global Promoter Targeting of a Conserved Lysine Deacetylase for Transcriptional Shutoff during Quiescence Entry. Mol. Cell 59, 732-743.

McLendon, R., Friedman, A., Bigner, D., Van Meir, E. G., Brat, D. J., M Mastrogianakis, G., Olson, J. J., Mikkelsen, T., Lehman, N., Aldape, K., et al. (2008). Comprehensive genomic characterization defines human glioblastoma genes and core pathways. Nature 455, 1061-1068.

Mehta, S., Huillard, E., Kesari, S., Maire, C. L., Golebiowski, D., Harrington, E. P., Alberta, J. A., Kane, M. F., Theisen, M., Ligon, K. L., et al. (2011). The central nervous system-restricted transcription factor Olig2 opposes p53 responses to genotoxic damage in neural progenitors and malignant glioma. Cancer Cell 19, 359-371.

Meyer, M., Reimand, J., Lan, X., Head, R., Zhu, X., Kushida, M., Bayani, J., Pressey, J. C., Lionel, A. C., Clarke, I. D., et al. (2015). Single cell-derived clonal analysis of human glioblastoma links functional and genomic heterogeneity. Proc Natl Acad Sci USA 112, 851-856.

Mizutani, K.-I., Yoon, K., Dang, L., Tokunaga, A., and Gaiano, N. (2007). Differential Notch signalling distinguishes neural stem cells from intermediate progenitors. Nature 449, 351-355.

Moore, N., and Lyle, S. (2011). Quiescent, slow-cycling stem cell populations in cancer: a review of the evidence and discussion of significance. J Oncol 2011.

Nathanson, D. A., Gini, B., Mottahedeh, J., Visnyei, K., Koga, T., Gomez, G., Eskin, A., Hwang, K., Wang, J., Masui, K., et al. (2014). Targeted therapy resistance mediated by dynamic regulation of extrachromosomal mutant EGFR DNA. Science 343, 72-76.

Ntziachristos, P., Tsirigos, A., Welstead, G. G., Trimarchi, T., Bakogianni, S., Xu, L., Loizou, E., Holmfeldt, L., Strikoudis, A., King, B., et al. (2014). Contrasting roles of histone 3 lysine 27 demethylases in acute lymphoblastic leukaemia. Nature 514, 513-517.

Pallini, R., Ricci-Vitiani, L., Montano, N., Mollinari, C., Biffoni, M., Cenci, T., Pierconti, F., Martini, M., De Maria, R., and Larocca, L. M. (2011). Expression of the stem cell marker CD133 in recurrent glioblastoma and its value for prognosis. Cancer 117, 162-174.

Park, D. H., Hong, S. J., Salinas, R. D., Liu, S. J., Sun, S. W., Sgualdino, J., Testa, G., Matzuk, M. M., Iwamori, N., and Lim, D. A. (2014). Activation of neuronal gene expression by the JMJD3 demethylase is required for postnatal and adult brain neurogenesis. Cell Rep 8, 1290-1299.

Patel, A. P., Tirosh, I., Trombetta, J. J., Shalek, A. K., Gillespie, S. M., Wakimoto, H., Cahill, D. P., Nahed, B. V., Curry, W. T., Martuza, R. L., et al. (2014). Single-cell RNA-seq highlights intratumoral heterogeneity in primary glioblastoma. Science 344, 1396-1401.

Pollard, S. M., Yoshikawa, K., Clarke, I. D., Danovi, D., Stricker, S., Russell, R., Bayani, J., Head, R., Lee, M., Bernstein, M., et al. (2009). Glioma stem cell lines expanded in adherent culture have tumor-specific phenotypes and are suitable for chemical and genetic screens. Cell Stem Cell 4, 568-580.

R Core Team (2014). R: A language and environment for statistical computing. R Foundation for Statistical Computing, Vienna, Austria.

Rada-Iglesias, A., Bajpai, R., Swigut, T., Brugmann, S. A., Flynn, R. A., and Wysocka, J. (2012). A unique chromatin signature uncovers early developmental enhancers in humans Nature 470, 279-283.

Ran, F. A., Hsu, P. D., Wright, J., Agarwala, V., Scott, D. A., and Zhang, F. (2013). Genome engineering using the CRISPR-Cas9 system. Nat Protoc 8, 2281-2308.

Rathert, P., Roth, M., Neumann, T, Muerdter, F., Roe, J.-S., Muhar, M., Deswal, S., Cerny-Reiterer, S., Peter, B., Jude, J., et al. (2015). Transcriptional plasticity promotes primary and acquired resistance to BET inhibition. Nature 525, 543-547.

Ravindran Menon, D., Das, S., Krepler, C., Vultur, A., Rinner, B., Schauer, S., Kashofer, K., Wagner, K., Zhang, G., Bonyadi Rad, E., et al. (2015). A stress-induced early innate response causes multidrug tolerance in melanoma. Oncogene 34, 4448-4459.

Rheinbay, E., Suvà, M. L., Gillespie, S. M., Wakimoto, H., Patel, A. P., Shahid, M., Oksuz, O., Rabkin, S. D., Martuza, R. L., Rivera, M. N., et al. (2013). An aberrant transcription factor network essential for Wnt signaling and stem cell maintenance in glioblastoma. Cell Rep 3, 1567-1579.

Roesch, A., Fukunaga-Kalabis, M., Schmidt, E. C., Zabierowski, S. E., Brafford, P. A., Vultur, A., Basu, D., Gimotty, P., Vogt, T., and Herlyn, M. (2010). A temporarily distinct subpopulation of slow-cycling melanoma cells is required for continuous tumor growth. Cell 141, 583-594.

Roesch, A., Vultur, A., Bogeski, I., Wang, H., Zimmermann, K. M., Speicher, D., Körbel, C., Laschke, M. W., Gimotty, P. A., Philipp, S. E., et al. (2013). Overcoming intrinsic multidrug resistance in melanoma by blocking the mitochondrial respiratory chain of slow-cycling JARID1B (high) cells. Cancer Cell 23, 811-825.

Saito, N., Fu, J., Zheng, S., Yao, J., Wang, S., Liu, D. D., Yuan, Y., Sulman, E. P., Lang, F. F., Colman, H., et al. (2014). A high Notch pathway activation predicts response to γ secretase inhibitors in proneural subtype of glioma tumor-initiating cells. Stem Cells 32, 301-312.

Sharma, S. V., Lee, D. Y., Li, B., Quinlan, M. P., Takahashi, F., Maheswaran, S., McDermott, U., Azizian, N., Zou, L., Fischbach, M. A., et al. (2010). A Chromatin-Mediated Reversible Drug-Tolerant State in Cancer Cell Subpopulations. Cell 141, 69-80.

Shen, L., Shao, N., Liu, X., and Nestler, E. (2014). ngs.plot: Quick mining and visualization of next-generation sequencing data by integrating genomic databases. BMC Genomics 15, 284.

Shi, J., Wang, E., Milazzo, J. P., Wang, Z., Kinney, J. B., and Vakoc, C. R. (2015). Discovery of cancer drug targets by CRISPR-Cas9 screening of protein domains. Nat Biotechnol 33, 661-667.

Singh, S. K., Hawkins, C., Clarke, I. D., Squire, J. A., and Bayani, J. (2004). Identification of human brain tumour initiating cells. Nature.

Singh, S. K., Clarke, I. D., Terasaki, M., Bonn, V. E., Hawkins, C., Squire, J., and Dirks, P. B. (2003). Identification of a cancer stem cell in human brain tumors. Cancer Research 63, 5821-5828.

Snuderl, M., Fazlollahi, L., Le, L. P., Nitta, M., Zhelyazkova, B. H., Davidson, C. J., Akhavanfard, S., Cahill, D. P., Aldape, K. D., Betensky, R. A., et al. (2011). Mosaic amplification of multiple receptor tyrosine kinase genes in glioblastoma. Cancer Cell 20, 810-817.

Son, M. J., Woolard, K., Nam, D.-H., Lee, J., and Fine, H. A. (2009). SSEA-1 is an enrichment marker for tumor-initiating cells in human glioblastoma. Cell Stem Cell 4, 440-452.

Stupp, R., Mason, W. P., van den Bent, M. J., Weller, M., Fisher, B., Taphoorn, M. J. B., Belanger, K., Brandes, A. A., Marosi, C., Bogdahn, U., et al. (2005). Radiotherapy plus concomitant and adjuvant temozolomide for glioblastoma. N. Engl. J. Med. 352, 987-996.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc Natl Acad Sci USA 102, 15545-15550.

Sun, C., Wang, L., Huang, S., Heynen, G. J. J. E., Prahallad, A., Robert, C., Haanen, J., Blank, C., Wesseling, J., Willems, S. M., et al. (2014). Reversible and adaptive resistance to BRAF(V600E) inhibition in melanoma. Nature 508, 118-122.

Suvà, M. L., Rheinbay, E., Gillespie, S. M., Patel, A. P., Wakimoto, H., Rabkin, S. D., Riggi, N., Chi, A. S., Cahill, D. P., Nahed, B. V., et al. (2014). Reconstructing and Reprogramming the Tumor-Propagating Potentialof Glioblastoma Stem-like Cells. Cell 157, 580-594.

Tamura, K., Aoyagi, M., Ando, N., Ogishima, T., Wakimoto, H., Yamamoto, M., and Ohno, K. (2013). Expansion of CD133-positive glioma cells in recurrent de novo glioblastomas after radiotherapy and chemotherapy. J. Neurosurg. 119, 1145-1155.

Tanaka, S., Louis, D. N., Curry, W. T., Batchelor, T. T., and Dietrich, J. (2012). Diagnostic and therapeutic avenuesfor glioblastoma: no longer a dead end? Nature Reviews Clinical Oncology 10, 14-26.

Vanner, R. J., Remke, M., Gallo, M., Selvadurai, H. J., Coutinho, F., Lee, L., Kushida, M., Head, R., Morrissy, S., Zhu, X., et al. (2014). Quiescent sox2(+) cells drive hierarchical growth and relapse in sonic hedgehog subgroup medulloblastoma. Cancer Cell 26, 33-47.

Venere, M., Fine, H. A., Dirks, P. B., and Rich, J. N. (2011). Cancer stem cells in gliomas: identifying and understanding the apex cell in cancer's hierarchy. Glia 59, 1148-1154.

Wakimoto, H., Kesari, S., Farrell, C. J., Curry, W. T., Zaupa, C., Aghi, M., Kuroda, T., Stemmer-Rachamimov, A., Shah, K., Liu, T.-C., et al. (2009). Human glioblastoma-derived cancer stem cells: establishment of invasive glioma models and treatment with oncolytic herpes simplex virus vectors. Cancer Research 69, 3472-3481.

Wang, J., Wakeman, T. P., Lathia, J. D., Hjelmeland, A. B., Wang, X.-F., White, R. R., Rich, J. N., and Sullenger, B. A. (2010). Notch promotes radioresistance of glioma stem cells. Stem Cells 28, 17-28.

Whitfield, M. L., Sherlock, G., Saldanha, A. J., Murray, J. I., Ball, C. A., Alexander, K. E., Matese, J. C., Perou, C. M., Hurt, M. M., Brown, P. O., et al. (2002). Identification of genes periodically expressed in the human cell cycle and their expression in tumors. Mol. Biol. Cell 13, 1977-2000.

Wickham, H. (2009). ggplot2: elegant graphics for data analysis, 1st edn (New York: Springer).

Williams, K., Christensen, J., Rappsilber, J., Nielsen, A. L., Johansen, J. V., and Helin, K. (2014). The histone lysine demethylase JMJD3/KDM6B is recruited to p53 bound promoters and enhancer elements in a p53 dependent manner PLoS ONE 9, e96545.

Xia, X., Lemieux, M. E., Li, W., Carroll, J. S., Brown, M., Liu, X. S., and Kung, A. L. (2009). Integrative analysis of HIF binding and transactivation reveals its role in maintaining histone methylation homeostasis. Proc Natl Acad Sci USA 106, 4260-4265.

Zhu, L. J., Gazin, C., Lawson, N. D., Pages, H., Lin, S. M., Lapointe, D. S., and Green, M. R. (2010). ChIPpeakAnno: a Bioconductor package to annotate ChIP-seq and ChIP-chip data. BMC Bioinformatics 11, 237.

Zhu, J., Adli, M., Zou, J. Y., Verstappen, G., Coyne, M., Zhang, X., Durham, T., Miri, M., Deshpande, V., De Jager, P. L., et al. (2013). Genome-wide chromatin state transitions associated with developmental and environmental cues. Cell 152, 642-654.

What is claimed is:

1. A method of increasing cell death in a glioblastoma stem cell population comprising measuring expression in the glioblastoma stem cell population of one or more biomarkers selected from the group consisting of SALL2, DLX2, ZFHX4, HEY1, HES5, and FABP7 in the glioblastoma stem cell population;

contacting the glioblastoma stem cell population with dasatinib, crenolanib, or a combination thereof, wherein dasatinib has the following structure:

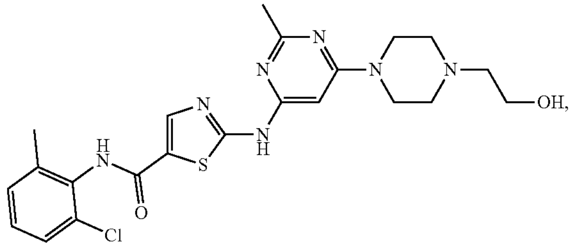 [SMILES: Cc1nc(Nc2ncc(C(=O)Nc3c(C)cccc3Cl)s2)cc(N2CCN(CCO)CC2)n1]

and crenolanib has the following structure:

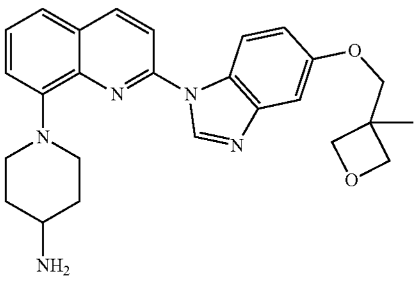 [SMILES: CC1(COc2ccc3c(c2)ncn3-c2ccc3cccc(N4CCC(N)CC4)c3n2)COC1]

measuring expression of said one or more biomarkers in in the glioblastoma stem cell population after said contacting with dasatinib, crenolanib, or a combination thereof; and contacting the glioblastoma stem cell persister population with GSKJ4 if there is increased expression of said one or more biomarkers after said contacting with dasatinib, crenolanib, or a combination thereof as compared to the first measuring step, wherein, GSKJ4 has the following structure:
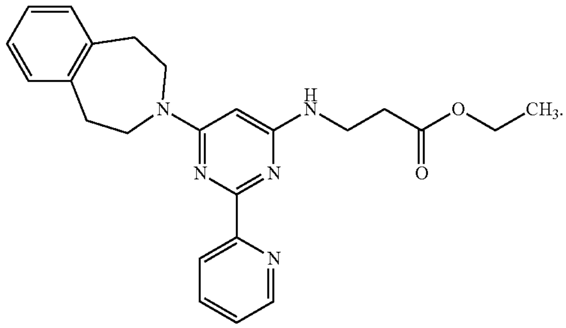 [SMILES: CCOC(=O)CCNc1cc(N2CCc3ccccc3CC2)nc(-c2ccccn2)n1]
* * * * *